United States Patent
Giovannini et al.

(10) Patent No.: US 9,789,082 B2
(45) Date of Patent: *Oct. 17, 2017

(54) SOMATOSTATIN RECEPTOR SUBTYPE 4 (SSTR4) AGONISTS

(71) Applicant: Centrexion Therapeutics Corporation, Baltimore, MD (US)

(72) Inventors: Riccardo Giovannini, Verona (IT); Yunhai Cui, Biberach an der Riss (DE); Henri Doods, Warthausen (DE); Marco Ferrara, San Donato (IT); Stefan Just, Biberach an der Riss (DE); Raimund Kuelzer, Mittelbiberach (DE); Iain Lingard, Monza (IT); Rocco Mazzaferro, San Giuliano (IT); Klaus Rudolf, Warthausen (DE)

(73) Assignee: Centrexion Therapeutics Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/157,624

(22) Filed: May 18, 2016

(65) Prior Publication Data
US 2017/0014381 A1   Jan. 19, 2017

Related U.S. Application Data

(63) Continuation of application No. 14/275,879, filed on May 12, 2014, now Pat. No. 9,371,282.

(30) Foreign Application Priority Data

May 17, 2013 (EP) .................................. 13168224

(51) Int. Cl.
| | | |
|---|---|---|
| A61K 31/403 | (2006.01) | |
| C07D 209/52 | (2006.01) | |
| C07D 487/04 | (2006.01) | |
| C07D 471/04 | (2006.01) | |
| C07D 401/12 | (2006.01) | |
| C07D 417/12 | (2006.01) | |
| C07D 403/12 | (2006.01) | |
| C07D 405/12 | (2006.01) | |
| C07D 413/12 | (2006.01) | |
| A61K 31/4155 | (2006.01) | |
| A61K 31/416 | (2006.01) | |
| A61K 31/423 | (2006.01) | |
| A61K 31/426 | (2006.01) | |
| A61K 31/429 | (2006.01) | |
| A61K 31/437 | (2006.01) | |
| A61K 31/4375 | (2006.01) | |
| A61K 31/4439 | (2006.01) | |
| A61K 31/4709 | (2006.01) | |
| A61K 31/4725 | (2006.01) | |
| A61K 31/497 | (2006.01) | |
| A61K 31/501 | (2006.01) | |

(Continued)

(52) U.S. Cl.
CPC .......... *A61K 31/403* (2013.01); *A61K 31/416* (2013.01); *A61K 31/4155* (2013.01); *A61K 31/423* (2013.01); *A61K 31/426* (2013.01); *A61K 31/429* (2013.01); *A61K 31/437* (2013.01); *A61K 31/4375* (2013.01); *A61K 31/4439* (2013.01); *A61K 31/4709* (2013.01); *A61K 31/4725* (2013.01); *A61K 31/497* (2013.01); *A61K 31/501* (2013.01); *A61K 31/502* (2013.01); *A61K 31/506* (2013.01); *A61K 31/5025* (2013.01); *A61K 31/517* (2013.01); *A61K 31/519* (2013.01); *C07D 209/52* (2013.01); *C07D 401/12* (2013.01); *C07D 403/12* (2013.01); *C07D 405/12* (2013.01); *C07D 413/12* (2013.01); *C07D 417/12* (2013.01); *C07D 471/04* (2013.01); *C07D 487/04* (2013.01)

(58) Field of Classification Search
CPC .............. A61K 31/403; A61K 31/4155; A61K 31/416; A61K 31/423; A61K 31/426; A61K 31/429; A61K 31/437; A61K 31/4375; A61K 31/4439; A61K 31/4709; A61K 31/4725; A61K 31/497; A61K 31/501; A61K 31/502; A61K 31/5025; A61K 31/506; A61K 31/517; A61K 31/519; C07D 209/52; C07D 487/04; C07D 471/04; C07D 401/12; C07D 417/12; C07D 403/12; C07D 405/12; C07D 413/12
See application file for complete search history.

(56) References Cited

U.S. PATENT DOCUMENTS

| | | | |
|---|---|---|---|
| 6,057,338 A | 5/2000 | Yang et al. | |
| 6,063,796 A | 5/2000 | Yang et al. | |

(Continued)

FOREIGN PATENT DOCUMENTS

| | | |
|---|---|---|
| CN | 102675290 A | 9/2012 |
| WO | WO-2005037216 A2 | 4/2005 |

(Continued)

OTHER PUBLICATIONS

Rai, Pharmacology & Therapeutics, vol. 152, 98-110, 2015.*

(Continued)

*Primary Examiner* — D M Seaman
(74) *Attorney, Agent, or Firm* — Goodwin Procter LLP

(57) ABSTRACT

3-aza-bicyclo[3.1.0]hexane-6-carboxylic acid amide derivatives which are agonists of somatostatin receptor subtype 4 (SSTR4), useful for preventing or treating medical disorders related to SSTR4.

38 Claims, No Drawings

(51) Int. Cl.
  *A61K 31/502*   (2006.01)
  *A61K 31/5025*  (2006.01)
  *A61K 31/506*   (2006.01)
  *A61K 31/517*   (2006.01)
  *A61K 31/519*   (2006.01)

(56) References Cited

U.S. PATENT DOCUMENTS

| | | |
|---|---|---|
| 6,159,941 A | 12/2000 | Ankersen et al. |
| 7,741,362 B2 | 6/2010 | Tomperi et al. |
| 8,895,602 B1 | 11/2014 | Nam et al. |
| 9,371,282 B2 * | 6/2016 | Giovannini ......... C07D 209/52 |
| 2002/0052315 A1 | 5/2002 | Hornik et al. |
| 2010/0004339 A1 | 1/2010 | Tomperi et al. |
| 2014/0005165 A1 | 1/2014 | Nair et al. |
| 2014/0343065 A1 | 11/2014 | Giovannini et al. |
| 2014/0343295 A1 | 11/2014 | Nam et al. |

FOREIGN PATENT DOCUMENTS

| | | |
|---|---|---|
| WO | WO-2008/075172 A2 | 6/2008 |
| WO | WO-2010059922 A1 | 5/2010 |
| WO | WO-2012028676 A1 | 3/2012 |
| WO | WO-2012125661 A1 | 9/2012 |
| WO | WO-2014/184275 A1 | 11/2014 |

OTHER PUBLICATIONS

European Search Report for corresponding application EP13168224.7, mailed Jun. 13, 2013.

International Search Report and Written Opinion for International Patent Application PCT/EP2014/059905 mailed on Jul. 23, 2014. (7 pages).

Sándor, K. et al. "Analgesic effects of the somatostatin sst4 receptor selective agonist J-2156 in acute and chronic pain models," Eur. J. Pharmacol. (2006) vol. 539, pp. 71-75. (Abstract Only).

* cited by examiner

SOMATOSTATIN RECEPTOR SUBTYPE 4 (SSTR4) AGONISTS

This application is a continuation of U.S. application Ser. No. 14/275,879, filed May 12, 2014, which claims priority to and the benefit of European Patent Application Serial No. 13168224.7, filed May 17, 2013, each of which is hereby incorporated by reference in its entirety.

FIELD OF THE INVENTION

The invention relates to 3-aza-bicyclo[3.1.0]hexane-6-carboxylic acid amide derivatives of general formula (I), which are agonists of somatostatin receptor subtype 4 (SSTR4), useful for preventing or treating medical disorders related to SSTR4. In addition, the invention relates to processes for preparing pharmaceutical compositions as well as processes for manufacture of the compounds according to the invention.

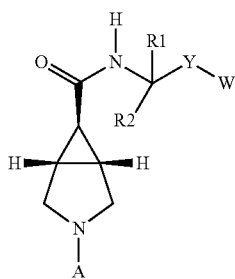

(I)

BACKGROUND OF THE INVENTION

Somatostatin, or somatotropin-release inhibitory factor (SRIF), is a cyclic peptide found in humans. It is produced widely in the human body and acts both systemically and locally to inhibit the secretion of various hormones, growth factors and neurotransmitters. The effects of somatostatin are mediated by a family of G protein-coupled receptors, of which five subtypes are known. These subtypes are divided into two subfamilies, the first comprising SSTR2, SSTR3 and SSTR5 and the second SSTR1 and SSTR4.

Somatostatin is involved in the regulation of processes such as for example cellular proliferation, glucose homeostasis, inflammation and pain.

In this aspect somatostatin or other members of the somatostatin peptide family are believed to inhibit nociceptive and inflammatory processes via the SSTR4 pathway.

A number of further therapeutic areas for SSTR4 agonists have been discussed (see e.g. Crider, A; Mini Rev. Med. Chem. 2002, 7, 213 (and references therein); WO 2010/059922 (and references therein).

Selective SSTR4 agonists have been disclosed, for instance, in J. Am. Chem. Soc. 1998, 120, 1368-1373.

WO 2010/059922 provides pyrrolidine carboxamide agonists of SSTR4.

However, there is further need for selective SSTR4 agonists, especially for non-peptidic agonists, which show high stability and other advantageous properties, such as oral efficacy and metabolic stability.

Substituted 3-azabicyclo[3.1.0]hexane derivatives have been discussed for the use as inhibitors of the glycine type-1 transporter (WO 2005/037216), for the use as CCR2 (chemokine receptor 2) antagonists (WO 2012/125661) or for the treatment of renal injuries and hypertension (CN 102675290).

AIM OF THE INVENTION

It has now been found that compounds of the present invention according to general formula (I) are effective agonists of somatostatin receptor 4 (SSTR4).

Besides the agonistic property toward somatostatin receptor 4, the compounds of the present invention provide advantageous pharmacokinetic properties. For example the compounds of the present invention show high metabolic stability.

Furthermore, the compounds according to the present invention show high selectivity for the SSTR4 receptor with respect to the other subtypes of the same subfamily including the SSTR1 receptor. As a consequence the probability of side effects is reduced.

Accordingly, one aspect of the invention refers to compounds according to formula (I) and salts, hydrates or solvates thereof as agonists of somatostatin receptor 4.

Another aspect of the invention refers to compounds according to formula (I) and salts, hydrates or solvates thereof as selective agonists of SSTR4 over other subtypes of the same family, including selectivity over the other subtype of the same subfamily (SSTR1).

A further aspect of the invention relates to the physiologically acceptable salts of the compounds of general formula (I) according to this invention with inorganic or organic acids.

In a further aspect this invention relates to pharmaceutical compositions, containing at least one compound according to formula (I) or a physiologically acceptable salt, hydrate or solvate thereof, optionally together with one or more inert carriers and/or diluents.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of disorders related to SSTR4.

Another aspect of the invention relates to processes of manufacture of the compounds of the present invention.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of diseases or conditions which can be influenced by activation of SSTR4. In this aspect the present invention relates to compounds according to formula (I) or a physiologically acceptable salt thereof for the treatment of pain of various origins and/or inflammation.

Other aims of the present invention will become apparent to the skilled man directly from the foregoing and following remarks.

DETAILED DESCRIPTION

In a first aspect the present invention relates to compounds of general formula (I)

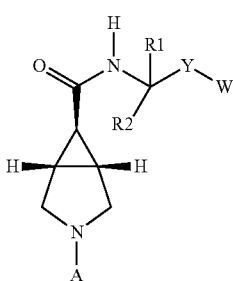

(I)

wherein
A is selected from the group $A^1$ consisting of H and $C_{1-6}$-alkyl;
$R^1$ and $R^2$ are independently selected from the group $R^{1.1a}$, $R^{2.1a}$ consisting of H, $C_{1-6}$-alkyl and $C_{3-6}$-cycloalkyl, wherein at least one of $R^1$ or $R^2$ is $C_{1-6}$-alkyl or $C_{3-6}$-cycloalkyl,
wherein the $C_{1-6}$-alkyl or the $C_{3-6}$-cycloalkyl is optionally substituted with halogens or MeO—, or
wherein $R^1$ and $R^2$ together form a 2- to 5-membered alkylene-bridge optionally substituted with halogens incorporating 0 to 2 heteroatoms independently selected from the group consisting of N, O or S;
W is selected from the group $W^1$ consisting of a mono- or bicyclic aryl, mono- or bicyclic heteroaryl, mono- or bicyclic heterocyclyl and mono- or bicyclic cycloalkyl.
wherein each of these ring systems are optionally substituted with one or more $R^3$, and wherein the heteroaryl comprises up to 4 heteroatoms and one or two 5- or 6-membered ring(s);
$R^3$ is independently selected from the group $R^{3.1}$ consisting of $C_{1-6}$-alkyl, $C_{3-8}$-cycloalkyl, $C_{1-6}$-alkyl-O—, benzyl, halogen, HO—, NC—, mono- or bicyclic heteroaryl, and 5- or 6-membered monocyclic heterocyclyl containing one heteroatom selected from the group consisting of N, O or $S(O)_r$, wherein the heteroaryl contains up to 4 heteroatoms and one or two 5- or 6-membered ring(s), and r is 0, 1 or 2,
wherein the $C_{1-6}$-alkyl, $C_{3-8}$-cycloalkyl, $C_{1-6}$-alkyl-O—, benzyl, heteroaryl and the heterocyclyl are optionally substituted with halogens, HO—, acetyl, $C_{1-6}$-alkyl-O—, oxo, $R^4$—$S(O)_2$—, with $R^4$ being aryl, $C_{3-6}$-cycloalkyl and/or $C_{1-6}$-alkyl;
Y is selected from the group $Y^1$ consisting of a bond, —$CH_2$—, —$CH_2CH_2$—, and —$CH_2O$—;
or a salt of any of the above compounds.

Unless otherwise stated, the groups, residues, and substituents, particularly $R^1$, $R^2$, $R^3$, $R^4$, A, W and Y are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^2$ consisting of H or $C_{1-3}$-alkyl.
In a further embodiment of the present invention
A is selected from the group $A^3$ consisting of H or $H_3C$—.
In a further embodiment of the present invention
A is selected from the group $A^4$ consisting of H.
$R^1$ and $R^2$ are independently selected from the group $R^{1.1}$, $R^{2.1}$ consisting of H and $C_{1-6}$-alkyl, wherein at least one of $R^1$ or $R^2$ is $C_{1-6}$-alkyl, or wherein $R^1$ and $R^2$ together form a 2- to 5-membered alkylene-bridge incorporating 0 to 2 heteroatoms independently selected from the group consisting of N, O or S;
In a further embodiment of the present invention
$R^1$ and $R^2$ are independently selected from the group $R^{1.2}$, $R^{2.2}$ consisting of H and $C_{1-3}$-alkyl optionally substituted with halogens, wherein at least one of $R^1$ or $R^2$ is independently $C_{1-3}$-alkyl optionally substituted with halogens, or wherein $R^1$ and $R^2$ together form a 2- to 5-membered alkylene-bridge optionally substituted with halogens incorporating 0 to 2 heteroatoms independently selected from the group consisting of N, O or S.
In a further embodiment of the present invention
$R^1$ and $R^2$ are selected from the group $R^{1.3}$ and $R^{2.3}$ consisting of $C_{1-3}$-alkyl or, wherein $R^1$ and $R^2$ together with the C atom, to which they are connected, form a 3-, 4-, 5- or 6-membered ring incorporating 0 to 2 heteroatoms selected from the group consisting of N, O and S.
In a further embodiment of the present invention
$R^1$ and $R^2$ are selected from the group $R^{1.4}$ and $R^{2.4}$ consisting of $H_3C$— or wherein $R^1$ and $R^2$ together form a 2- or 3-membered alkylene-bridge
In a further embodiment of the present invention
$R^1$ and $R^2$ are selected from the group $R^{1.5}$ and $R^{2.5}$ consisting of $H_3C$—.
In a further embodiment of the present invention
W is selected from the group $W^2$ consisting of a mono- or bicyclic aryl, a mono- or bicyclic heteroaryl and a mono- or bicyclic heterocyclyl, wherein each of these ring systems are optionally substituted with one or more $R^3$, and wherein the heteroaryl comprises up to 4 heteroatoms and one or two 5- or 6-membered ring(s).
In a further embodiment of the present invention
W is selected from the group $W^3$ consisting of a monocyclic aryl, a monocyclic heteroaryl and a monocyclic heterocyclyl,
wherein each of these ring systems are optionally substituted with one or more $R^3$, and wherein the heteroaryl comprises up to 4 heteroatoms and one 5- or 6-membered ring.
In a further embodiment of the present invention
W is selected from the group $W^4$ consisting of a bicyclic aryl, a bicyclic heteroaryl and a bicyclic heterocyclyl, wherein each of these ring systems are optionally substituted with one or more $R^3$, and wherein the heteroaryl comprises up to 4 heteroatoms and two 5- or 6-membered rings.
In a further embodiment of the present invention
W is a selected from the group $W^5$ consisting of

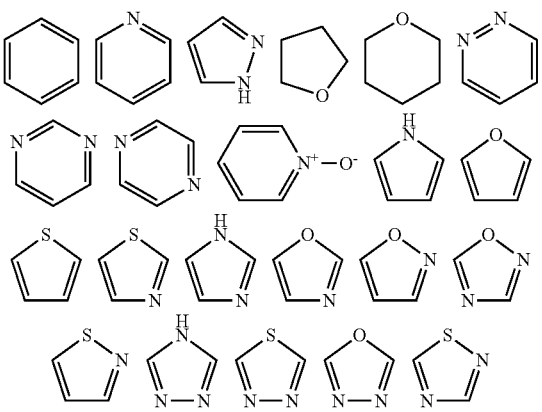

-continued
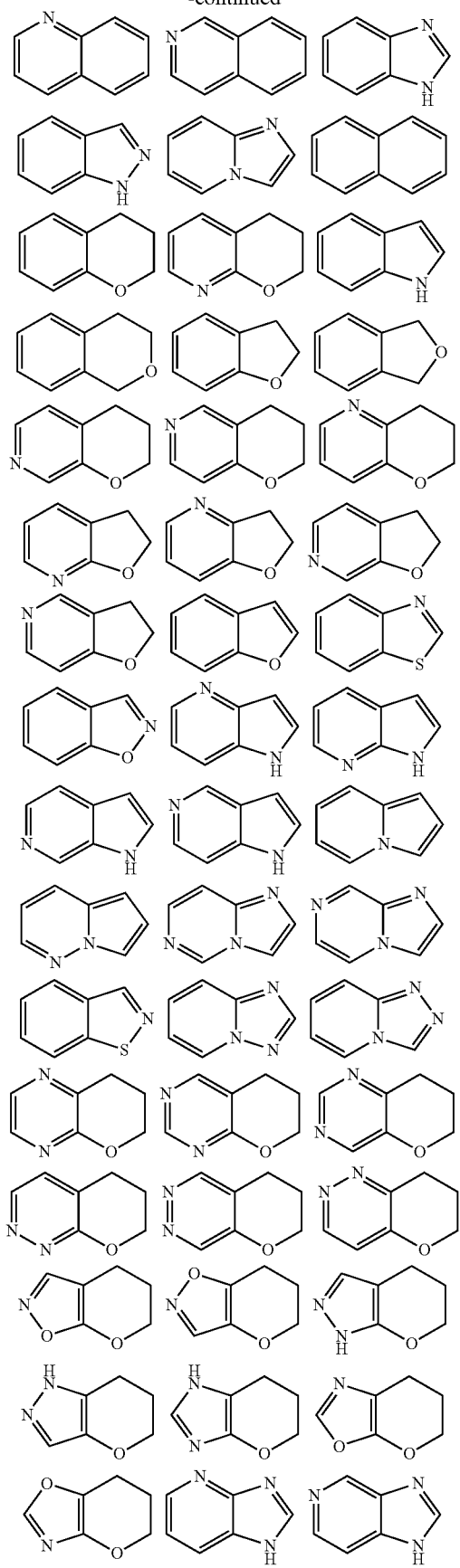
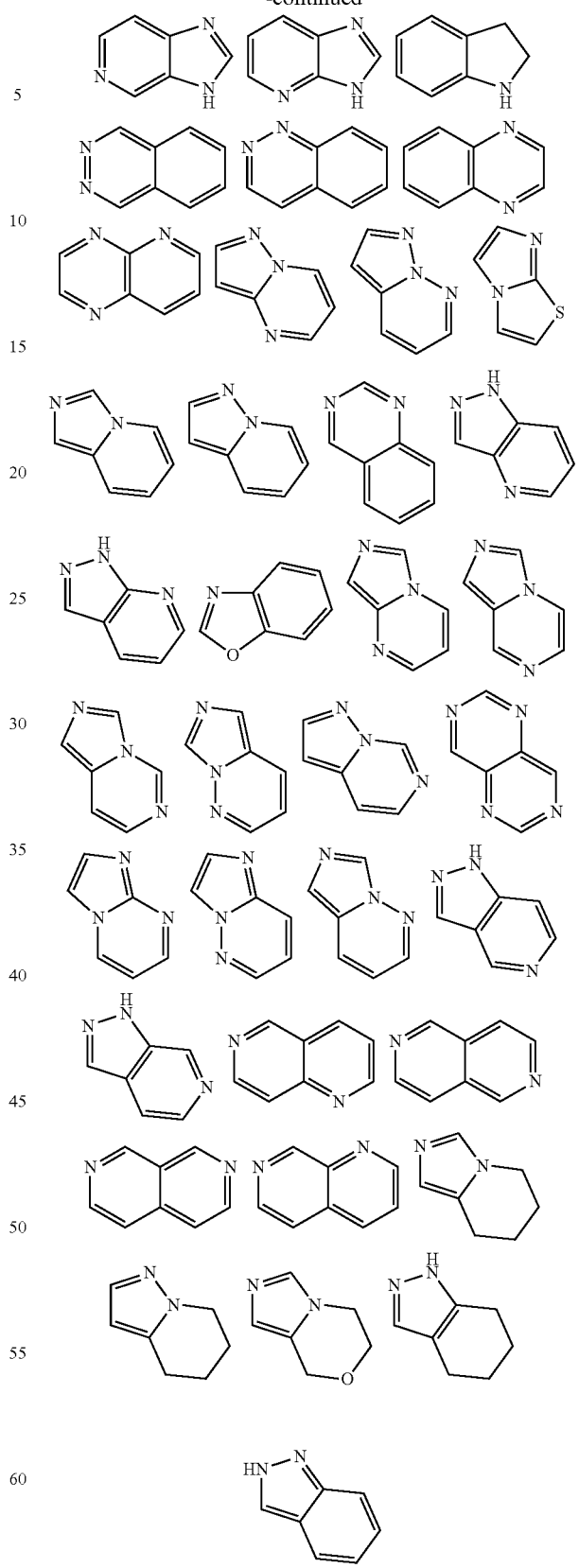
wherein each of these ring systems are optionally substituted with one or more $R^3$.

In a further embodiment of the present invention
W is a selected from the group $W^6$ consisting of
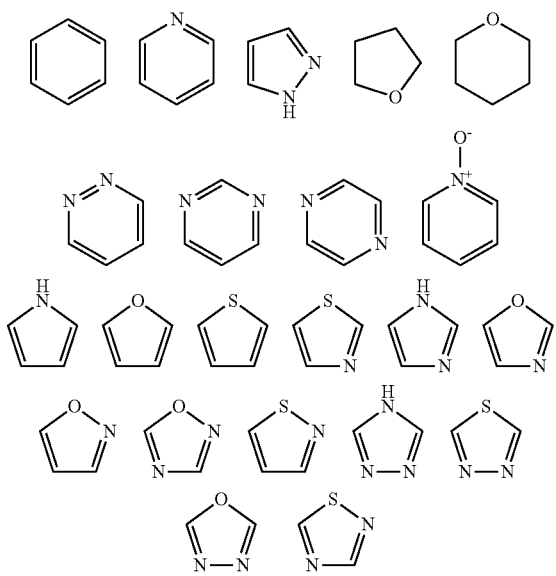
wherein each of these ring systems are optionally substituted with one or more $R^3$.
In a further embodiment of the present invention
W is a selected from the group $W^7$ consisting of
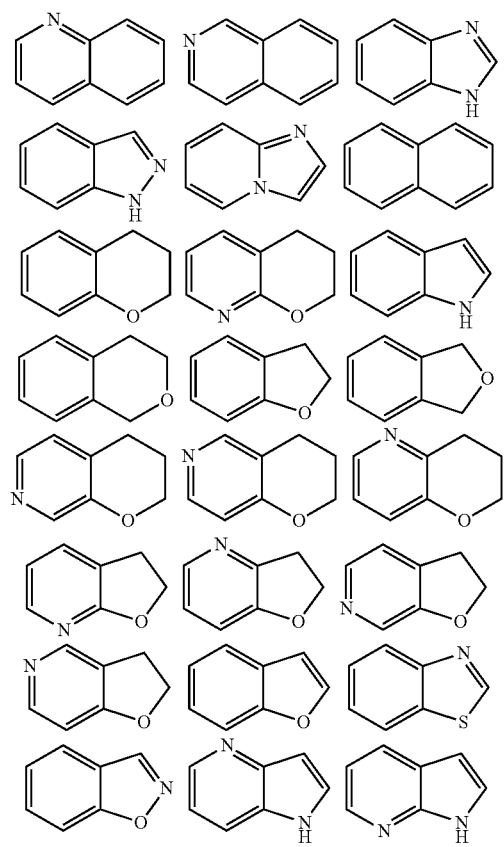
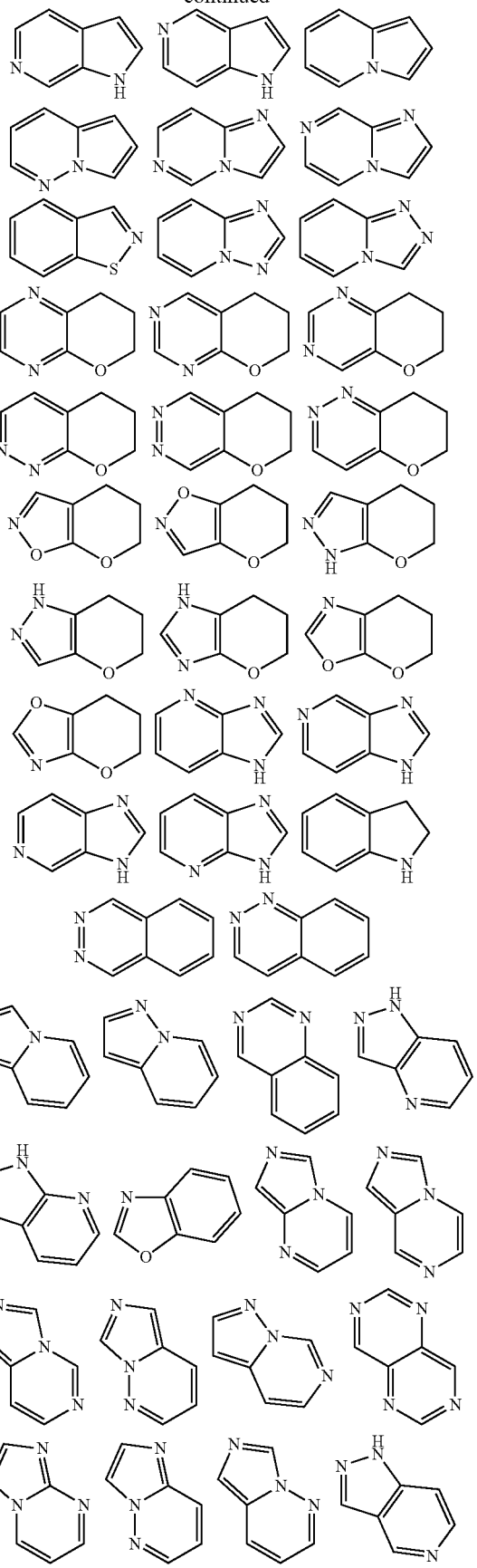

-continued

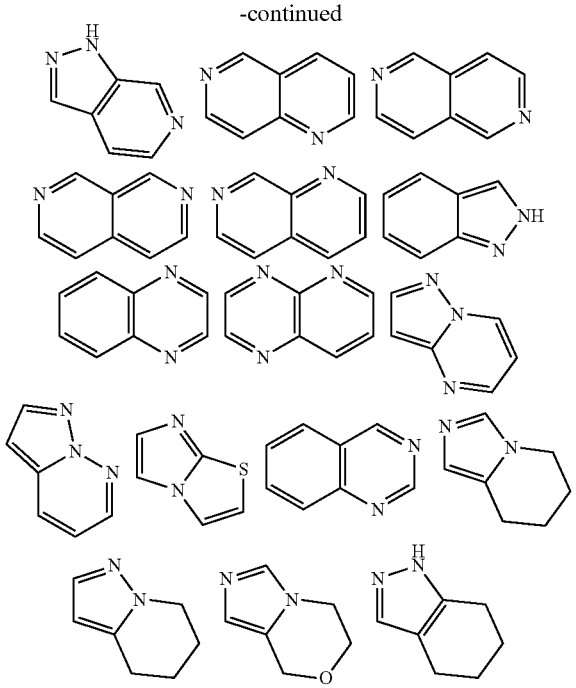

wherein each of these ring systems are optionally substituted with one or more R³.

In a further embodiment of the present invention W is selected from the group $W^8$ consisting of

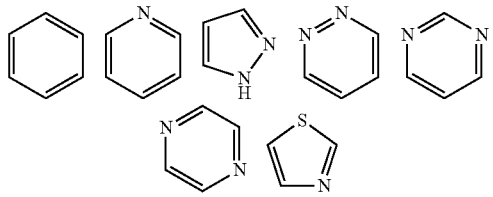

wherein each of these ring systems are optionally substituted with one or more R³.

In a further embodiment of the present invention W is selected from the group $W^9$ consisting of

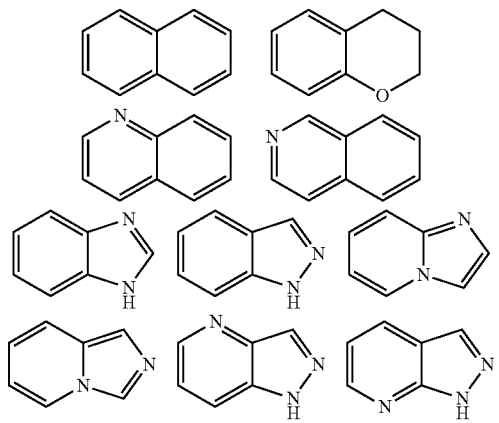

-continued

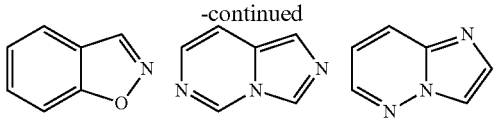

wherein each of these ring systems are optionally substituted with one or more R³.

In a further embodiment of the present invention W is selected from the group $W^{9a}$ consisting of

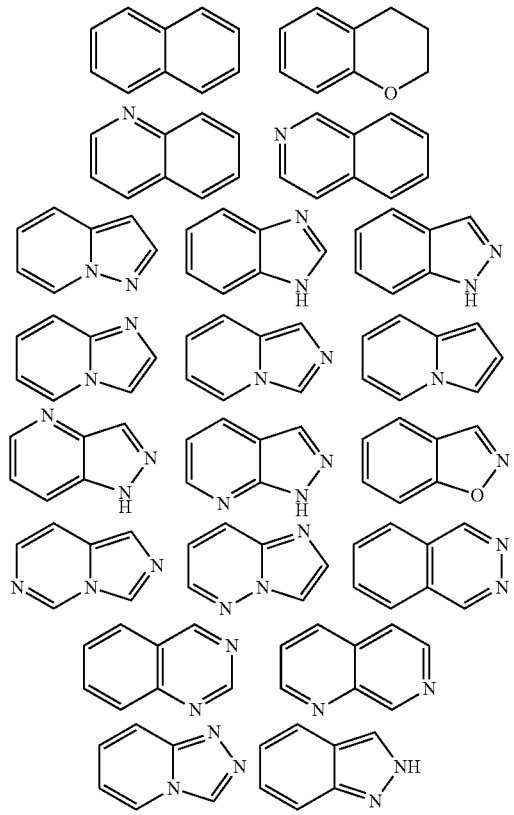

wherein each of these ring systems are optionally substituted with one or more R³.

In a further embodiment of the present invention W is selected from the group $W^{10}$ consisting of

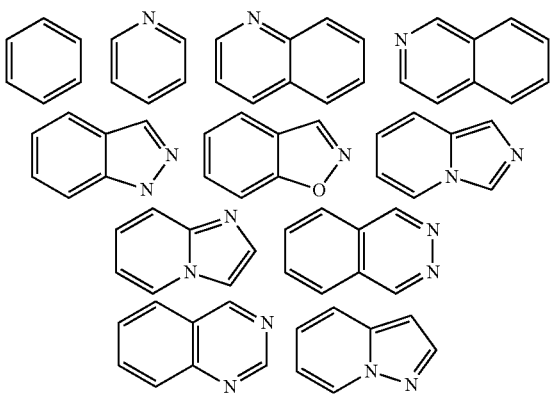

-continued

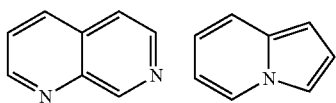

wherein each of these ring systems are optionally substituted with one or more R³.

In a further embodiment of the present invention W is selected from the group W¹¹ consisting of

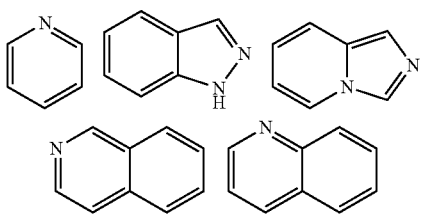

wherein each of these ring systems are optionally substituted with one or more R³.

In a further embodiment of the present invention W is selected from the group W¹¹ᵃ consisting of

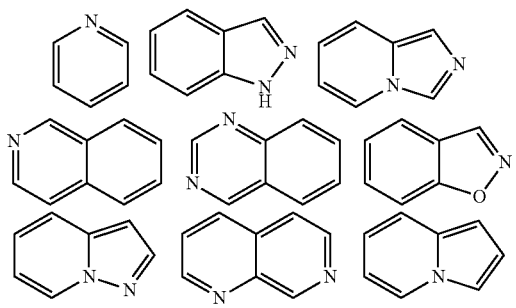

wherein each of these ring systems are optionally substituted with one or more R³.

In a further embodiment of the present invention W is selected from the group W¹² consisting of

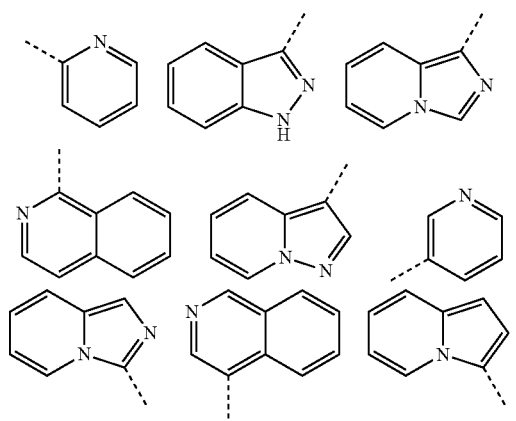

-continued

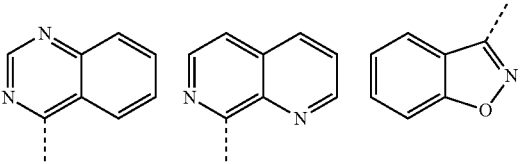

wherein each of these ring systems is preferentially attached as indicated by a dotted line and optionally substituted with one or more R³.

In a further embodiment of the present invention
R³ is independently selected from the group R³·² consisting of $C_{1-6}$-alkyl, $C_{3-8}$-cycloalkyl, $C_{1-6}$-alkyl-O—, benzyl, halogen, HO—, and NC—, wherein the $C_{1-6}$-alkyl, $C_{3-8}$-cycloalkyl, $C_{1-6}$-alkyl-O—, and the benzyl-substituents are optionally substituted with halogens and/or HO—;

In a further embodiment of the present invention
R³ is independently selected from the group R³·³ consisting of $C_{1-3}$-alkyl, $C_{3-6}$-cycloalkyl, $C_{1-3}$-alkyl-O—, halogen, NC—, wherein, in case R³ is connected to N-atoms of W, R³ is selected from the group consisting of $C_{1-3}$-alkyl and $C_{3-6}$-cycloalkyl, wherein the $C_{1-3}$-alkyl, $C_{3-6}$-cycloalkyl and $C_{1-3}$-alkyl-O-substituents are optionally substituted with halogens.

In a further embodiment of the present invention
R³ is independently selected from the group R³·⁴ consisting of H₃C—, cyclopropyl, H₃CO—, F—, Cl—, NC— and F₃C—, wherein N-atoms of W are optionally substituted with groups selected from H₃C— and cyclopropyl.

R³ is independently selected from the group R³·⁴ᵃ consisting of H₃C—, cyclopropyl, H₃CO—, F—, Cl—, NC— and F₃C—, wherein, in case R³ is connected to N-atoms of W, R³ is H₃C—.

In a further embodiment of the present invention
R³ is independently selected from the group R³·⁴ᵇ consisting of H₃C—, F₃C— and F—, wherein, in case R³ is connected to N-atoms of W, R³ is H₃C—.

In a further embodiment of the present invention
R³ is selected from the group R³·⁵ consisting of H₃C— and F₃C—.

In a further embodiment of the present invention
Y is selected from the group Y² consisting of a bond, —CH₂CH₂—, and —CH₂O—.

In a further embodiment of the present invention
Y is selected from the group Y³ consisting of —CH₂CH₂— and —CH₂O—.

In a further embodiment of the present invention
Y is selected from the group Y³ᵃ consisting of a bond and —CH₂O—.

In a further embodiment of the present invention
Y is selected from the group Y⁴ consisting of a bond.

In a further embodiment of the present invention
Y is selected from the group Y⁵ consisting of —CH₂O—.

In a further embodiment, if W is a monocyclic ring, at least one of R³ is preferably attached at the ortho-position or neighbouring position with respect to the attachment point of W to Y.

In a further embodiment, if W is a bicyclic ring, Y is preferably selected from Y⁴.

In a further embodiment, if W is a monocyclic ring, Y is preferably selected from Y³, more preferably from Y⁵.

In a further aspect the present invention relates to pharmaceutically acceptable salts, hydrates or solvates, more specifically to pharmaceutically acceptable salts, hydrates or solvates for use as a medicament.

In a further aspect, the present invention relates to pharmaceutical compositions containing at least one compound according to the specifications above or a pharmaceutically acceptable salt, hydrate or solvate thereof together with one or more pharmaceutically acceptable carrier.

In a further aspect, the present invention relates compounds according to the specifications above for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect, the present invention relates a pharmaceutically acceptable salt, hydrate or solvate of the compounds according to the specifications above for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect, the present invention relates to a pharmaceutical composition containing at least one compound according to the specifications above or a pharmaceutically acceptable salt, hydrate or solvate thereof together with one or more pharmaceutically acceptable carrier for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect the present invention relates to compounds of general formula (II)

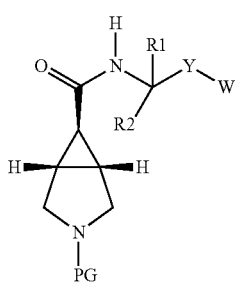

(II)

which are intermediates for the manufacture of compounds of general formula (I), wherein $R^1$, $R^2$, Y, W and $R^3$ have the meaning as defined for general formula (I), PG is a protecting group for an amino function such as outlined in: Peter G. M. Wuts, Theodora W. Greene, Greene's Protective Groups in Organic Synthesis, Wiley-Interscience; $4^{th}$ edition (Oct. 30, 2006), chapter 7.

Preferred protecting groups are tert-butoxycarbonyl-, benzyloxycarbonyl-, 9-fluorenylmethoxycarbonyl-, benzyl- and 2,4-di methoxybenzyl-, most preferred is tert-butoxycarbonyl.

In a further aspect the present invention relates to compounds of general formula (III)

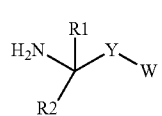

(III)

which are intermediates for the manufacture of compounds of general formula (I), wherein $R^1$, $R^2$, Y, W and $R^3$ have the meaning as defined for general formula (I), Each $R^{1.x}$, $R^{2.x}$, $R^{3.x}$, $A^x$, $W^x$, and a $Y^x$ represents a characterized, individual embodiment for the corresponding substituent as described above. Thus given the above definitions, substituents $R^1$, $R^2$, $R^3$, A, W, and Y are fully characterized by the term ($R^{1.x}$, $R^{2.x}$, $R^{3.x}$, $A^x$, $W^x$, and a $Y^x$) wherein for each index x an individual figure is given that ranges from "1" to the highest number given above. All individual embodiments described by the term in parentheses with full permutation of the indices x, referring to the definitions above, shall be comprised by the present invention.

The following Table 1 shows, exemplarily and generally in the order of increasing preference from the first line to the last line, such embodiments E-1 to E-53 of the invention that are considered preferred. This means that, for example, embodiments E-19 to E-28 are preferred over earlier entries, such as E-1 to E-7.

TABLE 1

Preferred embodiments E-1 to E- 53 of the invention.

| | A | W | $R^1/R^2$ | $R^3$ | Y |
|---|---|---|---|---|---|
| E-1 | $A^1$ | $W^2$ | $R^{1.1a}/R^{2.1a}$ | $R^{3.1}$ | $Y^1$ |
| E-2 | $A^1$ | $W^2$ | $R^{1.1a}/R^{2.1a}$ | $R^{3.2}$ | $Y^1$ |
| E-3 | $A^1$ | $W^1$ | $R^{1.1a}/R^{2.1a}$ | $R^{3.1}$ | $Y^1$ |
| E-4 | $A^1$ | $W^5$ | $R^{1.1a}/R^{2.1a}$ | $R^{3.1}$ | $Y^1$ |
| E-5 | $A^1$ | $W^5$ | $R^{1.1}/R^{2.1}$ | $R^{3.2}$ | $Y^2$ |
| E-6 | $A^2$ | $W^1$ | $R^{1.2}/R^{2.2}$ | $R^{3.1}$ | $Y^1$ |
| E-7 | $A^2$ | $W^1$ | $R^{1.2}/R^{2.2}$ | $R^{3.2}$ | $Y^1$ |
| E-8 | $A^3$ | $W^1$ | $R^{1.3}/R^{2.3}$ | $R^{3.2}$ | $Y^2$ |
| E-9 | $A^3$ | $W^2$ | $R^{1.3}/R^{2.3}$ | $R^{3.2}$ | $Y^3$ |
| E-10 | $A^3$ | $W^2$ | $R^{1.3}/R^{2.3}$ | $R^{3.2}$ | $Y^{3a}$ |
| E-11 | $A^4$ | $W^2$ | $R^{1.3}/R^{2.3}$ | $R^{3.2}$ | $Y^1$ |
| E-12 | $A^3$ | $W^2$ | $R^{1.4}/R^{2.4}$ | $R^{3.3}$ | $Y^1$ |
| E-13 | $A^4$ | $W^2$ | $R^{1.4}/R^{2.4}$ | $R^{3.4}$ | $Y^2$ |
| E-14 | $A^4$ | $W^3$ | $R^{1.4}/R^{2.4}$ | $R^{3.4}$ | $Y^3$ |
| E-15 | $A^4$ | $W^4$ | $R^{1.4}/R^{2.4}$ | $R^{3.4a}$ | $Y^4$ |
| E-16 | $A^4$ | $W^3$ | $R^{1.4}/R^{2.4}$ | $R^{3.4a}$ | $Y^5$ |
| E-17 | $A^4$ | $W^5$ | $R^{1.4}/R^{2.4}$ | $R^{3.4}$ | $Y^2$ |
| E-18 | $A^4$ | $W^5$ | $R^{1.4}/R^{2.4}$ | $R^{3.4}$ | $Y^{3a}$ |
| E-19 | $A^4$ | $W^5$ | $R^{1.4}/R^{2.4}$ | $R^{3.4}$ | $Y^4$ |
| E-20 | $A^4$ | $W^5$ | $R^{1.4}/R^{2.4}$ | $R^{3.4}$ | $Y^5$ |
| E-21 | $A^1$ | $W^6$ | $R^{1.1a}/R^{2.1a}$ | $R^{3.1}$ | $Y^3$ |
| E-22 | $A^4$ | $W^6$ | $R^{1.4}/R^{2.4}$ | $R^{3.4}$ | $Y^3$ |
| E-23 | $A^1$ | $W^7$ | $R^{1.1a}/R^{2.1a}$ | $R^{3.1}$ | $Y^4$ |
| E-24 | $A^4$ | $W^7$ | $R^{1.4}/R^{2.4}$ | $R^{3.4}$ | $Y^4$ |
| E-25 | $A^4$ | $W^6$ | $R^{1.4}/R^{2.4}$ | $R^{3.4}$ | $Y^5$ |
| E-26 | $A^4$ | $W^8$ | $R^{1.4}/R^{2.4}$ | $R^{3.4a}$ | $Y^3$ |
| E-27 | $A^4$ | $W^9$ | $R^{1.4}/R^{2.4}$ | $R^{3.4a}$ | $Y^4$ |
| E-28 | $A^4$ | $W^{9a}$ | $R^{1.4}/R^{2.4}$ | $R^{3.4a}$ | $Y^4$ |
| E-29 | $A^4$ | $W^8$ | $R^{1.4}/R^{2.4}$ | $R^{3.4a}$ | $Y^5$ |
| E-30 | $A^4$ | $W^{10}$ | $R^{1.4}/R^{2.4}$ | $R^{3.4a}$ | $Y^3$ |
| E-31 | $A^4$ | $W^{10}$ | $R^{1.4}/R^{2.4}$ | $R^{3.4a}$ | $Y^4$ |
| E-32 | $A^4$ | $W^{10}$ | $R^{1.4}/R^{2.4}$ | $R^{3.4a}$ | $Y^5$ |
| E-33 | $A^4$ | $W^{9a}$ | $R^{1.5}/R^{2.5}$ | $R^{3.4}$ | $Y^4$ |
| E-34 | $A^4$ | $W^8$ | $R^{1.5}/R^{2.5}$ | $R^{3.4b}$ | $Y^3$ |
| E-35 | $A^4$ | $W^9$ | $R^{1.5}/R^{2.5}$ | $R^{3.4b}$ | $Y^4$ |
| E-36 | $A^4$ | $W^8$ | $R^{1.5}/R^{2.5}$ | $R^{3.5}$ | $Y^3$ |
| E-37 | $A^4$ | $W^9$ | $R^{1.5}/R^{2.5}$ | $R^{3.5}$ | $Y^4$ |
| E-38 | $A^4$ | $W^{9a}$ | $R^{1.5}/R^{2.5}$ | $R^{3.5}$ | $Y^4$ |
| E-39 | $A^4$ | $W^8$ | $R^{1.5}/R^{2.5}$ | $R^{3.5}$ | $Y^5$ |
| E-40 | $A^4$ | $W^8$ | $R^{1.5}/R^{2.5}$ | $R^{3.4b}$ | $Y^5$ |
| E-41 | $A^4$ | $W^{10}$ | $R^{1.5}/R^{2.5}$ | $R^{3.4b}$ | $Y^4$ |
| E-42 | $A^4$ | $W^{10}$ | $R^{1.5}/R^{2.5}$ | $R^{3.4b}$ | $Y^5$ |
| E-43 | $A^4$ | $W^{11}$ | $R^{1.5}/R^{2.5}$ | $R^{3.4b}$ | $Y^{3a}$ |
| E-44 | $A^4$ | $W^{11}$ | $R^{1.5}/R^{2.5}$ | $R^{3.4b}$ | $Y^4$ |
| E-45 | $A^4$ | $W^{11}$ | $R^{1.5}/R^{2.5}$ | $R^{3.4b}$ | $Y^5$ |
| E-46 | $A^4$ | $W^{11}$ | $R^{1.5}/R^{2.5}$ | $R^{3.5}$ | $Y^4$ |
| E-47 | $A^4$ | $W^{11}$ | $R^{1.5}/R^{2.5}$ | $R^{3.5}$ | $Y^5$ |
| E-48 | $A^4$ | $W^{11a}$ | $R^{1.5}/R^{2.5}$ | $R^{3.4b}$ | $Y^{3a}$ |
| E-49 | $A^4$ | $W^{11a}$ | $R^{1.5}/R^{2.5}$ | $R^{3.4b}$ | $Y^4$ |
| E-50 | $A^4$ | $W^{11a}$ | $R^{1.5}/R^{2.5}$ | $R^{3.4b}$ | $Y^5$ |

TABLE 1-continued

Preferred embodiments E-1 to E- 53 of the invention.

| | A | W | R¹/R² | R³ | Y |
|---|---|---|---|---|---|
| E-51 | A⁴ | W¹² | R¹·⁵/R²·⁵ | R³·⁵ | Y³ᵃ |
| E-52 | A⁴ | W¹² | R¹·⁵/R²·⁵ | R³·⁵ | Y⁴ |
| E-53 | A⁴ | W¹² | R¹·⁵/R²·⁵ | R³·⁵ | Y⁵ | the tautomers thereof, the stereoisomers thereof, the mixtures thereof, the salts thereof, the hydrates thereof and the solvates thereof.

Accordingly, for example E-28 covers compounds of formula (I), wherein
A is H,
R¹ and R² are selected from the group consisting of H₃C— or wherein R¹ and R² together form a 2- or 3-membered alkylene-bridge,
W is selected from the group consisting of

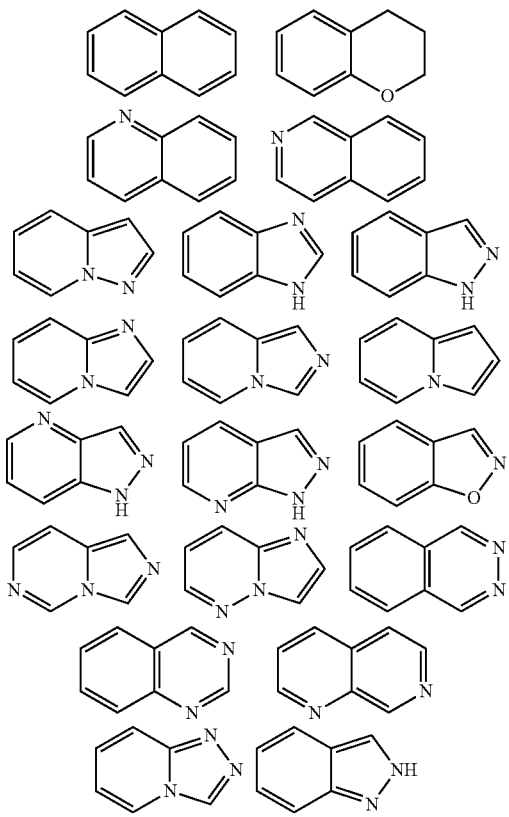

wherein each of these ring systems are optionally substituted with one or more R³,
R³ is independently selected from the group consisting of H₃C—, cyclopropyl, H₃CO—, F—, Cl—, NC— and F₃C—, wherein, in case R³ is connected to N-atoms of W, R³ is H₃C—,
Y is a bond.

Accordingly, for example E-29 covers compounds of formula (I), wherein
A is H,
R¹ and R² are selected from the group consisting of H₃C— or wherein R¹ and R² together form a 2- or 3-membered alkylene-bridge,
W is selected from the group consisting of

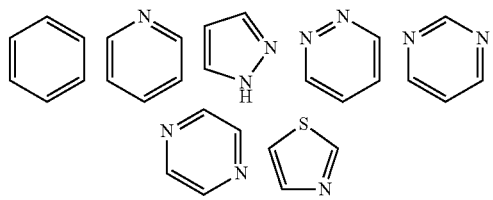

wherein each of these ring systems are optionally substituted with one or more R³,
R³ is independently selected from the group consisting of H₃C—, cyclopropyl, H₃CO—, F—, Cl—, NC— and F₃C—, wherein, in case R³ is connected to N-atoms of W, R³ is H₃C—,
Y is —CH₂O—.

The present invention preferably relates to the following compounds:

| Comp. | Structure |
|---|---|
| I | (structure) |
| II | (structure) |
| III | (structure) |
| IV | (structure) |
| V | (structure) |
| VII | (structure) |

-continued

| Comp. | Structure |
|-------|-----------|
| VIII | 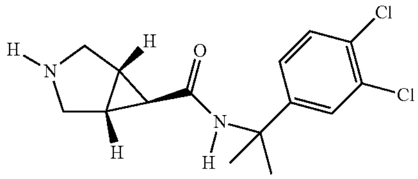 [SMILES: CC(C)(NC(=O)[C@H]1[C@@H]2CNC[C@@H]21)c1ccc(Cl)c(Cl)c1] |
| IX | 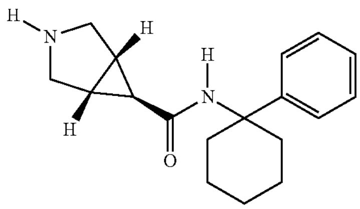 [SMILES: O=C(NC1(c2ccccc2)CCCCC1)[C@H]1[C@@H]2CNC[C@@H]21] |
| X | 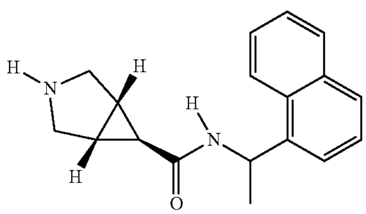 [SMILES: CC(NC(=O)[C@H]1[C@@H]2CNC[C@@H]21)c1cccc2ccccc12] |
| XI | 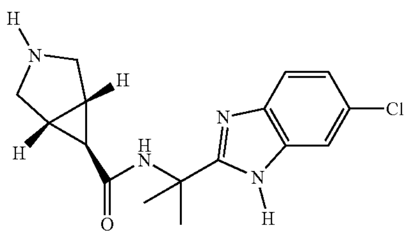 [SMILES: CC(C)(NC(=O)[C@H]1[C@@H]2CNC[C@@H]21)c1nc2ccc(Cl)cc2[nH]1] |
| XII | 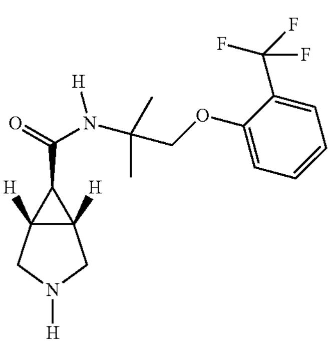 [SMILES: CC(C)(COc1ccccc1C(F)(F)F)NC(=O)[C@H]1[C@@H]2CNC[C@@H]21] |
| XIII | 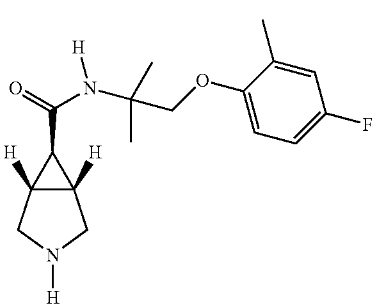 [SMILES: Cc1cc(F)ccc1OCC(C)(C)NC(=O)[C@H]1[C@@H]2CNC[C@@H]21] |

-continued

| Comp. | Structure |
|-------|-----------|
| XIV | 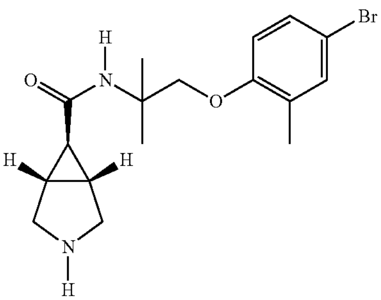 [SMILES: Cc1cc(Br)ccc1OCC(C)(C)NC(=O)[C@H]1[C@@H]2CNC[C@@H]21] |
| XV | 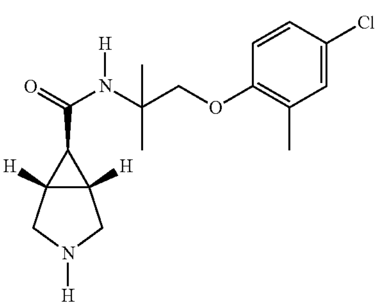 [SMILES: Cc1cc(Cl)ccc1OCC(C)(C)NC(=O)[C@H]1[C@@H]2CNC[C@@H]21] |
| XVI | 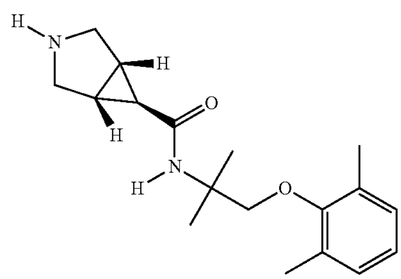 [SMILES: Cc1cccc(C)c1OCC(C)(C)NC(=O)[C@H]1[C@@H]2CNC[C@@H]21] |
| XVII | 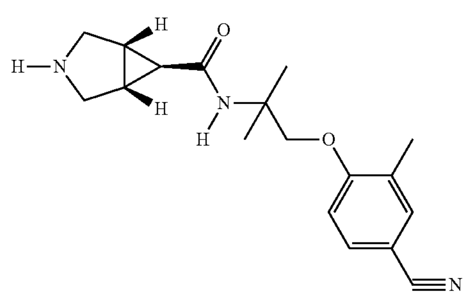 [SMILES: Cc1cc(C#N)ccc1OCC(C)(C)NC(=O)[C@H]1[C@@H]2CNC[C@@H]21] |
| XVIII | 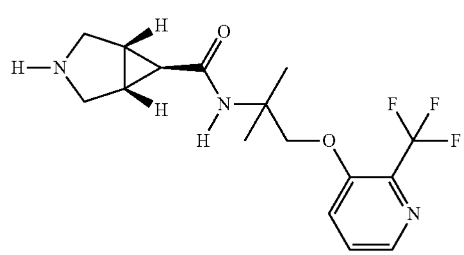 [SMILES: CC(C)(COc1cccnc1C(F)(F)F)NC(=O)[C@H]1[C@@H]2CNC[C@@H]21] |

| Comp. | Structure |
|---|---|
| XIX | 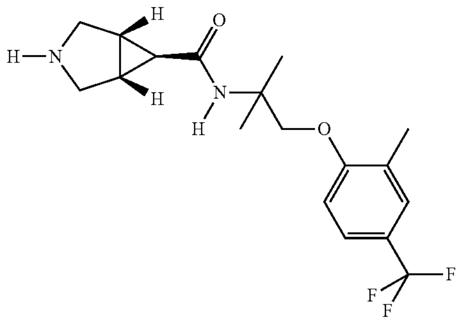 [SMILES: Cc1cc(C(F)(F)F)ccc1OCC(C)(C)NC(=O)[C@H]1[C@@H]2CNC[C@@H]21] |
| XX | 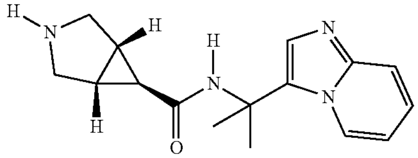 [SMILES: CC(C)(NC(=O)[C@H]1[C@@H]2CNC[C@@H]21)c1cnc2ccccn12] |
| XXI | 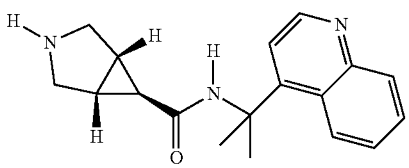 [SMILES: CC(C)(NC(=O)[C@H]1[C@@H]2CNC[C@@H]21)c1ccnc2ccccc12] |
| XXII | 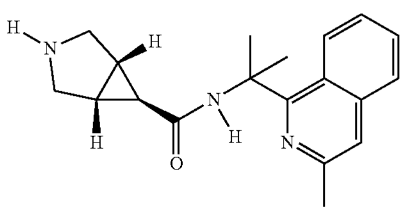 [SMILES: Cc1cc2ccccc2c(C(C)(C)NC(=O)[C@H]2[C@@H]3CNC[C@@H]32)n1] |
| XXIII | 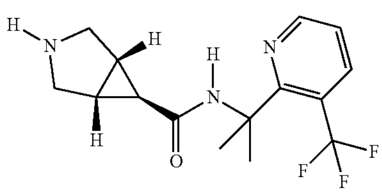 [SMILES: CC(C)(NC(=O)[C@H]1[C@@H]2CNC[C@@H]21)c1ncccc1C(F)(F)F] |
| XXIV | 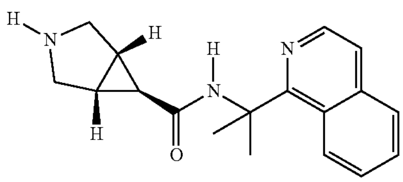 [SMILES: CC(C)(NC(=O)[C@H]1[C@@H]2CNC[C@@H]21)c1nccc2ccccc12] |
| XXV | 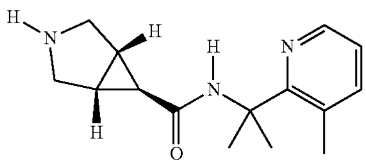 [SMILES: Cc1cccnc1C(C)(C)NC(=O)[C@H]1[C@@H]2CNC[C@@H]21] |
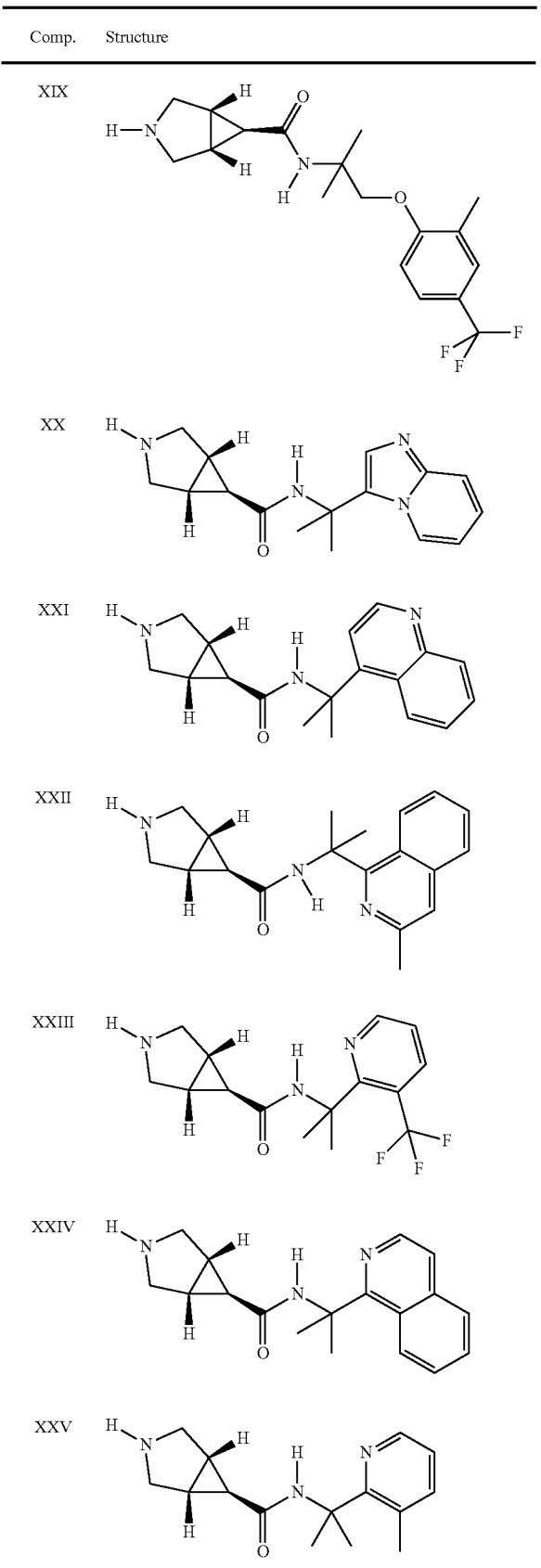
| Comp. | Structure |
|---|---|
| XXVI | 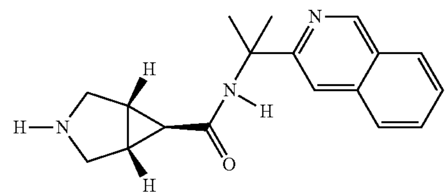 [SMILES: CC(C)(NC(=O)[C@H]1[C@@H]2CNC[C@@H]21)c1cc2ccccc2cn1] |
| XXVII | 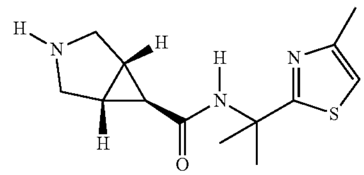 [SMILES: Cc1csc(C(C)(C)NC(=O)[C@H]2[C@@H]3CNC[C@@H]32)n1] |
| XXVIII | 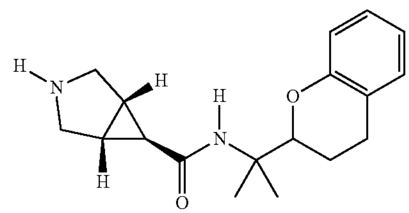 [SMILES: CC(C)(NC(=O)[C@H]1[C@@H]2CNC[C@@H]21)C1CCc2ccccc2O1] |
| XXIX | 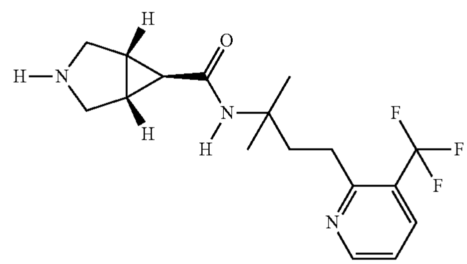 [SMILES: CC(C)(CCc1ncccc1C(F)(F)F)NC(=O)[C@H]1[C@@H]2CNC[C@@H]21] |
| XXX | 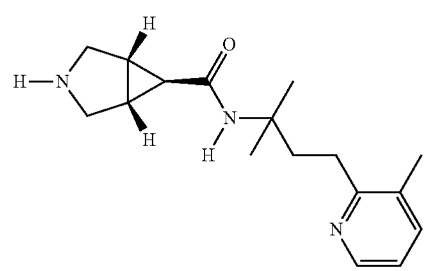 [SMILES: Cc1cccnc1CCC(C)(C)NC(=O)[C@H]1[C@@H]2CNC[C@@H]21] |
| XXXI | 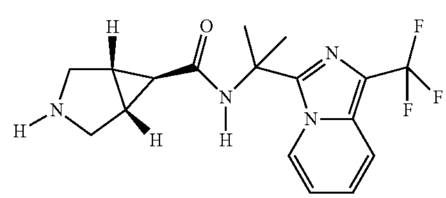 [SMILES: CC(C)(NC(=O)[C@H]1[C@@H]2CNC[C@@H]21)c1nc(C(F)(F)F)c2ccccn12] |
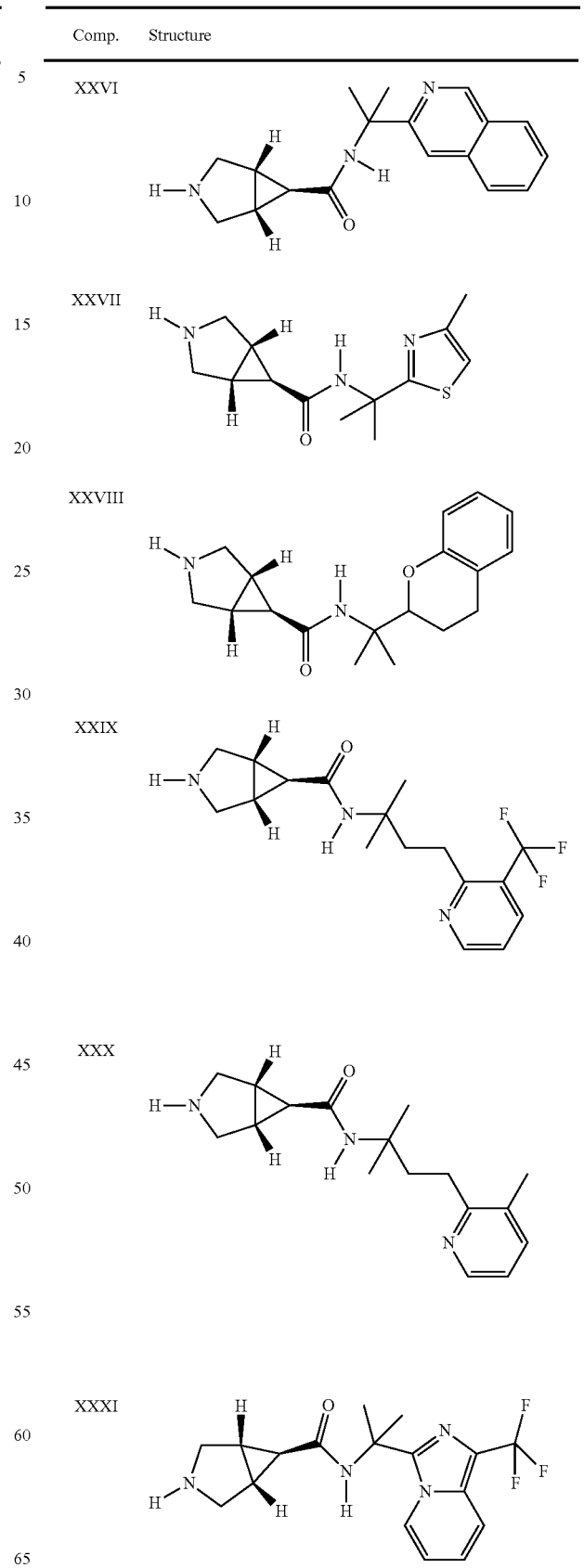

-continued

| Comp. | Structure |
|-------|-----------|
| XXXII | 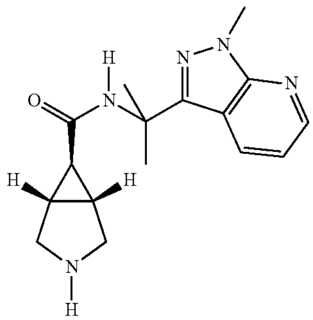 [SMILES: Cn1nc(C(C)(C)NC(=O)[C@H]2[C@@H]3CNC[C@@H]32)c2cccnc21] |
| XXXIII | 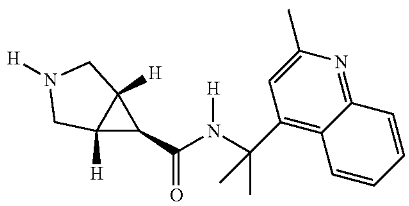 [SMILES: Cc1cc(C(C)(C)NC(=O)[C@H]2[C@@H]3CNC[C@@H]32)c2ccccc2n1] |
| XXXIV | 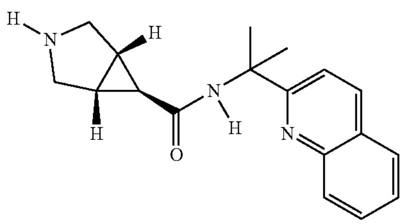 [SMILES: CC(C)(NC(=O)[C@H]1[C@@H]2CNC[C@@H]21)c1ccc2ccccc2n1] |
| XXXV | 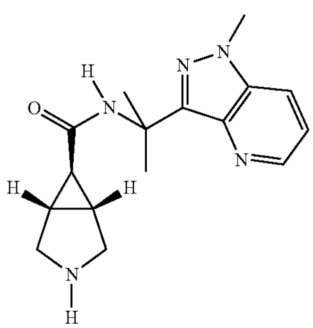 [SMILES: Cn1nc(C(C)(C)NC(=O)[C@H]2[C@@H]3CNC[C@@H]32)c2ncccc21] |
| XXXVI | 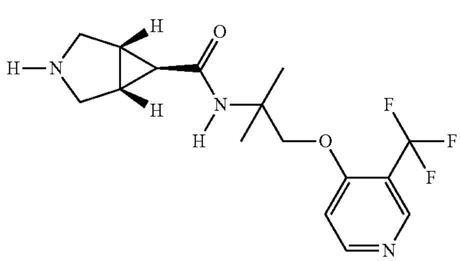 [SMILES: CC(C)(COc1ccncc1C(F)(F)F)NC(=O)[C@H]1[C@@H]2CNC[C@@H]21] |
| XXXVII | 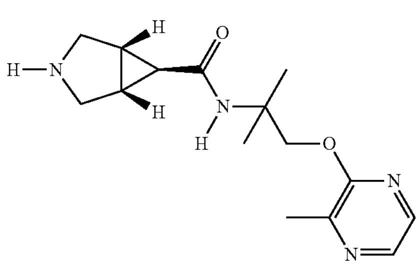 [SMILES: Cc1nccnc1OCC(C)(C)NC(=O)[C@H]1[C@@H]2CNC[C@@H]21] |
| XXXVIII | |
| XXXIX | |
| XL | |
| XLI | |
| XLII | |
| XLIII | |

-continued

| Comp. | Structure |
|---|---|
| XLIV | 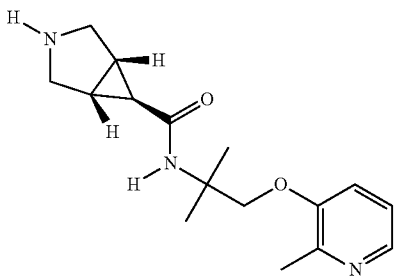 [SMILES: Cc1ncccc1OCC(C)(C)NC(=O)[C@H]1[C@@H]2CNC[C@@H]21] |
| XLV | 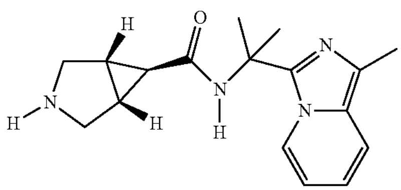 [SMILES: Cc1nc(C(C)(C)NC(=O)[C@H]2[C@@H]3CNC[C@@H]32)n2ccccc12] |
| XLVI | 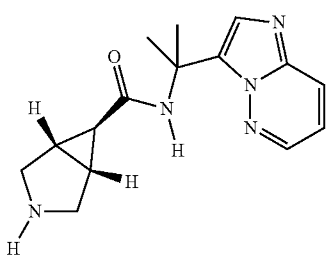 [SMILES: CC(C)(NC(=O)[C@H]1[C@@H]2CNC[C@@H]21)c1cnc2cccnn12] |
| XLVII | 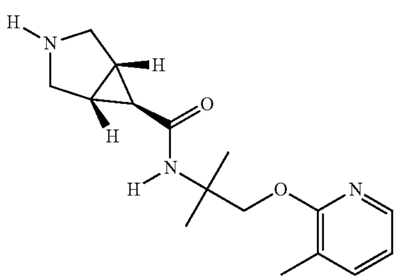 [SMILES: Cc1cccnc1OCC(C)(C)NC(=O)[C@H]1[C@@H]2CNC[C@@H]21] |
| XLVIII | 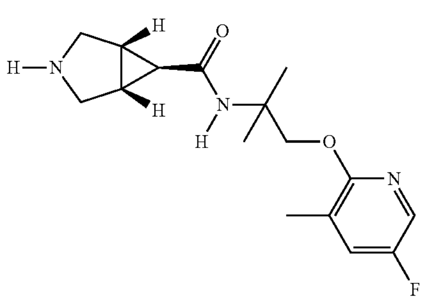 [SMILES: Cc1cc(F)cnc1OCC(C)(C)NC(=O)[C@H]1[C@@H]2CNC[C@@H]21] |
| XLIX | 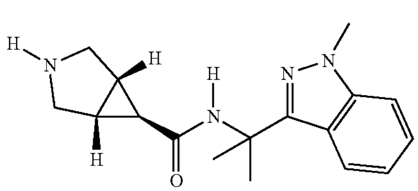 [SMILES: Cn1nc(C(C)(C)NC(=O)[C@H]2[C@@H]3CNC[C@@H]32)c2ccccc21] |

-continued

| Comp. | Structure |
|---|---|
| L | 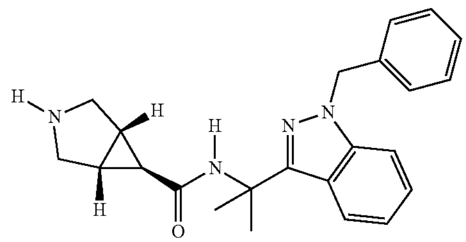 [SMILES: CC(C)(NC(=O)[C@H]1[C@@H]2CNC[C@@H]21)c1nn(Cc2ccccc2)c2ccccc12] |
| LI | 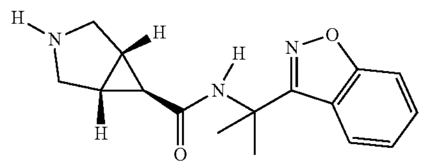 [SMILES: CC(C)(NC(=O)[C@H]1[C@@H]2CNC[C@@H]21)c1noc2ccccc12] |
| LII | 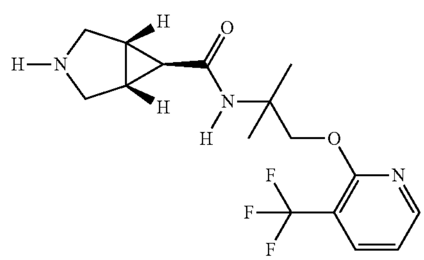 [SMILES: CC(C)(COc1ncccc1C(F)(F)F)NC(=O)[C@H]1[C@@H]2CNC[C@@H]21] |
| LIII | 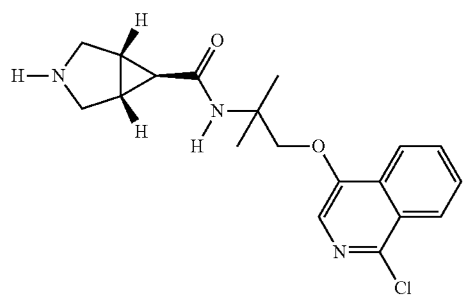 [SMILES: CC(C)(COc1cnc(Cl)c2ccccc12)NC(=O)[C@H]1[C@@H]2CNC[C@@H]21] |
| LIV | 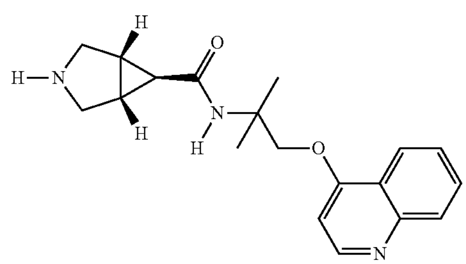 [SMILES: CC(C)(COc1ccnc2ccccc12)NC(=O)[C@H]1[C@@H]2CNC[C@@H]21] |
| LV | 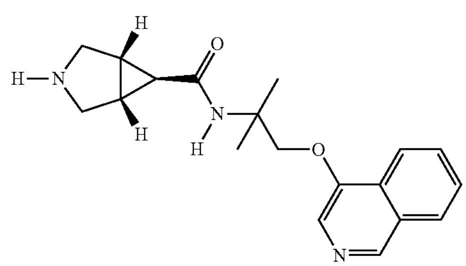 [SMILES: CC(C)(COc1cncc2ccccc12)NC(=O)[C@H]1[C@@H]2CNC[C@@H]21] |

| Comp. | Structure |
|---|---|
| LVI | 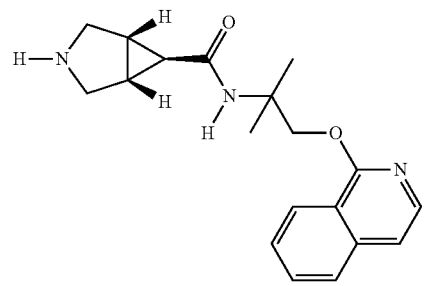 [SMILES: CC(C)(COc1nccc2ccccc12)NC(=O)[C@H]1[C@@H]2CNC[C@@H]21] |
| LVII | 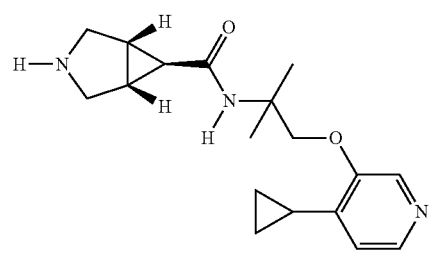 [SMILES: CC(C)(COc1cnccc1C1CC1)NC(=O)[C@H]1[C@@H]2CNC[C@@H]21] |
| LVIII | 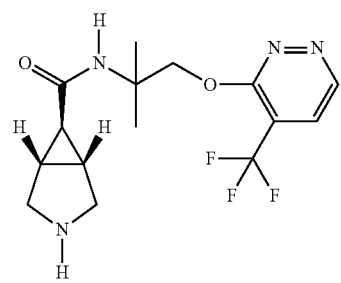 [SMILES: CC(C)(COc1nnccc1C(F)(F)F)NC(=O)[C@H]1[C@@H]2CNC[C@@H]21] |
| LIX | 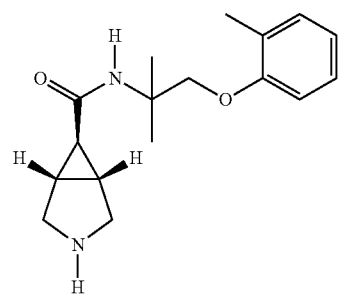 [SMILES: Cc1ccccc1OCC(C)(C)NC(=O)[C@H]1[C@@H]2CNC[C@@H]21] |
| LX | 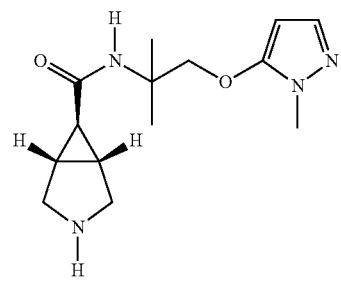 |
| Comp. | Structure |
|---|---|
| LXI | 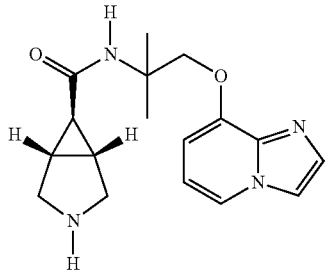 [SMILES: CC(C)(COc1cccn2ccnc12)NC(=O)[C@H]1[C@@H]2CNC[C@@H]21] |
| LXII | 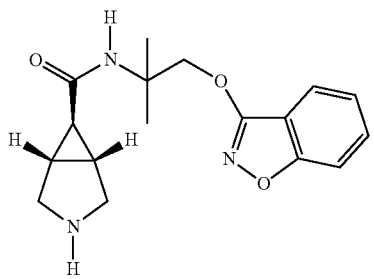 [SMILES: CC(C)(COc1noc2ccccc12)NC(=O)[C@H]1[C@@H]2CNC[C@@H]21] |
| LXIII | 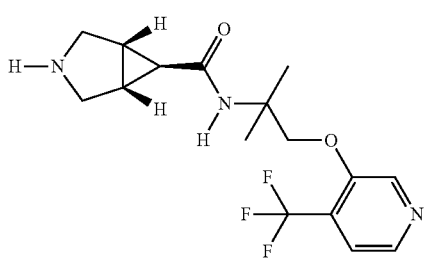 [SMILES: CC(C)(COc1cnccc1C(F)(F)F)NC(=O)[C@H]1[C@@H]2CNC[C@@H]21] |
| LXIV | 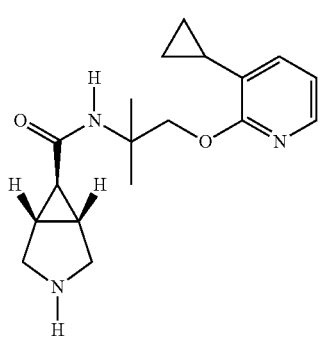 [SMILES: CC(C)(COc1ncccc1C1CC1)NC(=O)[C@H]1[C@@H]2CNC[C@@H]21] |
| LXV | 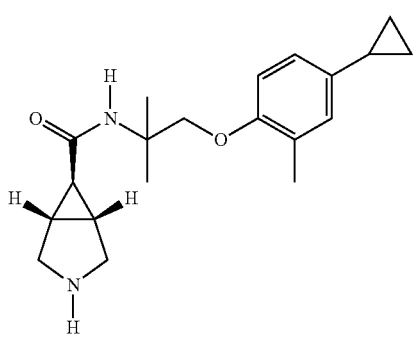 [SMILES: Cc1cc(C2CC2)ccc1OCC(C)(C)NC(=O)[C@H]1[C@@H]2CNC[C@@H]21] |

| Comp. | Structure |
|---|---|
| LXVI | 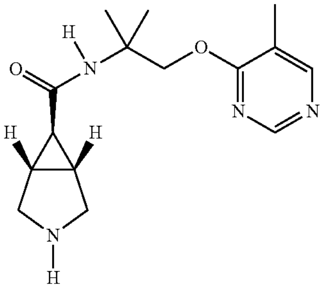 [SMILES: Cc1cncnc1OCC(C)(C)NC(=O)[C@H]1[C@@H]2CNC[C@@H]21] |
| LXVII | 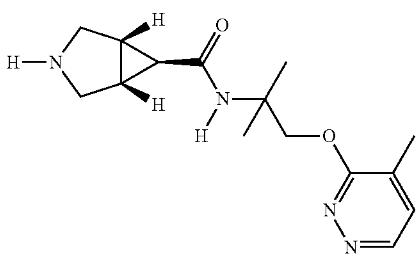 [SMILES: Cc1ccnnc1OCC(C)(C)NC(=O)[C@H]1[C@@H]2CNC[C@@H]21] |
| LXVIII | 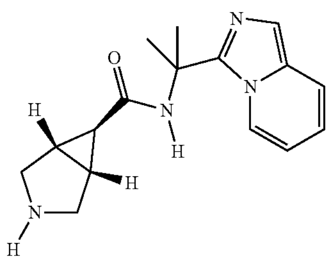 [SMILES: CC(C)(NC(=O)[C@H]1[C@@H]2CNC[C@@H]21)c1ncc2ccccn12] |
| LXIX | 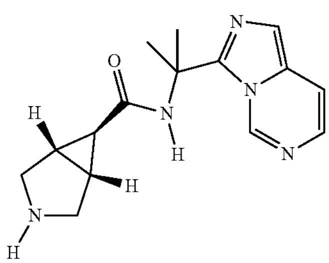 [SMILES: CC(C)(NC(=O)[C@H]1[C@@H]2CNC[C@@H]21)c1ncc2ccncn12] |
| LXX | 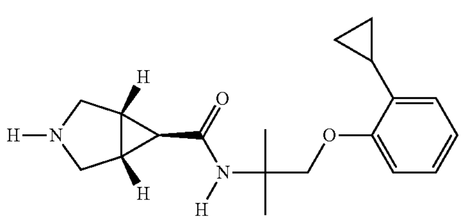 [SMILES: CC(C)(COc1ccccc1C1CC1)NC(=O)[C@H]1[C@@H]2CNC[C@@H]21] |
| LXXI | 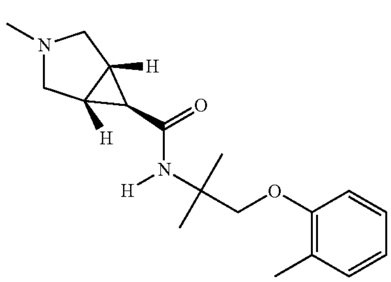 [SMILES: Cc1ccccc1OCC(C)(C)NC(=O)[C@H]1[C@@H]2CN(C)C[C@@H]21] |

| Comp. | Structure |
|---|---|
| LXXII | 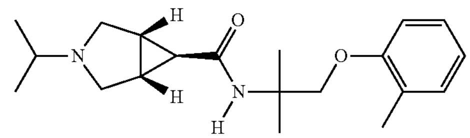 [SMILES: Cc1ccccc1OCC(C)(C)NC(=O)[C@H]1[C@@H]2CN(C(C)C)C[C@@H]21] |
| LXXIII | 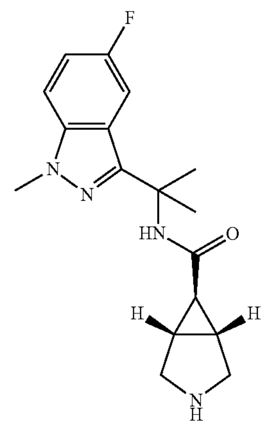 [SMILES: Cn1nc(C(C)(C)NC(=O)[C@H]2[C@@H]3CNC[C@@H]32)c2cc(F)ccc21] |
| LXXIV | 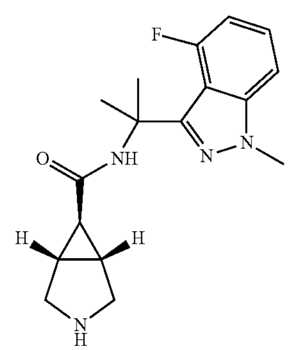 [SMILES: Cn1nc(C(C)(C)NC(=O)[C@H]2[C@@H]3CNC[C@@H]32)c2c(F)cccc21] |
| LXXV | 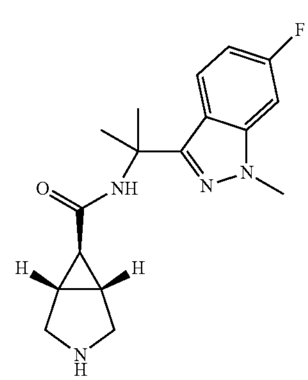 [SMILES: Cn1nc(C(C)(C)NC(=O)[C@H]2[C@@H]3CNC[C@@H]32)c2ccc(F)cc21] |

29
-continued
| Comp. | Structure |
|---|---|
| LXXVI | 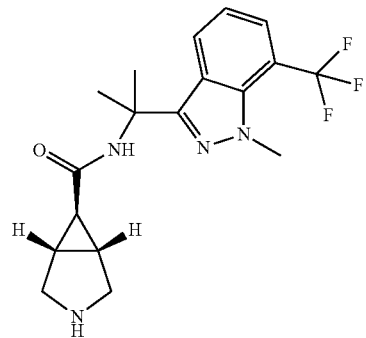 [SMILES: Cn1nc(C(C)(C)NC(=O)[C@H]2[C@@H]3CNC[C@@H]32)c2cccc(C(F)(F)F)c21] |
| LXXVII | 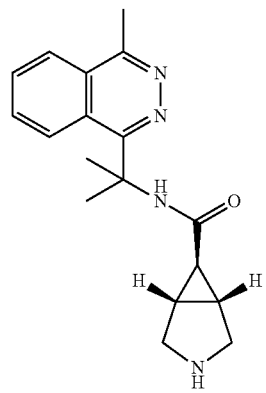 [SMILES: Cc1nnc(C(C)(C)NC(=O)[C@H]2[C@@H]3CNC[C@@H]32)c2ccccc12] |
| LXXVIII | 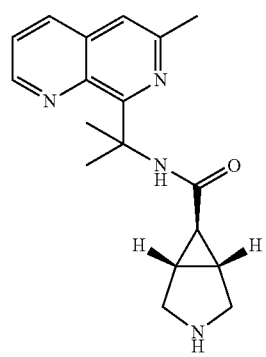 [SMILES: Cc1cc2cccnc2c(C(C)(C)NC(=O)[C@H]2[C@@H]3CNC[C@@H]32)n1] |
| LXXIX | 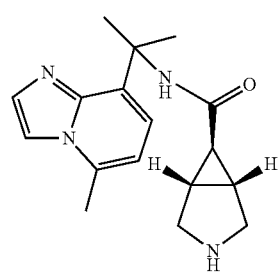 [SMILES: Cc1ccc(C(C)(C)NC(=O)[C@H]2[C@@H]3CNC[C@@H]32)c2nccn12] |
30
-continued
| Comp. | Structure |
|---|---|
| LXXX | 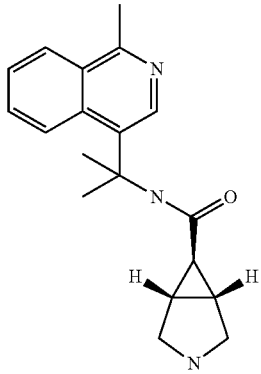 [SMILES: Cc1ncc(C(C)(C)NC(=O)[C@H]2[C@@H]3CNC[C@@H]32)c2ccccc12] |
| LXXXI | 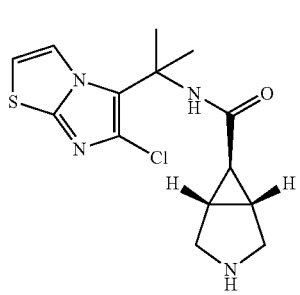 [SMILES: CC(C)(NC(=O)[C@H]1[C@@H]2CNC[C@@H]21)c1c(Cl)nc2sccn12] |
| LXXXII | 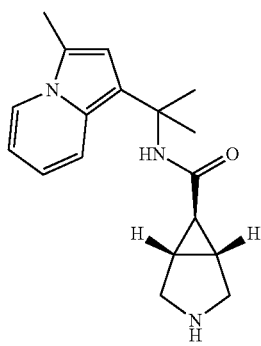 [SMILES: Cc1cc(C(C)(C)NC(=O)[C@H]2[C@@H]3CNC[C@@H]32)c2ccccn12] |
| LXXXIII | 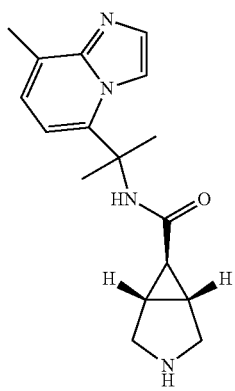 [SMILES: Cc1ccc(C(C)(C)NC(=O)[C@H]2[C@@H]3CNC[C@@H]32)n2ccnc12] |

| Comp. | Structure |
|---|---|
| LXXXIV | 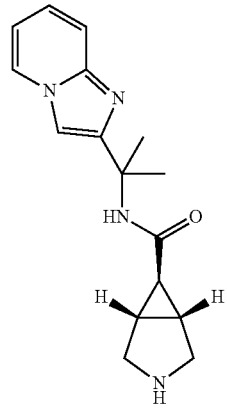 [SMILES: CC(C)(NC(=O)[C@H]1[C@@H]2CNC[C@@H]21)c1cn2ccccc2n1] |
| LXXXV | 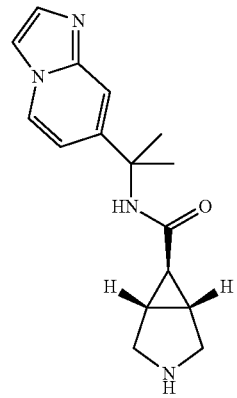 [SMILES: CC(C)(NC(=O)[C@H]1[C@@H]2CNC[C@@H]21)c1ccn2ccnc2c1] |
| LXXXVI | 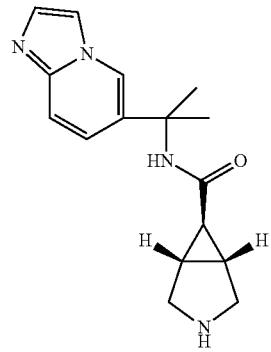 [SMILES: CC(C)(NC(=O)[C@H]1[C@@H]2CNC[C@@H]21)c1ccc2nccn2c1] |
| LXXXVII | 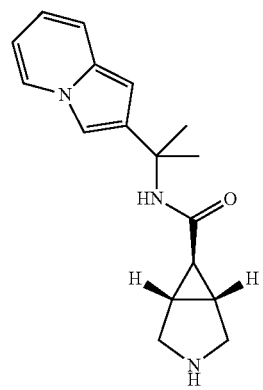 [SMILES: CC(C)(NC(=O)[C@H]1[C@@H]2CNC[C@@H]21)c1cc2ccccn2c1] |
| Comp. | Structure |
|---|---|
| LXXXVIII | 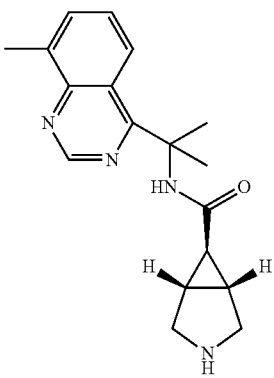 [SMILES: Cc1cccc2c(C(C)(C)NC(=O)[C@H]3[C@@H]4CNC[C@@H]43)ncnc12] |
| LXXXIX | 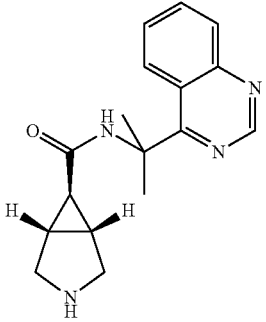 [SMILES: CC(C)(NC(=O)[C@H]1[C@@H]2CNC[C@@H]21)c1ncnc2ccccc12] |
| XC | 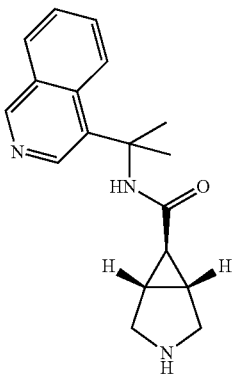 [SMILES: CC(C)(NC(=O)[C@H]1[C@@H]2CNC[C@@H]21)c1cncc2ccccc12] |
| XCI | 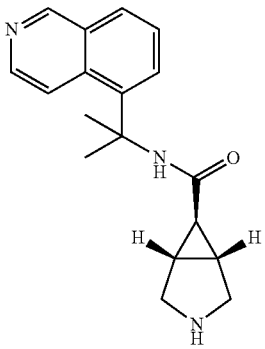 [SMILES: CC(C)(NC(=O)[C@H]1[C@@H]2CNC[C@@H]21)c1cccc2cnccc12] |

| Comp. | Structure |
|---|---|
| XCII | 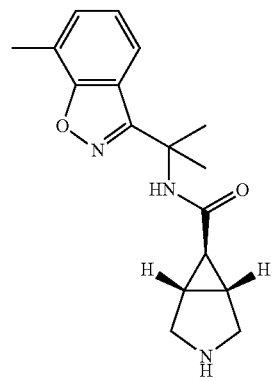 [SMILES: Cc1cccc2c(C(C)(C)NC(=O)[C@H]3[C@@H]4CNC[C@@H]43)noc12] |
| XCIII | 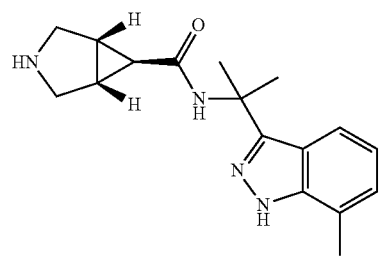 [SMILES: Cc1cccc2c(C(C)(C)NC(=O)[C@H]3[C@@H]4CNC[C@@H]43)n[nH]c12] |
| XCIV | 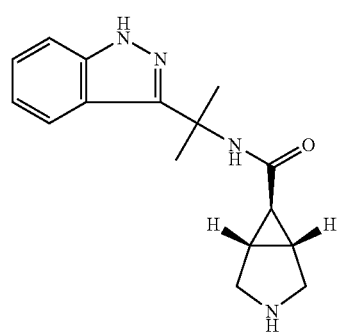 [SMILES: CC(C)(NC(=O)[C@H]1[C@@H]2CNC[C@@H]21)c1n[nH]c2ccccc12] |
| XCV | 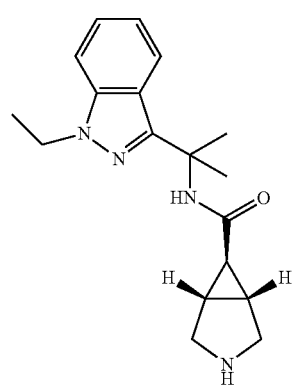 [SMILES: CCn1nc(C(C)(C)NC(=O)[C@H]2[C@@H]3CNC[C@@H]32)c2ccccc21] |
| XCVI | 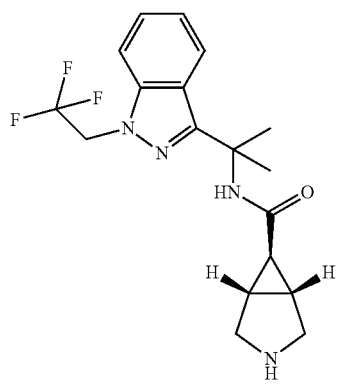 [SMILES: CC(C)(NC(=O)[C@H]1[C@@H]2CNC[C@@H]21)c1nn(CC(F)(F)F)c2ccccc12] |
| XCVII | 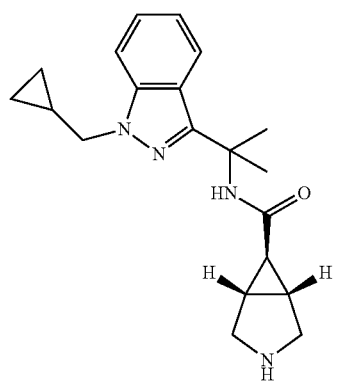 [SMILES: CC(C)(NC(=O)[C@H]1[C@@H]2CNC[C@@H]21)c1nn(CC2CC2)c2ccccc12] |
| XCVIII | 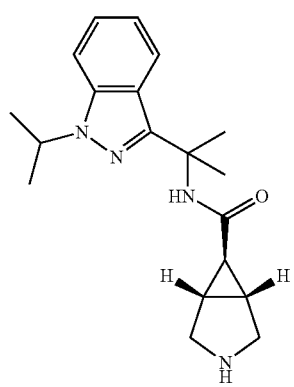 [SMILES: CC(C)n1nc(C(C)(C)NC(=O)[C@H]2[C@@H]3CNC[C@@H]32)c2ccccc21] |
| XCIX | 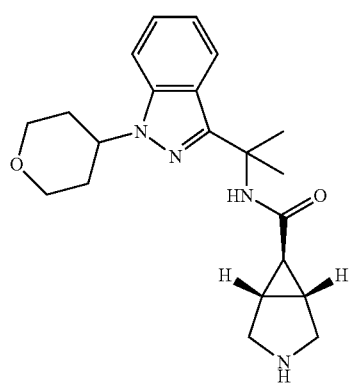 [SMILES: CC(C)(NC(=O)[C@H]1[C@@H]2CNC[C@@H]21)c1nn(C2CCOCC2)c2ccccc12] |

35
-continued
| Comp. | Structure |
|---|---|
| C | 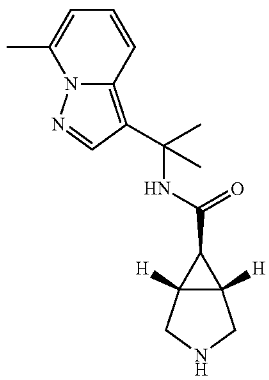 [SMILES: Cc1cccc2c(C(C)(C)NC(=O)[C@H]3[C@@H]4CNC[C@@H]43)cnn12] |
| CI | 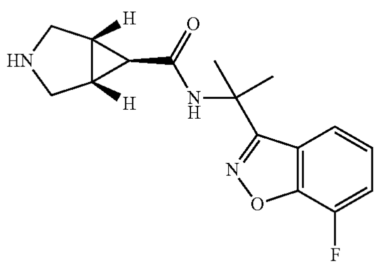 [SMILES: CC(C)(NC(=O)[C@H]1[C@@H]2CNC[C@@H]21)c1noc2c(F)cccc12] |
| CII | 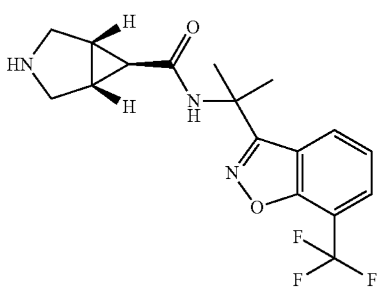 [SMILES: CC(C)(NC(=O)[C@H]1[C@@H]2CNC[C@@H]21)c1noc2c(C(F)(F)F)cccc12] |
| CIII | 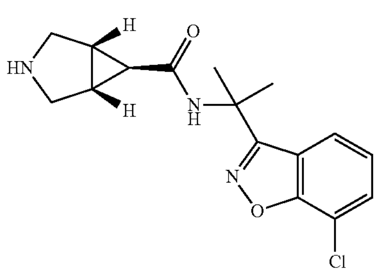 |
| CIV | 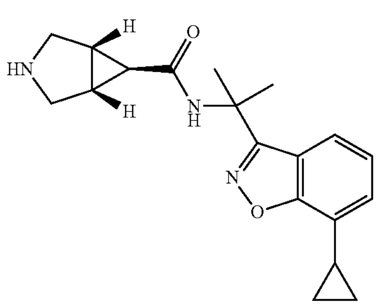 [SMILES: CC(C)(NC(=O)[C@H]1[C@@H]2CNC[C@@H]21)c1noc2c(C3CC3)cccc12] |
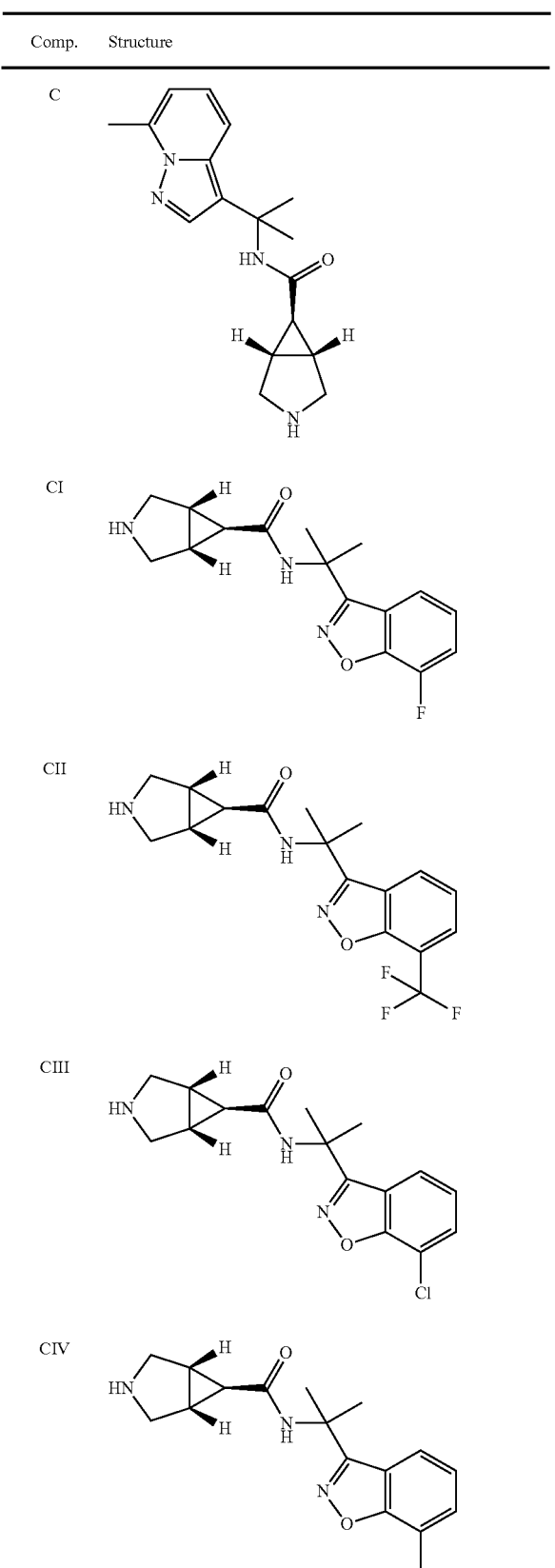
36
-continued
| Comp. | Structure |
|---|---|
| CV | 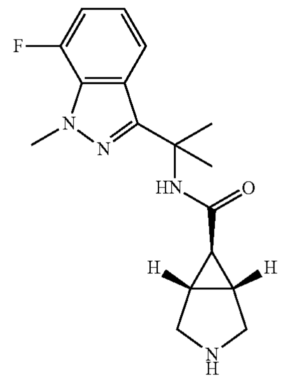 [SMILES: Cn1nc(C(C)(C)NC(=O)[C@H]2[C@@H]3CNC[C@@H]32)c2cccc(F)c21] |
| CVI | 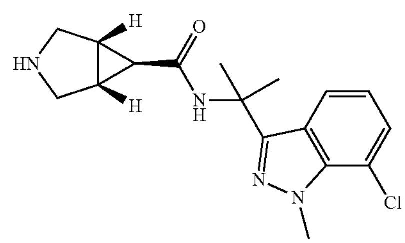 [SMILES: Cn1nc(C(C)(C)NC(=O)[C@H]2[C@@H]3CNC[C@@H]32)c2cccc(Cl)c21] |
| CVII | 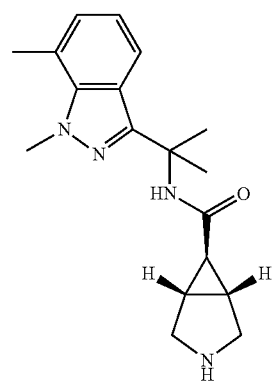 [SMILES: Cc1cccc2c(C(C)(C)NC(=O)[C@H]3[C@@H]4CNC[C@@H]43)nn(C)c12] |
| CVIII | 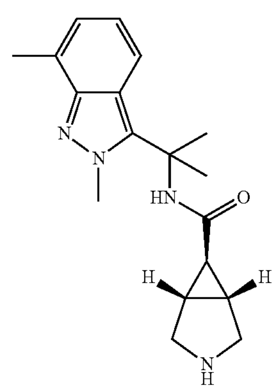 [SMILES: Cc1cccc2c(C(C)(C)NC(=O)[C@H]3[C@@H]4CNC[C@@H]43)n(C)nc12] |
| CVIV | 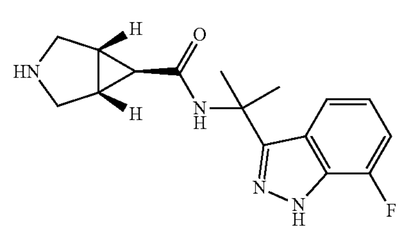 [SMILES: CC(C)(NC(=O)[C@H]1[C@@H]2CNC[C@@H]21)c1n[nH]c2c(F)cccc12] |
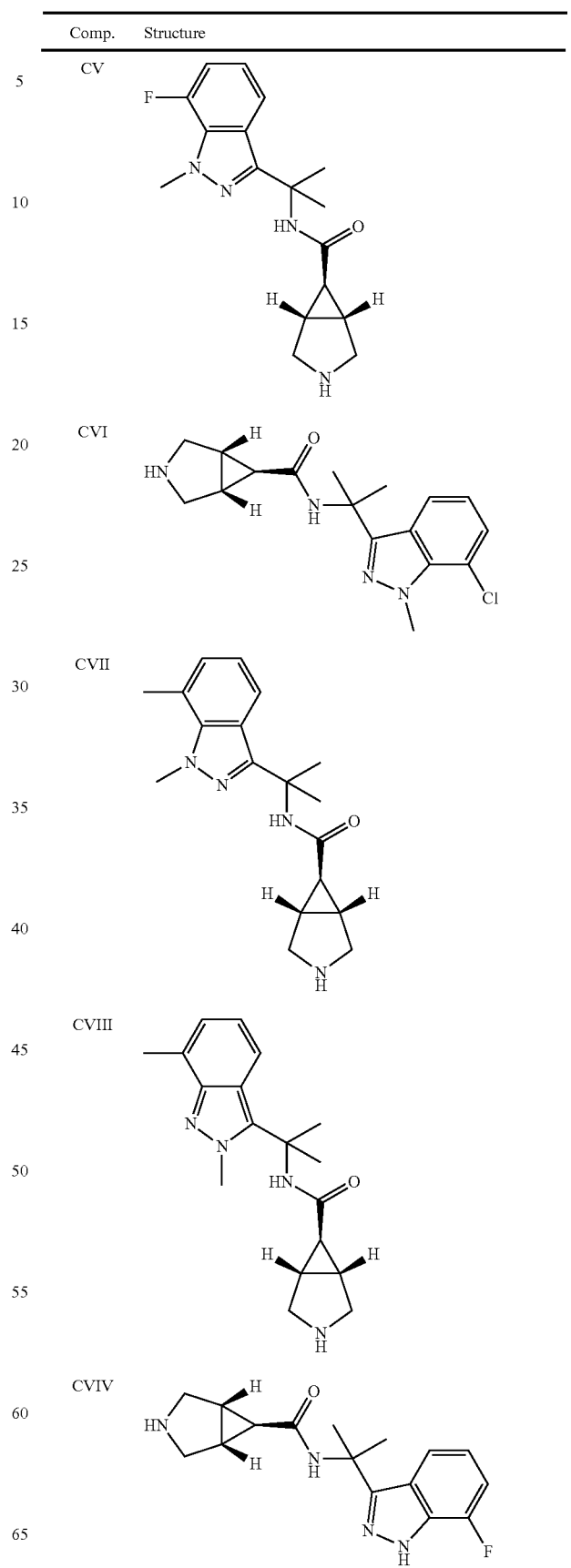

| Comp. | Structure |
|---|---|
| CX | 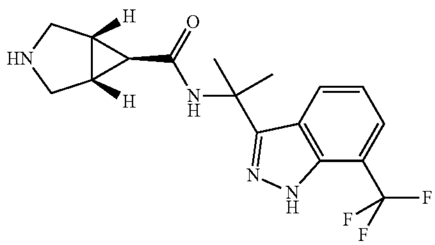 [SMILES: CC(C)(NC(=O)[C@H]1[C@@H]2CNC[C@@H]21)c1n[nH]c2c(C(F)(F)F)cccc12] |
| CXI | 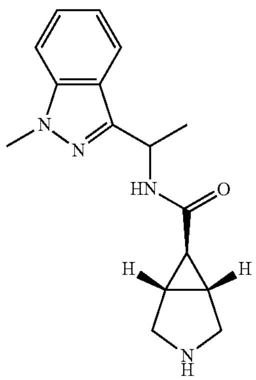 [SMILES: CC(NC(=O)[C@H]1[C@@H]2CNC[C@@H]21)c1nn(C)c2ccccc12] |
| CXII | 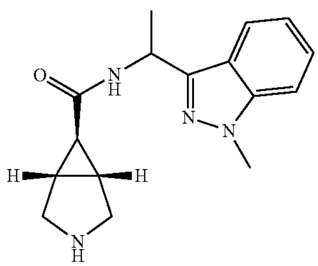 [SMILES: CC(NC(=O)[C@H]1[C@@H]2CNC[C@@H]21)c1nn(C)c2ccccc12] |
| CXIII | 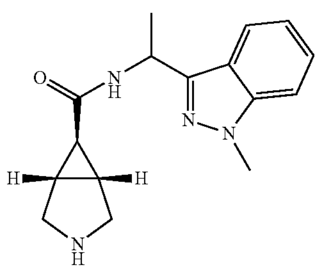 [SMILES: CC(NC(=O)[C@H]1[C@@H]2CNC[C@@H]21)c1nn(C)c2ccccc12] |
| CXIV | 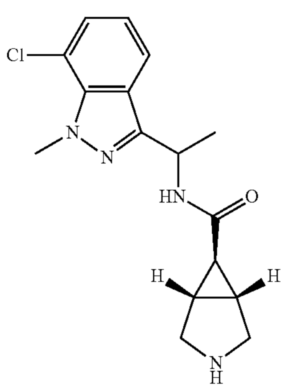 [SMILES: CC(NC(=O)[C@H]1[C@@H]2CNC[C@@H]21)c1nn(C)c2c(Cl)cccc12] |
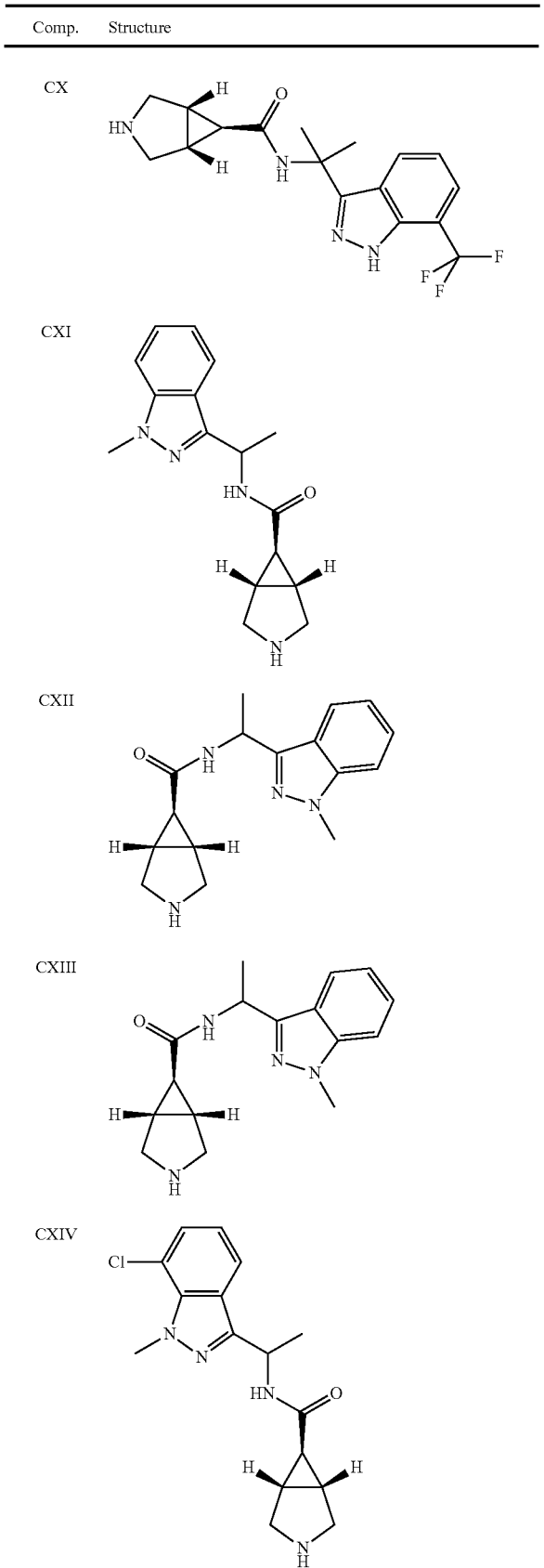
| Comp. | Structure |
|---|---|
| CXVII | 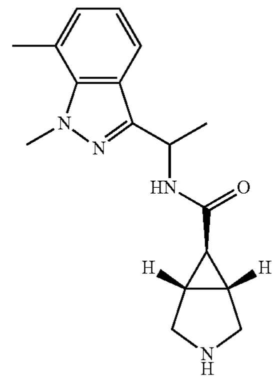 [SMILES: Cc1cccc2c(C(C)NC(=O)[C@H]3[C@@H]4CNC[C@@H]43)nn(C)c12] |
| CXX | 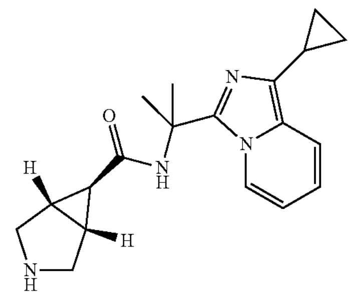 [SMILES: CC(C)(NC(=O)[C@H]1[C@@H]2CNC[C@@H]21)c1nc(C2CC2)c2ccccn12] |
| CXXI | 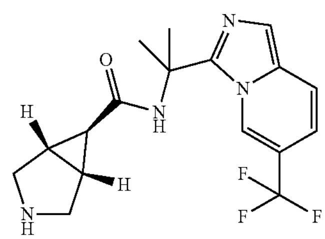 [SMILES: CC(C)(NC(=O)[C@H]1[C@@H]2CNC[C@@H]21)c1ncc2ccc(C(F)(F)F)cn12] |
| CXXII | 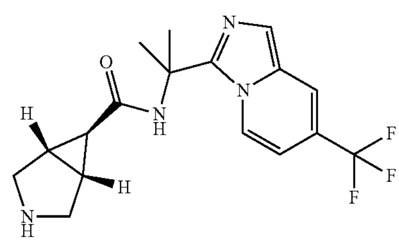 [SMILES: CC(C)(NC(=O)[C@H]1[C@@H]2CNC[C@@H]21)c1ncc2cc(C(F)(F)F)ccn12] |
| CXXIII | 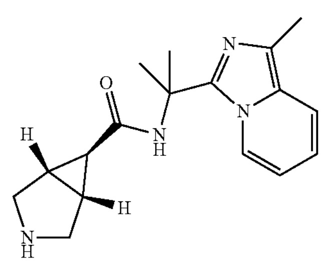 [SMILES: Cc1nc(C(C)(C)NC(=O)[C@H]2[C@@H]3CNC[C@@H]32)n2ccccc12] |
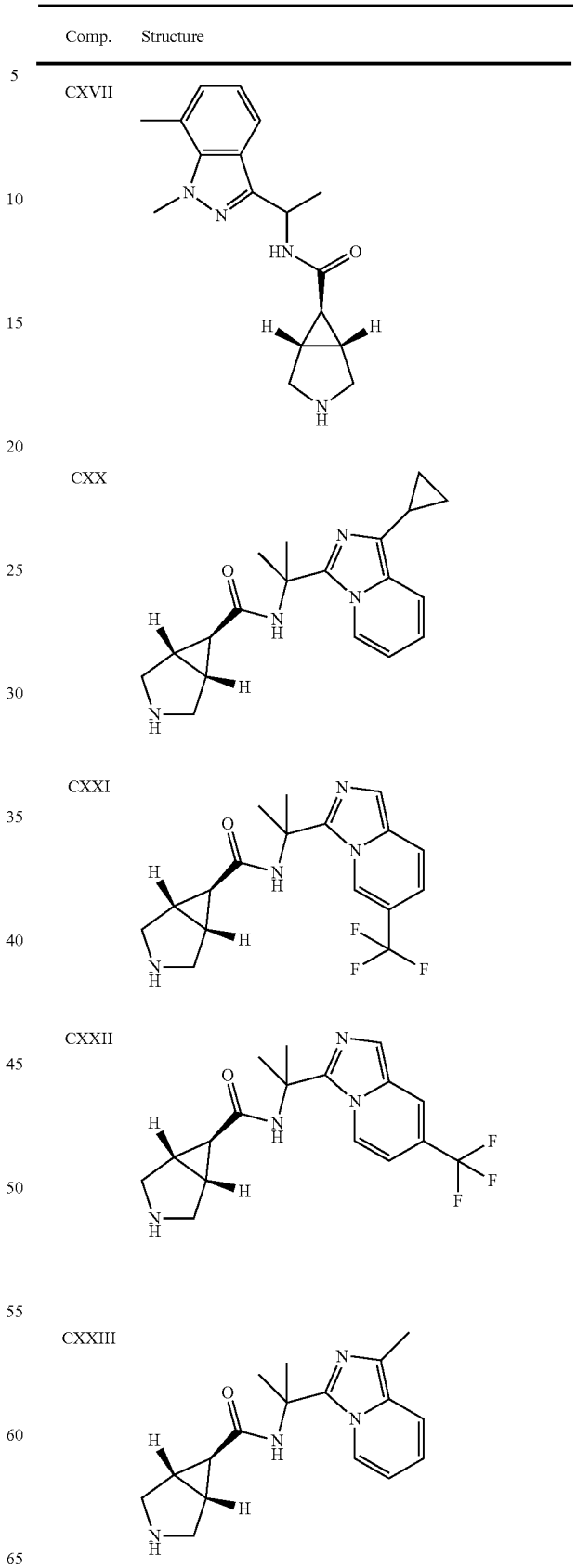

| Comp. | Structure |
|---|---|
| CXXIV | 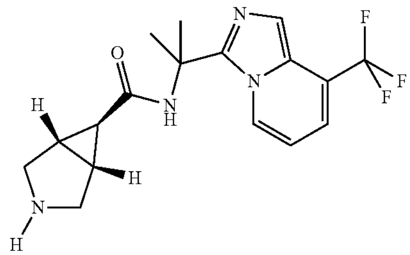 [SMILES: CC(C)(NC(=O)[C@H]1[C@@H]2CNC[C@@H]21)c1ncc2c(C(F)(F)F)cccn12] |
| CXXV | 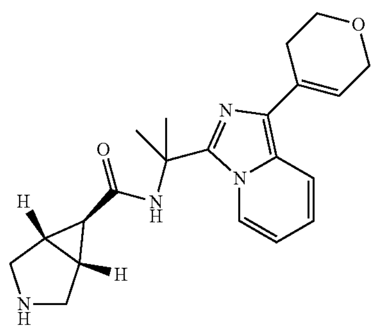 [SMILES: CC(C)(NC(=O)[C@H]1[C@@H]2CNC[C@@H]21)c1nc(C2=CCOCC2)c2ccccn12] |
| CXXVI | 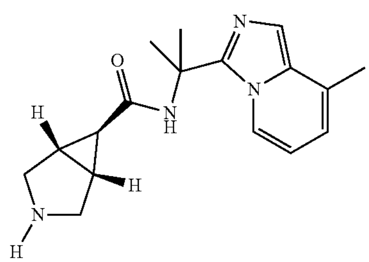 [SMILES: Cc1cccn2c(C(C)(C)NC(=O)[C@H]3[C@@H]4CNC[C@@H]43)ncc12] |
| CXXVII | 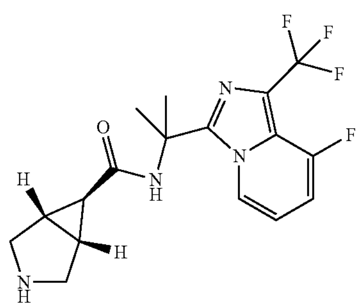 [SMILES: CC(C)(NC(=O)[C@H]1[C@@H]2CNC[C@@H]21)c1nc(C(F)(F)F)c2c(F)cccn12] |
| CXXVIII | 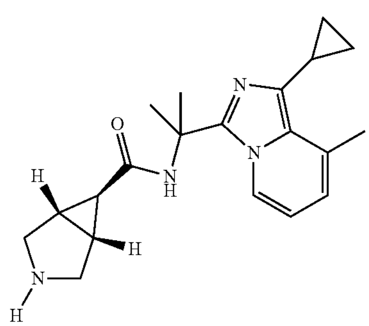 [SMILES: Cc1cccn2c(C(C)(C)NC(=O)[C@H]3[C@@H]4CNC[C@@H]43)nc(C3CC3)c12] |

| Comp. | Structure |
|---|---|
| CXXVIV | 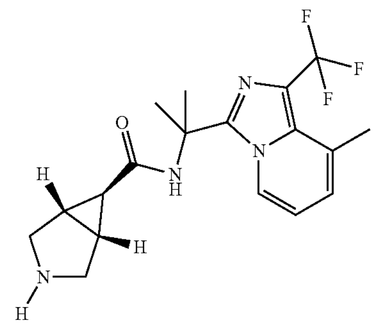 [SMILES: Cc1cccn2c(C(C)(C)NC(=O)[C@H]3[C@@H]4CNC[C@@H]43)nc(C(F)(F)F)c12] |
| CXXX | 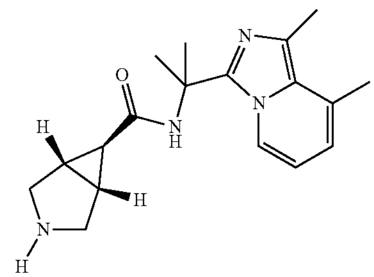 [SMILES: Cc1cccn2c(C(C)(C)NC(=O)[C@H]3[C@@H]4CNC[C@@H]43)nc(C)c12] |
| CXXXI | 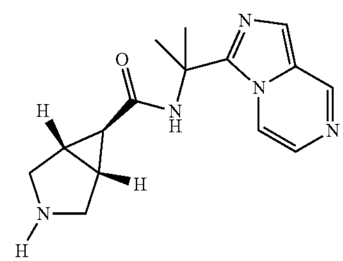 [SMILES: CC(C)(NC(=O)[C@H]1[C@@H]2CNC[C@@H]21)c1ncc2cnccn12] |
| CXXXII | 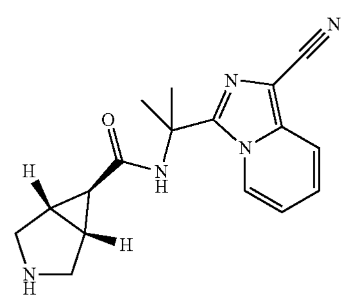 [SMILES: CC(C)(NC(=O)[C@H]1[C@@H]2CNC[C@@H]21)c1nc(C#N)c2ccccn12] |
| CXXXIII | 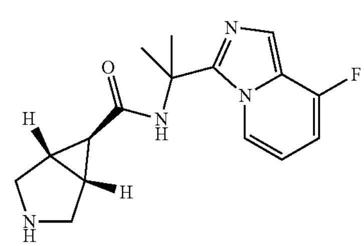 [SMILES: CC(C)(NC(=O)[C@H]1[C@@H]2CNC[C@@H]21)c1ncc2c(F)cccn12] |

| Comp. | Structure |
|---|---|
| CXXXIV | 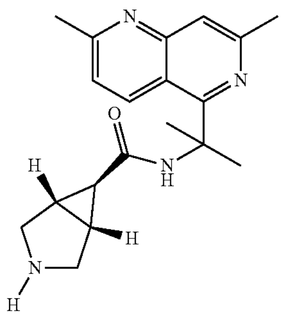 [SMILES: Cc1cc2nc(C)ccc2c(C(C)(C)NC(=O)[C@H]2[C@@H]3CNC[C@@H]32)n1] |
| CXXXV | 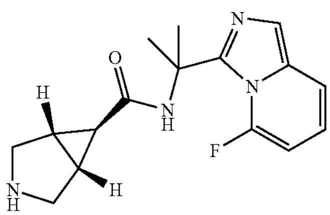 [SMILES: CC(C)(NC(=O)[C@H]1[C@@H]2CNC[C@@H]21)c1ncc2cccc(F)n12] |
| CXXXVI | 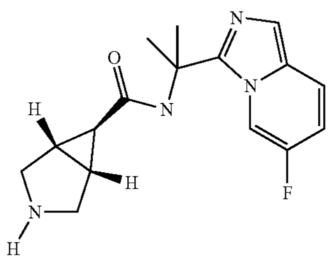 [SMILES: CC(C)(NC(=O)[C@H]1[C@@H]2CNC[C@@H]21)c1ncc2ccc(F)cn12] |
| CXXXVII | 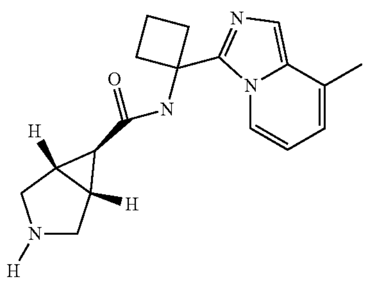 [SMILES: Cc1cccn2c(C3(NC(=O)[C@H]4[C@@H]5CNC[C@@H]54)CCC3)ncc12] |
| CXXXVIII | 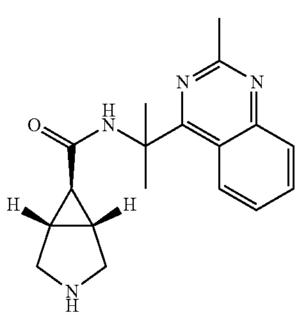 [SMILES: Cc1nc(C(C)(C)NC(=O)[C@H]2[C@@H]3CNC[C@@H]32)c2ccccc2n1] |

| Comp. | Structure |
|---|---|
| CXXXVIV | |
| CXL | |
| CXLI | |
| CXLII | |
| CXLIII | |

| Comp. | Structure |
|---|---|
| CXLIV | 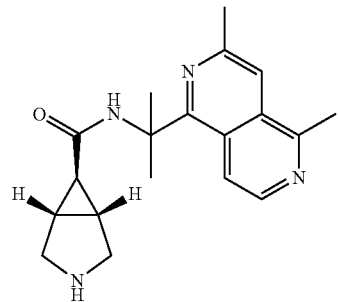 [SMILES: Cc1cc2c(C)nccc2c(C(C)(C)NC(=O)[C@H]2[C@@H]3CNC[C@@H]32)n1] |
| CXLV | 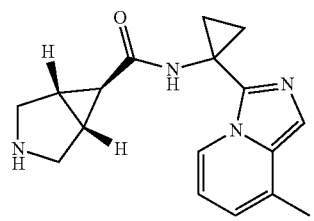 [SMILES: Cc1cccn2c(C3(NC(=O)[C@H]4[C@@H]5CNC[C@@H]54)CC3)ncc12] |
| CXLVI | 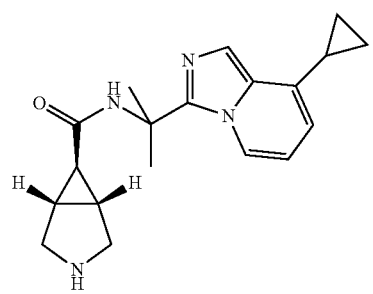 [SMILES: CC(C)(NC(=O)[C@H]1[C@@H]2CNC[C@@H]21)c1ncc2c(C3CC3)cccn12] |
| CXLVII | 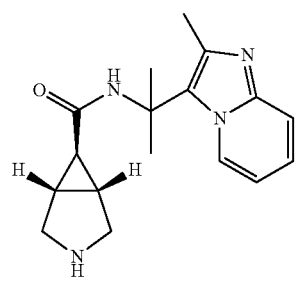 [SMILES: Cc1nc2ccccn2c1C(C)(C)NC(=O)[C@H]1[C@@H]2CNC[C@@H]21] |
| CXLVIII | 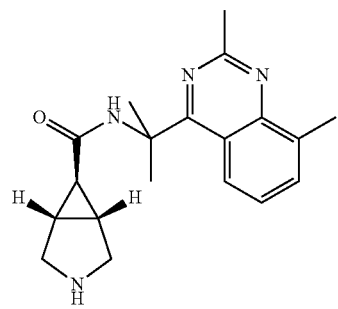 [SMILES: Cc1nc(C(C)(C)NC(=O)[C@H]2[C@@H]3CNC[C@@H]32)c2cccc(C)c2n1] |
| CXLVIV | 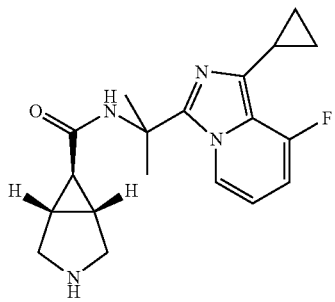 [SMILES: CC(C)(NC(=O)[C@H]1[C@@H]2CNC[C@@H]21)c1nc(C2CC2)c2c(F)cccn12] |
| CL | 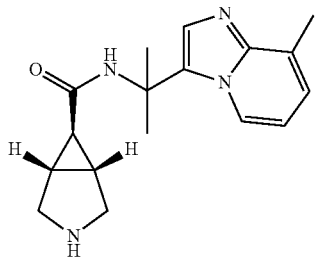 [SMILES: Cc1cccn2c(C(C)(C)NC(=O)[C@H]3[C@@H]4CNC[C@@H]43)cnc12] |
| CLI | 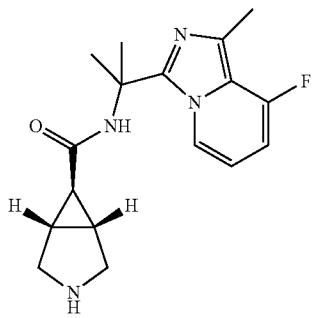 [SMILES: Cc1nc(C(C)(C)NC(=O)[C@H]2[C@@H]3CNC[C@@H]32)n2cccc(F)c12] |
| CLII | 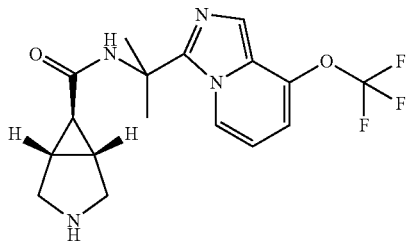 [SMILES: CC(C)(NC(=O)[C@H]1[C@@H]2CNC[C@@H]21)c1ncc2c(OC(F)(F)F)cccn12] |
| CLIII | 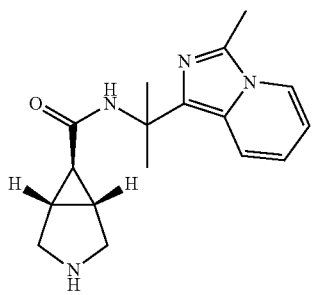 [SMILES: Cc1nc(C(C)(C)NC(=O)[C@H]2[C@@H]3CNC[C@@H]32)c2ccccn12] |

-continued
| Comp. | Structure |
|---|---|
| CLIV | 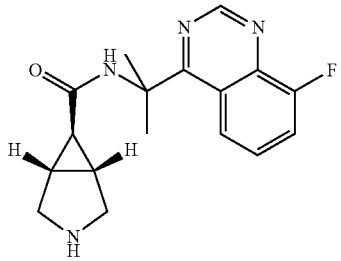 [SMILES: CC(C)(NC(=O)[C@H]1[C@@H]2CNC[C@@H]21)c1ncnc2c(F)cccc12] |
| CLV | 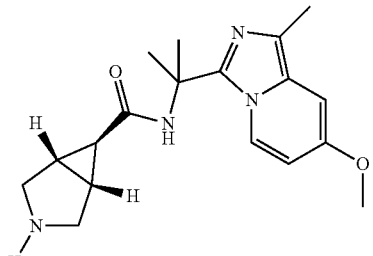 |
| CLVI | 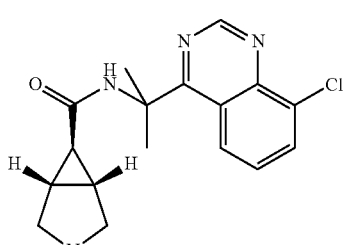 |
| CLVII | 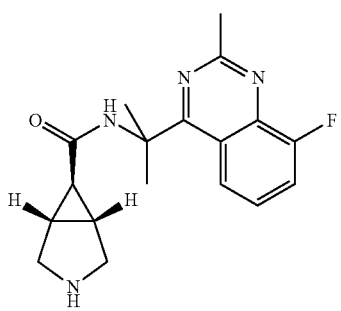 [SMILES: Cc1nc(C(C)(C)NC(=O)[C@H]2[C@@H]3CNC[C@@H]32)c2cccc(F)c2n1] |
| CLVIII | 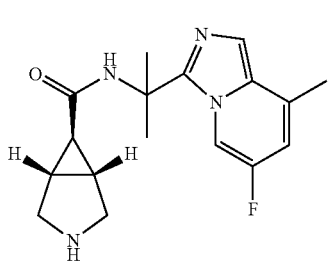 [SMILES: Cc1cc(F)cn2c(C(C)(C)NC(=O)[C@H]3[C@@H]4CNC[C@@H]43)ncc12] |
-continued
| Comp. | Structure |
|---|---|
| CLVIV | 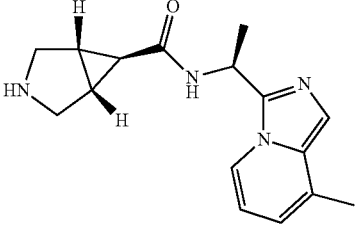 [SMILES: Cc1cccn2c([C@H](C)NC(=O)[C@H]3[C@@H]4CNC[C@@H]43)ncc12] |
| CLX | 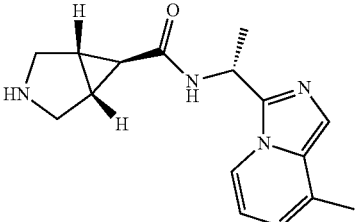 |
| CLXI | 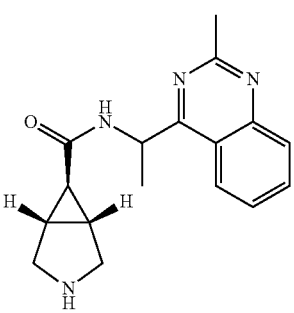 |
| CLXII | 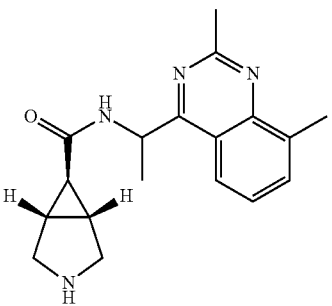 [SMILES: Cc1nc(C(C)NC(=O)[C@H]2[C@@H]3CNC[C@@H]32)c2cccc(C)c2n1] |
| CLXVII | 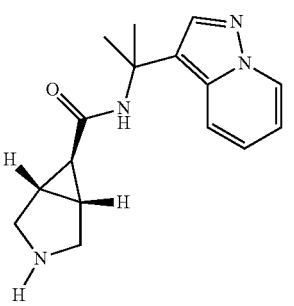 [SMILES: CC(C)(NC(=O)[C@H]1[C@@H]2CNC[C@@H]21)c1cnn2ccccc12] |

-continued
| Comp. | Structure |
|---|---|
| CLXVIII | 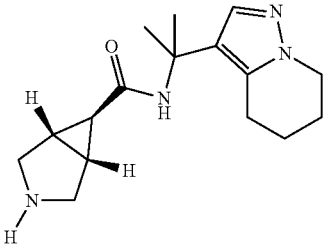 [SMILES: CC(C)(NC(=O)[C@H]1[C@@H]2CNC[C@@H]21)c1cnn2c1CCCC2] |
| CLXVIV | 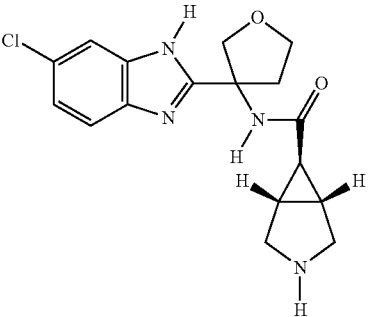 [SMILES: O=C(NC1(c2nc3ccc(Cl)cc3[nH]2)CCOC1)[C@H]1[C@@H]2CNC[C@@H]21] |
| CLXX | 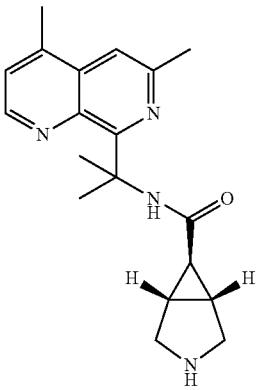 [SMILES: Cc1cc2c(C)ccnc2c(C(C)(C)NC(=O)[C@H]2[C@@H]3CNC[C@@H]32)n1] |
| CLXXI | 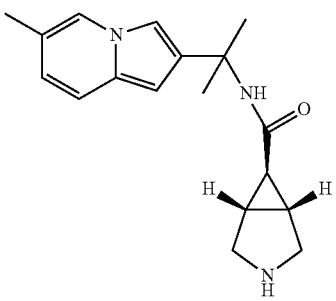 [SMILES: Cc1ccc2cc(C(C)(C)NC(=O)[C@H]3[C@@H]4CNC[C@@H]43)cn2c1] |
| CLXXII | 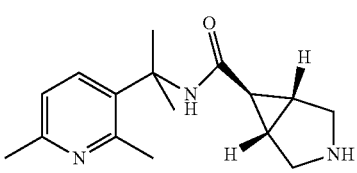 [SMILES: Cc1ccc(C(C)(C)NC(=O)[C@H]2[C@@H]3CNC[C@@H]32)c(C)n1] |//
-continued
| Comp. | Structure |
|---|---|
| CLXXIII | 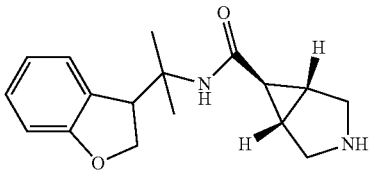 [SMILES: CC(C)(NC(=O)[C@H]1[C@@H]2CNC[C@@H]21)C1COc2ccccc21] |
| CLXXVI | 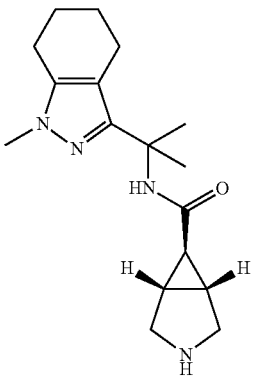 [SMILES: Cn1nc(C(C)(C)NC(=O)[C@H]2[C@@H]3CNC[C@@H]32)c2c1CCCC2] |
| CLXXVII | 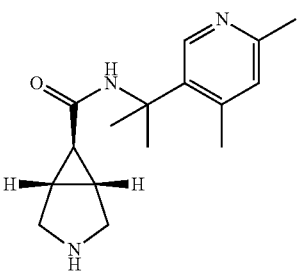 [SMILES: Cc1cc(C)c(C(C)(C)NC(=O)[C@H]2[C@@H]3CNC[C@@H]32)cn1] |
| CLXXVIII | 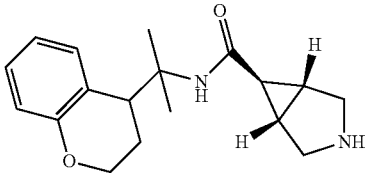 [SMILES: CC(C)(NC(=O)[C@H]1[C@@H]2CNC[C@@H]21)C1CCOc2ccccc21] |
| CLXXXI | 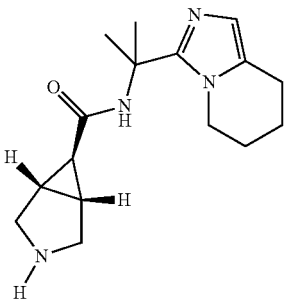 [SMILES: CC(C)(NC(=O)[C@H]1[C@@H]2CNC[C@@H]21)c1ncc2n1CCCC2] |

| Comp. | Structure |
|---|---|
| CLXXXII | (structure) |
| CLXXXIII | (structure) |
| CLXXXIV | (structure) |

Terms and Definitions Used

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

The number of substituents $R^3$ of W is preferably from 0 to 3, more preferably from 0 to 2, most preferably 1 or 2.

For the instances where Y is —CH$_2$O— this to be interpreted such that the oxygen atom of —CH$_2$O— is connected to W.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The prefix "meso" indicates the presence of a symmetry element of the second kind (mirror plane, centre of inversion, rotation-reflection axis) in a chemical species.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term "halogen" generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkylene:

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

Alkenyl:

The term "$C_{2-n}$-alkenyl" is used for a group as defined in the definition for "$C_{1-n}$-alkyl" with at least two carbon atoms, if at least two of those carbon atoms of said group are bonded to each other by a double bond.

Alkynyl:

The term "$C_{2-n}$-alkynyl" is used for a group as defined in the definition for "$C_{1-n}$-alkyl" with at least two carbon atoms, if at least two of those carbon atoms of said group are bonded to each other by a triple bond.

Cycloalkyl:

The term "$C_{3-n}$-cycloalkyl" wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Heterocyclyl:

The term "heterocyclyl" means a saturated or unsaturated mono- or polycyclic-ring systems including aromatic ring system containing one or more heteroatoms selected from N, O or S(O)r, wherein r=0, 1 or 2, consisting of 5 to 11 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

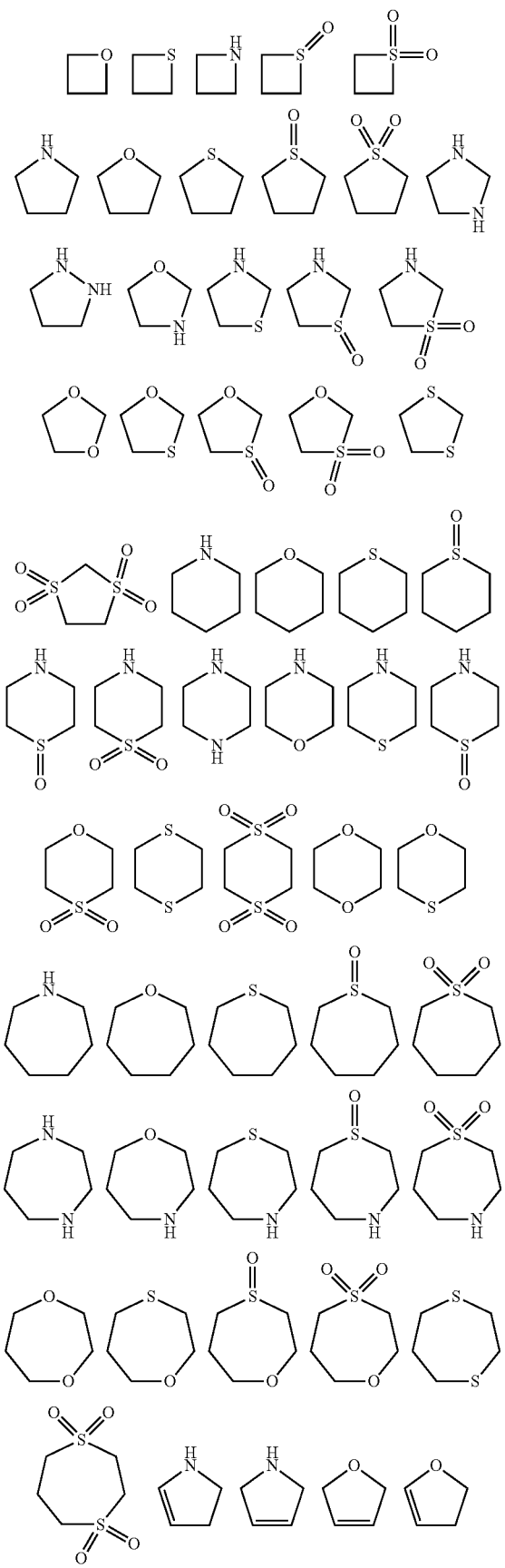

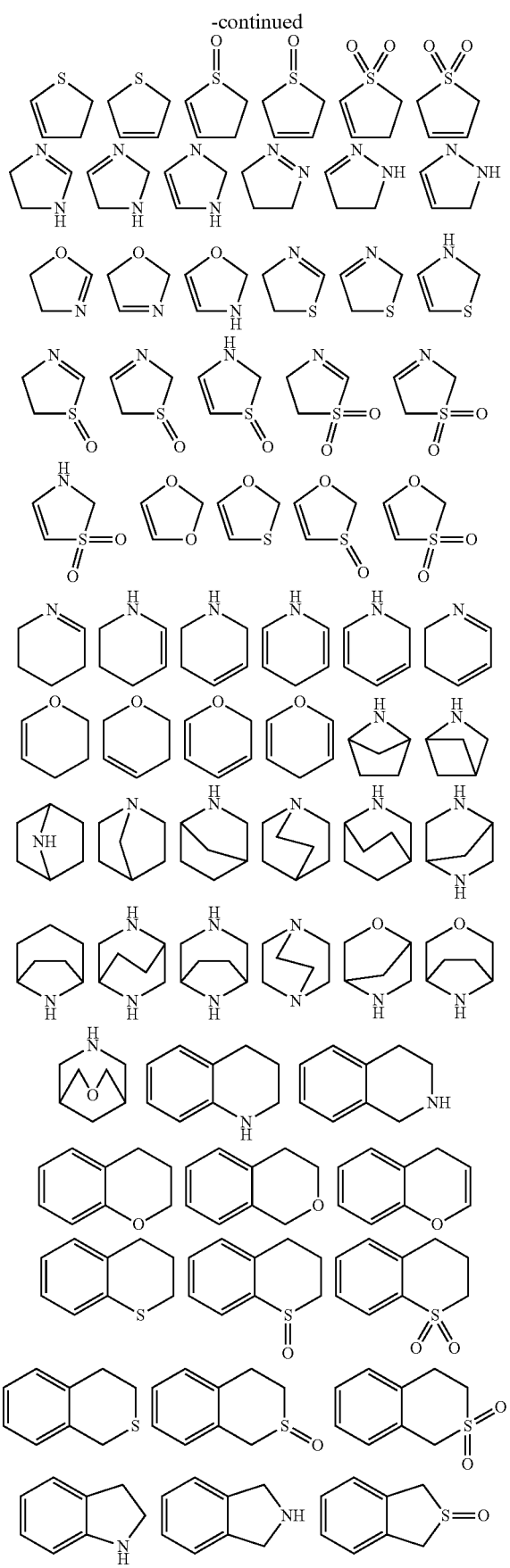
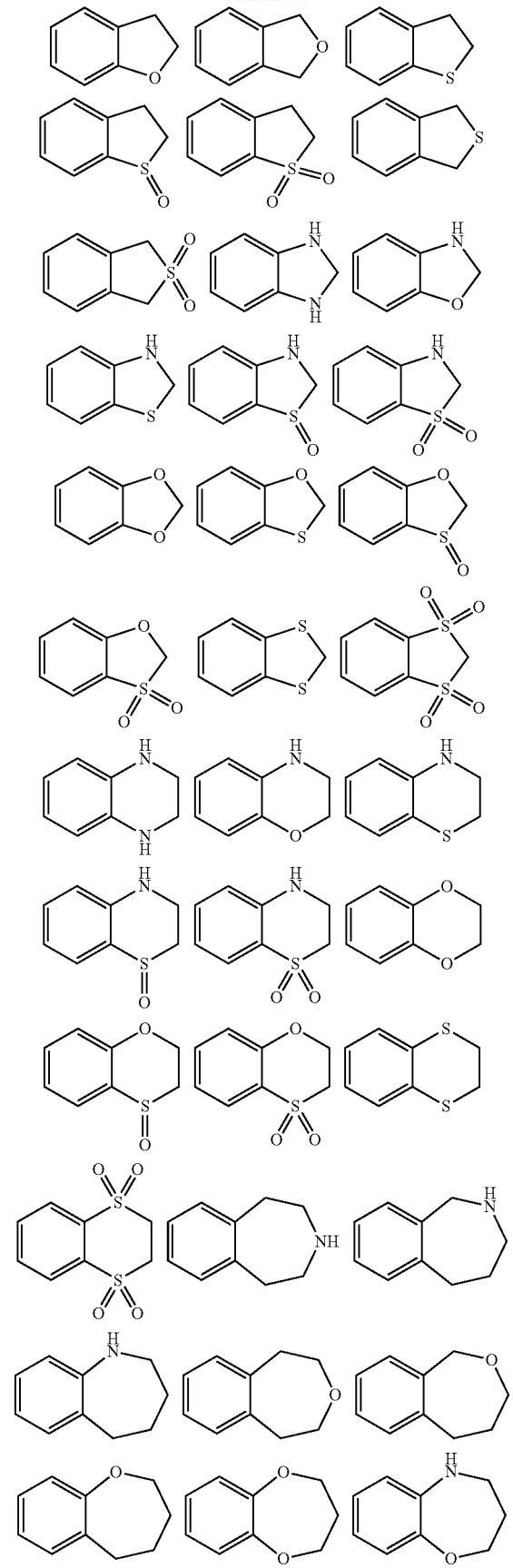

Aryl:

The term "aryl" as used herein, either alone or in combination with another radical, denotes a carbocyclic aromatic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heteroaryl:

The term "heteroaryl" means a mono- or bicyclic-ring systems containing one or more heteroatoms selected from N, O or S(O)$_r$, wherein r=0, 1 or 2, consisting of 5 to 10 ring atoms, wherein at least one of the heteroatoms is part of an aromatic ring. The term "heteroaryl" is intended to include all the possible isomeric forms. Preferred heteroaryls for the present invention comprise up to 4 heteroatoms and at least one 5- or 6-membered ring, more preferably at least one 6-membered ring.

Thus, the term "heteroaryl" includes the following exemplary structures which are not depicted as radicals as each form may be attached through a covalent bond to any atom so long as appropriate valences are maintained:

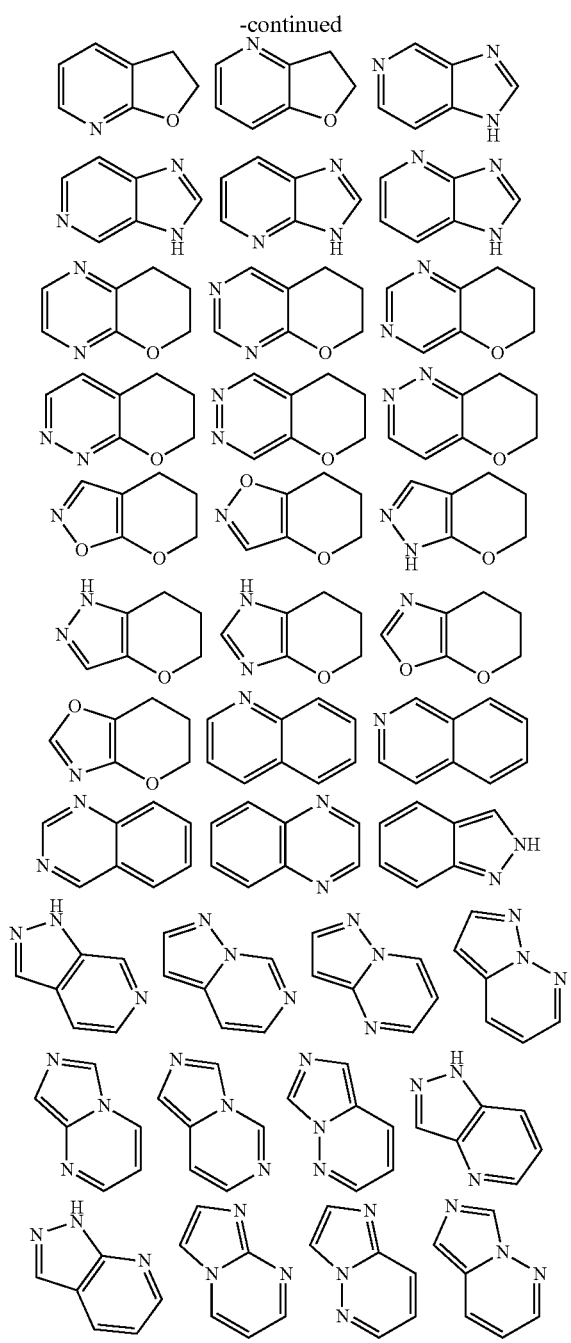

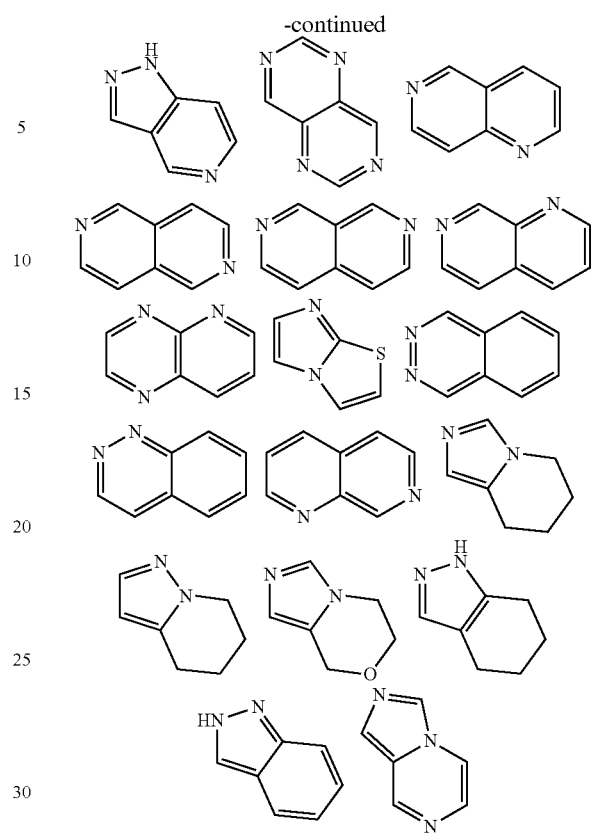

Many of the terms given above may be used repeatedly in the definition of a formula or group and in each case have one of the meanings given above, independently of one another.

Methods of Preparation

The compounds according to the invention may be obtained using methods of synthesis known in principle. Preferably, the compounds are obtained by the following methods according to the invention which are described in more detail hereinafter.

The following schemes shall illustrate generally how to manufacture the compounds according to general formula (I) and the corresponding intermediate compounds by way of example. The abbreviated substituents may be as defined above if not defined otherwise within the context of the schemes. For a list of abbreviations, see below.

Scheme 1

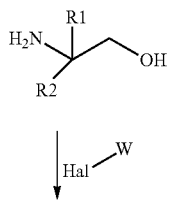

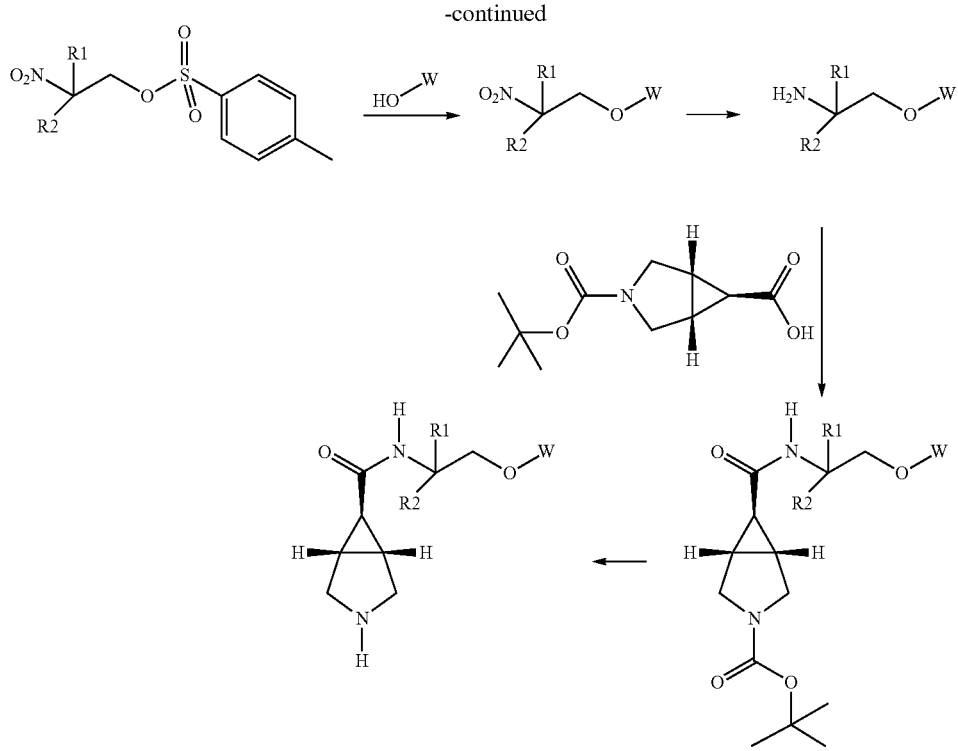

In scheme 1, Hal=halogen.

Scheme 1: In a first step a derivative of toluene-4-sulfonic acid 2-nitro-ethyl ester is reacted with an alcohol in the presence of an appropriate base such as Cesium carbonate in an appropriate solvent such as N,N-dimethylacetamide at elevated temperatures. The nitro group of the resulting product is converted in the corresponding primary amine by hydrogenation in the presence of an appropriate catalyst such as Raney Nickel in an appropriate solvent such as methanol or by treatment with Zinc in an appropriate solvent such as methanol in the presence of HCl or by treatment with Tin (II) chloride in an appropriate solvent such as ethanol at elevated temperatures. Alternatively, the amino ether is prepared reacting an amino alcohol with an halide in the presence of an appropriate base such as sodium hydride in an appropriate solvent such as dioxane. The amino ether is coupled with meso-(1R,5S,6r)-3-(tert-butoxycarbonyl)-3-azabicyclo[3.1.0]hexane-6-carboxylic acid (commercially available from ABCR or WuXi AppTec, $^1$H NMR (500 MHz, DMSO-$d_6$): δ 1.24 (t, J=3.2, 1H), 1.38 (s, 9H), 1.97 (t, J=2.5 Hz,2H), 3.34 (d, 2H), 3.48 (d, J=11.0 Hz, 2H), 12.21 (br, 1H)) in an appropriate solvent such as DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 2

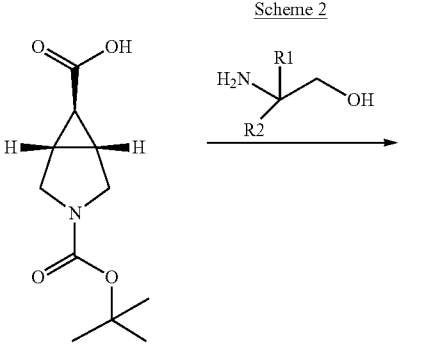

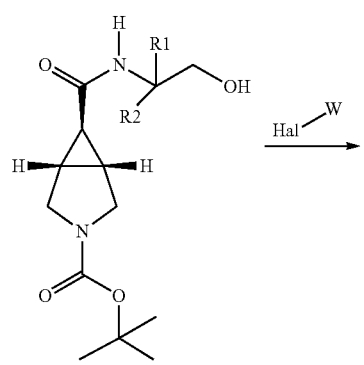

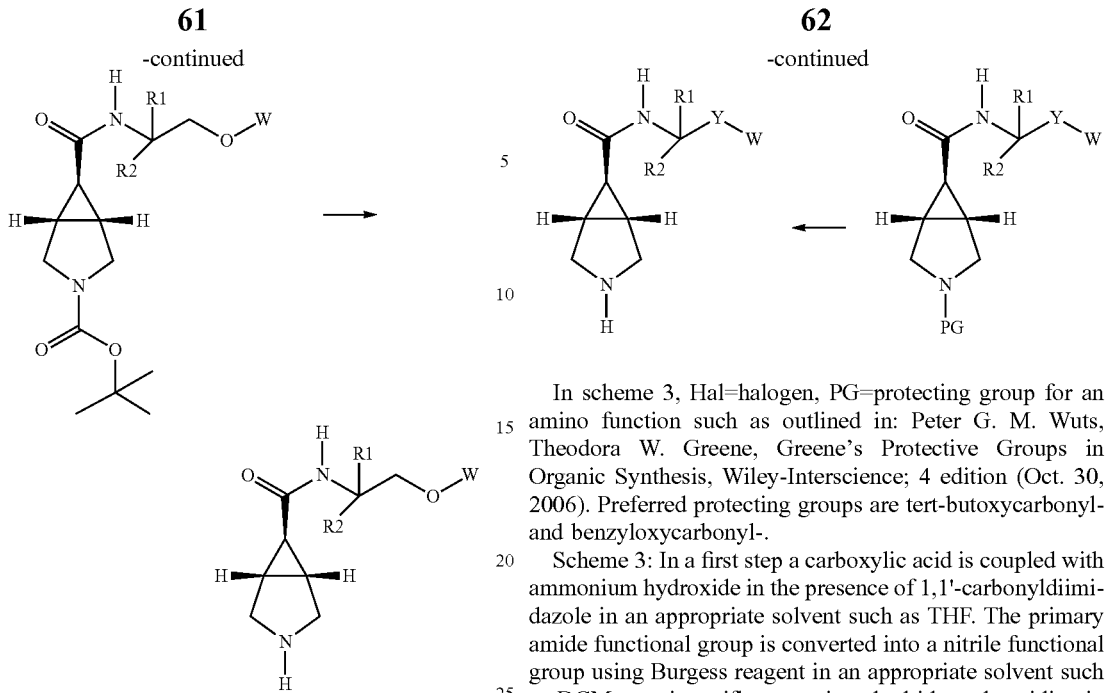

In scheme 2, Hal=halogen.

Scheme 2: In a first step an amino alcohol is coupled with meso-(1R,5S,6r)-3-(tert-butoxycarbonyl)-3-azabicyclo[3.1.0]hexane-6-carboxylic acid in an appropriate solvent such as DMF and in the presence of a coupling agent (e.g. HATU) and a base (e.g. DIPEA). The resulting alcohol is reacted with an halide in the presence of an appropriate base such as sodium hydride in an appropriate solvent such as dioxane. The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

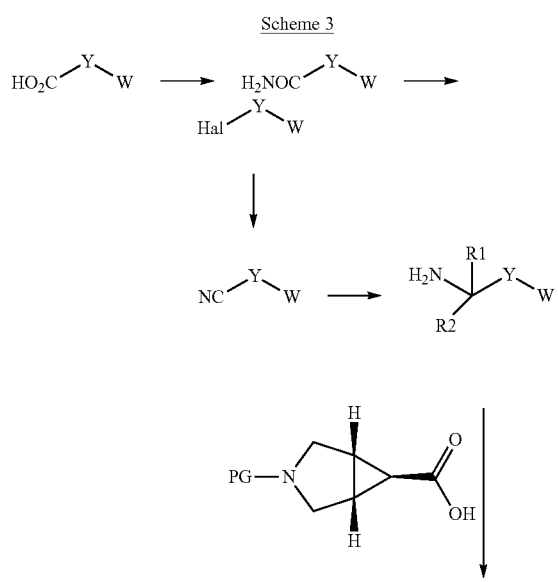

In scheme 3, Hal=halogen, PG=protecting group for an amino function such as outlined in: Peter G. M. Wuts, Theodora W. Greene, Greene's Protective Groups in Organic Synthesis, Wiley-Interscience; 4 edition (Oct. 30, 2006). Preferred protecting groups are tert-butoxycarbonyl- and benzyloxycarbonyl-.

Scheme 3: In a first step a carboxylic acid is coupled with ammonium hydroxide in the presence of 1,1'-carbonyldiimidazole in an appropriate solvent such as THF. The primary amide functional group is converted into a nitrile functional group using Burgess reagent in an appropriate solvent such as DCM or using trifluoroacetic anhydride and pyridine in an appropriate solvent such as DCM. Alternatively, a halogen-substituted derivative is converted into a nitrile upon treatment with Zinc cyanide in the presence of a Palladium source (e.g. tris(dibenzylideneacetone)dipalladium(0) or 1,1-bis(diphenylphosphino) ferrocenedichloro palladium (II)), a phosphine (e.g. 1,1'-bis(diphenylphosphino)ferrocene), optionally Zinc, in appropriate solvents such as DMF or N,N-dimethyl-acetamide at elevated temperatures. Nitriles are reacted with Cerium (III) chloride and alkyllithiums (see *J. Org. Chem.* 1992, 57, 4521-452) in an appropriate solvent such as THF or alternatively with Grignard reagents in an appropriate solvent such as toluene at elevated temperatures. The resulting amine is coupled with protected meso-(1R,5S,6r)-3-azabicyclo[3.1.0]hexane-6-carboxylic acid (meso-(1R,5S,6r)-3-(benzyloxycarbonyl)-3-azabicyclo[3.1.0]hexane-6-carboxylic acid is commercially available from Matrix Scientific) in an appropriate solvent such as DCM or DMF and in the presence of a coupling agent (e.g. HATU or TBTU) and a base (e.g. TEA or DIPEA). In case W is substituted with $R^3$=halogen, such group can be substituted upon treatment with a stannane or a boronic acid or a trifluoroborate or a boroxine in the presence of a Palladium source (e.g 1,1'-Bis(diphenylphosphino)ferrocene-palladium(II)dichloride dichloromethane complex), in appropriate solvents such as DMF at elevated temperatures.

The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol. Alternatively, Boc removal is accomplished by treatment with a silylating agent (e.g. tert-butyldimethylsilyl trifluoromethanesulfonate) in the presence of a base (e.g. 2,6-lutidine) in appropriate solvents such as DCM followed by reaction with a fluoride source (e.g. tetrabutylammonium fluoride) in appropriate solvents such as THF. The benzyloxycarbonyl-protecting group is removed by hydrogenation in the presence of a catalyst (e.g. palladium on carbon) in appropriate solvents such as MeOH and water.

Partial saturation of W is achieved by hydrogenation in the presence of a metal catalyst (e.g. platinum(IV) oxide hydrate) in an appropriate solvent such as acetic acid.

Scheme 4

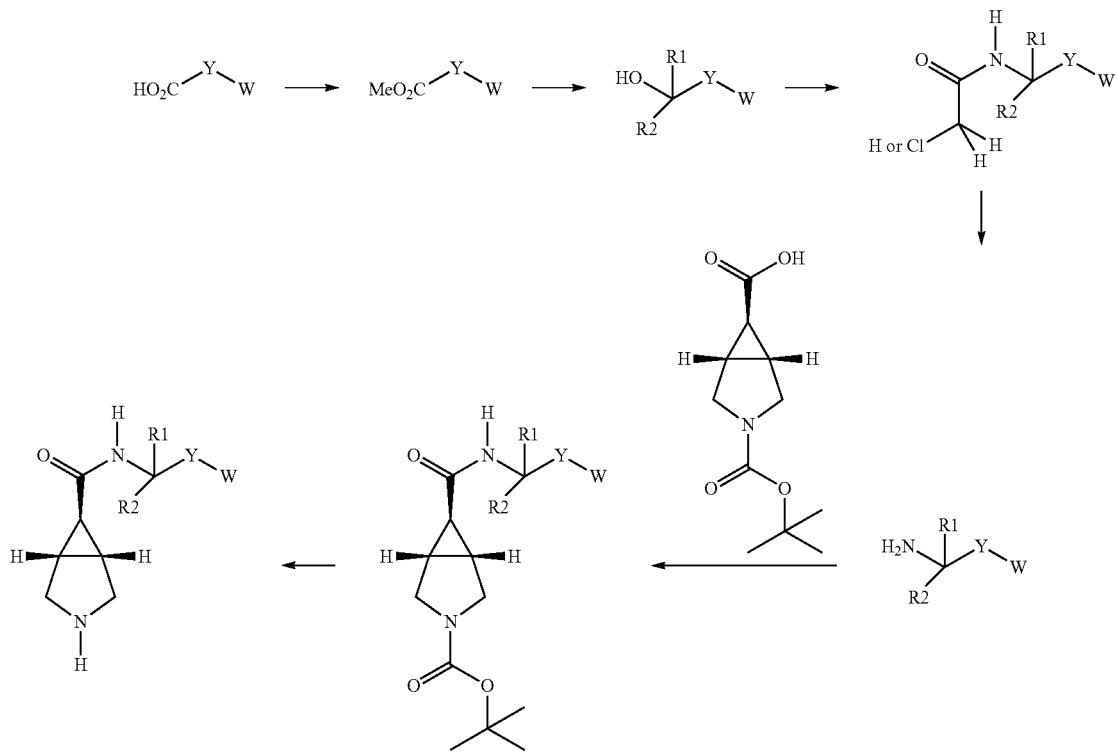

Scheme 4: In a first step a carboxylic acid is esterified with trimethylsilyldiazomethane in appropriate solvents such as DCM and MeOH. The ester is reacted with an appropriate organometallic reagent such as a Grignard reagent in an appropriate solvent such as THF to afford an alcohol, which in turn is treated with acetonitrile or chloroacetonitrile in appropriate acids such as sulfuric acid, acetic acid or trifluoroacetic acid. Acetamide cleavage is carried out in the presence of a base (e.g. Potassium hydroxide) in appropriate solvents such as 1,2 methoxyethanol and ethylene glycol or in concentrated aqueous acid (e.g. 6M HCl). The resulting amine is coupled with meso-(1R,5S,6r)-3-(tert-butoxycarbonyl)-3-azabicyclo[3.1.0]hexane-6-carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 5

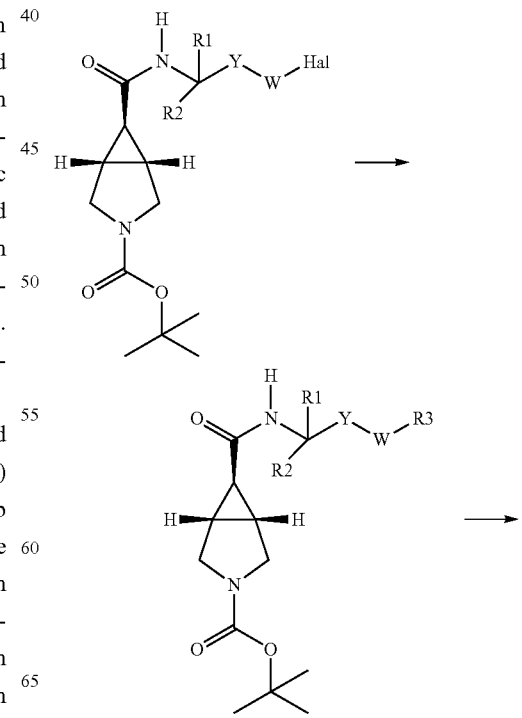

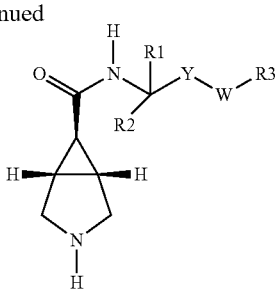

In scheme 5, Hal=halogen, $R^3$=substituent as defined for W.

Scheme 5: A halogen-substituted derivative is functionalised with $R^3$ upon treatment with a boronic acid or a trifluoroborate in the presence of a Palladium source (e.g. tetrakis (triphenylphosphine)palladium(0) or palladium (II) acetate and tricyclohexylphosphine), a base (e.g. potassium carbonate or tri potassium phosphate) in appropriate solvents such as 1,2-dimethoxyethane, toluene and water at elevated temperatures. Alternatively, the halogen-substituted derivative is hydrogenated in the presence of a Palladium in an appropriate solvent such as EtOH. The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 6

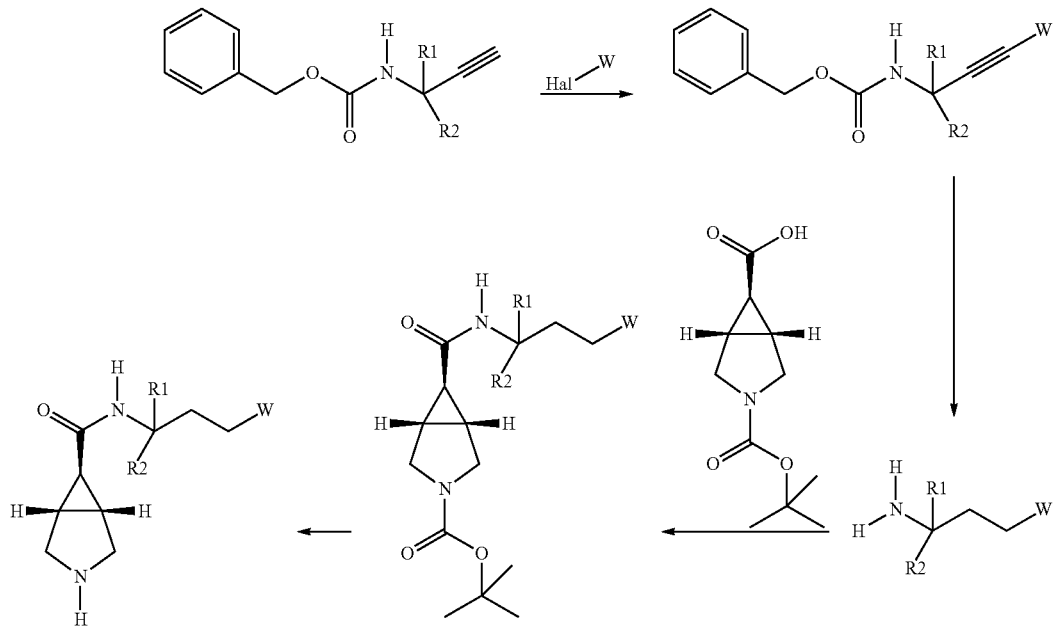

In scheme 6, Hal=halogen

Scheme 6: In a first step a derivative of prop-2-ynyl-carbamic acid benzyl ester is substituted upon treatment with an halide in the presence of a Copper source (e.g. Copper (I) iodide), a Palladium source (e.g. dichlorobis (triphenylphosphine)-palladium(II)) and a base (e.g. triethylamine) in an appropriate solvent such as acetonitrile. The resulting product is hydrogenated in the presence of Palladium in an appropriate solvent such as MeOH. The resulting amine is coupled with meso-(1R,5S,6r)-3-(tert-butoxycarbonyl)-3-azabicyclo[3.1.0]hexane-6-carboxylic acid in an appropriate solvent such as DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 7

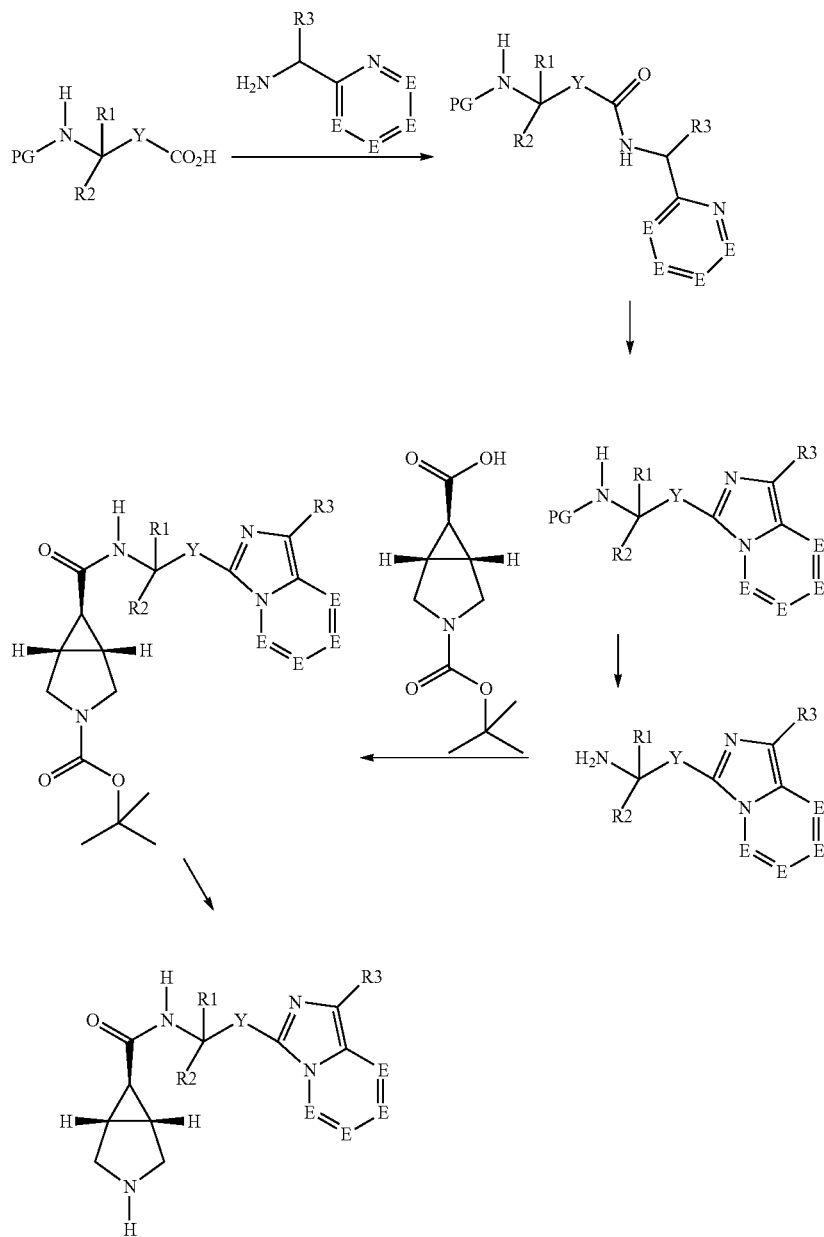

In scheme 7, R3=substituent as defined for W; E=C or N, independently; PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting groups are tert-butoxycarbonyl-, benzyloxycarbonyl- and 9-fluorenyl methoxycarbonyl-.

Scheme 7: In a first step a carboxylic acid is coupled with 2-(aminomethyl)-substituted heterocycle in an appropriate solvent such as THF or DCM and in the presence of a coupling agent (e.g. TBTU or HATU) and a base (e.g. TEA). Condensation is achieved using Burgess reagent in an appropriate solvent such as DCM or using phosphorus oxychloride and DMF at elevated temperatures. The tert-butoxycarbonyl-protecting group is removed with hydrochloric acid in an appropriate solvent such as ethyl ether while the benzyloxycarbonyl-is removed by hydrogenation in the presence of a catalyst (e.g. palladium on carbon) in appropriate solvents such as MeOH and water. The resulting amine is coupled with meso-(1R,5S,6r)-3-(tert-butoxycarbonyl)-3-azabicyclo[3.1.0]hexane-6-carboxylic acid in an appropriate solvent such as THF or DCM and in the presence of a coupling agent (e.g. HATU) and a base (e.g. TEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 8

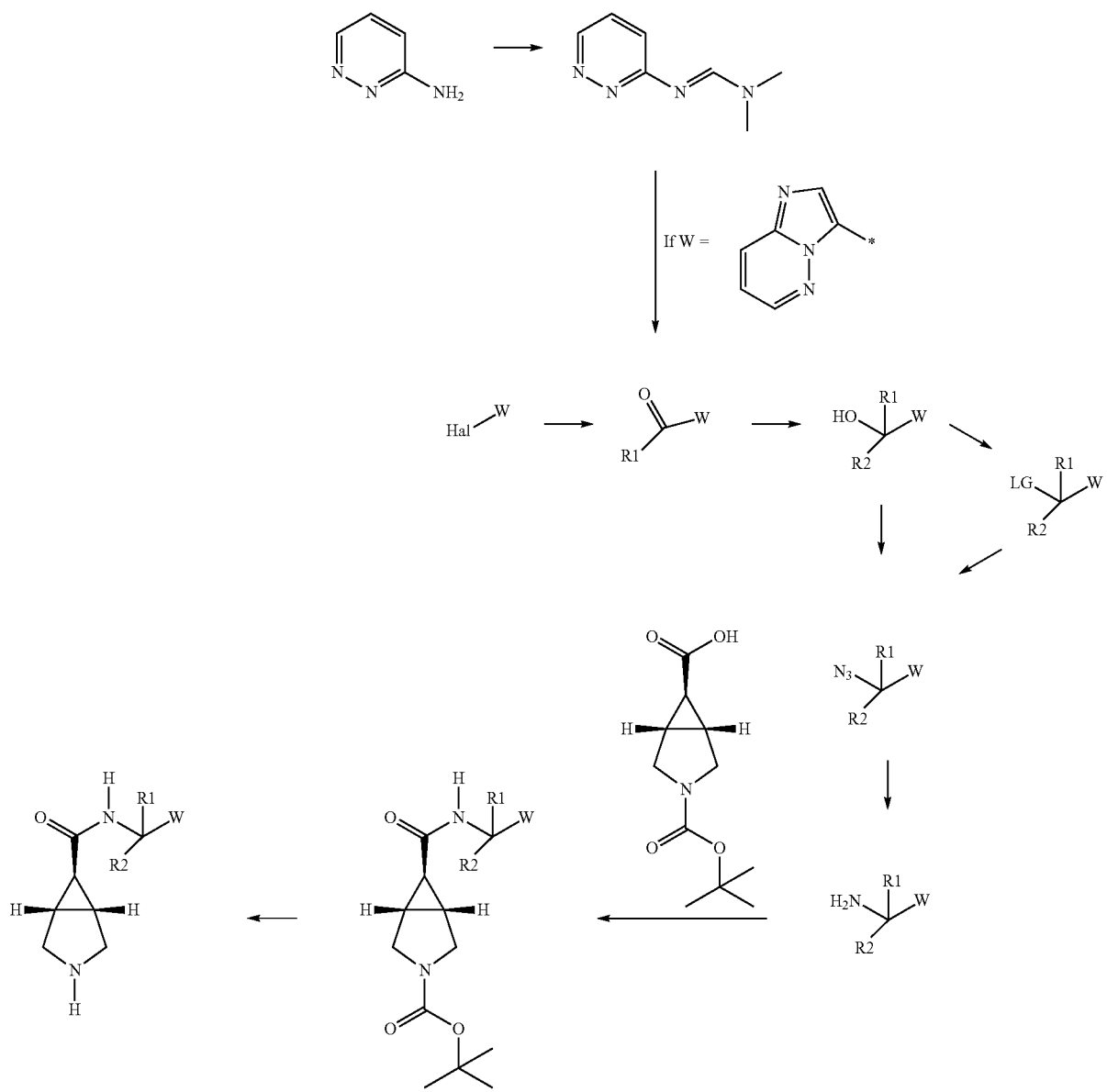

In scheme 8, Hal=halogen; LG=sulfonic ester or halogen

Scheme 8: In a first step a ketone is obtained by coupling of a halide with an appropriate tin reagent (e.g. tributyl(1-ethoxyvinyl)tin) in the presence of a palladium source (e.g. tetrakis(triphenylphosphine)palladium(0)) in an appropriate solvent such as toluene at high temperatures followed by acidic treatment (e.g. aqueous HCl in THF). Alternatively, a ketone is synthesised from an amine by treatment with N.N-dimethylformamide dimethyl acetal in an appropriate solvent such as toluene at elevated temperatures followed by reaction with chloroacetone and sodium iodide in an appropriate solvent such as DMF at elevated temperatures. The resulting ketone is reacted with an appropriate organometallic reagent such as a Grignard reagent in an appropriate solvent such as THF to afford an alcohol, which in turn is treated with sodium azide in an appropriate acid such as TFA. Alternatively, the alcohol is converted to a leaving group, such as a sulfonic ester by treatment with a sulfonyl chloride (e.g. methanesulfonyl chloride), a base (e.g. triethylamine) in an appropriate solvent such as THF. The leaving group is displaced with Sodium azide in DMF to afford an azide. Azide reduction is carried out by hydrogenation in the presence of palladium in an appropriate solvent such as EtOAc. The resulting amine is coupled with meso-(1R,5S,6r)-3-(tert-butoxycarbonyl)-3-azabicyclo[3.1.0]hexane-6-carboxylic acid in an appropriate solvent such as THF or DMF or DCM and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 9

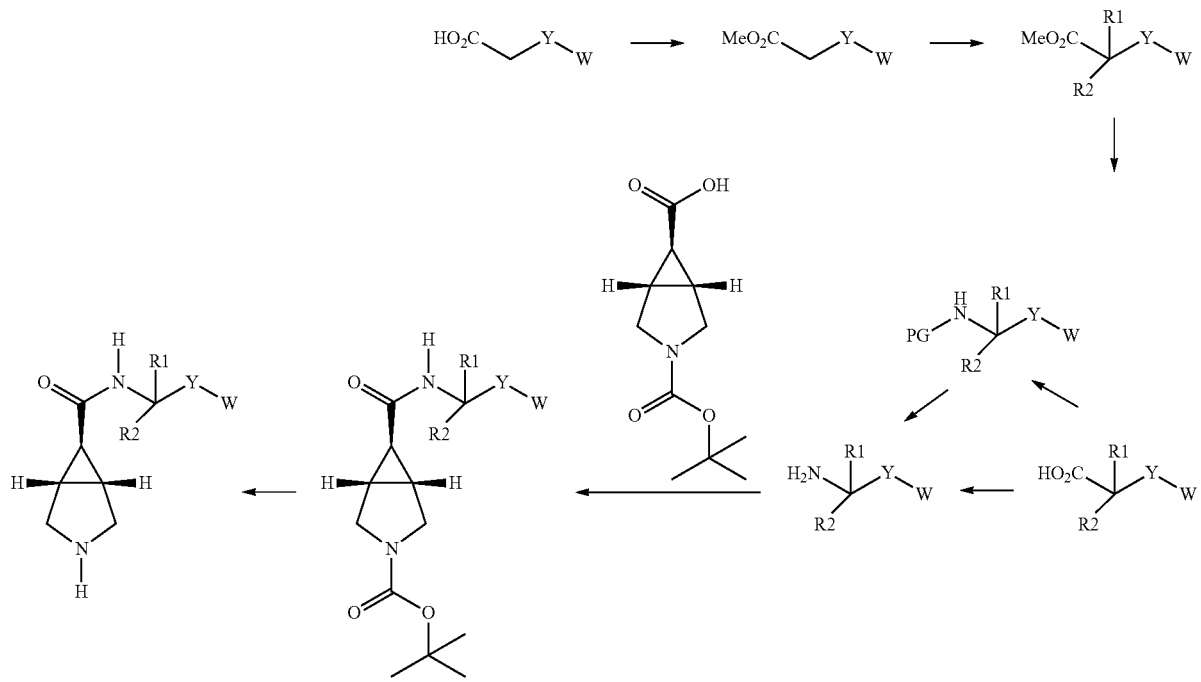

In scheme 9, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting group is 4-methoxy-benzyloxycarbonyl-.

Scheme 9: In a first step a carboxylic is converted into the corresponding ester (e.g. with trimethylsilyldiazomethane in DCM/MeOH). The ester is bis-alkylated by treatment with a base (e.g. Lithium bis(trimethylsilyl)amide) in an appropriate solvent such as THF followed by treatment with alkylating agent(s) (e.g. iodomethane). The bis-alkylated ester is hydrolysed to the carboxylic acid with a base (e.g. lithium hydroxide) in appropriate solvent such as THF and water. The carboxylic acid is treated with diphenylphosphoryl azide and a base (e.g. TEA) in an appropriate solvent such as toluene at high temperatures followed by acidic treatment (e.g. 4M aqueous HCl). Alternatively, the carboxylic acid is treated with diphenylphosphoryl azide, a base (e.g. TEA) and an alcohol (e.g. 4-methoxybenzyl alcohol) in an appropriate solvent such as toluene at high temperatures. The 4-methoxy-benzyloxycarbonyl protecting group is deprotected with TFA in an appropriate solvent such as DCM. The amine is coupled with meso-(1R,5S,6r)-3-(tert-butoxycarbonyl)-3-azabicyclo[3.1.0]hexane-6-carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 10

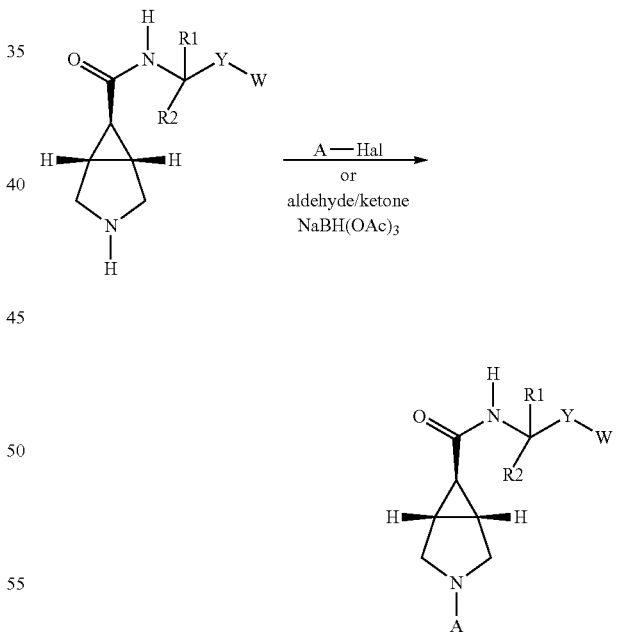

In scheme 10, Hal=halogen.

Scheme 10: A secondary amine is coupled with an halide in the presence of an appropriate base such as triethylamine in an appropriate solvent such as DMF. Alternatively, a reductive amination is carried out by reaction with an appropriate aldehyde or ketone, a reducing agent such as sodium triacetoxyborohydride and acetic acid in an appropriate solvent such as DMF.

Scheme 11

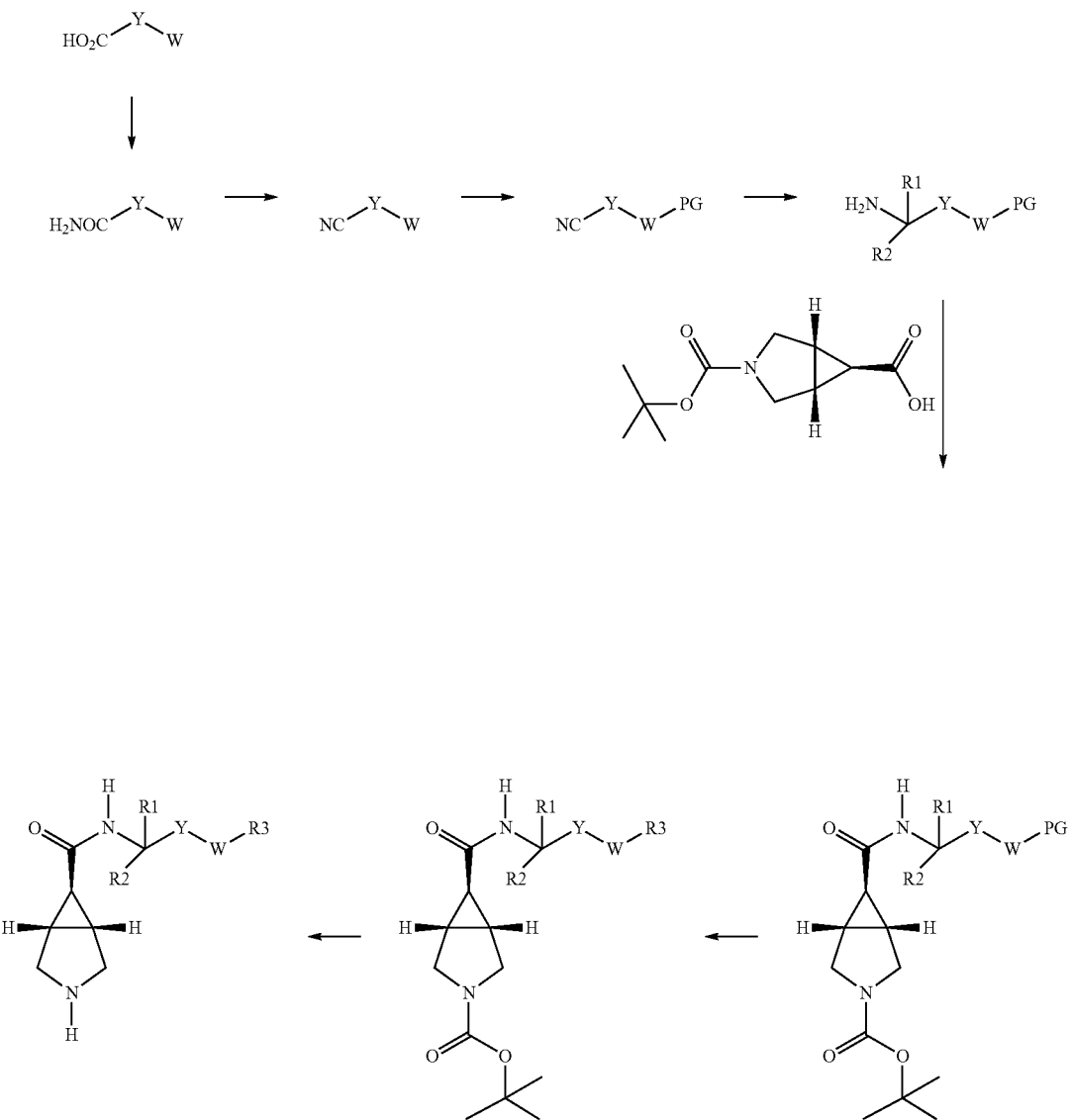

In scheme 11, PG=protecting group for a heteroaryl or heterocyclyl Nitrogen such as outlined in: Peter G. M. Wuts, Theodora W. Greene, Greene's Protective Groups in Organic Synthesis, Wiley-Interscience; 4 edition (Oct. 30, 2006).

Preferred protecting group is trimethylsilylethoxymethyl-, $R^3$=substituent as defined for W.

Scheme 11: in a first step a carboxylic acid is coupled with ammonium hydroxide in the presence of 1,1'-carbonyldiimidazole in an appropriate solvent such as THF. The primary amide functional group is converted into a nitrile functional group using Burgess reagent in an appropriate solvent such as DCM. The trimethylsilylethoxymethyl-protecting group is installed by reaction with 2-(trimethylsilyl)ethoxymethyl chloride, a base (e.g. Sodium hydride) in an appropriate solvent such as DMF. Protected nitriles compounds are reacted with Cerium (III) chloride and alkyllithiums (see *J. Org. Chem.* 1992, 57, 4521-452) in an appropriate solvent such as THF or alternatively with Grignard reagents in an appropriate solvent such as toluene at elevated temperatures. The resulting amine is coupled with meso-(1R,5S,6r)-3-(tert-butoxycarbonyl)-3-azabicyclo[3.1.0]hexane-6-carboxylic acid in an appropriate solvent such as DCM or DMF and in the presence of a coupling agent (e.g. HATU or TBTU) and a base (e.g. TEA or DIPEA). The trimethylsilylethoxymethyl-protecting group is removed with tetrabutylammonium fluoride and ethylenediamine. An $R^3$ other than H is introduced by treatment with a halide in the presence of a base (e.g. cesium carbonate) in appropriate solvents such as DMF or N,N-dimethyl-acetamide. The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 12
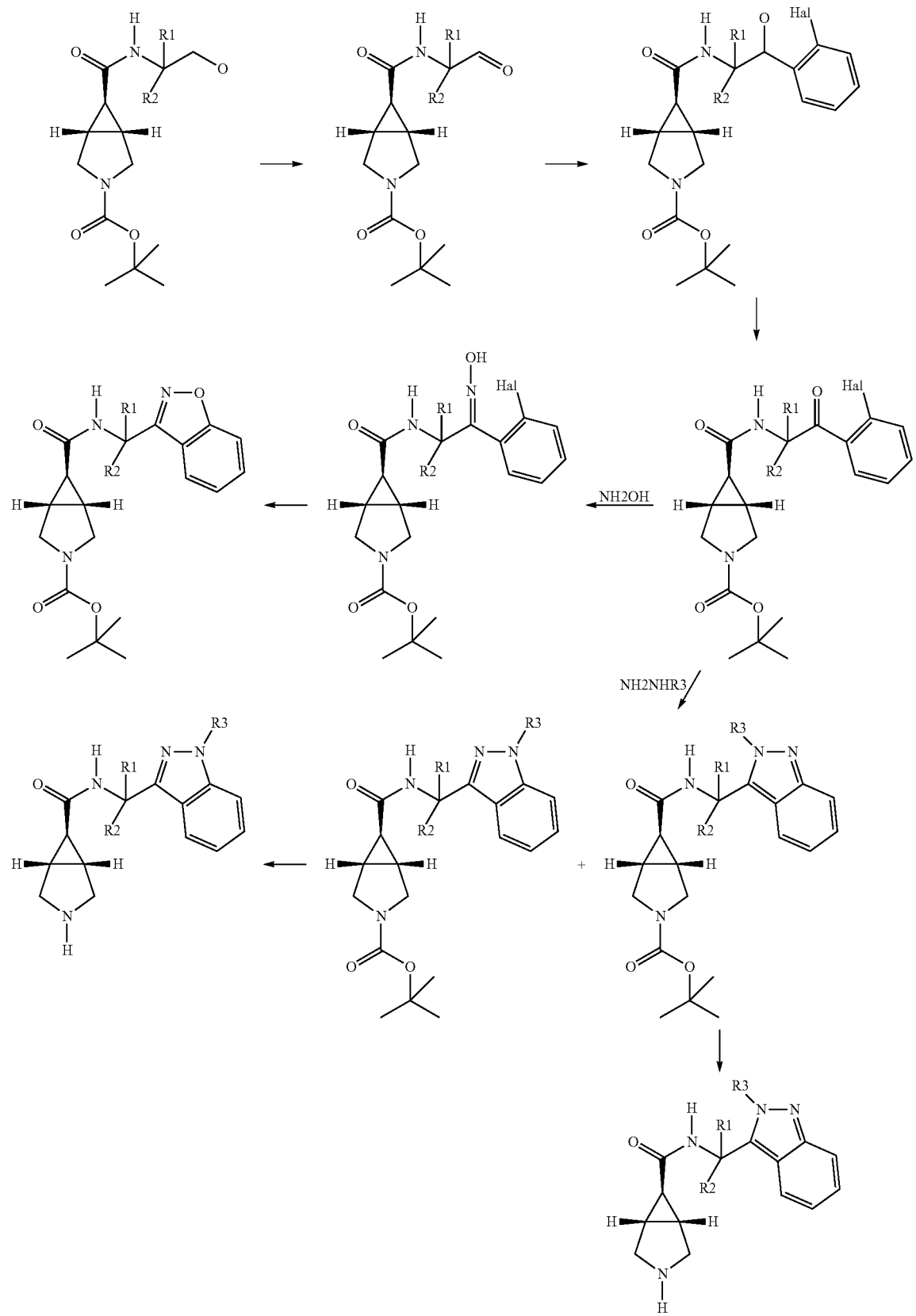

In scheme 12, Hal=halogen; R³=substituent as defined for W.

Scheme 12: in a first step an alcohol is oxidized to the aldehyde with Dess-Martin periodinane in DCM. The aldehyde is reacted with an ortho-metallated halide in an appropriate solvent such as THF at low temperatures to afford an alcohol, which in turn is oxidized to the ketone with Dess-Martin periodinane in DCM. The ketone is converted to the oxime upon treatment with hydroxylamine hydrochloride in an appropriate solvent such as pyridine. Reaction with a base (e.g. potassium tert-butoxide) in an appropriate solvent such as THF gives rise to a benzoisoxazole optionally substituted with one or more R³. In case R³=halogen, such group can be substituted upon treatment with a stannane or a boronic acid or a trifluoroborate in the presence of a Palladium source (e.g. tetrakis (triphenylphosphine)palladium(0)), in appropriate solvents such as DCM or DMF at elevated temperatures.

The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Alternatively, the ketone is converted to the 1H-indazole optionally substituted with one or more R³ upon treatment with optionally substituted hydrazine in an appropriate solvent such as ethanol at high temperatures. 2H-Indazole optionally substituted with one or more R³ is obtained upon treatment with optionally substituted hydrazine, a base (e.g. potassium carbonate) and catalytic amounts of copper (II) oxide. In case R³=halogen, such group can be substituted upon treatment with a stannane or a boronic acid or a trifluoroborate in the presence of a Palladium source (e.g. Palladium(II) acetate), a phosphine (e.g. X-Phos), a base (e.g. potassium carbonate) in appropriate solvents such as cyclopentyl methyl ether and water at elevated temperatures.

The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 13

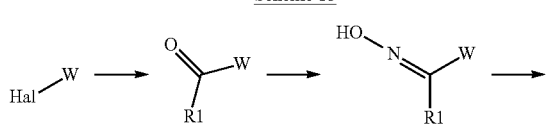

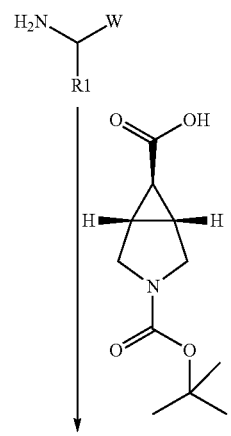

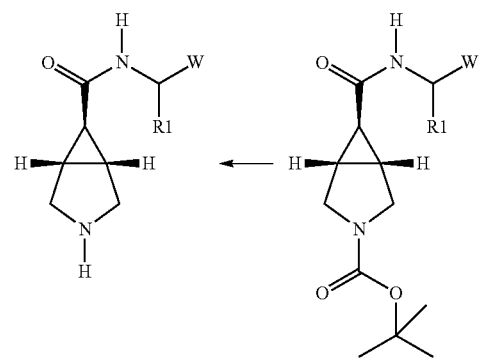

In scheme 13, Hal=halogen.

Scheme 13: In a first step a ketone is obtained by coupling of a halide with an appropriate tin reagent (e.g. tributyl(1-ethoxyvinyl)tin) in the presence of a palladium source (e.g. tetrakis(triphenylphosphine)palladium(0)) in an appropriate solvent such as toluene at high temperatures optionally followed by acidic treatment (e.g. aqueous HCl in THF). The ketone is converted to the oxime upon treatment with hydroxylamine hydrochloride and a base (e.g. TEA) in an appropriate solvent such as EtOH at elevated temperatures. The oxime is converted in the corresponding primary amine by hydrogenation in the presence of an appropriate catalyst such as Raney Nickel and of ammonium hydroxide in an appropriate solvent such as EtOH. The resulting amine is coupled with meso-(1R,5S,6r)-3-(tert-butoxycarbonyl)-3-azabicyclo[3.1.0]hexane-6-carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 14

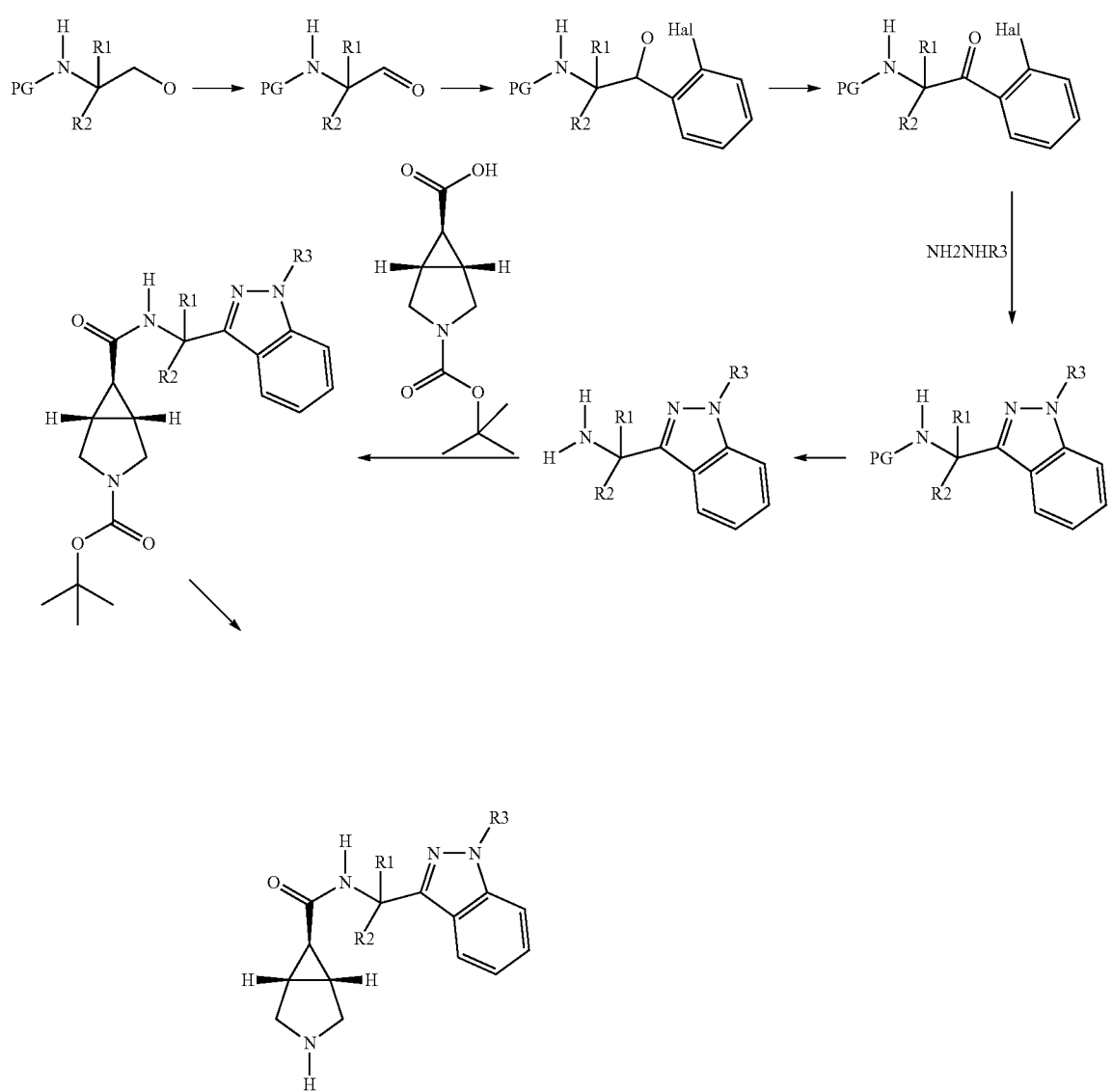

In scheme 14, PG=protecting group for an amino function such as outlined in: Peter G. M. Wuts, Theodora W. Greene, Greene's Protective Groups in Organic Synthesis, Wiley-Interscience; 4 edition (Oct. 30, 2006). Preferred protecting group is tert-butoxycarbonyl-.

Hal=halogen; $R^3$=substituent as defined for W.

Scheme 14: in a first step an alcohol is oxidized to the aldehyde with Dess-Martin periodinane in DCM. The aldehyde is reacted with an ortho-metallated halide in an appropriate solvent such as THF at low temperatures to afford an alcohol, which in turn is oxidized to the ketone with Dess-Martin periodinane in DCM. The ketone is converted to the 1H-indazole optionally substituted with one or more $R^3$ upon treatment with optionally substituted hydrazine in an appropriate solvent such as ethanol at high temperatures. In case $R^3$=halogen, such group can be substituted upon treatment with a stannane or a boronic acid or a trifluoroborate in the presence of a Palladium source (e.g. 1,1'-Bis(diphenylphosphino)ferrocene-palladium(II)dichloride dichloromethane complex), a base (e.g. potassium carbonate) in appropriate solvents such as DMF at elevated temperatures. When the resulting product is Boc-protected, deprotection is accomplished with hydrochloric acid in an appropriate solvent such as dioxane, methanol or ethyl ether. Alternatively, Boc cleavage is carried out upon heating at elevated temperatures in appropriate solvents such as water and methanol. The resulting amine is coupled with meso-(1R,5S,6r)-3-(tert-butoxycarbonyl)-3-azabicyclo[3.1.0]hexane-6-carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 15

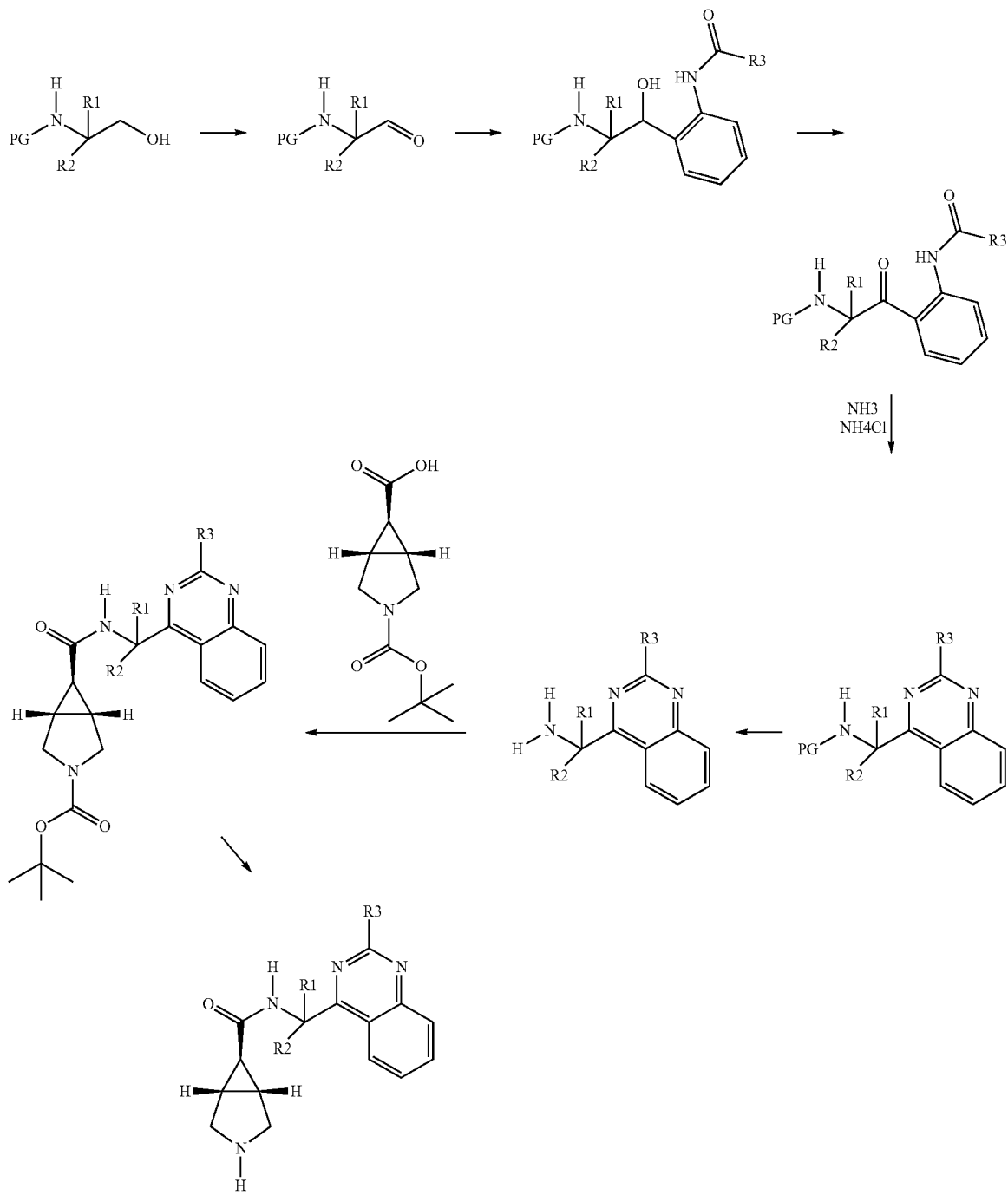

In scheme 15, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting group is tert-butoxycarbonyl-.

$R^3$=substituent as defined for W.

Scheme 15: in a first step an alcohol is oxidized to the aldehyde with Dess-Martin periodinane in DCM. The aldehyde is reacted with an ortho-metallated acetanilide prepared from a corresponding 2-halo acetanilide by halogen-metal exchange in an appropriate solvent such as THF at low temperatures to afford an alcohol, which in turn is oxidized to the ketone with Dess-Martin periodinane in DCM. The ketone is converted to the quinazoline optionally substituted with one or more $R^3$ upon treatment with ammonia and ammonium chloride in an appropriate solvent such as methanol at high temperatures. When the resulting product is Boc-protected, deprotection is accomplished with hydrochloric acid in an appropriate solvent such as dioxane, methanol or ethyl ether. Alternatively, Boc cleavage is carried out upon heating at elevated temperatures in appropriate solvents such as water and methanol. The resulting amine is coupled with meso-(1R,5S,6r)-3-(tert-butoxycarbonyl)-3-azabicyclo[3.1.0]hexane-6-carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Method of Treatment

Indications

The present invention relates to the use of a compound of formula (I) for the treatment and/or prevention of a disease or medical condition.

The present invention relates to compounds of formula (I) or pharmaceutically acceptable salts thereof, which are useful in the prevention and/or treatment of a disease and/or condition in which the activation of SSTR4 receptors is of therapeutic benefit, including improvement of symptoms, including but not limited to the treatment and/or prevention of pain of any kind and/or inflammatory diseases and/or associated conditions.

In a further aspect the present invention encompasses the compounds of the above-mentioned general formula (I) or pharmaceutically acceptable salts thereof, according to the invention for use as medicaments.

In view of their pharmacological effect the substances are suitable for the treatment of (1) acute pain such as for example toothache, peri- and post-operative pain, traumatic pain, muscle pain, the pain caused by burns, sunburn, trigeminal neuralgia, pain caused by colic, as well as spasms of the gastro-intestinal tract or uterus; sprains (2) visceral pain such as for example chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(3) neuropathic pain such as lumbosacral radiculopathy, low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, post-thoracotomy syndrome, stump pain, repetitive motion pain, neuropathic pain associated hyperalgesia and allodynia, alcoholism and other drug-induced pain;

(4) inflammatory pain/receptor-mediated pain in connection with diseases such as for example osteoarthritis, rheumatoid arthritis, inflammatory arthropathy, rheumatic fever, tendo-synovitis, bursitis, tendonitis, gout and gout-arthritis, traumatic arthritis, vulvodynia, damage to and diseases of the muscles and fascia, juvenile arthritis, spondylitis, psoriasis-arthritis, myositides, dental disease, influenza and other viral infections such as colds, systemic lupus erythematodes or pain caused by burns;

(5) tumour pain associated with cancers such as for example lymphatic or myeloid leukaemia, Hodgkin's disease, non-Hodgkin's lymphomas, lymphogranulomatosis, lymphosarcomas, solid malignant tumours and extensive metastases;

(6) headache diseases of various origins, such as for example cluster headaches, migraine (with or without aura) and tension headaches;

(7) sympathetically maintained pain like complex regional pain syndrome Type I and II;

(8) painful conditions of mixed origin, such as for example chronic back pain including lumbago, or fibromyalgia, sciatica, endometriosis, kidney stones.

The compounds are also suitable for treating (9) inflammatory and/or oedematous diseases of the skin and mucous membranes, such as for example allergic and non-allergic dermatitis, atopic dermatitis, psoriasis, burns, sunburn, bacterial inflammations, irritations and inflammations triggered by chemical or natural substances (plants, insects, insect bites), itching; inflammation of the gums, oedema following trauma caused by burns, angiooedema or uveitis;

(10) Vascular and heart diseases which are inflammation-related like arteriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

(11) inflammatory changes connected with diseases of the airways and lungs such as bronchial asthma, including allergic asthma (atopic and non-atopic) as well as bronchospasm on exertion, occupationally induced asthma, viral or bacterial exacerbation of an existing asthma and other non-allergically induced asthmatic diseases; chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round) vasomotor rhinitis and diseases caused by dust in the lungs such as aluminosis, anthracosis, asbestosis, chalicosis, siderosis, silicosis, tabacosis and byssinosis, exogenous allergic alveolitis, pulmonary fibrosis, bronchiectasis, pulmonary diseases in alpha1-antitrypsin deficiency and cough;

(12) inflammatory diseases of the gastrointestinal tract including Crohn's disease and ulcerative colitis, irritable bowel syndrome, pancreatitis;

(13) inflammation associated diseases of ear, nose, mouth and throat like influenza and viral/bacterial infections such as the common cold, allergic rhinitis (seasonal and perennial), pharyngitis, tonsillitis, gingivitis, laryngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;

(14) diabetes mellitus and its effects (such as e.g. diabetic vasculopathy, diabetic neuropathy, diabetic retinopathy, diabetic nephropathy) and diabetic symptoms in insulitis (for example hyperglycaemia, diuresis, proteinuria and increased renal excretion of nitrite and kallikrein); Doan syndrome and orthostatic hypotension;

(15) sepsis and septic shock after bacterial infections or after trauma;

(16) inflammatory diseases of the joints and connective tissue such as vascular diseases of the connective tissue, sprains and fractures, and musculoskeletal diseases with inflammatory symptoms such as acute rheumatic fever, polymyalgia rheumatica, reactive arthritis, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren syndrome, Still's disease or Felty syndrome; as well as vascular diseases such as panarteriitis nodosa, polyarthritis nodosa, periarteriitis nodosa, arteriitis temporalis, Wegner's granulomatosis, giant cell arteriitis, arteriosclerosis and erythema nodosum;

(17) diseases of and damage to the central nervous system such as for example cerebral oedema and the treatment and prevention of psychiatric diseases such as depression, for example, and for the treatment and prevention of epilepsy;

(18) disorders of the motility or spasms of respiratory, genito-urinary, gastro-intestinal including biliary or vascular structures and organs;

(19) post-operative fever;

(20) for the treatment and prevention of arteriosclerosis and related complaints;

(21) for the treatment and prevention of diseases of the genito-urinary tract such as for example urinary incontinence and related complaints, benign prostatic hyperplasia and hyperactive bladder, nephritis, cystitis (interstitial cystitis);

(22) for the treatment and prevention of morbid obesity and related complaints;

(23) neurological diseases such as cerebral oedema and angioedema, cerebral dementia like e.g. Parkinson's and Alzheimers disease, senile dementia; multiple sclerosis, epilepsy, temporal lobe epilepsy, drug resistant epilepsy, stroke, myasthenia gravis, brain and meningeal infections like encephalomyelitis, meningitis, HIV as well as schizophrenia, delusional disorders, autism, affective disorders and tic disorders;

(24) cognitive impairments associated with schizophrenia, Alzheimer's Disease and other neurological and psychiatric disorders. With respect to Alzheimer's disease, the compounds of general formula (I) may also be useful as disease modifying agent;

(25) work-related diseases like pneumoconiosis, including aluminosis, anthracosis, asbestosis, chalicosis, ptilosis, siderosis, silicosis, tabacosis and byssinosis;

(26) benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, large bowel cancer, small bowel cancer, stomach cancer, colon cancer, gastroenteropancreatic tumours, gastric carcinomas, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; the proliferation of adenoma cells, thyroid cancer, GI tumours, cholan-giocarcinoma, hepatic cancer, vesical cancer, chondrosarcoma, malignant pheochromocytoma, neuroblastoma, thymoma, paragangliomas, phaeochromocytomas, ependymomas, leukemia e.g., leukemia of basophilic leukemia, chronic lymphocytic leukemia, chronic myeloid leukemia, Hodgkin disease and non-Hodgkin lymphoma; adenomatous polyps, including familial adenomatous polyposis (FAP) as well preventing polyps from forming in patients at risk of FAP. Suitable uses may include use in the treatment of acromegaly, cancer, arthritis, carcinoid tumours, and vasoactive intestinal peptide tumours;

(27) various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching;

(28) anxiety, depression, schizophrenia, epilepsy, attention deficit and hyperactive disorders and neurodegenerative diseases such as dementia, Alzheimer's disease and Parkinson's disease. The treatment of affective disorders includes bipolar disorders, e.g. manic-depressive psychoses, extreme psychotic states, e.g. mania and excessive mood swings for which a behavioural stabilization is being sought. The treatment of anxiety states includes generalized anxiety as well as social anxiety, agoraphobia and those behavioural states characterized by social withdrawal, e.g. negative symptoms;

(29) diseases involving pathological vascular proliferation, e.g. angiogenesis, restenosis, smooth muscle proliferation, endothelial cell proliferation and new blood vessel sprouting or conditions requiring the activation of neovascularization. The angiogenic disease may for example be age-related macular degeneration or vascular proliferation associated with surgical procedures, e.g. angioplasty and AV shunts. Other possible uses are the treatments of arteriosclerosis, plaque neovascularization, hypertrophic cardiomyopathy, myocardial angiogenesis, valvular disease, myo-cardiac infarction, coronary collaterals, cerebral collaterals and ischemic limb angiogenesis;

(30) pathological condition in the retina and/or iris-ciliary body of mammals. Such conditions may be high intraocular pressure (IOP) and/or deep ocular infections. Treatable diseases may e.g. be glaucoma, stromal keratitis, iritis, retinitis, cataract and conjunctivitis. Other diseases connected to the eye may be ocular and corneal angiogenic conditions, for example, corneal graft rejection, retrolental fibroplasia, Osier-Webber Syndrome or rubeosis.

(31) compounds of the invention, after incorporation of a label (e.g. 35-S, 123-I, 125-I, 111-In, 11-C, etc.) either directly in the compound or via a suitable spacer, can also be used for the imaging of healthy or diseased tissues and/or organs, such as prostate, lung, brain, blood vessels or tumours possessing ssti and/or SSTR4 receptors.

Preferred according to the present invention is the use of a compound of formula (I) for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula (I) to a human being.

Dosage:

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions:

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

A further aspect of the invention is a pharmaceutical formulation including a compound of formula (I) in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

non-steroidal antiinflammatory drugs (NSAIDs) including COX-2 inhibitors;
opiate receptor agonists;
Cannabionoid agonists or inhibitors of the endocannabinoid pathway
Sodium channel blockers;
N-type calcium channel blockers;
serotonergic and noradrenergic modulators;
corticosteroids;
histamine H1, H2, H3 and H4 receptor antagonists;
proton pump inhibitors;
leukotriene antagonists and 5-lipoxygenase inhibitors;
local anesthetics;
VR1 agonists and antagonists;
Nicotinic acetylcholine receptor agonists;
P2X3 receptor antagonists;
NGF agonists and antagonists or anti-NGF antibodies;
NK1 and NK2 antagonists;
Bradykinin B1 antagonists
CCR2 antagonists
iNOS or nNOS or eNOS inhibitors
NMDA antagonist;
potassium channel modulators;
GABA modulators;
serotonergic and noradrenergic modulators;
anti-migraine drugs;
neuropathic pain drugs such as pregabaline or duloxetine.

Said list is not considered to have a limiting character.

In the following representative examples of such treatment options shall be given:

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like;

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs including but not limited to hydroxychloroquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like;

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Histamine H3 receptor antagonists: ciproxifan and the like

Histamine H4 receptor antagonists: thioperamide and the like

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators, like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

Chemical Manufacture

Abbreviations:

Ac Acetyl
ACN acetonitrile
APCI Atmospheric pressure chemical ionization
Boc tert-butyloxycarbony
Burgess reagent: methoxycarbonylsulfamoyl-triethyl ammonium hydroxide inner salt
CDI 1,1'-carbonyldiimidazole
d day
dba dibenzylideneacetone
DCM dichloromethane
DIPEA diisopropylethylamine
DME 1,2-dimethoxyethane
DMF dimethylformamide
DMSO dimethyl sulfoxide
ESI electrospray ionization (in MS)
EtOAc ethylacetate
EtOH ethanol
Exp. example
h hour(s)
HATU O-(7-azabenzotriazol-1-yl)-N,N,N',N'-tetramethyl-uronium-hexafluorophosphate
HPLC high performance liquid chromatography
HPLC-MS coupled high performance liquid chromatography-mass spectrometry
LC liquid chromatography
LC-MS coupled liquid chromatography-mass spectrometry
M molar (mol/L)
MeOH methanol
min minute(s)
MS mass spectrometry
NMP 1-methyl-2-pyrrolidinone
RP reverse phase
rt room temperature
$R_t$ retention time (in HPLC/LC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography-mass spectrometry Methods:

UPLC-MS and HPLC-MS Methods:

Method 1

Instrument: LC/MS Waters Acquity UPLC System DAD, SQD single quadrupole; column: HSS C18 1.8 μm 2.1×50 mm, Temp 35° C.; mobile phase: A=H$_2$O 90%+10% CH$_3$CN+CF$_3$COOH 0.1%, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ES+/ES−; scan range: 90-900 amu Method 2

Instrument: LC/MS Waters Acquity UPLC System DAD, SQD single quadrupole; column: BEH C18 1.7 μm 2.1×50 mm, Temp 35° C.; mobile phase: A=H$_2$O 90%+10% CH$_3$CN+NH$_4$COOH 5 mmol, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 ml/min; detection: UV 254 nm; detection: SQD, single quadrupole; ion source: ES+/ES−; scan range: 90-900 amu Method 3

Instrument: LC/MS Waters Acquity UPLC System DAD, ELSD detector, SQD single quadrupole; column: HSS C18 1.8 μm 2.1×50 mm, Temp 35° C.; mobile phase: A=H$_2$O 90%+10% CH$_3$CN+CF$_3$COOH 0.1%, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 ml/min; detection: UV 254 nm; detection: ELSD detector; detection: SQD, single quadrupole; ion source: ES+/ES−; scan range: 90-900 amu Method 4

Instrument: LC/MS Waters Acquity UPLC System DAD, ELSD detector, SQD single quadrupole; column: BEH C18 1.7 μm 2.1×50 mm; mobile phase: A=H$_2$O 90%+CH$_3$CN 10%+NH$_4$COOH 5 mM, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu Method 5

Instrument: LC/MS Waters Acquity UPLC System DAD, ELSD detector, SQD single quadrupole; column: HSS C18 1.8 μm 2.1×50 mm, Temp 35° C.; mobile phase: A=H$_2$O 90%+CH$_3$CN 10%+CF$_3$COOH 0.1%, B=CH$_3$CN 90%+ H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu Method 6

Instrument: LC/MS ThermoFinnigan HPLC Surveyor DAD, LCQ Fleet Ion Trap; column: Simmetry Shield RP8, 5 μm, 4.6×150 mm; eluent A: 90% water+10% ACN+ HCOOH 0.1%; eluent B=ACN 90%+10% H$_2$O+HCOOH 0.1%; gradient: 0.0 min 5% B→1.5 min 5% B→11.5 min 95% B→13.0 min 95% B→13.3 min 5% B→15.0 min 5% B; flow rate: 1.0 mL/min; UV Detection: 254 nm; Detection: Finnigan Fleet, Ion Trap; ion source: ES+; scan range: 100-900 amu Method 7

Instrument: LC/MS ThermoFinnigan. Hplc Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% H$_2$O+ NH$_4$COOH 10 mM; gradient: 0.0 min 0% B→1.50 min 0% B→8.00 min 100% B→10.00 min 100% B→11.00 min 0% B→12.00 min 0% B; flow rate: 0.7 mL/min; UV Detection: 254 nm; Ion source: APCI+/APCI−.

Method 7a

Instrument: LC/MS ThermoFinnigan. Hplc Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% H$_2$O+ NH$_4$COOH 10 mM; gradient: 0.0 min 0% B→0.50 min 0% B→6.50 min 100% B→7.50 min 100% B→8.00 min 0% B→9.00 min 0% B; flow rate: 1.2 mL/min; UV Detection: 254 nm; Ion source: APCI+/APCI−.

Method 7b

Instrument: LC/MS ThermoFinnigan. Hplc Surveyor DAD, MSQ Quadrupole; column: Synergi Hydro RP100A, 2.5 um, 3×50 mm; eluent A: 90% water+10% ACN+ammonium formate 5 mM; eluent B=ACN 90%+10% H$_2$O; gradient: 0.0 min 0% B→4.00 min 100% B→5.30 min 100% B→5.50 min 0% B→6.00 min 0% B; flow rate: 1.2 mL/min; UV Detection: 254 nm; Ion source: APCI+/APCI−.

Method 8

Instrument: LC/MS ThermoFinnigan. Hplc Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% H$_2$O+ NH$_4$COOH 10 mM; gradient: 0.0 min 0% B→4.00 min 100% B→5.30 min 100% B→5.50 min 0% B→6.00 min 0% B; flow rate: 1.2 mL/min; UV Detection: 254 nm; Ion source: APCI+/APCI−.

Method 9

Instrument: LC/MS Waters Alliance 2695 HPLC System DAD, Quattro Micro Triple quadrupole; column: SunFire C18 3.5 μm 4.6×50 mm; eluent A: H$_2$O 90%+10% CH$_3$CN+ CF$_3$COOH 0.05%; eluent B=CH$_3$CN 90%+10% H$_2$O; gradient: 0.0 min 0% B→4.50 min 100% B→5.80 min 100% B→6.00 min 0% B; flow rate: 1.3 mL/min; UV Detection: 254 nm; Ion source: ES+.

Method 10

Instrument: LC/MS Waters Alliance 2695 HPLC System DAD, Quattro Micro Triple quadrupole; column: Atlantis dC18 5 μm 4.6×50 mm; eluent A: H$_2$O 90%+10% CH$_3$CN+ CF$_3$COOH 0.05%; eluent B=CH$_3$CN 90%+10% H$_2$O; gradient: 0.0 min 0% B→0.70 min 0% B→4.50 min 100% B→5.80 min 100% B→6.00 min 0% B; flow rate: 1.3 mL/min; UV Detection: 254 nm; Ion source: ES+.

Method 11

Instrument: LC/MS Waters Alliance 2695 HPLC System DAD, Quattro Micro Triple quadrupole; column: Xbridge Phenyl 3.5 μm 3×30 mm; eluent A: H$_2$O 90%+10% CH$_3$CN+NH$_4$HCO$_3$ 5 mM; eluent B=CH$_3$CN 90%+10% H$_2$O; gradient: 0.0 min 0% B→4.50 min 100% B→5.80 min 100% B→6.00 min 0% B; flow rate: 1.3 mL/min; UV Detection: 254 nm; Ion source: ES+/−

Method 12

Instrument: LC/MS ThermoFinnigan HPLC Surveyor DAD, LCQFleet Ion Trap; column: Xselect CSH, 2.5 μm, 4.6×50 mm; eluent A: H$_2$O 90%+10% CH$_3$CN+HCOOH 0.1%; eluent B=CH$_3$CN 90%+H$_2$O 10%+HCOOH 0.1%; gradient: 0.0 min 0% B→4.00 min 100% B→5.30 min 100% B→5.50 min 0% B→6.00 min 0% B; flow rate: 1.4 mL/min; UV Detection: 254 nm; Ion source: ES+/−

Method 12a

Instrument: LC/MS Waters Alliance 2695 HPLC System DAD, Quattro Micro Triple quadrupole; column: Zorbax Eclipse XDB-C18 3.5 μm 4.6×50 mm, Temp 35° C.; eluent A: H$_2$O 90%+10% CH$_3$CN+NH$_4$COOH 5 mM; eluent B=CH$_3$CN 90%+10% H$_2$O; gradient: 0.0 min 0% B→4.50 min 100% B→5.80 min 100% B→6.00 min 0% B; flow rate: 1.3 mL/min; UV Detection: 254 nm; Ion source: ES+/−

GC-MS Methods:

Method 13

Instrument: GC/MS Thermo Scientific TRACE GC ULTRA, DSQ II MS single quadrupole; column: Agilent DB-5MS, 25 m×0.2 5 mmol×0.25 μm; carrier gas: Helium, 1 mL/min constant flow; oven program: 50° C., to 100° C. in 10° C./min, to 200° C. in 20° C./min, to 320° C. in 30° C./min (hold 10 min); detection: DSQ II MS single quadrupole; ion source: EI; scan range: 50-450 amu Chiral HPLC Methods:

Method 14

HPLC apparatus type: Agilent 1100; column: Daicel chiralpack AD-H, 5.0 μm, 250 mm×4.6 mm; method: eluent hexane/IPA 70:30; flow rate: 1 mL/min, Temperature: 25° C.; UV Detection: 230 nm Method 15

HPLC apparatus type: Agilent 1100; column: Daicel chiralpack AD-H, 5.0 μm, 250 mm×4.6 mm; method: eluent hexane/IPA 85:15; flow rate: 1 mL/min, Temperature: 25° C.; UV Detection: 230 nm Method 16

HPLC apparatus type: Agilent 1100; column: Daicel chiralpack AD-H, 5.0 μm, 250 mm×4.6 mm; method: eluent hexane/IPA 75:25; flow rate: 1 mL/min, Temperature: 25° C.; UV Detection: 230 nm Method 17

HPLC apparatus type: Agilent 1100; column: Daicel chiralpack OJ-H, 5.0 μm, 250 mm×4.6 mm; method: eluent hexane/ethanol 93:7; flow rate: 1 mL/min, Temperature: 25° C.; UV Detection: 230 nm Method 18
HPLC apparatus type: Agilent 1100; column: Daicel chiralpack AS-H, 5.0 μm, 250 mm×4.6 mm; method: eluent hexane/ethanol 95:5; flow rate: 1 mL/min, Temperature: 25° C.; UV Detection: 230 nm Microwave Heating:
Discover® CEM instruments, equipped with 10 and 35 mL vessels NMR Equipment:
The $^1$H NMR spectra were recorded on a Bruker Avance III (500 MHz) or a Varian 400 (400 MHz) instrument using deuterated dimethylsulfoxide (DMSO-d6) as the solvent with tetramethylsilane (TMS) as an internal standard. Chemical shifts are reported in δ values (ppm) relative to TMS.

EXPERIMENTAL

Example 1a

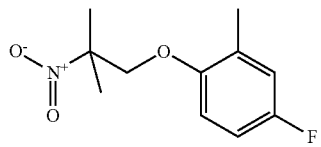 [SMILES: Cc1cc(F)ccc1OCC(C)(C)[N+](=O)[O-]]

2-Methyl-2-nitropropyl-p-toluenesulfonate (250 mg, 0.915 mmol), 4-fluoro-2-methylphenol (115 mg, 0.915 mmol) and cesium carbonate (358 mg, 1.098 mmol) are heated in dry N,N-dimethylacetamide (5 mL) at 80° C. overnight. Cesium carbonate (596 mg, 1.830 mmol) is added and the reaction mixture heated at 150° C. for 2 h. The reaction mixture is treated with water (5 mL) and 4M HCl (5 mL) and extracted with ethyl acetate. The organic layer is washed with brine, dried over $Na_2SO_4$ and evaporated under reduced pressure to furnish a residue that is purified by flash chromatography (eluent 0-30% EtOAc/cyclohexane) to furnish the title compound (155 mg, 75%).

$^1$H NMR (300 MHz, DMSO-$d_6$): δ 1.66 (s, 6H), 2.07 (s, 3H), 4.31 (s, 2H), 6.94-7.03 (m, 3H)

UPLC-MS (Method 2): $R_t$=1.31 min

MS (ESI pos): m/z=228 (M+H)$^+$

The following examples are synthesized in analogy to the preparation of example 1a:

| Example | Structure | Reactant(s) | HPLC-MS or UPLC-MS or GC-MS or $^1$H-NMR |
|---|---|---|---|
| 1b | 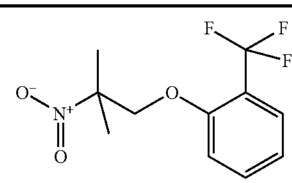 | 2-hydroxy-benzo-trifluoride (148 mg, 0.915 mmol) | $^1$H NMR (300 MHz, DMSO-$d_6$),: δ 1.66 (s, 6H); 4.5 (s, 2H), 7.14 (dd, J = 7.0, 7.6 Hz, 1H), 7.29 (d, J = 8.2 Hz, 1H), 7.60-7.65 (m, 2H) |
| 1c | 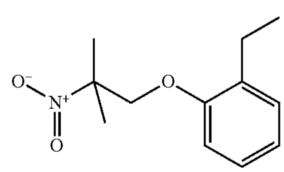 [SMILES: CCc1ccccc1OCC(C)(C)[N+](=O)[O-]] | 2-ethyl-phenol (78 μL. 0.659 mmol) | method: 1<br>R$_t$ [min]: 1.40<br>MS (ESI pos or APCI, m/z)<br>(M + H)$^+$: 224 |
| 1d | 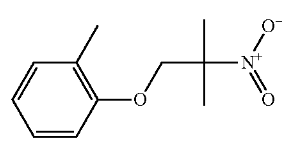 | 2-methyl-phenol (1,3 g, 12.07 mmol) | method: 2<br>R$_t$ [min]: 1.31<br>MS (ESI pos or APCI, m/z)<br>(M + H)$^+$: 210 |
| 1e | 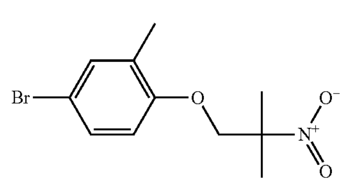 [SMILES: Cc1cc(Br)ccc1OCC(C)(C)[N+](=O)[O-]] | 4-bromo-2-methylphenol (1.3 g, 7.32 mmol) | $^1$H NMR (500 MHz, DMSO-$d_6$),: δ 1.66 (s, 6H), 2.06 (s, 3H), 4.33 (s, 2H), 6.93 (d. J = 8.5 Hz, 1H), 7.31-7.33 (m, 2H) |
| 1f | 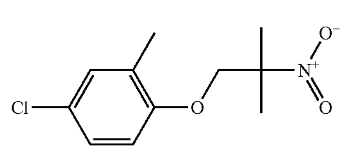 [SMILES: Cc1cc(Cl)ccc1OCC(C)(C)[N+](=O)[O-]] | 4-chloro-2-methylphenol (574 mg, 4.02 mmol) | $^1$H NMR (400 MHz, DMSO-$d_6$): δ 1.66 (s, 6H), 2.06 (s, 3H), 4.33 (s, 2H), 6.97 (d, J = 8.4 Hz 1H), 7.18-7.22 (m, 2H) |

| Example | Structure | Reactant(s) | HPLC-MS or UPLC-MS or GC-MS or ¹H-NMR |
|---------|-----------|-------------|----------------------------------------|
| 1g | 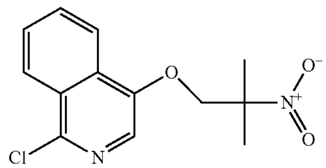 [SMILES: CC(C)(COc1cnc(Cl)c2ccccc12)[N+](=O)[O-]] | 1-chloro-4-hydroxy-isoquinoline (394 mg, 2.19 mmol) | method: 8<br>R$_t$ [min]: 3.50<br>MS (ESI pos or APCI, m/z)<br>(M + H)$^+$: 281 |
| 1h | 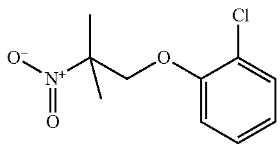 | 2-chlorophenol (0.13 ml, 1.207 mmol) | method: 1<br>R$_t$ [min]: 1.29<br>MS (ESI pos or APCI, m/z)<br>(M + H)$^+$: 230 |
| 1i | 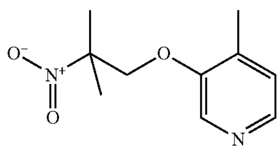 | 4-methyl-pyridin-3-ol (100 mg, 0.915 mmol) | method: 7<br>R$_t$ [min]: 5.73<br>MS (ESI pos or APCI, m/z)<br>(M + H)$^+$: 211 |
| 1j | 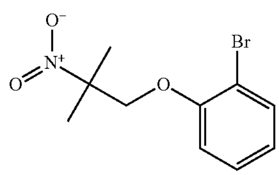 | 2-bromophenol (2 ml, 18.29 mmol) | method: 1<br>R$_t$ [min]: 1.34<br>MS (ESI pos or APCI, m/z)<br>(M + H)$^+$: 275 |
| 1k | 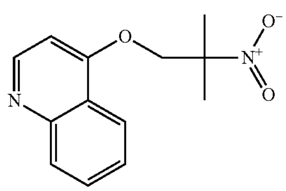 [SMILES: CC(C)(COc1ccnc2ccccc12)[N+](=O)[O-]] | 4-hydroxy-quinoline (223 mg, 1.537 mmol) | method: 13<br>R$_t$ [min]: 12.33<br>MS (EI pos, m/z)<br>[M]$^+$: 246 |
| 1l | 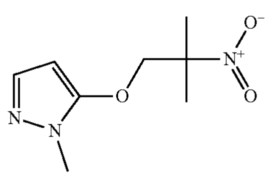 | 5-hydroxy-1-methyl-1H-pyrazole (718 mg, 7.31 mmol) | method: 2<br>R$_t$ [min]: 0.90<br>MS (ESI pos or APCI, m/z)<br>(M + H)$^+$: 200 |
| 1m | 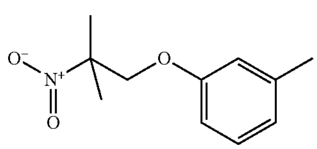 | 3-methylphenol (71 mg, 0.659 mmol) | method: 1<br>R$_t$ [min]: 1.33<br>MS (ESI pos or APCI, m/z)<br>(M + H)$^+$: 210 |
| 1n | 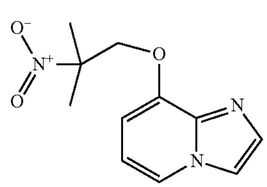 [SMILES: CC(C)(COc1cccn2ccnc12)[N+](=O)[O-]] | Imidazo[1,2-a]pyridin-8-ol (491 mg, 3.66 mmol) | ¹H NMR (500 MHz, DMSO-d$_6$): δ 1.70 (s, 6H), 4.59 (s, 2H), 6.71 (dd, J = 1.1, 7.7 Hz, 1H), 6.80 (dd, J = 6.6, 7.4 Hz, 1H), 7.47 (d, J = 1.2 Hz, 1H), 7.92 (d, J = 1.2 Hz, 1H), 8.19 (dd, J = 1.0, 6.7 Hz, 1H) |
| 1o | 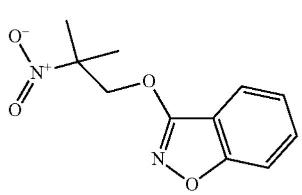 [SMILES: CC(C)(COc1noc2ccccc12)[N+](=O)[O-]] | Benzo[d]-isoxazol-3-ol (494 mg, 3.66 mmol) | ¹H NMR (500 MHz, DMSO-d$_6$): δ 1.72 (s, 6H), 4.82 (s, 2H), 7.38 (ddd, J = 1.4, 6.5, 8.0 Hz, 1H), 7.64-7.78 (m, 2H), 7.72 (ddd, J = 1.2, 2.0, 8.0 Hz, 1H) |

| Example | Structure | Reactant(s) | HPLC-MS or UPLC-MS or GC-MS or $^1$H-NMR |
|---|---|---|---|
| 1p | 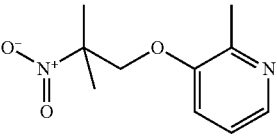 | 3-hydroxy-2-methylpyridine (72 mg, 0.659 mmol) | method: 1<br>$R_t$ [min]: 0.64<br>MS (ESI pos or APCI, m/z)<br>$(M + H)^+$: 211 |

Example 1q

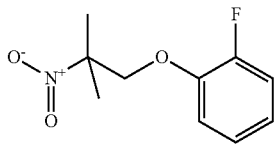

Example 1q is prepared as described for example 1a using 2-fluorophenol (148 mg, 1.317 mmol) as starting material and the reaction is heated for 90 minutes at 130° C. The reaction mixture is treated with water and extracted with ethyl ether. The organic layer is washed with brine and 5% K$_2$CO$_3$, dried and evaporated under reduced pressure to furnish the title compound (170 mg, 62%).

UPLC-MS (Method 2): $R_t$=1.24 min
MS (ESI pos): m/z=214 (M+H)$^+$

Example 1r

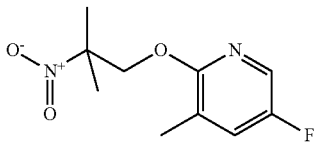 [SMILES: Cc1cc(F)cnc1OCC(C)(C)[N+](=O)[O-]]

2-chloro-5-fluoro-3-methylpyridine (1 g, 6.870 mmol) is dissolved in hydrochloric acid (37%, 20 mL) and the reaction is heated under microwave irradiation at 150° C. for 15 h. The mixture is diluted with water and washed with DCM. The aqueous layer is basified with NaOH and re-extracted with DCM several times. The organic layer is separated, dried and evaporated to furnish 5-fluoro-3-methyl-pyridin-2-ol (140 mg, content 74%, 12%).

UPLC-MS (Method 2): $R_t$=0.50 min
MS (ESI pos): m/z=128 (M+H)$^+$

5-Fluoro-3-methyl-pyridin-2-ol (139 mg, 1.098 mmol), 2-methyl-2-nitropropyl-p-toluenesulfonate (300 mg, 1.098 mmol and cesium carbonate (429 mg, 1.317 mmol) are heated in dry N,N-dimethylacetamide (5 mL) at 150° C. for 7 h. The reaction mixture is treated with water (10 mL) and extracted with ethyl acetate (20 mL). The organic layer is dried and evaporated under reduced pressure to furnish a residue that is purified by flash chromatography (eluent 0-25% EtOAc/cyclohexane) to furnish the title compound (70 mg, 25%).

UPLC-MS (Method 2): $R_t$=1.20 min
MS (ESI pos): m/z=229 (M+H)$^+$

Example 2a

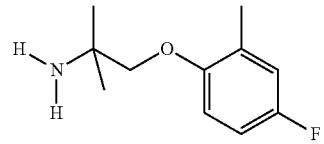

Raney Nickel (28 mg, 0.330 mmol) is added to example 1a (150 mg, 0.660 mmol) dissolved in MeOH (10 mL) and the mixture is hydrogenated at 3 bar overnight. The catalyst is removed by filtration and the reaction evaporated under reduced pressure to furnish the title compound (96 mg, 74%) that is used as such.

HPLC-MS (Method 7): $R_t$=4.82 min
MS (APCI): m/z=198 (M+H)$^+$

The following examples are synthesized in analogy to the preparation of example 2a:

| Example | Structure | Reactant(s) | HPLC-MS or UPLC-MS or $^1$H-NMR |
|---|---|---|---|
| 2b | 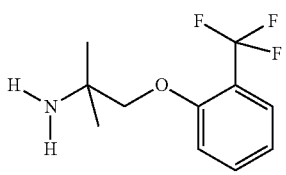 [SMILES: CC(C)(N)COc1ccccc1C(F)(F)F] | Example 1b (200 mg, 0.760 mmol) | $^1$H NMR (300 MHz, DMSO-d$_6$),: δ 1.11 (s, 6H), 1.51 (s, br, 2H), 3.76 (s, 2H), 7.07 (dd, J = 7.7, 8.4 Hz, 1H). 7.19 (d, J = 8.8 Hz, 1H), 7.58-7.64 (m. 2H) |

-continued

| Example | Structure | Reactant(s) | HPLC-MS or UPLC-MS or $^1$H-NMR |
|---|---|---|---|
| 2c | 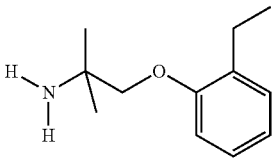 | Example 1c (65 mg, 90% content, 0.262 mmol) | method: 1 R$_t$ [min]: 0.76 MS (ESI pos or APCI, m/z) (M + H)$^+$: 194 |
| 2d | 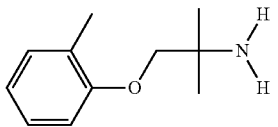 | Example 1d (2.1 g, 96% content, 9.63 mmol) | method: 2 R$_t$ [min]: 0.73 MS (ESI pos or APCI, m/z) (M + H)$^+$: 180 |
| 2e | 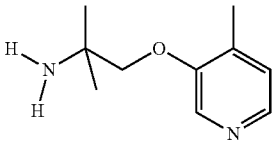 | Example 1i (150 mg, 0.714 mmol) | method: 7 R$_t$ [min]: 4.37 MS (ESI pos or APCI, m/z) (M + H)$^+$: 181 |
| 2f | 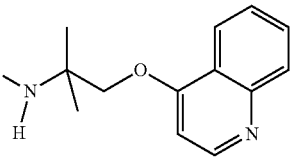 | Example 1k (173 mg, 0.703 mmol) | method: 8 R$_t$ [min]: 1.82 MS (ESI pos or APCI, m/z) (M + H)$^+$: 217 |
| 2g | 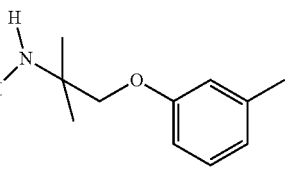 | Example 1m (62 mg, 93% content, 0.276 mmol) | method: 1 R$_t$ [min]: 0.74 MS (ESI pos or APCI, m/z) (M + H)$^+$: 180 |
| 2h | 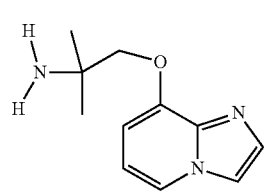 | Example 1n (230 mg, 0.978 mmol) | method: 2 R$_t$ [min]: 0.53 MS (ESI pos or APCI, m/z) (M + H)$^+$: 206 |
| 2i | 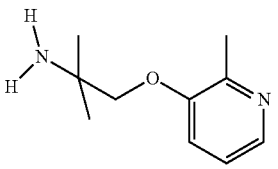 | Example 1p (128 mg 0.572 mmol) | method: 1 R$_t$ [min]: 0.27 MS (ESI pos or APCI, m/z) (M + H)$^+$: 181 |
| 2j | 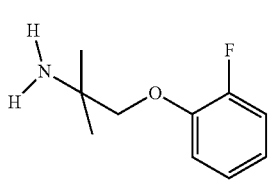 | Example 1q (170 mg, 0.678 mmol) | method: 1 R$_t$ [min]: 0.66 MS (ESI pos or APCI, m/z) (M + H)$^+$: 184 |

Example 2k

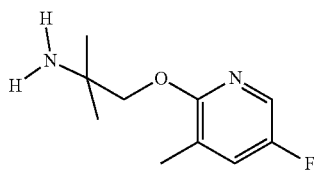

Example 2k is prepared from example 1 r (70 mg, 0.273 mmol) in analogy to the example 2a. The work-up residue is purified over SCX cartridge, washed with MeOH and eluted with methanolic ammonia. Volatiles are removed under reduced pressure to furnish the title compound (17 mg, 28%)

UPLC-MS (Method 2): $R_t$=0.66 min
MS (ESI pos): m/z=199 (M+H)$^+$

Example 2l and Example 2m

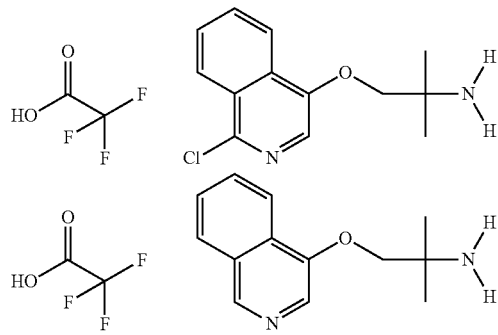

Raney Nickel (50 mg, 0.584 mmol) is added to example 1g (200 mg, 0.712 mmol) dissolved in MeOH (10 mL) and the mixture is hydrogenated at 3 bar for 2 h. The catalyst is removed by filtration and the reaction evaporated to furnish a residue purified by preparative HPLC (stationary phase: Sunfire C18 ODB 5 µm 19×100 mm. Mobile phase: ACN/H$_2$O+CF$_3$COOH 0.05%). Fractions containing the title compound are combined and evaporated to furnish example 2l (90 mg, 35%) and example 2m (152 mg, 65%).

Example 2l: HPLC-MS (Method 10): $R_t$=3.22 min
MS (ESI pos): m/z=234 (M+H)$^+$
Example 2m: HPLC-MS (Method 10): $R_t$=1.07 min
MS (ESI pos): m/z=200 (M+H)$^+$

Example 2n

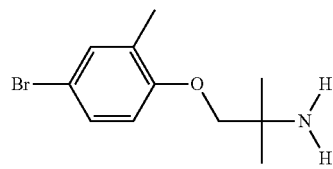

The example 1e (1.4 g, 4.86 mmol) is dissolved in dry MeOH (30 mL), then HCl 4M in dioxane (18 mL, 73 mmol) is added and the mixture is cooled at 0° C. Zinc (1.9 g, 29.15 mmol) is added portionwise and the reaction is allowed to reach RT and stirred overnight.

The mixture is filtered over a celite pad, then the solution is basified with NaOH 1N and The solids are removed by filtration. DCM is added and the reaction is washed with water. The organic layer is separated, dried and evaporated under reduced pressure to give the title compound (380 mg, 30%).

UPLC-MS (Method 2): $R_t$=1.00 min
MS (ESI pos): m/z=259 (M+H)$^+$

The following examples are synthesized in analogy to the preparation of example 2n:

| Example | Structure | Reactant(s) | UPLC-MS $R_t$ [min], method | MS (ESI pos, m/z) (M + H)$^+$ |
|---|---|---|---|---|
| 2o | ![structure] | Example 1f (800 mg, 3.28 mmol) | 0.98, 2 | 214 |
| 2p | ![structure] | Example 1h (260 mg, 90% content, 1.019 mmol) | 0.72, 1 | 200 |
| 2q | ![structure] | Example 1j (5 g, 18.24 mmol) | 0.76, 1 | 245 |

-continued

| Example | Structure | Reactant(s) | UPLC-MS $R_t$ [min], method | MS (ESI pos, m/z) $(M + H)^+$ |
|---|---|---|---|---|
| 2r | 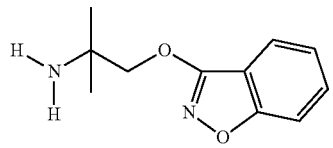 | Example 1l (580 mg, 2.91 mmol) | 0.45 1 | 170 |

Example 2s

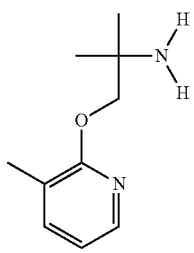

Example 1o (110 mg, 0.466 mmol) and tin (II) chloride dihydrate (420 mg, 1.86 mmol are dissolved in dry absolute ethanol (20 mL) and heated to reflux for 8 h.

The reaction mixture is cooled and saturated $Na_2CO_3$ solution is added. The solids are removed by filtration through a celite pad and EtOAc added to the resulting mixture.

The organic layer is washed with water, then with brine, then is separated, dried and evaporated under reduced pressure to give the title compound (100 mg, 94%).

UPLC-MS (Method 1): $R_t$=0.68 min

MS (ESI pos): m/z=207 $(M+H)^+$

Example 2t

2-Amino-2-methyl-propan-1-ol (11 mL, 118.8 mmol) is dissolved in dioxane (20 mL) and sodium hydride (60% suspension in mineral oil, 5.0 g, 124.7 mmol) is added portionwise at 0° C. and after 15 minutes 2-fluoro-3-methyl-pyridine (3 mL, 29.7 mmol) is added. The resulting mixture is heated at 100° C. for 1 h. The reaction is diluted with DCM and washed with water. The organic layer is separated, dried and evaporated under reduced pressure to furnish the title compound (5.1 g, 95%) that is used as such.

HPLC-MS (Method 8): $R_t$=1.78 min

MS (AFCI): m/z=181 $(M+H)^+$

Example 2u

Example 2u is prepared in analogy to example 2t using 3-fluoro-4-(trifluoromethyl)-pyridine (8 g, 48.46 mmol) as starting material with the exception that the final residue is dissolved in MeOH and washed with n-heptane. Volatiles are removed under reduce pressure to give the title compound (9.5 g, 84%)

HPLC-MS (Method 11): $R_t$=1.97 min

MS (ESI pos): m/z=235 $(M+H)^+$

Example 3a

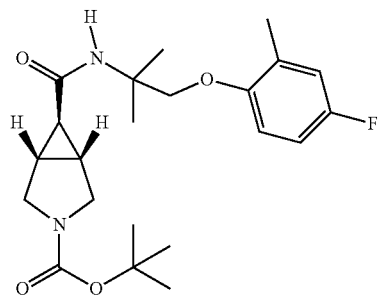 [SMILES: Cc1cc(F)ccc1OCC(C)(C)NC(=O)[C@H]1[C@@H]2CN(C(=O)OC(C)(C)C)C[C@@H]21]

HATU (95 mg, 0.251 mmol) is added to meso-(1R,5S,6r)-3-(tert-butoxycarbonyl)-3-azabicyclo[3.1.0]hexane-6-carboxylic acid (52 mg, 0.228 mmol, commercially available from ABCR or WuXi AppTec, $^1$H NMR (500 MHz, DMSO-$d_6$): δ 1.24 (t, J=3.2, 1H), 1.38 (s, 9H), 1.97 (t, J=2.5 Hz, 2H), 3.34 (d, 2H), 3.48 (d, J=11.0 Hz, 2H), 12.21 (br, 1H)), example 2a (45 mg, 0.228 mmol) and DIPEA (118 µl, 0.684 mmol) in DMF (1 mL) and stirring is continued overnight. Volatiles are evaporated under reduced pressure to afford a residue that is purified by flash chromatography (eluent 0-40% EtOAc/cyclohexane) to furnish the title compound (72 mg, 78%).

HPLC-MS (Method 7): $R_t$=7.37 min

MS (APCI): m/z=407 $(M+H)^+$

The following examples are synthesized in analogy to the preparation of example 3a:

| Example | Structure | Reactant(s) | HPLC-MS or UPLC-MS R$_t$ [min], method | MS (ESI pos or APCI, m/z) (M + H)$^+$ |
|---|---|---|---|---|
| 3b | 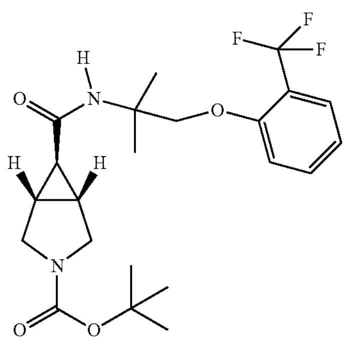 [SMILES: CC(C)(COc1ccccc1C(F)(F)F)NC(=O)[C@H]1[C@@H]2CN(C(=O)OC(C)(C)C)C[C@@H]21] | Example 2b (55 mg, 0.236 mmol) | 7.55 7 | 443 |
| 3c | 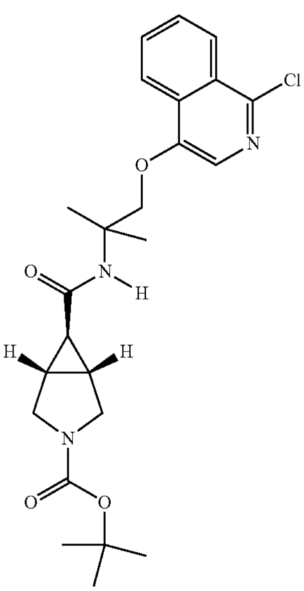 [SMILES: CC(C)(COc1cnc(Cl)c2ccccc12)NC(=O)[C@H]1[C@@H]2CN(C(=O)OC(C)(C)C)C[C@@H]21] | Example 2l (90 mg, 0.246 mmol) | 3.86 8 | 460 |
| 3d | 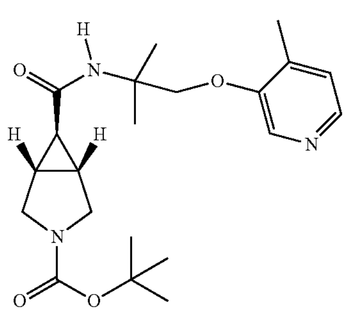 [SMILES: Cc1ccncc1OCC(C)(C)NC(=O)[C@H]1[C@@H]2CN(C(=O)OC(C)(C)C)C[C@@H]21] | Example 2e (59 mg, 88% content, 0.288 mmol) | 6.28 7 | 390 |

-continued

| Example | Structure | Reactant(s) | HPLC-MS or UPLC-MS R$_t$ [min], method | MS (ESI pos or APCI, m/z) (M + H)$^+$ |
|---------|-----------|-------------|----------------------------------------|---------------------------------------|
| 3e | 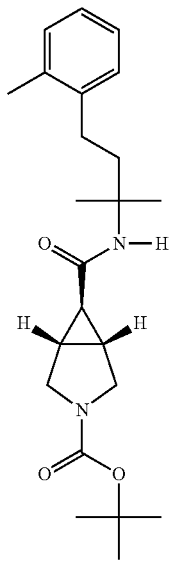 [SMILES: Cc1ccccc1CCC(C)(C)NC(=O)[C@H]1[C@@H]2CN(C(=O)OC(C)(C)C)C[C@@H]21] | Example 2q (161 mg. 0.66 mmol) | 1.37 2 | 454 |
| 3f | 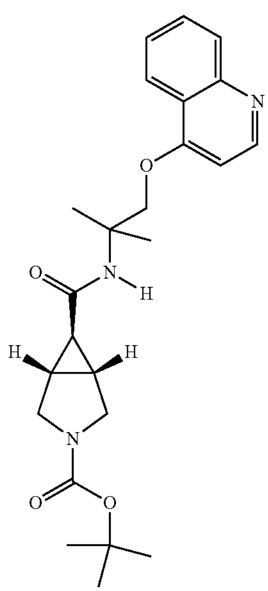 [SMILES: CC(C)(COc1ccnc2ccccc12)NC(=O)[C@H]1[C@@H]2CN(C(=O)OC(C)(C)C)C[C@@H]21] | Example 2f (147 mg, 0.682 mmol) using HPLC preparative purification after purification by flash chromatography | 3.42/4.06 8 | 426 |

-continued

| Example | Structure | Reactant(s) | HPLC-MS or UPLC-MS R$_t$ [min], method | MS (ESI pos or APCI, m/z) (M + H)$^+$ |
|---------|-----------|-------------|----------------------------------------|---------------------------------------|
| 3g | 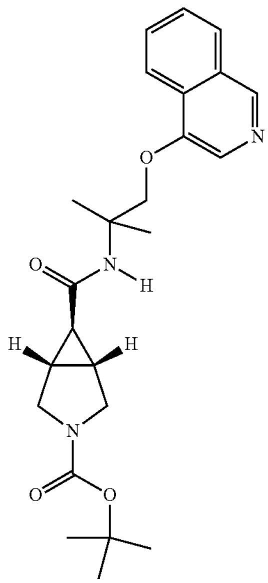 [SMILES: CC(C)(COc1cncc2ccccc12)NC(=O)[C@H]1[C@@H]2CN(C(=O)OC(C)(C)C)C[C@@H]21] | Example 2m (152 mg. 0.460 mmol) | 3.43 8 | 426 |
| 3h | 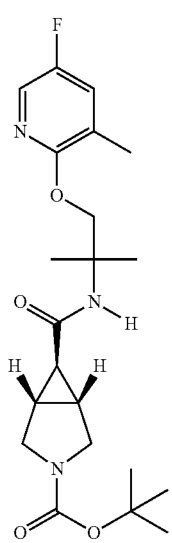 [SMILES: Cc1cc(F)cnc1OCC(C)(C)NC(=O)[C@H]1[C@@H]2CN(C(=O)OC(C)(C)C)C[C@@H]21] | Example 2k (17 mg, 89% content, 0.076 mmol) | 3.55 8 | 408 |

Example 3i

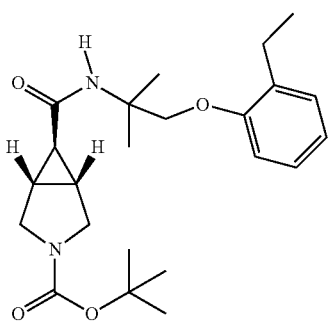 [SMILES: CCc1ccccc1OCC(C)(C)NC(=O)[C@H]1[C@@H]2CN(C(=O)OC(C)(C)C)C[C@@H]21]

TBTU (70 mg, 0.218 mmol) is added to meso-(1R,5S,6r)-3-(tert-butoxycarbonyl)-3-azabicyclo[3.1.0]hexane-6-carboxylic acid (45 mg, 0.198 mmol), example 2c (46 mg, 91% content, 0.218 mmol) and TEA (80 µl, 0.594 mmol) in dry DMF (1.5 mL) and stirring is continued for 3 h. The reaction is diluted with water and washed with ethyl ether. The organic layer is washed with $NaHCO_3$ saturated solution and water, then is separated, dried and evaporated under reduced pressure to furnish the title compound (85 mg, 86%) that is used as such.

UPLC-MS (Method 1): $R_t$=1.46 min

MS (ESI pos): m/z=403 $(M+H)^+$

The following examples are synthesized in analogy to the preparation of example 3i:

| Example | Structure | Reactant(s) | UPLC-MS $R_t$ [min], method | MS (ESI pos, m/z) $(M + H)^+$ |
|---|---|---|---|---|
| 3j | 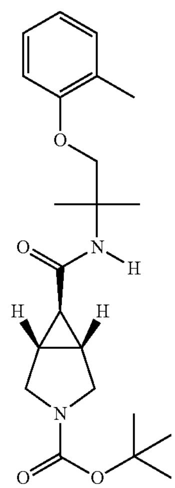 [SMILES: Cc1ccccc1OCC(C)(C)NC(=O)[C@H]1[C@@H]2CN(C(=O)OC(C)(C)C)C[C@@H]21] | Example 2d (79 mg. 0.440 mmol) | 1.34 2 | 389 |
| 3k | 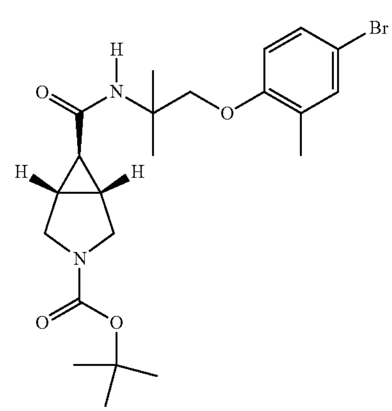 [SMILES: Cc1cc(Br)ccc1OCC(C)(C)NC(=O)[C@H]1[C@@H]2CN(C(=O)OC(C)(C)C)C[C@@H]21] | Example 2n (370 mg, 1.43 mmol) | 1.47 2 | 468 |

-continued
| Example | Structure | Reactant(s) | UPLC-MS R$_t$ [min], method | MS (ESI pos, m/z) (M + H)$^+$ |
|---|---|---|---|---|
| 3l | 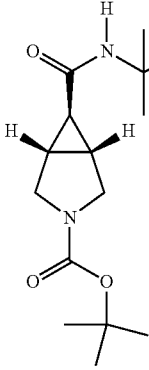 | Example 2o (580 mg, 2.71 mmol) | 1.50 2 | 423 |
| 3m | 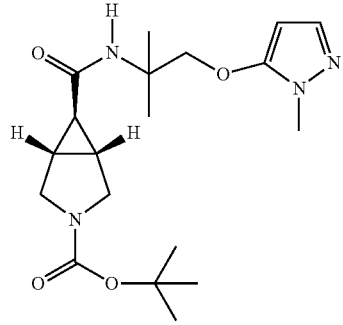 [SMILES: Cn1nccc1OCC(C)(C)NC(=O)[C@H]1[C@@H]2CN(C(=O)OC(C)(C)C)C[C@@H]21] | Example 2r (100 mg, 0.591 mmol) | 1.01 2 | 379 |
| 3n | 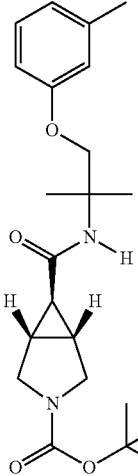 | Example 2g (43 mg, 83% content, 0.198 mmol) | 1.42 1 | 349 |
| 3o | 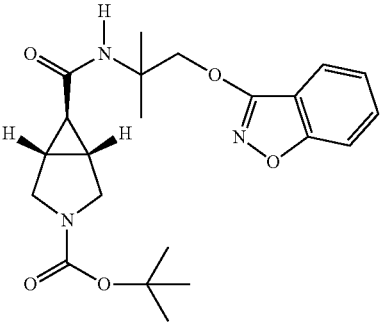 [SMILES: CC(C)(COc1noc2ccccc12)NC(=O)[C@H]1[C@@H]2CN(C(=O)OC(C)(C)C)C[C@@H]21] | Example 2s (100 mg, 90% content, 0.436 mmol) | 1.27 2 | 416 |

-continued

| Example | Structure | Reactant(s) | UPLC-MS R_t [min], method | MS (ESI pos, m/z) (M + H)+ |
|---|---|---|---|---|
| 3p | 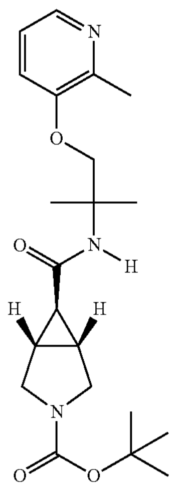 [SMILES: Cc1ncccc1OCC(C)(C)NC(=O)[C@H]1[C@@H]2CN(C(=O)OC(C)(C)C)C[C@@H]21] | Example 2i (61 mg, 0.242 mmol, 71% content) | 0.82 1 | 390 |
| 3q | 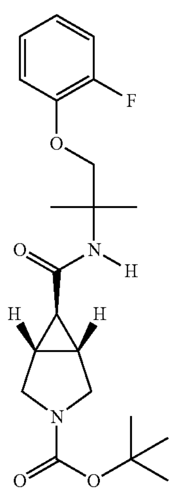 [SMILES: CC(C)(COc1ccccc1F)NC(=O)[C@H]1[C@@H]2CN(C(=O)OC(C)(C)C)C[C@@H]21] | Example 2j (40 mg, 0.218 mmol) | 1.31 1 | 393 |
| 3r | 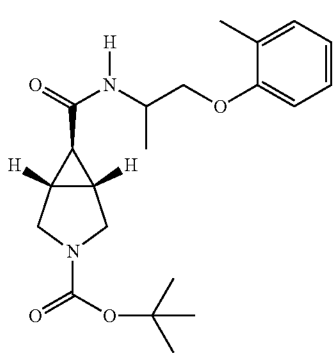 [SMILES: Cc1ccccc1OCC(C)NC(=O)[C@H]1[C@@H]2CN(C(=O)OC(C)(C)C)C[C@@H]21] | 1-Methyl-2-o-tolyloxy-ethylamine (300 mg, 50% content, 0.908 mmol) | 1.36 2 | 375 |

Example 3s

Example 3v

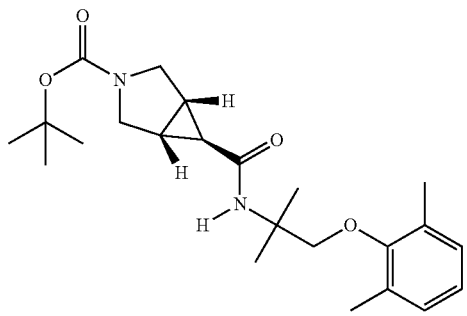 [SMILES: Cc1cccc(C)c1OCC(C)(C)NC(=O)[C@H]1[C@@H]2CN(C(=O)OC(C)(C)C)C[C@@H]21]

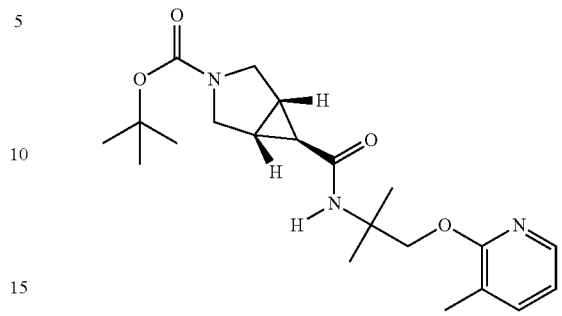

Example 3s is prepared as described for example 3i using 1-(2,6-dimethylphenoxy)-2-methyl-propan-2-amine (68 mg, 0.352 mmol) as starting material. The reaction is stirred for 2 days. After the usual work-up, the residue is purified by preparative HPLC (stationary phase: Sunfire C18 ODB 5 μm 19×100 mm. Mobile phase: ACN/H$_2$O+CF$_3$COOH 0.05%). Fractions containing the title compound are combined, and evaporated to furnish the title compound (95 mg, 62%).

UPLC-MS (Method 1): R$_t$=1.45 min
MS (ESI pos): m/z=403 (M+H)$^+$

The following examples are synthesized in analogy to the preparation of example 3s:

Example 2t (5.1 g, 28.29 mmol), HATU (10.8 g, 28.295 mmol) and DIPEA (15.5 g, 56.589 mmol) are added to meso-(1R,5S,6r)-3-(tert-butoxycarbonyl)-3-azabicyclo [3.1.0]hexane-6-carboxylic acid (6.4 g, 28.295 mmol) in DMF (10 mL) and stirring is continued for 3 h. Volatiles are evaporated under reduced pressure. EtOAc is added and the reaction mixture is washed with NaHCO$_3$ saturated solution and then with brine. The organic layer is separated by Phase separator cartridge and solvent evaporated affording a residue that is purified by flash chromatography (eluent 20-50% EtOAc/cyclohexane) to furnish the title compound (8.4 g, 76%).

| Example | Structure | Reactant(s) | UPLC-MS R$_t$ [min], method | MS (ESI pos, m/z) (M + H)$^+$ |
|---|---|---|---|---|
| 3t | 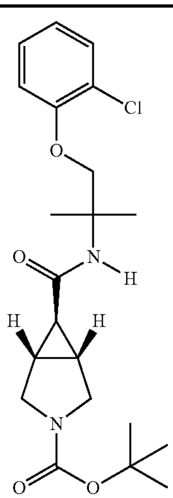 | Example 2p (47 mg, content 93%, 0.218 mmol) | 2.17 5 | 409 |
| 3u | 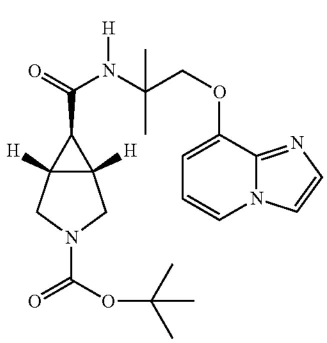 [SMILES: CC(C)(COc1cccn2ccnc12)NC(=O)[C@H]1[C@@H]2CN(C(=O)OC(C)(C)C)C[C@@H]21] | Example 2h (120 mg, 0.585 mmol) | 1.03 2 | 415 |

HPLC-MS (Method 8): $R_t$=3.30 min
MS (AFCI): m/z=390 (M+H)$^+$

Example 3w

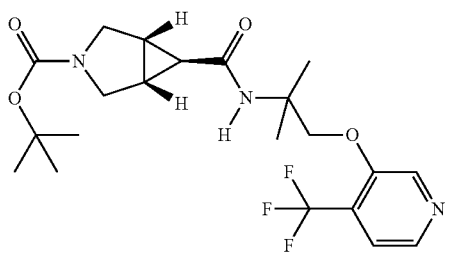 [SMILES: CC(C)(COc1cnccc1C(F)(F)F)NC(=O)[C@H]1[C@@H]2CN(C(=O)OC(C)(C)C)C[C@@H]21]

Example 2u (3 g, 12.80 mmol), HATU (4.87 g, 12.809 mmol) and DIPEA (4.46 mL, 25.617 mmol) are added to meso-(1R,5S,6r)-3-(tert-butoxycarbonyl)-3-azabicyclo[3.1.0]hexane-6-carboxylic acid (2.62 g, 11.528 mmol) in DMF (15 mL) and stirring is continued for 2 h. Volatiles are evaporated under reduced pressure, the crude is taken up with EtOAc and the organic layer is washed with NaHCO$_3$ saturated solution and brine. The organic layer is dried and evaporated to furnish a residue that is purified by flash chromatography (eluent 40-70% EtOAc/cyclohexane) to furnish the title compound (4 g, 98% content, 69%).

UPLC-MS (Method 2): $R_t$=1.12 min
MS (ESI pos): m/z=444 (M+H)$^+$

Example 4a

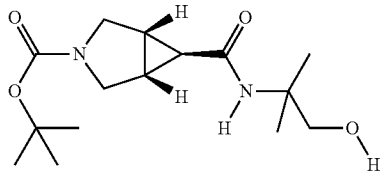 [SMILES: CC(C)(CO)NC(=O)[C@H]1[C@@H]2CN(C(=O)OC(C)(C)C)C[C@@H]21]

HATU (12 g, 31.682 mmol), DIPEA (6 mL, 34.322 mmol) and 2-amino-2-methyl-1-propanol (2.5 g, 27.722 mmol) are added to meso-(1R,5S,6r)-3-(tert-butoxycarbonyl)-3-azabicyclo[3.1.0]hexane-6-carboxylic acid (6 g, 26.402 mmol) in dry DMF (40 mL) and stirring is continued overnight. Volatiles are evaporated under reduced pressure to furnish a residue that is taken up in EtOAc, washed with 10% citric acid, sat. NaHCO$_3$ and dried using a phase separator cartridge. The resulting solution is evaporated under reduced pressure to furnish a residue that is purified by flash chromatography (eluent 50-90% EtOAc/cyclohexane) to furnish the title compound (6.2 g, 79%).

$^1$H NMR (500 MHz, DMSO-d$_6$): δ 1.15 (s, 6H), 1.38 (s, 9H), 1.43 (t, J=3.3 Hz, 1H), 1.77 (m, 2H), 3.27-3.31 (m, 2H), 3.35 (d, J=5.3 Hz, 2H), 3.45-3.48 (m, 2H), 4.82 (t, J=5.8 Hz, 1H), 7.54 (s, 1H)

Example 5a

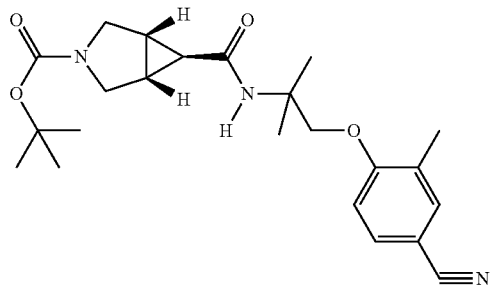 [SMILES: Cc1cc(C#N)ccc1OCC(C)(C)NC(=O)[C@H]1[C@@H]2CN(C(=O)OC(C)(C)C)C[C@@H]21]

Under nitrogen atmosphere, sodium hydride (60% suspension in mineral oil, 32 mg, 0.804 mmol) is added to example 4a (120 mg, 0.402 mmol) and 4-fluoro-3-methylbenzonitrile (109 mg, 0.804 mmol) in dry 1,4-dioxane (2 mL) cooled to 0° C. and stirring is continued for 3 h at rt. Volatiles are evaporated under reduced pressure to furnish a residue that is purified by preparative HPLC (stationary phase: Sunfire C18 ODB 5 μm 19×100 mm. Mobile phase: ACN/H$_2$O+CF3COOH 0.05%). Fractions containing the title compound are combined, acetonitrile is evaporated under reduced pressure, the aqueous layer is basified with sat. NaHCO$_3$ and extracted with DCM. The organic layer is dried using a phase separator cartridge and the resulting solution is evaporated under reduced pressure to furnish the title compound (105 mg, 63%).

UPLC-MS (Method 2): $R_t$=1.28 min
MS (ESI pos): m/z=414 (M+H)$^+$

The following examples are synthesized in analogy to the preparation of example 5a:

| Example | Structure | Reactant(s) | HPLC-MS or UPLC-MS Rt [min], method | MS (ESI pos or APCI, m/z) (M + H)$^+$ |
|---|---|---|---|---|
| 5b | 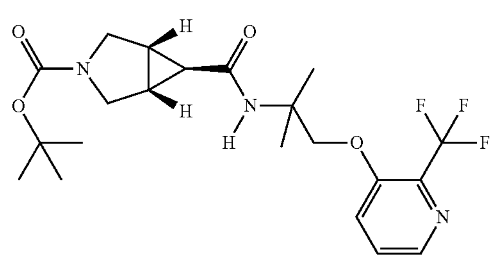 [SMILES: CC(C)(COc1cccnc1C(F)(F)F)NC(=O)[C@H]1[C@@H]2CN(C(=O)OC(C)(C)C)C[C@@H]21] | 3-fluoro-2-(trifluoromethyl)pyridine (111 mg, 0.670 mmol) | 1.20 2 | 444 |

-continued

| Example | Structure | Reactant(s) | HPLC-MS or UPLC-MS Rt [min], method | MS (ESI pos or APCI, m/z) (M + H)+ |
|---|---|---|---|---|
| 5c | 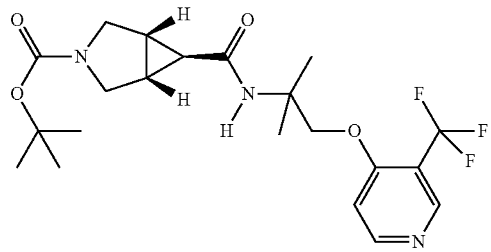 [SMILES: CC(C)(COc1ccncc1C(F)(F)F)NC(=O)[C@H]1[C@@H]2CN(C(=O)OC(C)(C)C)C[C@@H]21] | 4-chloro-3-trifluoromethyl-pyridine hydrochloride (146 mg, 0.670 mmol) + TEA (70 μL, 0.503 mmol) | 3.15 8 | 444 |
| 5d | 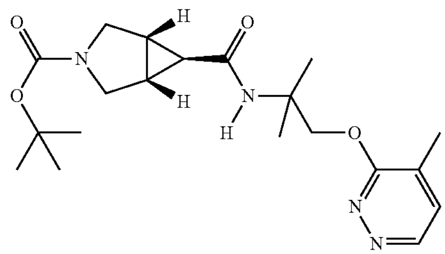 [SMILES: Cc1ccnnc1OCC(C)(C)NC(=O)[C@H]1[C@@H]2CN(C(=O)OC(C)(C)C)C[C@@H]21] | 3-chloro-4-methyl-pyridazine (86 mg, 0.670 mmol) | 2.72 8 | 391 |
| 5e | 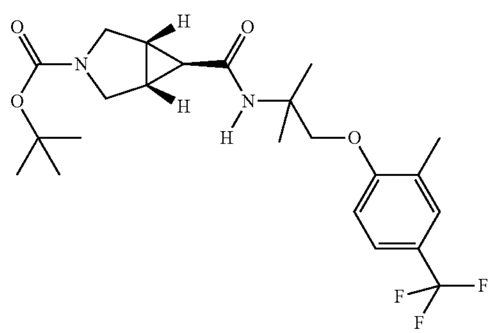 [SMILES: Cc1cc(C(F)(F)F)ccc1OCC(C)(C)NC(=O)[C@H]1[C@@H]2CN(C(=O)OC(C)(C)C)C[C@@H]21] | 4-fluoro-3-methylbenzo-trifluoride (119 mg, 0.670 mmol) | 3.99 8 | 457 |

Example 5f

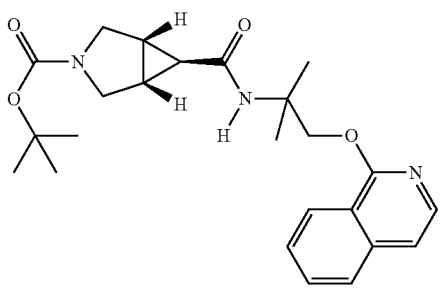 [SMILES: CC(C)(COc1nccc2ccccc12)NC(=O)[C@H]1[C@@H]2CN(C(=O)OC(C)(C)C)C[C@@H]21]

Example 5f is prepared as described for example 5a using 1-chloroisoquinoline (164 mg, 1 mmol) as starting material with the exception that the mixture is stirred for 2 h at rt and then heated at 60° C. for 3 h. Volatiles are evaporated under reduced pressure to furnish a residue that is purified by flash chromatography (eluent 20-50% EtOAc/cyclohexane) to furnish the title compound (159 mg, 74%).

HPLC-MS (Method 8): $R_t$=3.57

MS (APCI): m/z=426 (M+H)+

The following example is synthesized in analogy to the preparation of example 5f:

| Example | Structure | Reactant(s) | UPLC-MS $R_t$ [min], method | MS (ESI pos, m/z) (M + H)+ |
|---|---|---|---|---|
| 5g | 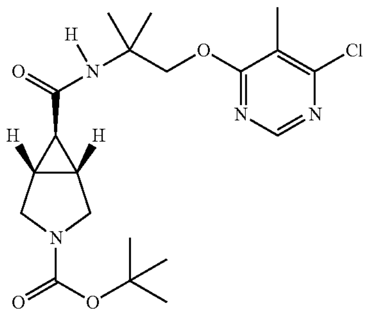 [SMILES: Cc1c(Cl)ncnc1OCC(C)(C)NC(=O)[C@H]1[C@@H]2CN(C(=O)OC(C)(C)C)C[C@@H]21] | 4,6-dichloro-5-methylpyrimidine (273 mg, 1.676 mmol) | 1.28 8 | 425 |

Example 5h

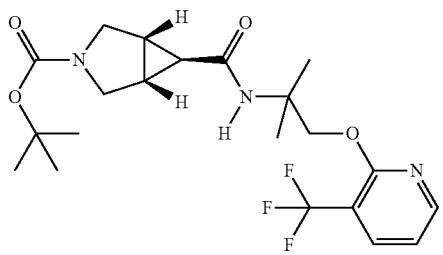 [SMILES: CC(C)(COc1ncccc1C(F)(F)F)NC(=O)[C@H]1[C@@H]2CN(C(=O)OC(C)(C)C)C[C@@H]21]

Under nitrogen, sodium hydride (60% suspension in mineral oil, 62 mg, 1.54 mmol) is added to example 4a (200 mg, 0.670 mmol) and 2-fluoro-3-(trifluoro-methyl)pyridine (221 mg, 1.34 mmol) in dry 1,4-dioxane (4 mL) cooled to 0° C. The reaction mixture is allowed to reach rt and then is heated at 110° C. under microwave irradiation for 50 minutes. The reaction mixture is diluted with DCM and washed with water, and then with saturated NH$_4$Cl, dried and concentrated under reduced pressure giving a residue that is purified by flash chromatography (eluent 0-40% EtOAc/cyclohexane) to furnish the title compound (200 mg, 64%).

UPLC-MS (Method 2): $R_t$=1.26 min

MS (ESI pos): m/z=444 (M+H)+

The following examples are synthesized in analogy to the preparation of example 5h:

| Example | Structure | Reactant(s) | HPLC-MS or UPLC-MS $R_t$ [min], method | MS (ESI pos, m/z) (M + H)+ |
|---|---|---|---|---|
| 5i | 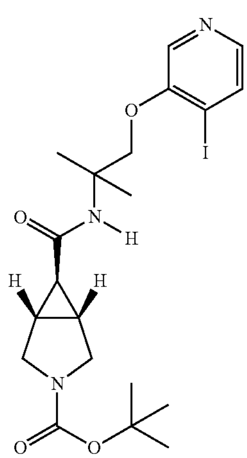 [SMILES: CC(C)(COc1cnccc1I)NC(=O)[C@H]1[C@@H]2CN(C(=O)OC(C)(C)C)C[C@@H]21] | 3-fluoro-4-iodopyridine (299 mg, 1.34 mmol) | 3.20 12 | 502 |

| Example | Structure | Reactant(s) | HPLC-MS or UPLC-MS $R_t$ [min], method | MS (ESI pos, m/z) (M + H)+ |
|---|---|---|---|---|
| 5j | 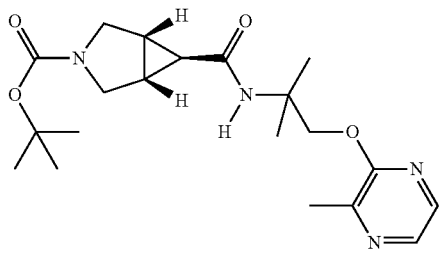 [SMILES: Cc1nccnc1OCC(C)(C)NC(=O)[C@H]1[C@@H]2CN(C(=O)OC(C)(C)C)C[C@@H]21] | 3-chloro-4-(trifluoro-methyl)pyridazine (synthesised as described in WO2009/086130, 305.8 mg, 1.67 mmol) | 1.09 2 | 445 |

Example 5k

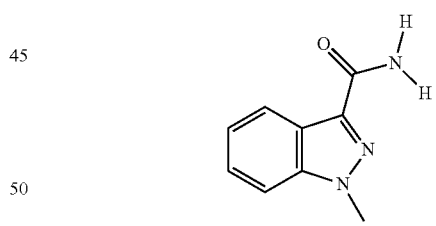

Example 5k is prepared as described for example 5a using 2-chloro-3-methylpyrazine (86 mg, 0.67 mmol) as starting material with the exception that the mixture is stirred for 2 h at rt and then heated at 60° C. overnight. Following preparative HPLC purification, the resulting material is purified by flash chromatography (eluent 20-50% EtOAc/cyclohexane) to furnish the title compound (42 mg, 32%).

HPLC-MS (Method 8): $R_t$=2.90
MS (APCI): m/z=391 (M+H)+

Example 5l

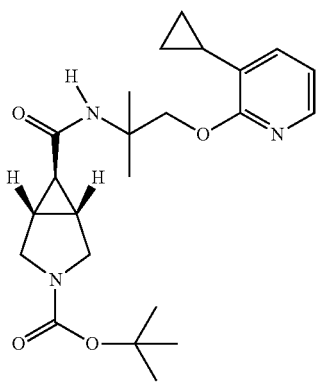 [SMILES: CC(C)(COc1ncccc1C1CC1)NC(=O)[C@H]1[C@@H]2CN(C(=O)OC(C)(C)C)C[C@@H]21]

2-Fluoro-3-iodopyridine (300 mg, 1.34 mmol), potassium cyclopropyltrifluoroborate (498 mg, 3.36 mmol), palladium (II) acetate (30 mg, 0.135 mmol) are dissolved in toluene (4 mL) under a nitrogen flow. Tricyclohexylphosphine (75 mg, 0.27 mmol), tri-potassium phosphate (1.1 g, 5.38 mmol) and water (0.4 mL) are added and the reaction mixture is heated under microwave irradation (130° C.) for 2 h. At rt, water is added and the aqueous layer is extracted with DCM. Then the organic layer is washed with water and brine, separated and dried to furnish 3-cyclopropyl-2-fluoro-pyridine (200 mg, 97%).

UPLC-MS (Method 2): $R_t$=0.94 min
MS (ESI pos): m/z=138 (M+H)+

Example 5l is prepared as described for example 5h using 3-cyclopropyl-2-fluoro-pyridine as starting material (184 mg, 1.34 mmol).

UPLC-MS (Method 2): $R_t$=1.28 min
MS (ESI pos): m/z=416 (M+H)+

Example 6a

To a solution of 1-methylindazole-3-carboxylic acid (1 g, 5.67 mmol) in dry THF (15 mL), CDI (1 g, 6.24 mmol) is added. The mixture is stirred at rt for 1.5 h, then ammonium hydroxide (13 mL of a 30% solution in water) is added and the mixture stirred for additional 15 min. Solvents are evaporated, the crude dissolved in EtOAc, washed with 0.1 N hydrochloric acid, sat. NaHCO$_3$ and brine. The organic layer is separated, dried and evaporated under vacuum to obtain the title compound (840 mg, 83%) used in the next step without any further purification.

$^1$H NMR (300 MHz, DMSO-d$_6$): δ 4.12 (s, 3H), 7.26 (ddd, J=1.0, 6.7, 7.6 Hz, 1H), 7.33 (br, s, 1H), 7.46 (ddd, J=1.0, 6.8, 8.0 Hz, 1H), 7.65 (br, s, 1H), 7.71 (dd, J=8.2 Hz, 1H), 8.16 (dd, J=8.2 Hz, 1H)

The following examples are synthesized in analogy to the preparation of example 6a:

| Example | Structure | Reactant(s) | ¹H NMR |
|---|---|---|---|
| 6b | 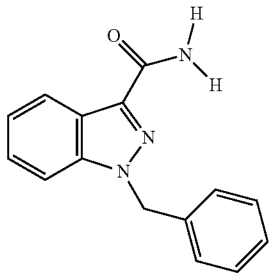 [SMILES: NC(=O)c1nn(Cc2ccccc2)c2ccccc12] | 1-benzyl-1H-indazole-3-carboxylic acid (1 g, 3.96 mmol) | ¹H NMR (300 MHz, DMSO-$d_6$): δ 5.73 (s, 2H), 7.23-7.35 (m, 6H), 7.39 (s, br, 1H), 7.39 (ddd, J = 1.2, 7.0, 8.1 Hz, 1H), 7.70 (s, br, 1H), 7.76 (ddd, J = 1.0, 1.6, 8.7 Hz, 1H), 8.19 (ddd, J = 1.1, 2.0, 8.1 Hz, 1H) |

| Example | Structure | Reactant(s) | HPLC-MS $R_t$ [min], method, MS (APCI, m/z) (M + H)⁺ |
|---|---|---|---|
| 6c | 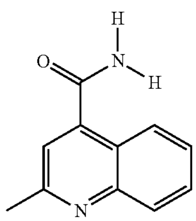 | 2-methyl-quinoline-4-carboxylic acid (1.2 g, 6.410 mmol) | 1.35<br>8<br>187 |

| Example | Structure | Reactant(s) | ¹H NMR |
|---|---|---|---|
| 6d | 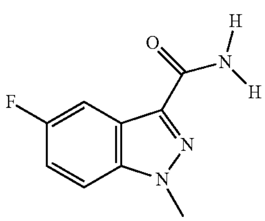 | 5-Fluoro-1-methyl-1H-indazole-3-carboxylic acid (1 g, 5, 15 mmol) | ¹H NMR (300 MHz, DMSO-$d_6$): δ 4.13 (3H,s), 7.33-7.42 (2H, m), 7.69(1 H, s), 7.77-7.82 (2H, m) |

| Example | Structure | Reactant(s) | HPLC-MS $R_t$ [min], method, MS (ESI pos or APCI, m/z) (M + H)⁺ |
|---|---|---|---|
| 6e | 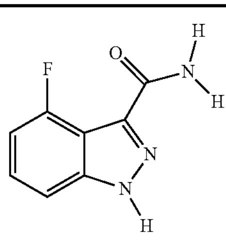 | 4-fluoro-1H-indazole-3-carboxylic acid (1.1 g, 5, 80 mmol) | 0.62<br>2<br>180 |
| 6f | 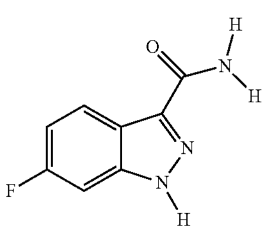 [SMILES: NC(=O)c1n[nH]c2cc(F)ccc12] | 6-fluoro-1H-indazole-3-carboxylic acid (3.0 g, 16, 65 mmol) | 0.69<br>1<br>180 |

-continued

| | | | |
|---|---|---|---|
| 6g | (structure) | 7-Methyl-pyrazolo[1,5-a]pyridine-3-carboxylic acid (synthesised as described in J. Comb. Chem., 2005, 7, 309-316; 160 mg, 0.91 mmol) | 0.59 2 176 |
| 6h | (structure) | 7-(trifluoromethyl)-1H-indazole-3-carboxylic acid (2.0 g, 6.08 mmol) | 0.77 2 230 |

Example 6i

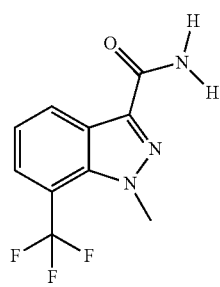 [SMILES: Cn1nc(C(N)=O)c2cccc(C(F)(F)F)c21]

Cesium carbonate (1.37 g, 4.19 mmol) is added to a solution of 6h (800 mg, 3.49 mmol) in DMF (10 mL). After 15 min, Iodomethane (215 µl, 3.49 mmol) is added dropwise to the reaction mixture. After 5 min the reaction is diluted with EtOAc, washed with saturated ammonium chloride and water. The organic layer is separated and dried with a Phase separator cartridge and evaporated under vacuum to obtain a the title compound (800 mg, 85% content, 80%), that is used as such.

UPLC-MS (Method 2): $R_t$=0.93
MS (ESI pos): m/z=244 (M+H)$^+$

The following example is synthesized in analogy to the preparation of example 6a:

Example 7a

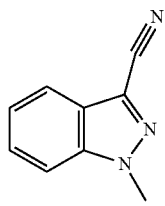

Burgess reagent (1.7 g, 7.19 mmol) is added to a solution of 6a (840 mg, 4.79 mmol) in DCM (15 mL), and the mixture is heated for 3 h at 35° C. The reaction is diluted with DCM, washed with 0.2N hydrochloric acid and brine. The organic layer is separated and dried with a Phase separator cartridge and evaporated under vacuum to obtain a crude that is purified by flash chromatography (eluent 0-20% EtOAc/cyclohexane) to furnish the title compound (680 mg, 90%).

GC-MS (Method 13): $R_t$=9.74 min
MS (EI pos): m/z=157 [M]$^+$

| Example | Structure | Reactant(s) | HPLC-MS $R_t$ [min], method, MS (APCI, m/z) (M + H)$^+$ |
|---|---|---|---|
| 6j | (structure) | 6-bromoindolizine-2-carboxylic acid (975 mg, 4.0 mmol) | 3.20 7a 239 |

The following examples are synthesized in analogy to the preparation of example 7a:

| Example | Structure | Reactant(s) | HPLC-MS or UPLC-MS $R_t$ [min], method | MS (ESI pos, m/z) $(M + H)^+$ |
|---|---|---|---|---|
| 7b | (1-benzyl-1H-indazole-3-carbonitrile) | Example 6b (979 mg, 3.81 mmol) | 1.24 2 | 234 |
| 7c | (2-methylquinoline-4-carbonitrile) | Example 6c (935 mg, 5.021 mmol) | 9.49 13 (GC-MS) | 168 [M]$^+$ |
| 7d | (5-fluoro-1-methyl-1H-indazole-3-carbonitrile) | Example 6d (640 mg, 3, 31 mmol) | 2.33 11 | 176 |

Example 7e

Trifluoroacetic anhydride (1.16 mL, 8.37 mmol) is added to a solution of 6e (600 mg, 3.35 mmol) in pyridine (6 mL) and DCM (15 mL). After 30 min the reaction is diluted with EtOAc, washed with saturated NaHCO$_3$, saturated NH$_4$Cl, water and brine. The organic layer is separated and dried with a Phase separator cartridge and evaporated under vacuum to furnish the title compound (500 mg, 93%), that is used as such.

UPLC-MS (Method 2): $R_t$=0.91

MS (ESI pos): m/z=162 (M+H)$^+$

The following examples are synthesized in analogy to the preparation of example 7e:

| Example | Structure | Reactant(s) | HPLC-MS or UPLC-MS $R_t$ [min], method | MS (ESI pos, m/z) $(M + H)^+$ |
|---|---|---|---|---|
| 7f | (6-fluoro-1H-indazole-3-carbonitrile) | Example 6f (1.20 g, 6, 70 mmol) | 0.85 2 | 162 |

-continued

| Example | Structure | Reactant(s) | | |
|---|---|---|---|---|
| 7g | 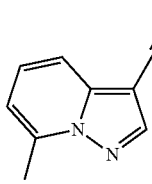 | Example 6g (109 mg, 0.62 mmol) | 0.89 2 | 158 |

| Example | Structure | Reactant(s) | ¹H NMR |
|---|---|---|---|
| 7h | 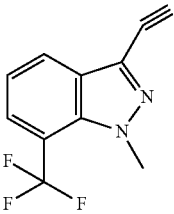 | Example 6i (800 mg, 90% content, 2, 96 mmol) | ¹H NMR (500 MHz, DMSO-$d_6$): δ 4.26-4.28 (3H, m), 7.59 (1H, dd, J = 7.8, 7.8 Hz), 8.08 (1H, d, J = 7.5 Hz), 8.28 (1H, d, J = 8.2 Hz) |

Example 7i

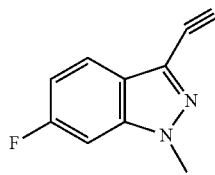

Cesium carbonate (1.31 g, 4.03 mmol) is added to a solution of 7e (500 mg, 3.10 mmol) in DMF (10 mL). After 15 min, iodomethane (192 µl, 3.10 mmol) is added dropwise to the reaction mixture. After stirring overnight the reaction is diluted with EtOAc, washed with saturated ammonium chloride and water. The organic layer is separated and dried with a Phase separator cartridge and evaporated under vacuum to obtain a crude that is purified by flash chromatography (eluent 0-20% EtOAc/cyclohexane) to furnish the title compound (340 mg, 63%).

UPLC-MS (Method 2): $R_t$=0.99

MS (ESI pos): m/z=176 (M+H)⁺

The following example is synthesized in analogy to the preparation of example 7i:

| Example | Structure | Reactant(s) | HPLC-MS or UPLC-MS $R_t$ [min], method | MS (ESI pos, m/z) (M + H)⁺ |
|---|---|---|---|---|
| 7j | 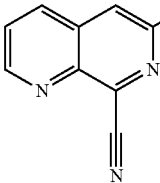 | Example 7f (600 mg, 3.72 mmol) | 1.09 1 | 176 |

Example 7k

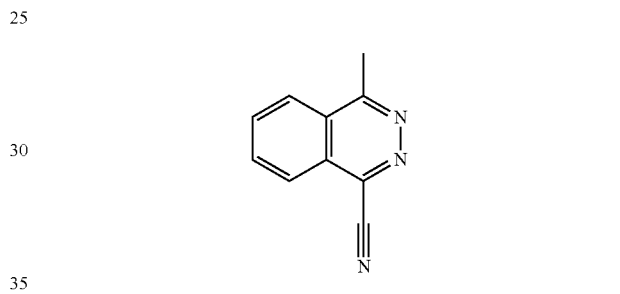

1-Chloro-4-methylphthalazine (5.00 g, 28.00 mmol), Zinc cyanide (3.62 g, 30.79 mmol), 1,1'-Bis(diphenylphosphino)ferrocene (1.40 g, 2.52 mmol), Tris(dibenzylideneacetone)dipalladium(0) (1.03 g, 1.12 mmol) in DMF (50 mL) were heated at 100° C. for 3 h. The reaction is diluted with EtOAc/water. The organic layer is separated, washed with brine, dried and evaporated under reduce pressure to give a residue that is purified by flash chromatography (eluent 0-60% EtOAc/cyclohexane) to furnish the title compound (4.17 g, 88%).

GC-MS (Method 13): $R_t$=10.85 min

MS (ESI pos): m/z=169 [M]⁺

The following example is synthesized in analogy to the preparation of example 7k:

| Example | Structure | Reactant(s) | HPLC-MS or UPLC-MS $R_t$ [min], method | MS (ESI pos, m/z) (M + H)⁺ |
|---|---|---|---|---|
| 7l | 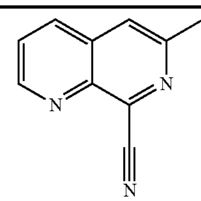 | 8-Chloro-6-methyl-1,7-naphthyridine (700 mg, 3, 92 mmol) | 3.26 10 | 170 |

Example 7m

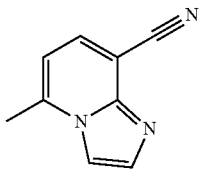

Ammonia in methanol (7M, 3.5 ml, 24 mmol) is added to 8-Bromo-5-methylimidazo[1,2-a]pyridine hydrochloride (3.00 g, 12.1 mmol) in DCM (5 mL). Volatiles are evaporated, DCM and water are added, the organic layer is separated, washed with brine, dried and evaporated under reduce pressure to give a residue (2.55 g). Part of such material (1.00 g, 4.74 mmol), Zinc cyanide (601 mg, 5.12 mmol), Zinc (31 mg, 0.47 mmol), 1,1'-Bis(diphenylphosphino)ferrocene]dichloropalladium(II) (347 mg, 0.47 mmol), 1,1'-Bis(diphenylphosphino)ferrocene (263 mg, 0.47 mmol) in N,N-dimethyl acetamide (10 mL) are heated at 150° C. for 1 h under microwave irradiation. The reaction is diluted with EtOAc/water. The organic layer is separated, washed with brine, dried and evaporated under reduce pressure to give a residue that is washed with DCM and the resulting solid collected by filtration to furnish the title compound (650 mg, 98% content, 86%).

HPLC-MS (Method 7a): $R_t$=2.43 min

MS (APCI): m/z=158 (M+H)$^+$

Example 7n

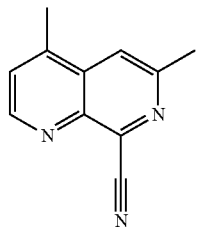

n-Butyllithium (2.5 M in hexanes, 29 mL, 72 mmol) is added dropwise to N-tert-butyl-4-chloropyridine-2-carboxamide (7.00 g, 32.9 mmol) in THF (70 mL) at −78° C. After 1 h at −78° C. iodomethane (6.8 mL, 109 mmol) is added and stirring is continued for 1 h. Saturated NH$_4$Cl (10 mL) is added and the organic layer is separated, dried and evaporated under reduce pressure to give a residue that is purified by flash chromatography (eluent 0-20% EtOAc/cyclohexane) to furnish N-tert-butyl-4-chloro-3-methyl-pyridine-2-carboxamide (5.7 g, 76%).

UPLC-MS (Method 2): $R_t$=1.08

MS (ESI pos): m/z=227 (M+H)$^+$ n-Butyllithium (2.5 M in hexanes, 28 mL, 70 mmol) is added dropwise to diisopropylamine (10 mL, 70 mmol) in THF (100 mL) at −78° C. After 1 h at −78° C. and 15 min at 0° C. the reaction mixture is cooled to −50° C. and N-tert-butyl-4-chloro-3-methyl-pyridine-2-carboxamide (5.7 g, 25 mmol) in THF (50 mL) is added dropwise and stirring is continued for 30 min at −40° C. Methyl acetate (2.2 mL, 28 mmol) is added and stirring is continued for 30 min at −40° C. Saturated NH$_4$Cl (2 mL), water (6 mL) and ethyl acetate are added and the organic layer is separated, dried and evaporated under reduce pressure to give a residue that is purified by flash chromatography (eluent 0-10% EtOAc/cyclohexane) to furnish 4-chloro-3-(2-oxo-propyl)-pyridine-2-carboxylic acid tert-butylamide (3.7 g, 55%).

UPLC-MS (Method 2): $R_t$=1.05

MS (ESI pos): m/z=269 (M+H)$^+$

Trimethylboroxine (5.7 mL, 41 mmol) is added to 4-chloro-3-(2-oxo-propyl)-pyridine-2-carboxylic acid tert-butylamide (3.63 g, 13.5 mmol), potassium carbonate (9.33 g, 67.5 mmol) and 1,1'-bis(diphenylphosphino)ferrocene-palladium(II)dichloride dichloromethane complex (1.10 g, 1.35 mmol) in DMF (60 mL) and the reaction mixture is heated at 100° C. overnight. Volatiles are evaporated under reduced pressure and the residue dissolved with EtOAc/water. The organic layer is separated, dried and evaporated under reduce pressure to give a residue that is purified by flash chromatography (eluent 0-30% EtOAc/cyclohexane) to furnish 4-methyl-3-(2-oxo-propyl)-pyridine-2-carboxylic acid tert-butylamide (2.61 g, 78%).

UPLC-MS (Method 2): $R_t$=0.96 min

MS (ESI pos): m/z=249 (M+H)$^+$

Ammonium acetate (10.0 g, 130 mmol) followed by 4-methyl-3-(2-oxo-propyl)-pyridine-2-carboxylic acid tert-butylamide (1.61 g, 6.48 mmol) are added to acetic acid (20 mL) and the reaction mixture is heated at 110° C. for 3 h. The reaction mixture is cooled to RT and 20% NaOH is added until pH 6-7. The aqueous layer is extracted with DCM (3 times) and the combined organic layers are washed with brine, dried and evaporated under reduce pressure to furnish 4,6-dimethyl-[1,7]naphthyridin-8-ol (1.12 g, 99%) that is used as such.

UPLC-MS (Method 2): $R_t$=0.62 min

MS (ESI pos): m/z=175 (M+H)$^+$ 4,6-Dimethyl-[1,7]naphthyridin-8-ol (1.26 g, 7.23 mmol) and phosphorus oxychloride (6.7 mL, 72 mmol) in toluene (18 mL) are heated at 100° C. overnight. Phosphorus oxychloride (20 mL, 215 mmol) is added and the reaction mixture is heated at 104° C. for 1d. The reaction mixture is cooled to RT and poured in a mixture of ice and water under stirring. After 30 min 20% NaOH is added until pH 6-7. The aqueous layer is extracted with DCM and the combined organic layers are washed with brine, dried and evaporated under reduce pressure to give a residue that is purified by flash chromatography (eluent 0-50% EtOAc/cyclohexane) to furnish 8-chloro-4,6-dimethyl-[1,7]naphthyridine (920 mg, 66%).

UPLC-MS (Method 2): $R_t$=0.96 min

MS (ESI pos): m/z=193 (M+H)$^+$

8-Chloro-4,6-dimethyl-[1,7]naphthyridine (1.34 g, 6.96 mmol), Zinc cyanide (898 mg, 7.65 mmol), 1,1'-bis(diphenylphosphino)ferrocene (347 mg, 0.63 mmol), tris(dibenzylideneacetone)dipalladium(0) (255 mg, 0.28 mmol) in DMF (20 mL) were heated at 100° C. overnight. The reaction is diluted with EtOAc/water. The organic layer is separated, washed with brine, dried and evaporated under reduce pressure to give a residue that is purified by flash chromatography (eluent 0-50% EtOAc/cyclohexane) to furnish the title compound (1.02 g, 80%).

UPLC-MS (Method 2): $R_t$=0.88 min

MS (ESI pos): m/z=184 (M+H)$^+$

The following example is synthesized in analogy to the preparation of example 7a:

| Example | Structure | Reactant(s) | HPLC-MS or UPLC-MS $R_t$ [min], method | MS (ESI pos, m/z) $(M + H)^+$ |
|---|---|---|---|---|
| 7o | 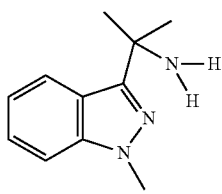 | Example 6j (806 mg, 3.37 mmol) | 1.15 2 | 221 |

Example 8a

Under nitrogen atmosphere, dry THF (22 mL) is added to anhydrous Cerium (III) chloride (3.2 g, 13 mmol) at 0° C. The reaction is allowed to reach RT and stirred for 2 h. At −78° C. methyllithium as a complex with Lithium Iodide (1.6M in ethyl ether, 8.1 mL, 13.1 mmol) is added and stirring is continued for 30 minutes at −78° C. A solution of 7a (680 mg, 4.32 mmol) in THF dry (3 mL) is added to the mixture and stirring is continued for 30 minutes at −78° C. and then overnight at RT. Saturated NH₄Cl and NaOH (50% in water) are added to the mixture until a precipitate forms. Undissolved material is filtered away on a celite pad. The filtrate is washed with water, separated and dried with a phase separator cartridge. The solvent is evaporated under reduce pressure to obtain a crude (350 mg, 30%) used in the next step without any further purification.

GC-MS (Method 13): $R_t$=9.85 min

MS (ESI pos): m/z=189 [M]⁺

The following examples are synthesized in analogy to the preparation of example 8a:

| Example | Structure | Reactant(s) | UPLC-MS $R_t$ [min], method | MS (ESI pos, m/z) $(M + H)^+$ |
|---|---|---|---|---|
| 8b | 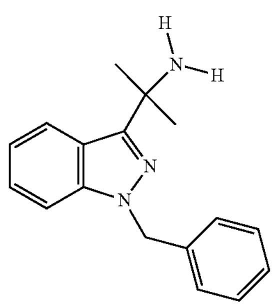 [SMILES: CC(C)(N)c1nn(Cc2ccccc2)c2ccccc12] | Example 7b (900 mg, 3.78 mmol) | 0.84 2 | 249 |
| 8c | 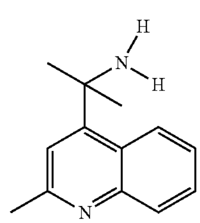 | Example 7c (370 mg, 2.20 mmol) | 0.58 2 | 201 |
| 8d | 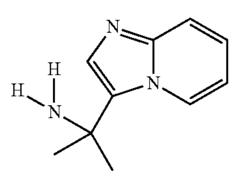 | Imidazo[1,2-a]pyridine-3-carbonitrile (350 mg, 2.44 mmol) | 0.55 2 | 176 |

| Example | Structure | Reactant(s) | UPLC-MS $R_t$ [min], method | MS (ESI pos, m/z) (M + H)+ |
|---|---|---|---|---|
| 8e | 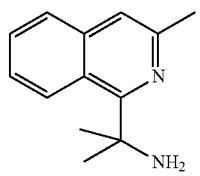 | 4-cyanoquinoline (400 mg, 2.595 mmol) | 0.62 2 | 187 |

Example 8f

Example 8f is prepared as described for example 8a using 3-methylisoquinoline-1-carbonitrile (350 mg, 2.08 mmol) as starting material. Following work-up, the resulting residue is purified by flash chromatography (eluent 100% DCM to 95:5:0.5 DCM/MeOH/NH$_4$OH) to furnish the title compound (162 mg, 39%).

GC-MS (Method 13): $R_t$=10.28
MS (ESI pos): m/z=200 [M]+

The following example are synthesized in analogy to the preparation of example 8f:

| Example | Structure | Reactant(s) | UPLC-MS $R_t$ [min], method | MS (ESI pos, m/z) (M + H)+ |
|---|---|---|---|---|
| 8g | 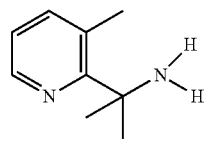 | 3-trifluoromethyl-pyridine-2-carbonitrile (300 mg, 1.74 mmol) | 0.64 2 | 205 |

Example 8h

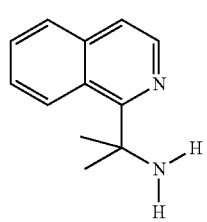

Example 8h is prepared as described for example 8a using 1-cyanoisoquinoline (400 mg, 2.6 mmol) as starting material. At the reaction completion, 3-propanol (3 mL) is added to the mixture. The reaction mixture is partitioned between DCM and water.

Organic phase is separated and dried with a phase separator cartridge. The solvent is evaporated under reduce pressure to obtain a crude (350 mg, 30%) that is purified by flash chromatography (eluent 100% DCM to 95:5:0.5 DCM/MeOH/NH$_4$OH) to furnish the title compound (37 mg, 6%).

UPLC-MS (Method 2): $R_t$=0.65
MS (ESI pos): m/z=187 (M+H)+

Example 8i

Methylmagnesium bromide in 2-methyltetrahydrofuran (3.2M, 6.3 mL, 20.10 mmol) is added dropwise to 2-cyano-3-methyl-pyridine (1 g, 8.04 mmol) in dry toluene (7 mL) at 0° C. The reaction is allowed to reach RT and heating is continued for 72 h at 90° C. 2N HCl is added and the aqueous layer is separated and then basified with 4N NH$_4$OH. Ethyl acetate is added and the organic layer is separated, dried using a phase separator cartridge and the resulting solution is evaporated under reduced pressure to furnish a residue that is used as such (840 mg, 30%)

UPLC-MS (Method 2): $R_t$=0.55
MS (ESI pos): m/z=151 (M+H)+

The following examples are synthesized in analogy to the preparation of example 8i:

| Example | Structure | Reactant(s) | UPLC-MS R$_t$ [min], method | MS (ESI pos, m/z) (M + H)$^+$ |
|---|---|---|---|---|
| 8j | 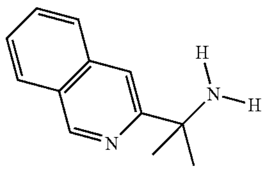 | Isoquinoline-carbonitrile (500 mg, 3.243 mmol) | 0.60 2 | 187 |
| 8k | 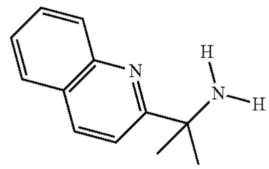 | 2-quinoline-carbonitrile (500 mg, 3.243 mmol) | 0.63 2 | 187 |

The following examples are synthesized in analogy to the preparation of example 8a:

| Example | Structure | Reactant(s) | UPLC-MS R$_t$ [min], method | MS (ESI pos, m/z) (M + H)$^+$ |
|---|---|---|---|---|
| 8l | 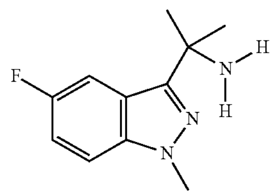 | Example 7d (350 mg, 2.00 mmol) | 0.62 2 | 191 (M − NH$_2$)$^+$ |
| 8m | 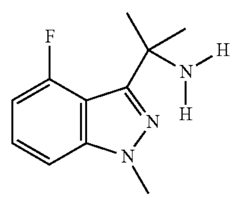 | Example 7i (300 mg, 1, 71 mmol) | 0.64 2 | 191 (M − NH$_2$)$^+$ |
| 8n | 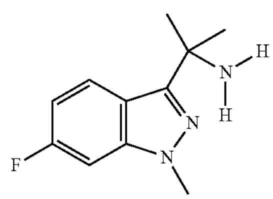 | Example 7j (300 mg, 1, 71 mmol) | 0.68 1 | 191 (M − NH$_2$)$^+$ |
| 8o | 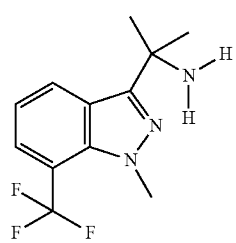 [SMILES: Cn1nc(C(C)(C)N)c2cccc(C(F)(F)F)c21] | Example 7h (400 mg, 1.78 mmol) | 0.77 2 | 241 (M − NH$_2$)$^+$ |
| 8p | 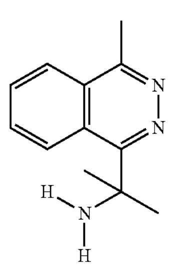 | Example 7k (2.80 g, 16.6 mmol) | 0.57 2 | 202 |

| Example | Structure | Reactant(s) | UPLC-MS R$_t$ [min], method | MS (ESI pos, m/z) (M + H)$^+$ |
|---|---|---|---|---|
| 8q | 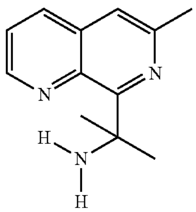 | Example 7l (300 mg, 1.77 mmol) | 0.62 2 | 202 |
| 8r | 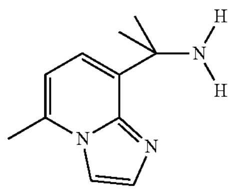 | Example 7m (300 mg, 98% content, 1.87 mmol) | 0.29 2 | 190 |
| 8s | 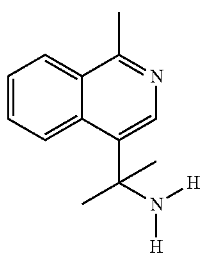 | 1-Methyl-4-Isoquinolinecarbonitrile (500 mg, 2.97 mmol) | 0.60 2 | 201 |
| 8t | 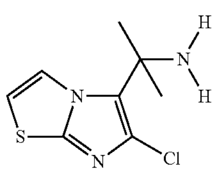 | 6-Chloroimidazo[2,1-b][1,3]thiazole-5-carbonitrile (500 mg, 2.72 mmol) | 0.60 2 | 216 |
| 8u | 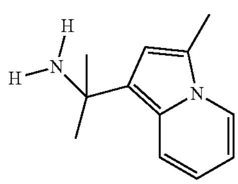 | 3-Methylindolizine-1-carbonitrile (prepared as described in WO 2003/000688, 600 mg, 3.84 mmol) | 0.96 2 | 172 (M − NH$_2$)$^+$ |
| 8v | 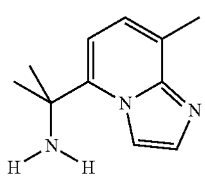 | 8-Methylimidazo[1,2-a]pyridine-5-carbonitrile (400 mg, 2.55 mmol) | 0.53 2 | 190 |
| 8w | 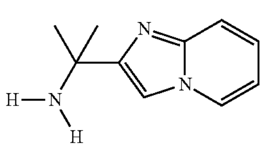 | Imidazo[1,2-a]pyridine-2-carbonitrile (800 mg, 5.59 mmol) | 0.43 2 | 176 |

-continued

| Example | Structure | Reactant(s) | UPLC-MS R_t [min], method | MS (ESI pos, m/z) (M + H)+ |
|---|---|---|---|---|
| 8x | 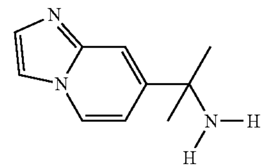 | Imidazo[1,2-a]pyridine-7-carbonitrile (400 mg, 2.79 mmol) | 0.27 2 | 176 |
| 8y | 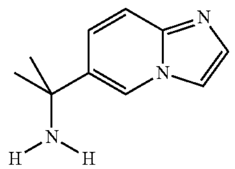 | Imidazo[1,2-a]pyridine-6-carbonitrile (400 mg, 2.79 mmol) | 0.25 2 | 176 |
| 8z | 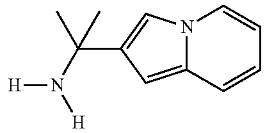 | Indolizine-2-carbonitrile (400 mg, 2.81 mmol) | 0.63 2 | 158 (M − NH$_2$)+ |
| 8aa | 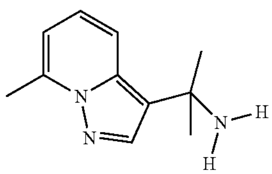 | Example 7g (97 mg, 0.62 mmol) | 0.61 2 | 173 (M − NH$_2$)+ |
| 8ab | 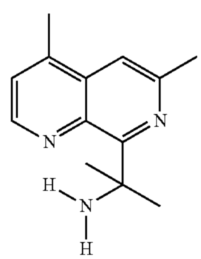 [SMILES: Cc1cc2c(C)ccnc2c(C(C)(C)N)n1] | Example 7n (300 mg, 1.64 mmol) | 0.74 2 | 216 |
| 8ac | 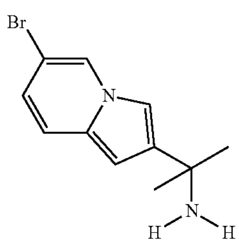 | Example 7o (400 mg, 1.81 mmol) | 0.78 2 | 236 (M − NH$_2$)+ |
| 8ad | 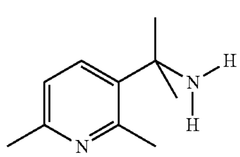 | 2,6-Dimethylnicotinonitrile (200 mg, 1.51 mmol) | 0.52, 0.57 2 | 165 |
| 8ae (racemic mixture) | 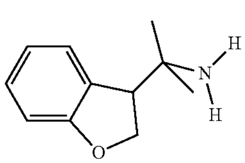 | 2,3-Dihydrobenzofuran-3-carbonitrile (racemic mixture) (220 mg, 1.52 mmol) | 0.63 2 | 178 |

-continued

| Example | Structure | Reactant(s) | UPLC-MS $R_t$ [min], method | MS (ESI pos, m/z) (M + H)+ |
|---|---|---|---|---|
| 8af (racemic mixture) | 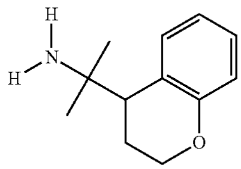 | 3,4-Dihydro-2H-1-benzopyran-4-carbonitrile (racemic mixture) (500 mg, 3.14 mmol) | 0.65 2 | 192 |
| 8ag | 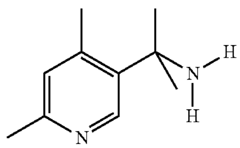 | 4,6-Dimethylnicotino-nitrile (355 mg, 2.69 mmol) | 0.54-0.61 2 | 165 |

Example 9a

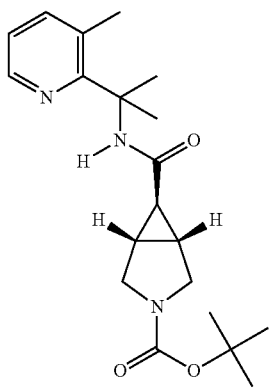 [SMILES: Cc1cccnc1C(C)(C)NC(=O)[C@H]1[C@@H]2CN(C(=O)OC(C)(C)C)C[C@@H]21]

HATU (326 mg, 0.858 mmol) is added to meso-(1R,5S, 6r)-3-(tert-butoxycarbonyl)-3-azabicyclo[3.1.0]hexane-6-carboxylic acid (150 mg, 0.660 mmol), example 8i (397 mg, 30% content, 0.92 mmol) and DIPEA (345 µl, 1.98 mmol) in dry DMF (2 mL) and stirring is continued for 2 h. Volatiles are evaporated under reduced pressure to furnish a residue that is diluted with ethyl acetate and washed with saturated NaHCO₃ and brine. The organic layers is separated, dried on a Phase separator cartridge and evaporated under reduce pressure to give a residue purified by flash chromatography (eluent DCM 100% to DCM\MeOH\NH₄OH 95\5\0.5) to furnish the title compound (104 mg, 95%).

¹H NMR (300 MHz, DMSO-d₆): δ 1.39 (s, 9H), 1.49 (t, J=3.5 Hz, 1H), 1.54 (s, 6H), 1.69 (br t, 2H), 2.35 (s, 3H), 3.26-3.30 (br d, J=11.7, Hz 2H), 3.45-3.49 (br d, J=11.7, Hz 2H), 7.08 (dd, J=4.7, 7.5 Hz, 1H), 7.39 (dd, J=1.5, 7.6 Hz, 1H), 8.25 (dd, J=1.6, 5 Hz, 1H), 8.35 (s, 1H)

The following examples are synthesized in analogy to the preparation of example 9a:

| Example | Structure | Reactant(s) | HPLC-MS or UPLC-MS $R_t$ [min], method | MS (ESI pos or APCI, m/z) (M + H)+ |
|---|---|---|---|---|
| 9b | 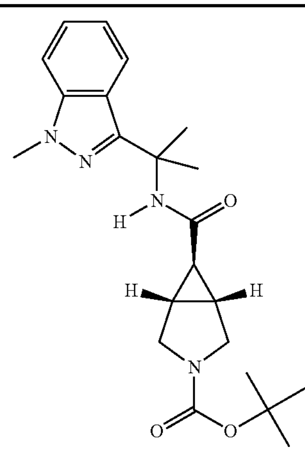 | Example 8a (1,060 g, 70% content, 3,921 mmol) | 3.03 8 | 399 |

-continued

| Example | Structure | Reactant(s) | HPLC-MS or UPLC-MS $R_t$ [min], method | MS (ESI pos or APCI, m/z) (M + H)+ |
|---|---|---|---|---|
| 9c | 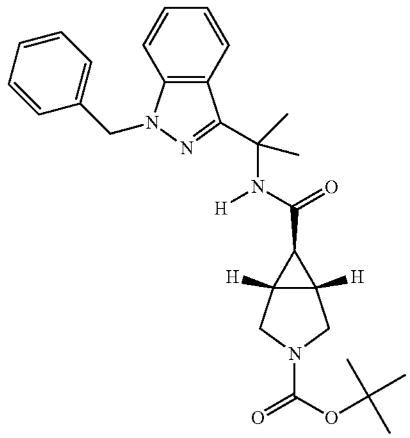 [SMILES: CC(C)(C)OC(=O)N1C[C@@H]2[C@H](C1)[C@H]2C(=O)NC(C)(C)c1nn(Cc2ccccc2)c2ccccc12] | Example 8b (972 mg, 30% content, 1.099 mol) | 1.32 2 | 475 |
| 9d | 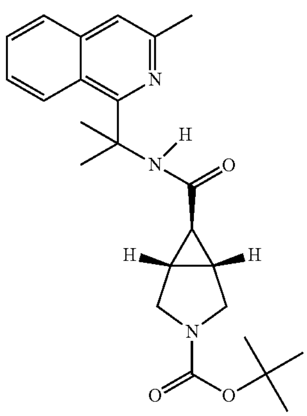 [SMILES: Cc1cc2ccccc2c(C(C)(C)NC(=O)[C@H]2[C@@H]3CN(C(=O)OC(C)(C)C)C[C@@H]32)n1] | Example 8f (161 mg, 0.804 mmol) | 3.61 8 | 410 |
| 9e | 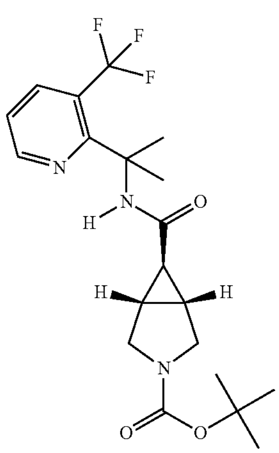 [SMILES: CC(C)(C)OC(=O)N1C[C@@H]2[C@H](C1)[C@H]2C(=O)NC(C)(C)c1ncccc1C(F)(F)F] | Example 8g (70 mg, 60% content, 0.206 mol) | 3.11 8 | 414 |

-continued

| Example | Structure | Reactant(s) | HPLC-MS or UPLC-MS $R_t$ [min], method | MS (ESI pos or APCI, m/z) $(M + H)^+$ |
|---|---|---|---|---|
| 9f | 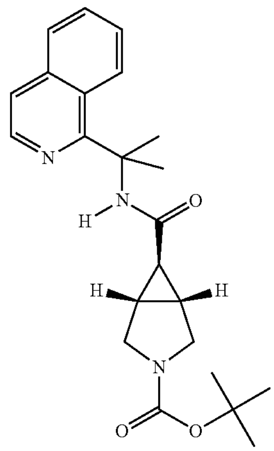 [SMILES: CC(C)(C)OC(=O)N1C[C@@H]2[C@H](C1)[C@H]2C(=O)NC(C)(C)c1nccc2ccccc12] | Example 8h (37 mg, 0.165 mmol) | 1.14 2 | 396 |

Example 9g

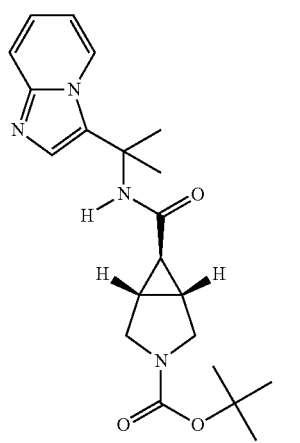 [SMILES: CC(C)(C)OC(=O)N1C[C@@H]2[C@H](C1)[C@H]2C(=O)NC(C)(C)c1cnc2ccccn12]

Example 9h

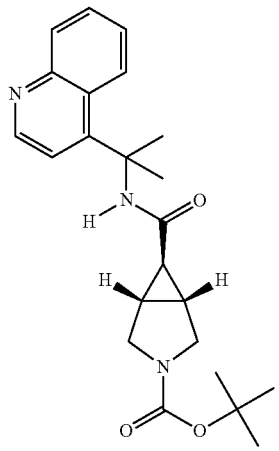 [SMILES: CC(C)(C)OC(=O)N1C[C@@H]2[C@H](C1)[C@H]2C(=O)NC(C)(C)c1ccnc2ccccc12]

Example 9g is prepared as described for the example 9a using 8d (130 mg, 60% content, 0.445 mmol) as starting material. Following the work-up, the residue is purified by preparative HPLC (stationary phase: Sunfire C18 ODB 5 μm 19×100 mm. Mobile phase: ACN/H₂O+CF₃COOH 0.05%). Fractions containing the title compound are combined, acetonitrile is evaporated under reduced pressure, the aqueous layer is basified with sat. NaHCO₃ and extracted with DCM. The organic layer is separated and dried using a phase separator cartridge and the resulting solution is evaporated under reduced pressure to furnish the title compound (142 mg, 83%).

HPLC-MS (Method 8): $R_t$=2.62 min

MS (AFCI): m/z=385 (M+H)⁺

Example 9h is prepared as described for the example 9a using 8e (100 mg, 90% content, 0.483 mmol) as starting material. Following the work-up, the residue is purified by flash chromatography (eluent 60-100% EtOAc/cyclohexane). Fractions containing the title compound are combined, the solvent is evaporated under reduced pressure to furnish the title compound (144 mg, 76%).

HPLC-MS (Method 8): $R_t$=2.85

MS (AFCI): m/z=396 (M+H)⁺

The following examples are synthesized in analogy to the preparation of example 9h:

| Example | Structure | Reactant(s) | HPLC-MS R$_t$ [min], method | MS (ESI pos or APCI, m/z) (M + H)$^+$ |
|---|---|---|---|---|
| 9i | 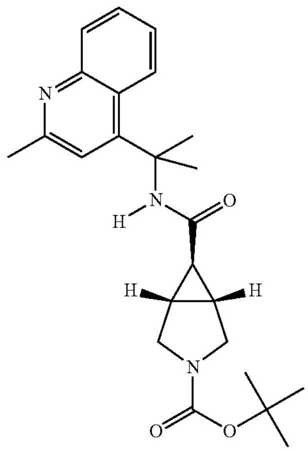 [SMILES: Cc1cc(C(C)(C)NC(=O)[C@H]2[C@@H]3CN(C(=O)OC(C)(C)C)C[C@@H]32)c2ccccc2n1] | Example 8c (454 mg, 33% content, 0.748 mmol) | 2.67 11 | 408 (M − H) |
| 9j | 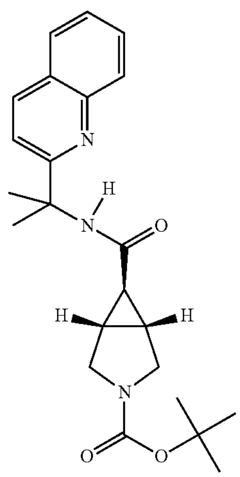 [SMILES: CC(C)(C)OC(=O)N1C[C@@H]2[C@H](C1)[C@H]2C(=O)NC(C)(C)c1ccc2ccccc2n1] | Example 8k (300 mg, 75% content, 1.208 mmol) | 3.09 11 | 396 |
| 9k | 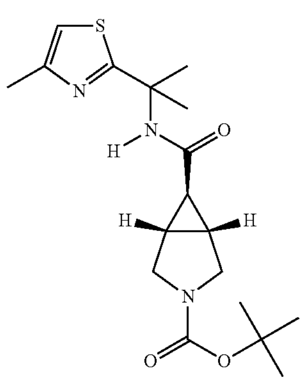 [SMILES: Cc1csc(C(C)(C)NC(=O)[C@H]2[C@@H]3CN(C(=O)OC(C)(C)C)C[C@@H]32)n1] | 2-(4-methyl-1,3-thiazol-2-yl)propan-2-amine (69 mg, 0.440 mmol) | 2.80 8 | 366 |

Example 91

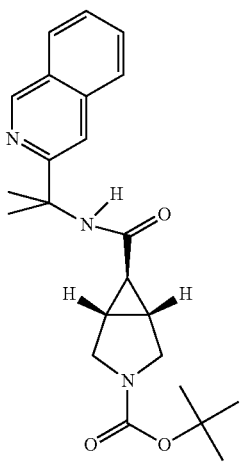 [SMILES: CC(C)(C)OC(=O)N1C[C@@H]2[C@H](C1)[C@H]2C(=O)NC(C)(C)c1cc2ccccc2cn1]

Example 91 is prepared as described for the example 9a using 8j (620 mg, 30% content, 0.964 mmol) as starting material. Following the work-up, the residue is purified by flash chromatography (eluent 30-100% EtOAc/cyclohexane). Fractions containing the title compound are combined, the solvent is evaporated under reduced pressure to furnish a residue that is re purified by preparative HPLC (stationary phase: Xbridge C18 5 μm 19×100 mm. Mobile phase: ACN/H$_2$O+NH$_4$COOH 5 mM). Fractions containing the title compound are combined and ACN is evaporated under reduced pressure. The aqueous layer is extracted with DCM, separated and the DCM is evaporated to furnish the title compound (62 mg, 16%)

HPLC-MS (Method 10): R$_t$=2.84
MS (ESI pos): m/z=396 (M+H)$^+$

The following examples are synthesized in analogy to the preparation of example 9h:

| Example | Structure | Reactant(s) | HPLC-MS R$_t$ [min], method | MS (ESI pos or APCI, m/z) (M + H)$^+$ |
|---|---|---|---|---|
| 9m | 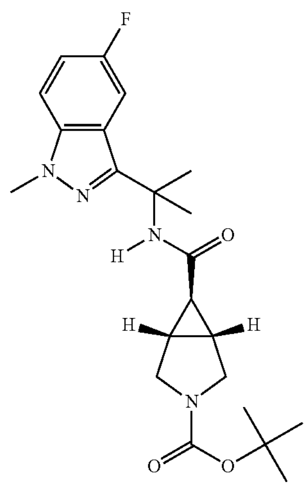 [SMILES: Cn1nc(C(C)(C)NC(=O)[C@H]2[C@@H]3CN(C(=O)OC(C)(C)C)C[C@@H]32)c2cc(F)ccc21] | Example 8l (358 mg, 65% content, 1.12 mmol) | 1.11 2 | 417 |
| 9n | 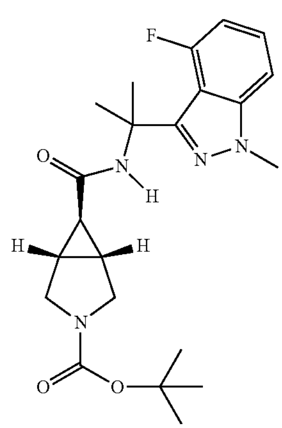 [SMILES: Cn1nc(C(C)(C)NC(=O)[C@H]2[C@@H]3CN(C(=O)OC(C)(C)C)C[C@@H]32)c2c(F)cccc21] | Example 8m (70 mg, 40% content, 0.14 mmol) | 1.13 2 | 417 |

-continued

| Example | Structure | Reactant(s) | HPLC-MS $R_t$ [min], method | MS (ESI pos or APCI, m/z) $(M + H)^+$ |
|---|---|---|---|---|
| 9o | 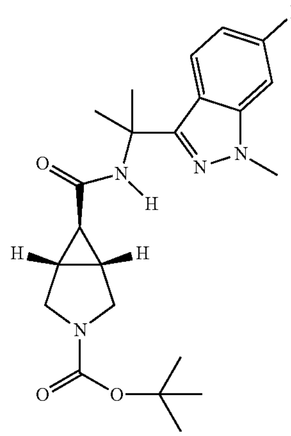 | Example 8n (90 mg, 40% content, 0.17 mmol) | 1.69 4 | 417 |
| 9p | 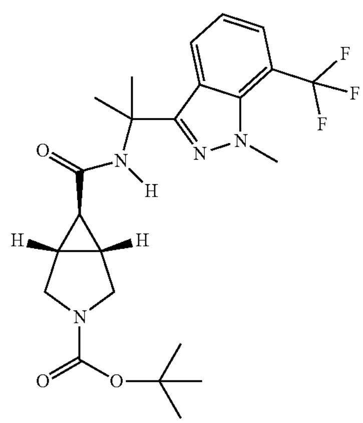 [SMILES: Cn1nc(C(C)(C)NC(=O)[C@H]2[C@@H]3CN(C(=O)OC(C)(C)C)C[C@@H]32)c2cccc(C(F)(F)F)c21] | Example 8o (200 mg, 72% content, 0.56 mmol) | 1.29 2 | 467 |

Example 9q

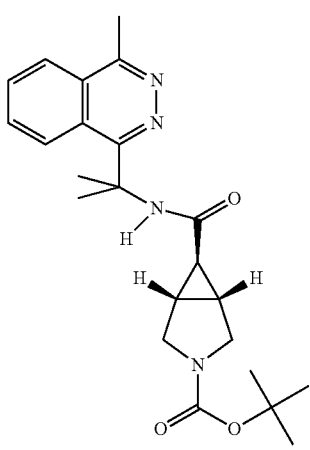 [SMILES: Cc1nnc(C(C)(C)NC(=O)[C@H]2[C@@H]3CN(C(=O)OC(C)(C)C)C[C@@H]32)c2ccccc12]

Example 9q is prepared as described for the example 9a using 8p (1.70 g, 13% content, 1.10 mmol) as starting material. Following the work-up, the residue is purified by flash chromatography (eluent EtOAc, then 5% MeOH in DCM). Fractions containing the title compound are combined, the solvent is evaporated under reduced pressure to furnish a residue that is further purified by preparative HPLC (stationary phase XTerra C18 OBD 5 μm 30×100 mm. Mobile phase: ACN/H$_2$O+NH$_4$COOH 5 mM). Fractions containing the title compound are combined and ACN is evaporated under reduced pressure. The aqueous layer is extracted with DCM, separated and the DCM is evaporated to furnish the title compound (110 mg, 98% content, 24%)

HPLC-MS (Method 7a): $R_t$=4.05
MS (APCI): m/z=411 (M+H)$^+$

Example 9r

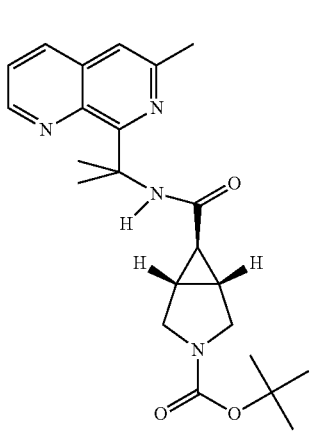 [SMILES: Cc1cc2cccnc2c(C(C)(C)NC(=O)[C@H]2[C@@H]3CN(C(=O)OC(C)(C)C)C[C@@H]32)n1]

Example 9r is prepared as described for the example 9a using 8q (190 mg, 80% content, 0.76 mmol) as starting material. Following the work-up, the residue is purified by preparative HPLC (stationary phase XTerra C18 OBD 5 μm 30×100 mm. Mobile phase: ACN/H₂O+NH₄COOH 5 mM). Fractions containing the title compound are combined and ACN is evaporated under reduced pressure. The aqueous layer is extracted with DCM, separated and the DCM is evaporated to furnish the title compound (240 mg, 98% content, 76%)

HPLC-MS (Method 4): $R_t$=2.00

MS (ESI pos): m/z=411 (M+H)⁺

Example 9s

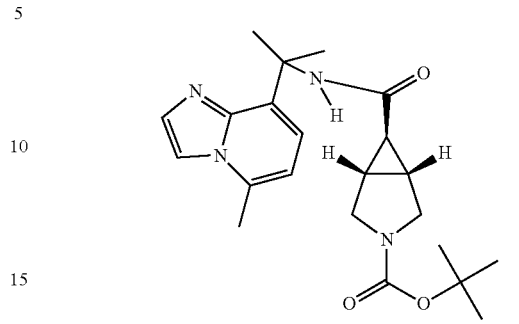

Example 9s is prepared as described for the example 9a using 8r (390 mg, 6% content, 0.12 mmol) as starting material. Following the work-up, the residue is purified by preparative HPLC (stationary phase XTerra C18 OBD 5 μm 30×100 mm. Mobile phase: ACN/H₂O+NH₄COOH 5 mM). Fractions containing the title compound are combined and ACN is evaporated under reduced pressure. The aqueous layer is extracted with DCM, separated and the DCM is evaporated to furnish the residue, that is further purified by flash chromatography (eluent 0-10% MeOH/DCM). Fractions containing the title compound are combined, volatiles are evaporated under reduced pressure to furnish the title compound (20 mg, 41%).

¹H NMR (500 MHz, DMSO-d₆): 1.39 (9H, s), 1.48 (1H, dd, J=3.2, 3.2 Hz), 1.64 (6H, s), 1.67-1.70 (2H, m), 2.68 (3H, s), 3.25 (2H, dd, J=9.5, 9.5 Hz), 3.46 (2H, dd, J=10.6, 10.6 Hz), 7.32 (1H, d, J=9.7 Hz), 7.40 (1H, d, J=9.4 Hz), 7.59 (1H, d, J=1.2 Hz), 7.79 (1H, t, J=1.2 Hz), 8.52 (1H, s).

The following example is synthesized in analogy to the preparation of example 9h:

| Example | Structure | Reactant(s) | HPLC-MS $R_t$ [min], method | MS (ESI pos or APCI, m/z) (M + H)⁺ |
|---|---|---|---|---|
| 9t | 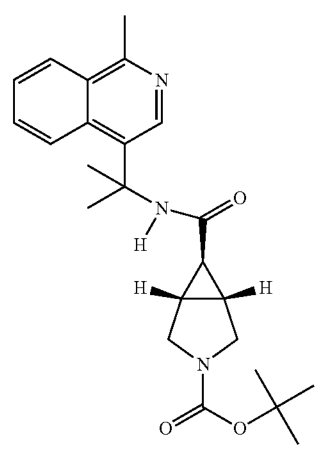 [SMILES: Cc1ncc(C(C)(C)NC(=O)[C@H]2[C@@H]3CN(C(=O)OC(C)(C)C)C[C@@H]32)c2ccccc12] | Example 8s (540 mg, 90% content, 2.43 mmol) | 3.50 10 | 410 |

The following example is synthesized in analogy to the preparation of example 9q:

| Example | Structure | Reactant(s) | HPLC-MS $R_t$ [min], method | MS (ESI pos or APCI, m/z) $(M + H)^+$ |
|---|---|---|---|---|
| 9u | 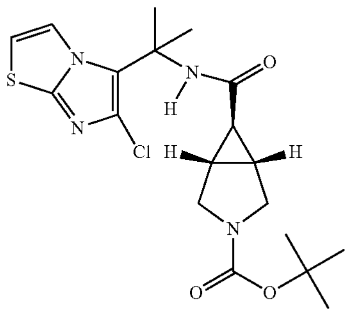 [SMILES: CC(C)(C)OC(=O)N1C[C@@H]2[C@H](C1)[C@H]2C(=O)NC(C)(C)c1c(Cl)nc2sccn12] | Example 8t (850 mg, 33% content, 1.30 mmol) | 3.23 12 | 425 |

Example 9v

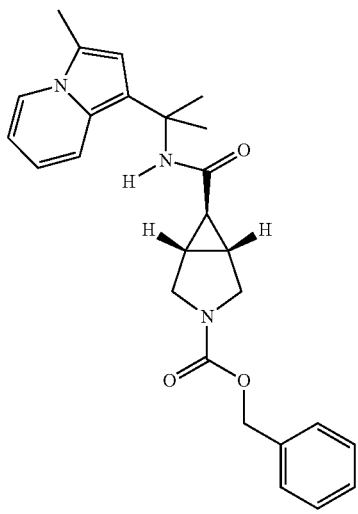 [SMILES: Cc1cc(C(C)(C)NC(=O)[C@H]2[C@@H]3CN(C(=O)OCc4ccccc4)C[C@@H]32)c2ccccn12]

HATU (223 mg, 0.587 mmol) is added to meso-(1R,5S,6r)-3-(benzyloxycarbonyl)-3-azabicyclo[3.1.0]hexane-6-carboxylic acid (commercially available from Matrix Scientific, 118 mg, 0.451 mmol), example 8u (100 mg, 85% content, 0.451 mmol) and DIPEA (236 µl, 1.35 mmol) in dry DMF (5 mL) and stirring is continued for 2 h. Volatiles are evaporated under reduced pressure to furnish a residue that is diluted with ethyl acetate and washed with saturated $NaHCO_3$ and brine. The organic layers is separated, dried on a Phase separator cartridge and evaporated under reduce pressure to give a residue purified by flash chromatography (eluent 0-25% EtOAc/cyclohexane) to furnish the title compound (135 mg, 98% content, 68%).

UPLC-MS (Method 2): $R_t$=1.26 min

MS (ESI pos): m/z=432 $(M+H)^+$

The following examples are synthesized in analogy to the preparation of example 9h:

| Example | Structure | Reactant(s) | HPLC-MS $R_t$ [min], method | MS (ESI pos, m/z) $(M + H)^+$ |
|---|---|---|---|---|
| 9w | 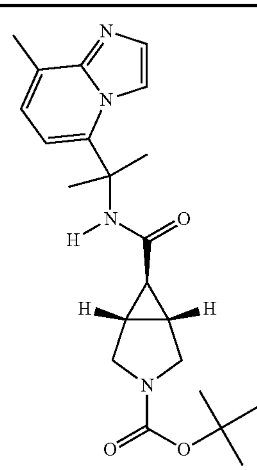 | Example 8v (200 mg, 83% content, 0.88 mmol) | 0.93 2 | 399 |

-continued

| Example | Structure | Reactant(s) | HPLC-MS R_t [min], method | MS (ESI pos, m/z) (M + H)+ |
|---|---|---|---|---|
| 9x | 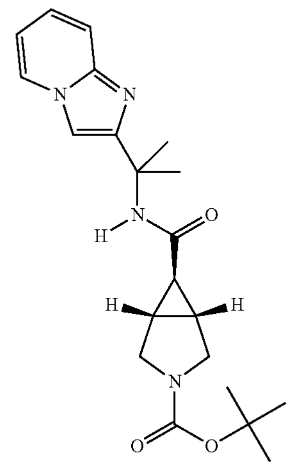 [SMILES: CC(C)(C)OC(=O)N1C[C@@H]2[C@H](C1)[C@H]2C(=O)NC(C)(C)c1cn2ccccc2n1] | Example 8w (300 mg, 70% content, 1.20 mmol) | 0.93 2 | 385 |
| 9y | 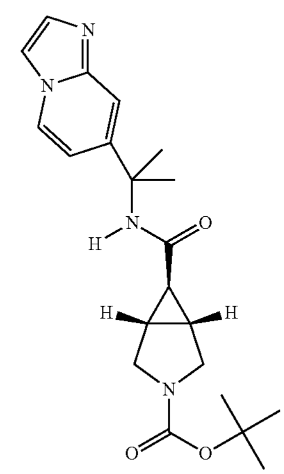 [SMILES: CC(C)(C)OC(=O)N1C[C@@H]2[C@H](C1)[C@H]2C(=O)NC(C)(C)c1ccn2ccnc2c1] | Example 8x (530 mg, 50% content, 1,51 mmol) | 0.80 2 | 385 |
| 9z | 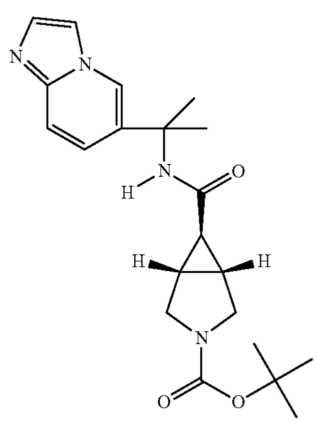 [SMILES: CC(C)(C)OC(=O)N1C[C@@H]2[C@H](C1)[C@H]2C(=O)NC(C)(C)c1ccc2nccn2c1] | Example 8y (480 mg, 34% content, 0.93 mmol) | 0.87 2 | 385 |

-continued

| Example | Structure | Reactant(s) | HPLC-MS R$_t$ [min], method | MS (ESI pos, m/z) (M + H)$^+$ |
|---|---|---|---|---|
| 9aa | 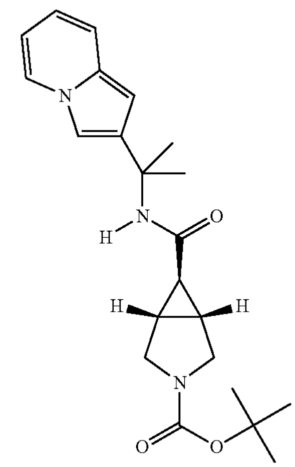 [SMILES: CC(C)(C)OC(=O)N1C[C@@H]2[C@H](C1)[C@H]2C(=O)NC(C)(C)c1cc2ccccn2c1] | Example 8z (600 mg, 32% content, 1.10 mmol) | 1.22 2 | 384 |
| 9ab | 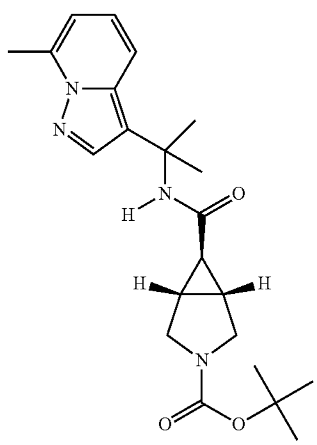 [SMILES: Cc1cccc2c(C(C)(C)NC(=O)[C@H]3[C@@H]4CN(C(=O)OC(C)(C)C)C[C@@H]43)cnn12] | Example 8aa (100 mg, 50% content, 0.26 mmol) | 1.08 2 | 399 |
| 9ac | 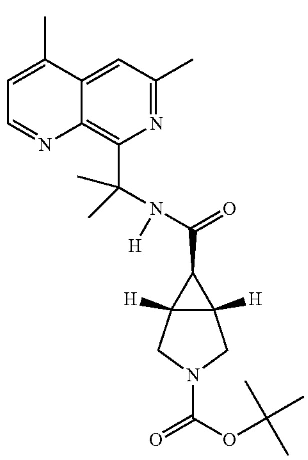 [SMILES: Cc1cc2c(C)ccnc2c(C(C)(C)NC(=O)[C@H]2[C@@H]3CN(C(=O)OC(C)(C)C)C[C@@H]32)n1] | Example 8ab (290 mg, 49% content, 0.66 mmol) | 1.40 2 | 425 |

-continued

| Example | Structure | Reactant(s) | HPLC-MS R$_t$ [min], method | MS (ESI pos, m/z) (M + H)$^+$ |
|---|---|---|---|---|
| 9ad | 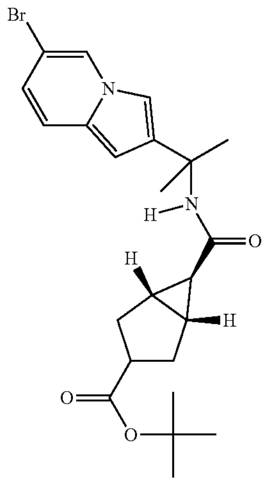 [SMILES: CC(C)(C)OC(=O)C1C[C@@H]2[C@H](C1)[C@H]2C(=O)NC(C)(C)c1cc2ccc(Br)cn2c1] | Example 8ac (458 mg, 20% content, 0.36 mmol) | 1.37 2 | 462 |
| 9ae | 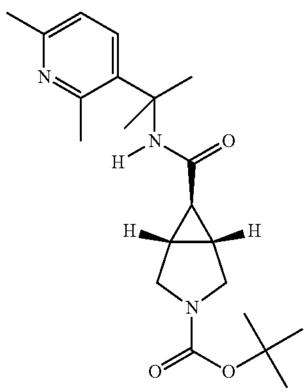 [SMILES: Cc1ccc(C(C)(C)NC(=O)[C@H]2[C@@H]3CN(C(=O)OC(C)(C)C)C[C@@H]32)c(C)n1] | Example 8ad (203 mg, 70% content, 0.87 mmol) | 0.96 2 | 374 |

The following example is synthesized in analogy to the preparation of example 9h:

| Example | Structure | Reactant(s) | HPLC-MS R$_t$ [min], method | MS (ESI pos, m/z) (M + H)$^+$ |
|---|---|---|---|---|
| 9af (mixture of stereo- isomers) | 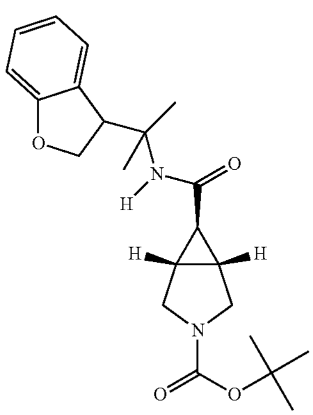 [SMILES: CC(C)(C)OC(=O)N1C[C@@H]2[C@H](C1)[C@H]2C(=O)NC(C)(C)C1COc2ccccc21] | Example 8ae (275 mg, 65% content, 1.01 mmol) | 1.25 2 | 387 |

The stereoisomers of the example 9af are separated by HPLC using a chiral stationary phase.

Method for Separation:

HPLC apparatus type: Waters 600 Pump, 2767 Autosampler, UV Detector 2489; column: Daicel chiralpack AD-H, 5.0 µm, 250 mm×20 mm; method: eluent hexane/IPA 80:20; flow rate: 15 mL/min, temperature: 25° C.; UV Detection: 230 nm.

Example 9ag: stereoisomer 1
Unknown absolute stereochemistry at OCH$_2$C marked with an asterisk

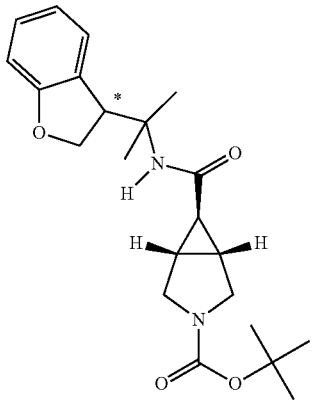 [SMILES: CC(C)(C)OC(=O)N1C[C@@H]2[C@H](C1)[C@H]2C(=O)NC(C)(C)C1COc2ccccc21]

Example 9ah: stereoisomer 2
Unknown absolute stereochemistry at OCH$_2$C marked with an asterisk

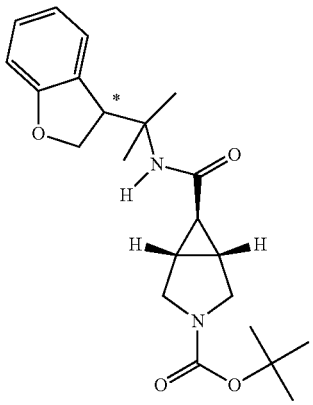 [SMILES: CC(C)(C)OC(=O)N1C[C@@H]2[C@H](C1)[C@H]2C(=O)NC(C)(C)C1COc2ccccc21]

| Example | Chiral HPLC (Method 16) R$_t$ [min] | HPLC-MS (Method 7a): R$_t$ [min] | MS (AFCl): m/z |
|---------|---|---|---|
| 9ag | 3.91 | 4.91 | 387 |
| 9ah | 4.95 | 4.92 | 387 |

The following example is synthesized in analogy to the preparation of example 9h:

| Example | Structure | Reactant(s) | HPLC-MS R$_t$ [min], method | MS (ESI pos, m/z) (M + H)$^+$ |
|---------|-----------|-------------|---|---|
| 9ai | 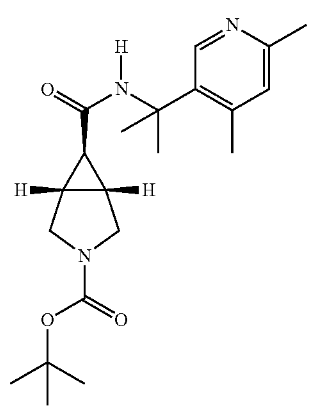 [SMILES: Cc1cc(C)c(C(C)(C)NC(=O)[C@H]2[C@@H]3CN(C(=O)OC(C)(C)C)C[C@@H]32)cn1] | Example 8ag (180 mg, 60% content, 0.66 mmol) | 0.96 2 | 374 |

The following example is synthesized in analogy to the preparation of example 9h:

| Example | Structure | Reactant(s) | HPLC-MS R$_t$ [min], method | MS (ESI pos, m/z) (M + H)$^+$ |
|---|---|---|---|---|
| 9aj (mixture of stereoisomers) | 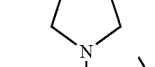 | Example 8af (520 mg, 46% content, 1.25 mmol) | 3.17 11 | 401 |

The stereoisomers of the example 9aj are separated by HPLC using a chiral stationary phase.

Method for Separation:

HPLC apparatus type: Waters 600 Pump, 2767 Autosampler, UV Detector 2489; column: Deicel chiralpack AD-H, 5.0 μm, 250 mm×20 mm; method: eluent hexane/IPA 75:25; flow rate: 15 mL/min, temperature: 25° C.; UV Detection: 230 nm.

Example 9ak: stereoisomer 1
Unknown absolute stereochemistry at CH$_2$CH$_2$C marked with an asterisk

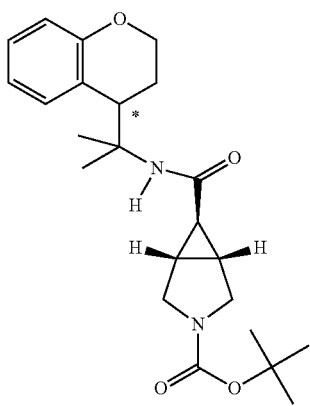 [SMILES: CC(C)(C)OC(=O)N1C[C@@H]2[C@H](C1)[C@H]2C(=O)NC(C)(C)C1CCOc2ccccc21]

-continued

Example 9al: stereoisomer 2
Unknown absolute stereochemistry at CH$_2$CH$_2$C marked with an asterisk

| Example | Chiral HPLC (Method 14) R$_t$ [min] | HPLC-MS (Method 11): R$_t$ [min] | MS (ESI pos, m/z) (M + H)$^+$ |
|---|---|---|---|
| 9ak | 3.54 | 3.16 | 401 |
| 9al | 4.17 | 3.16 | 401 |

Example 10a

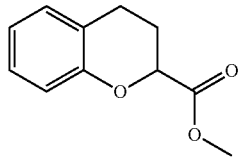

Trimethylsilyldiazomethane (10% in ethyl ether, 10.5 mL, 6.17 mmol) is added dropwise to 2-chromanecarboxylic acid (1 g, 5.61 mmol) in dry DCM (8 mL) and MeOH (0.8 mL) cooled to 0° C. Stirring is continued for 60 min, then the solvents are evaporated under reduced pressure to furnish the title compound (1 g, 95%).

UPLC-MS (Method 2): R$_t$=1.06 min
MS (ESI pos): m/z=193 (M+H)$^+$

Example 11a

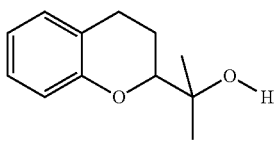

Under nitrogen flow, methylmagnesium bromide in 2-methyltetrahydrofuran (3.2M, 3 mL, 9.74 mmol) is added dropwise to example 10a (1 g, 4.82 mmol) dissolved in dry THF (20 mL) cooled to 0° C. Stirring is continued at 0° C. for 5 min followed by 2 h at rt. The reaction mixture is cooled to 0° C. and a saturated solution of NH$_4$Cl is added dropwise. EtOAc is added, the organic layer separated, washed with brine, dried over Na$_2$SO$_4$ and concentrated under reduced pressure to furnish the title compound (915 mg, 89%).

HPLC-MS (Method 8): R$_t$=2.72 min
MS (APCI): m/z=193 (M+H)$^+$

Example 12a

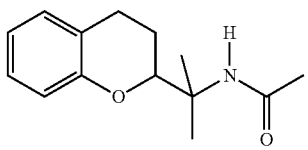 [SMILES: CC(=O)NC(C)(C)C1CCc2ccccc2O1]

Sulfuric acid (0.27 mL, 4.71 mmol) is added dropwise to example 11a (1 g, 4.82 mmol) dissolved in dry ACN (0.900 mL) and acetic acid (0.51 mL, 8.56 mmol) cooled to 0° C. Stirring is continued at 0° C. for 5 min followed by overnight at rt. 5M NH$_4$OH followed by EtOAc are added to the reaction mixture. The organic layer is washed with brine, dried over a phase separator cartridge and concentrated under reduced pressure to furnish a residue that is purified by flash chromatography (eluent 30-60% EtOAc/cyclohexane) to furnish the title compound (215 mg, 21%).

HPLC-MS (Method 8): R$_t$=2.82 min
MS (APCI): m/z=234 (M+H)$^+$

Example 13a

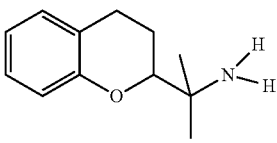

Potassium hydroxide (289 mg, 5.14 mmol) is added to example 12a (150 mg, 0.643 mmol) dissolved in 1,2 methoxyethanol (1 mL) and ethylene glycol (1 mL). The reaction mixture is heated at reflux overnight. Water and EtOAc are added to the reaction mixture cooled to rt and the organic layer is separated and dried using a phase separator cartridge. Solvents are removed under reduce pressure to furnish a residue, purified by preparative HPLC (stationary phase: Sunfire C18 ODB 5 μm 19×100 mm. Mobile phase: ACN/H$_2$O+CF3COOH 0.05%). Fractions containing the title compound are combined, acetonitrile is evaporated under reduced pressure, the aqueous layer is basified with sat. NaHCO$_3$ and extracted with DCM. The organic layer is separated and dried using a phase separator cartridge and the resulting solution is evaporated under reduced pressure to furnish the title compound (40 mg, 32%)

HPLC-MS (Method 8): R$_t$=2.20 min
MS (APCI): m/z=192 (M+H)$^+$

Example 14a

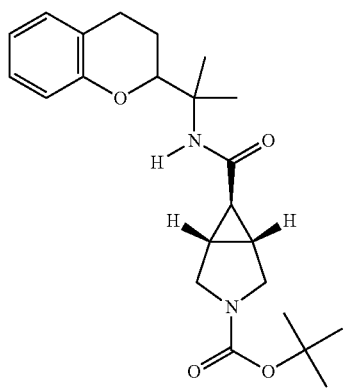 [SMILES: CC(C)(C)OC(=O)N1C[C@@H]2[C@H](C1)[C@H]2C(=O)NC(C)(C)C1CCc2ccccc2O1]

HATU (103 mg, 0.272 mmol) is added to meso-(1R,5S,6r)-3-(tert-butoxycarbonyl)-3-azabicyclo[3.1.0]hexane-6-carboxylic acid (48 mg, 0.21 mmol), example 13a (40 mg, 0.21 mmol) and DIPEA (109 μl, 0.627 mmol) in dry DMF (1 mL) and stirring is continued for 2 h at rt. Volatiles are evaporated under reduced pressure to furnish a residue that is diluted with ethyl acetate and washed with saturated NaHCO$_3$ and brine. The organic layer is separated, dried on a Phase separator cartridge and evaporated under reduce pressure to give a residue purified by flash chromatography (eluent 30-50% EtOAc/cyclohexane) to furnish the title compound (48 mg, 56%).

HPLC-MS (Method 8): R$_t$=3.73 min
MS (AFCI): m/z=401 (M+H)

Example 15a

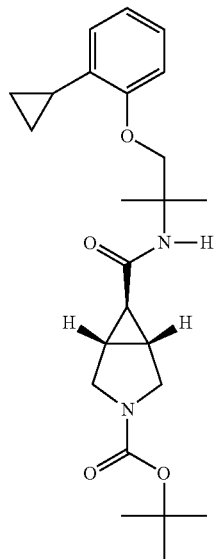 [SMILES: CC(C)(COc1ccccc1C1CC1)NC(=O)[C@H]1[C@@H]2CN(C(=O)OC(C)(C)C)C[C@@H]21]

Example 3e (150 mg, 0.330 mmol), potassium cyclopropyltrifluoroborate (122 mg, 0.827 mmol), palladium (II) acetate (22 mg, 0.099 mmol), tricyclohexylphosphine (56 mg, 0.199 mmol) and tri potassium phosphate (246 mg, 1.16 mmol) are dissolved in Toluene (2 mL) and water (0.200 mL) and the reaction mixture is heated at 120° C. for 2 h under microwave irradiation. The reaction is diluted with DCM/water. The organic layer is separated, dried and evaporated under reduce pressure to give a residue that is purified by preparative HPLC (stationary phase: Xbridge C18 5 μm 19×100 mm. Mobile phase: ACN/H$_2$O+NH$_4$COOH 5 mM). Fractions containing the title compound are combined, evaporated under reduced pressure and freeze-dried to furnish the title compound (105 mg, 77%).

UPLC-MS (Method 2): R$_t$=1.42 min
MS (ESI pos): m/z=415 (M+H)$^+$

The following example is synthesized in analogy to the preparation of example 15a:

Example 15c

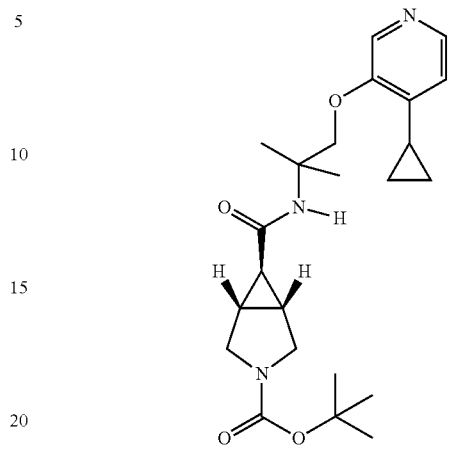

Example 5i (85 mg, 0.17 mmol) and cyclopropylboronic acid (22 mg, 0.254 mmol) in dry 1,2-dimethoxyethane (1 mL) are degassed with a flow of nitrogen for 5 minutes. Potassium carbonate (0.25 mL, 0.51 mmol) and tetrakis (triphenylphosphine) palladium(0) (20 mg, 0.017 mmol) are added and the reaction mixture is heated at 90° C. overnight. Cyclopropylboronic acid (43 mg, 0.50 mmol) and tetrakis (triphenylphosphine) palladium(0) (39 mg, 0.034 mmol) are added and the reaction mixture is heated under microwave irradiations at 120° C. for 40 min. Solvents are removed under reduce pressure to give a residue that is purified by preparative HPLC (stationary phase: Sunfire C18 ODB 5 μm 19×100 mm. Mobile phase: ACN/H$_2$O+CF3COOH 0.05%). Fractions containing the title compound are combined and evaporated under reduced pressure to furnish the title compound (48 mg, 83% content, 57%).

UPLC-MS (Method 2): R$_t$=1.12 min
MS (ESI pos): m/z=416 (M+H)$^+$

| Example | Structure | Reactant(s) | UPLC-MS R$_t$ [min], method | MS (ESI pos, m/z) (M + H)$^+$ |
|---|---|---|---|---|
| 15b | 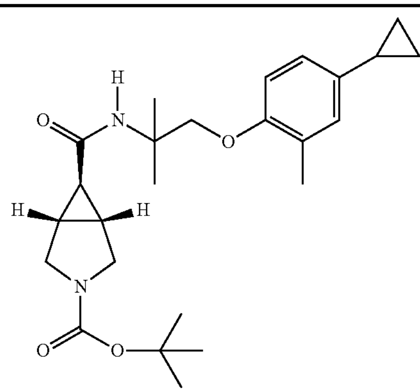 | Example 3k (300 mg, 0.629 mmol) | 1.52 2 | 429 |

Example 15d

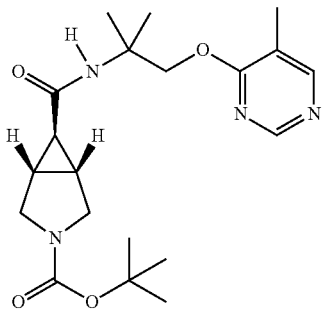 [SMILES: Cc1cncnc1OCC(C)(C)NC(=O)[C@H]1[C@@H]2CN(C(=O)OC(C)(C)C)C[C@@H]21]

Example 5g (140 mg, 0.283 mmol) is dissolved in EtOH (15 mL) and palladium (30 mg, 0.028 mmol) is added. The mixture is hydrogenated at 2 bar for 3 h. The catalyst is removed by filtration and washed with MeOH. The resulting solution is evaporated under reduced pressure to furnish a residue that is purified by flash chromatography (eluent 60-90% EtOAc/cyclohexane) to furnish the title compound (60 mg, 54%).
HPLC-MS (Method 8): $R_t$=2.83 min
MS (AFCI): m/z=391 (M+H)$^+$ Example 16a

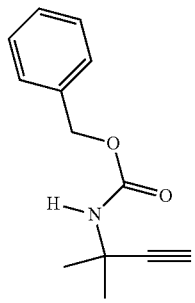 [SMILES: C#CC(C)(C)NC(=O)OCc1ccccc1]

N-(Benzyloxycarbonyloxy)succinimide (5.2 g, 20.90 mmol) is added to a solution of 1,1-dimethylpropargylamine (2 mL, 19 mmol) and TEA (3 mL, 20.90 mmol) in dry THF (60 mL) at 0° C. The mixture is allowed to reach rt and stirring is continued overnight. Volatiles are evaporated under reduced pressure and the resulting residue taken up with EtOAc and washed with water and brine. The organic layer is dried and evaporated under reduced pressure to furnish a residue that is purified by flash chromatography (eluent 0-20% EtOAc/cyclohexane) to furnish the title compound (2.7 g, 65%).
HPLC-MS (Method 8): $R_t$=2.87 min
MS (APCI): m/z=218 (M+H)$^+$ Example 17a 2-Bromo-3-(trifluoromethyl)pyridine (1.5 g, 6.63 mmol) is added to a solution of example 16a (500 mg, 2.21 mmol) in TEA (3.5 mL, 25.25 mmol) and dry ACN (14 mL) at rt. Then Copper (I) Iodide (84 mg, 0.442 mmol) and dichlorobis(triphenylphosphine)palladium(II) (155 mg, 0.221 mmol) are added and stirring is continued overnight. Solvent is evaporated under reduced pressure and the crude is purified by flash chromatography (eluent 0-40% EtOAc/cyclohexane) to furnish the title compound (800 mg, 99%).
UPLC-MS (Method 2): $R_t$=1.23 min
MS (ESI pos): m/z=363 (M+H)$^+$ The following example is synthesized in analogy to the preparation of example 17a:

| Example | Structure | Reactants(s) | UPLC-MS $R_t$ [min], method | MS (ESI pos, m/z) (M + H)$^+$ |
|---|---|---|---|---|
| 17b | 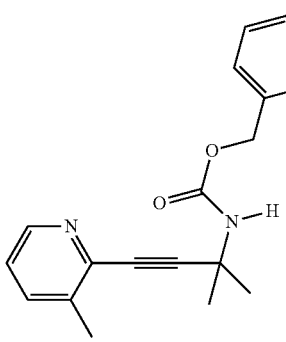 | 2-Bromo-3-methylpyridine (0.74 mL, 6.628 mmol) | 1.152 | 309 |

Example 18a

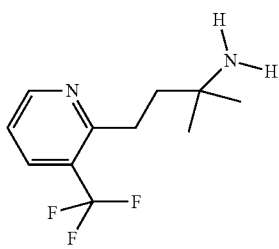 [SMILES: CC(C)(N)CCc1ncccc1C(F)(F)F]

Example 17a (800 mg, 2.075 mmol) is dissolved in MeOH (30 mL) and palladium (50 mg, 0.470 mmol) is added. The mixture is hydrogenated at 1 bar overnight and then at 3 bar for 72 h. The catalyst is removed by filtration and washed with MeOH. The resulting solution is evaporated under reduced pressure to furnish the title compound (432 mg, 90%).

HPLC-MS (Method 8): $R_t$=1.93 min

MS (AFCI): m/z=233 (M+H)$^+$

The following example is synthesized in analogy to the preparation of example 18a:

| Example | Structure | Reactants(s) | UPLC-MS $R_t$ [min], method | MS (ESI pos, m/z) (M + H)$^+$ |
|---|---|---|---|---|
| 18b | 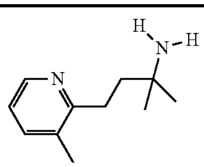 | Example 17b (540 mg, 1.751 mmol) | 0.602 | 179 |

Example 19a

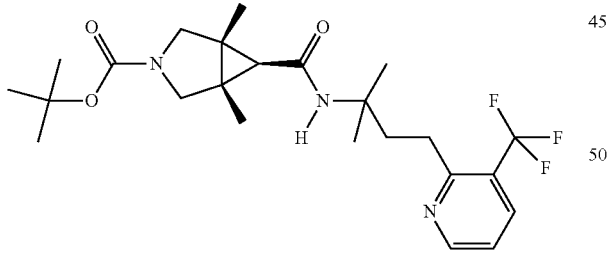

HATU (184 mg, 0.484 mmol) is added to meso-(1R,5S,6r)-3-(tert-butoxycarbonyl)-3-azabicyclo[3.1.0]hexane-6-carboxylic acid (100 mg, 0.440 mmol), example 18a (102 mg, 0.440 mmol) and DIPEA (228 μl, 1.32 mmol) in dry DMF (6 mL) and stirring is continued for 2 h. Volatiles are evaporated under reduced pressure and the crude is taken up with ethyl acetate and washed with saturated NaHCO$_3$ and brine. The organic layers is separated, dried on a Phase separator cartridge and evaporated under reduce pressure to give a residue that is purified by flash chromatography (eluent 0-70% EtOAc/cyclohexane) to furnish the title compound (142 mg, 73%).

UPLC-MS (Method 2): $R_t$=1.24 min

MS (ESI pos): m/z=442 (M+H)$^+$

The following example is synthesized in analogy to the preparation of example 19a:

| Example | Structure | Reactant(s) | HPLC-MS $R_t$ [min], method | MS (APCI, m/z) (M + H)$^+$ |
|---|---|---|---|---|
| 19b | 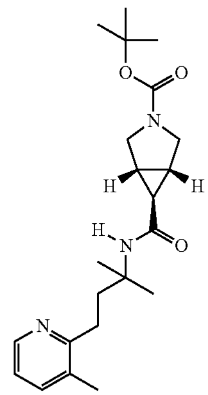 [SMILES: Cc1cccnc1CCC(C)(C)NC(=O)[C@H]1[C@@H]2CN(C(=O)OC(C)(C)C)C[C@@H]21] | Example 18b (78 mg, 0.440 mmol) | 3.038 | 388 |

Example 20a

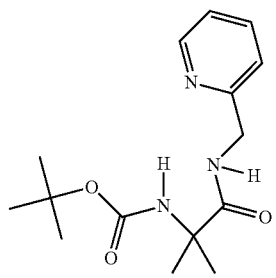 [SMILES: CC(C)(C)OC(=O)NC(C)(C)C(=O)NCc1ccccn1]

2-(aminomethyl)pyridine (532 mg, 4.920 mmol), TEA (2 mL, 14.760 mmol) and TBTU (1.6 g, 4.920 mmol) are added in sequence to 2-tert-butoxycarbonylamino-2-methylpropionic acid (1 g, 4.920 mmol) dissolved in dry THF (10 mL). Stirring is continued overnight at rt. The solvent is evaporated, the residue is diluted with ethyl acetate and washed with 1N NaOH solution and brine. The organic layer is dried, filtered and evaporated under reduced pressure to give a residue that is purified by flash chromatography (eluent 50-100% EtOAc/cyclohexane) to furnish the title compound (835 mg, 58%).

UPLC-MS (Method 2): $R_t$=0.79 min

MS (ESI pos): m/z=294 (M+H)$^+$

The following example is synthesized in analogy to the preparation of example 20a:

| Example | Structure | Reactants(s) | UPLC-MS R$_t$ [min], method | MS (ESI pos, m/z) (M + H)$^+$ |
|---|---|---|---|---|
| 20b | 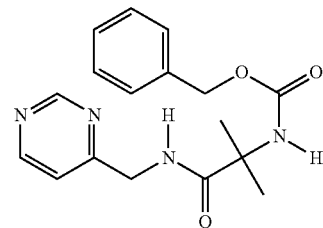 [SMILES: CC(C)(NC(=O)OCc1ccccc1)C(=O)NCc1ccncn1] | 1-Pyridin-2-yl-ethylamine (285 mg) | 0.872 | 308 |

Example 20c

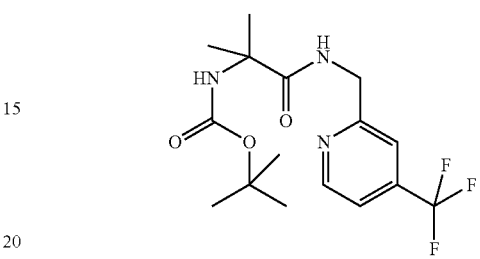

4-aminomethylpyrimidine (1 g, 9.16 mmol) is dissolved in dry DCM (20 mL), TEA (3.8 mL, 27.849 mmol), HATU (3.5 g, 9.16 mmol), N-carbobenzyloxy-2-methylalanine (2.1 g, 9.16 mmol) are added and the mixture is stirred at rt overnight. The reaction is diluted with water, the organic layer is washed with 1N NaOH and brine, dried, filtered and evaporated to give a residue that is purified by flash chromatography (eluent EtOAc 100%) to furnish the title compound (1.6 g)

UPLC-MS (Method 2): R$_t$=0.76 min
MS (ESI pos): m/z=329 (M+H)$^+$

Example 20d

C-(4-Trifluoromethyl-pyridin-2-yl)-methylamine dihydrochloride (0.5 g, 2.01 mmol), 2-tert-butoxycarbonylamino-2-methylpropionic acid (0.45 g, 2.21 mmol), TBTU (0.71 g, 2.21 mmol) and triethylamine (1.15 mL, 8.23 mmol) are combined in dichloromethane (10 mL) and the mixture stirred for 1 hour. The mixture is washed with 0.2M aqueous NaOH, dried over sodium sulphate and the solvent removed under vacuum. The residue is purified by flash chromatography (eluent 0-100% ethyl acetate in cyclohexane) to give the title compound (703 mg, 97%).

UPLC-MS (Method 2): R$_t$=1.00 min
MS (ESI pos): m/z=362 (M+H)$^+$

The following examples are synthesized in analogy to the preparation of example 20d (using HATU as the coupling agent where specified):

| Example | Structure | Reactant(s) Conditions | LC-MS R$_t$ [min], method | MS (ESI pos or APCI, m/z) (M + H)$^+$ |
|---|---|---|---|---|
| 20e | 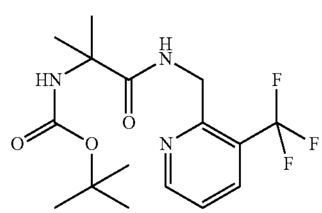 [SMILES: CC(C)(C)OC(=O)NC(C)(C)C(=O)NCc1ncccc1C(F)(F)F] | C-(3-trifluoromethyl-pyridin-2-yl)methylamine hydrochloride (300 mg) | 1.02 Method 2 | 362 |
| 20f | 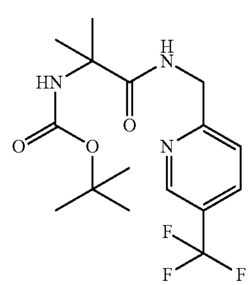 [SMILES: CC(C)(C)OC(=O)NC(C)(C)C(=O)NCc1ccc(C(F)(F)F)cn1] | C-(5-trifluoromethyl-pyridin-2-yl)methylamine hydrochloride (500 mg) | 1.04 Method 2 | 362 |

| Example | Structure | Reactant(s) Conditions | LC-MS R$_t$ [min], method | MS (ESI pos or APCI, m/z) (M + H)$^+$ |
|---|---|---|---|---|
| 20g | 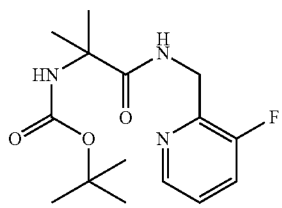 [SMILES: CC(C)(C)OC(=O)NC(C)(C)C(=O)NCc1ncccc1F] | 1-(3-fluoropyridin-2-yl)methanamine (1 g) | 0.82 Method 2 | 312 |
| 20h | 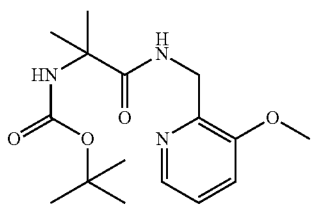 [SMILES: COc1cccnc1CNC(=O)C(C)(C)NC(=O)OC(C)(C)C] | C-(3-Methoxy-pyridin-2-yl)-methylamine dihydrochloride (1 g) HATU overnight reaction | 0.68 Method 1 | 324 |
| 20i | 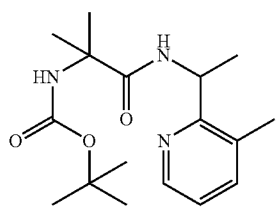 [SMILES: Cc1cccnc1C(C)NC(=O)C(C)(C)NC(=O)OC(C)(C)C] | 1-(3-methyl-2-pyridinyl)ethanamine (1 g) HATU 4 day reaction | 0.98 Method 2 | 322 |
| 20j | 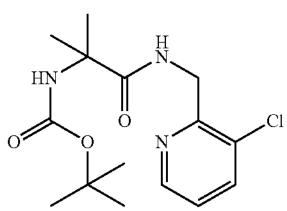 [SMILES: CC(C)(C)OC(=O)NC(C)(C)C(=O)NCc1ncccc1Cl] | (3-chloropyridin-2-yl)methanamine (1 g) HATU overnight reaction | 0.91 Method 1 | 328/330 |
| 20k | 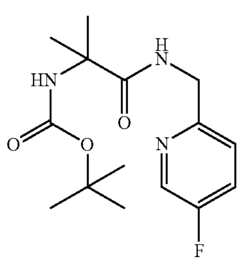 [SMILES: CC(C)(C)OC(=O)NC(C)(C)C(=O)NCc1ccc(F)cn1] | (5-fluoropyridin-2-yl)methanamine dihydrochloride (1 g) HATU 4 day reaction | 0.85 Method 2 | 312 |
| 20l | 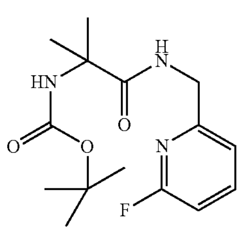 [SMILES: CC(C)(C)OC(=O)NC(C)(C)C(=O)NCc1cccc(F)n1] | (6-fluoropyridin-2-yl)methanamine (1 g) overnight reaction | 2.05 Method 11 | 310 (ES−) [M − H]− |

| Example | Structure | Reactant(s) Conditions | LC-MS R$_t$ [min], method | MS (ESI pos or APCI, m/z) (M + H)$^+$ |
|---|---|---|---|---|
| 20m | 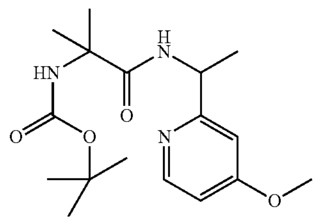 [SMILES: COc1ccnc(C(C)NC(=O)C(C)(C)NC(=O)OC(C)(C)C)c1] | 1-(4-Methoxy-pyridin-2-yl)-ethylamine hydrochloride prepared as described in DE2415063 (317 mg) HATU overnight reaction | 0.98 Method 2 | 338 |
| 20n | 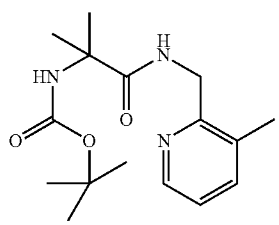 [SMILES: Cc1cccnc1CNC(=O)C(C)(C)NC(=O)OC(C)(C)C] | C-(3-Methyl-pyridin-2-yl)-methylamine (509 mg) overnight reaction | 3.60 Method 7a | 308 |
| 20o | 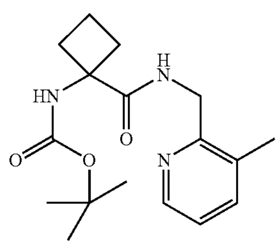 [SMILES: Cc1cccnc1CNC(=O)C1(NC(=O)OC(C)(C)C)CCC1] | C-(3-Methyl-pyridin-2-yl)-methylamine (500 mg) Boc-1-amino-1-cyclobutane-carboxylic acid (880 mg) overnight reaction | 0.90 Method 2 | 320 |
| 20p | 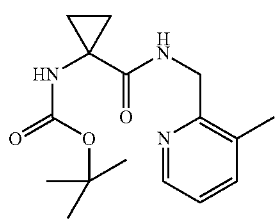 [SMILES: Cc1cccnc1CNC(=O)C1(NC(=O)OC(C)(C)C)CC1] | C-(3-Methyl-pyridin-2-yl)-methylamine (500 mg) Boc-1-amino-1-cyclopropane-carboxylic acid (823 mg) overnight reaction | 0.66 Method 1 | 306 |
| 20q | 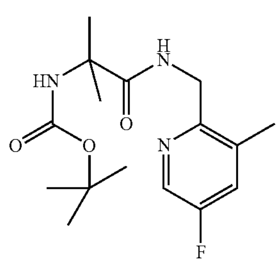 [SMILES: Cc1cc(F)cnc1CNC(=O)C(C)(C)NC(=O)OC(C)(C)C] | C-(5-fluoro-3-methyl-pyridin-2-yl)-methylamine (202 mg) HATU overnight reaction | 1.04 Method 2 | 326 |
| 20r | 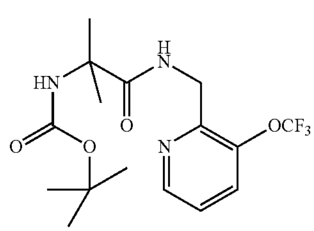 [SMILES: CC(C)(C)OC(=O)NC(C)(C)C(=O)NCc1ncccc1OC(F)(F)F] | C-(3-trifluoromethoxy pyridin-2-yl)-methylamine (860 mg) overnight reaction | 1.09 Method 2 | 378 |

-continued

| Example | Structure | Reactant(s) Conditions | LC-MS R$_t$ [min], method | MS (ESI pos or APCI, m/z) (M + H)$^+$ |
|---|---|---|---|---|
| 20s | 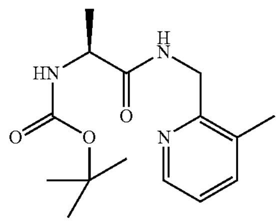 [SMILES: Cc1cccnc1CNC(=O)[C@H](C)NC(=O)OC(C)(C)C] | C-(3-Methyl-pyridin-2-yl)-methylamine (1.94 g) Boc-Ala-OH (3.0 g) overnight reaction | 0.93 Method 2 | 294 |
| 20t | 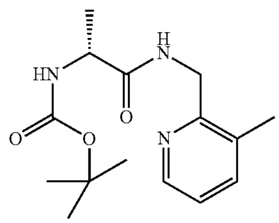 [SMILES: Cc1cccnc1CNC(=O)[C@@H](C)NC(=O)OC(C)(C)C] | C-(3-Methyl-pyridin-2-yl)-methylamine (1.61 g) Boc-D-Ala-OH (2.50 g) overnight reaction | 0.93 Method 2 | 294 |
| 20u | 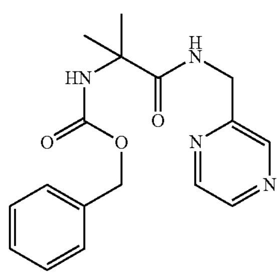 [SMILES: CC(C)(NC(=O)OCc1ccccc1)C(=O)NCc1cnccn1] | 2-Aminomethyl pyrazine (1.00 g) Cbz-Aib-OH (2.17 g) overnight reaction | 0.78 Method 2 | 329 |
| 20v | 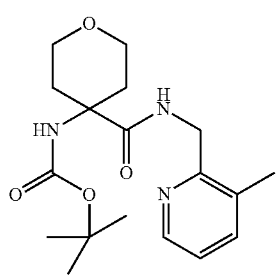 [SMILES: Cc1cccnc1CNC(=O)C1(NC(=O)OC(C)(C)C)CCOCC1] | C-(3-Methyl-pyridin-2-yl)-methylamine (470 mg) 4-N-Boc-amino-4-carboxytetrahydro pyran (945 mg) 3 day reaction | 0.86 Method 2 | 350 |
| 20w | 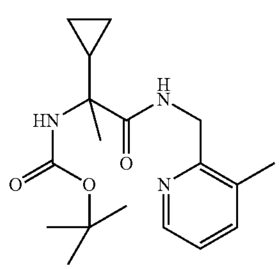 [SMILES: Cc1cccnc1CNC(=O)C(C)(NC(=O)OC(C)(C)C)C1CC1] | C-(3-Methyl-pyridin-2-yl)-methylamine (530 mg) 2-([(tert-butoxy)carbonyl] amino)-2-cyclopropyl propanoic acid (1.0 g) overnight reaction | 1.02 Method 2 | 334 |

Example 21a

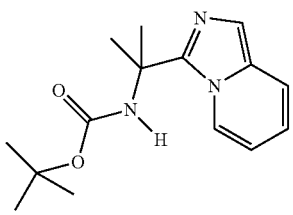 [SMILES: CC(C)(C)OC(=O)NC(C)(C)c1ncc2ccccn12]

Example 20a (685 mg, 2.335 mmol) is dissolved in DCM (10 mL) and cooled to 0° C., then Burgess reagent (610 mg, 2.560 mmol) is added. The mixture is allowed to reach rt and stirring is continued overnight. The reaction mixture is washed with water and brine. The organic layer is dried, filtered and evaporated under reduced pressure to give a residue that is purified by flash chromatography (eluent EtOAc/cyclohexane 30:70) to furnish the title compound (258 mg, 40%).

UPLC-MS (Method 2): $R_t$=0.91 min
MS (ESI pos): m/z=276 (M+H)$^+$

The following example is synthesized in analogy to the preparation of example 21a:

Example 21d

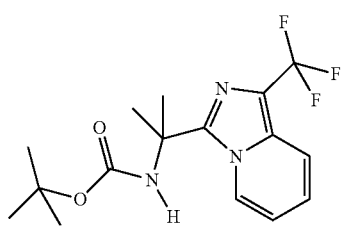

Example 21c (260 mg, 90% content, 0.583 mmol), 2,2-difluoro-2-(fluorosulfonyl)acetate (0.370 mL, 2.916 mmol) and copper (I) iodide (133 mg, 0.700 mmol) are dissolved in 1-methyl-2-pyrrolidinone (4 mL) and the reaction is stirred at 110° for 90 minutes. The mixture is cooled, diluted with water and extracted with ethyl acetate. The organic extracts are dried and the solvent removed. The residue is purified by flash chromatography (0-50% EtOAc in cyclohexane) to give the title compound (51 mg, 90% content, 23%)

UPLC-MS (Method 2): $R_t$=1.21 min
MS (ESI pos): m/z=344 (M+H)$^+$

| Example | Structure | Reactant(s) | UPLC-MS $R_t$ [min], method | MS (ESI pos, m/z) (M + H)$^+$ |
|---|---|---|---|---|
| 21b | 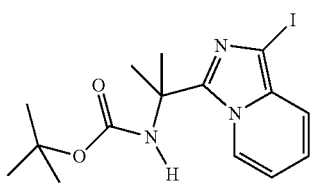 [SMILES: CC(C)(C)OC(=O)NC(C)(C)c1nc(I)c2ccccn12] | Example 20b (470 mg, 1.53 mmol) | 0.97  2 | 290 |

Example 21c

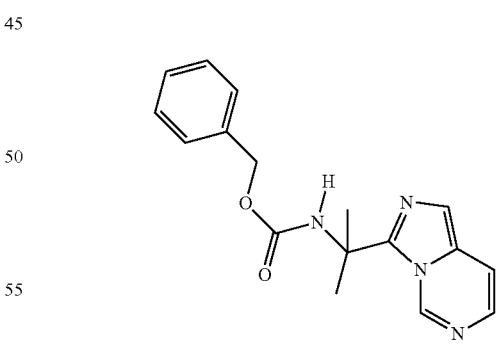

Example 21a (400 mg, 1.453 mmol), N-iodosuccinimide (654 mg, 2.905 mmol) and pyridinium p-toluenesulfonate (36 mg, 0.15 mmol) are dissolved in DCM (5 mL) and the reaction is stirred for 1 h.

The mixture is shaken with 10% sodium thiosulfate solution, the phases separated, the organic phase dried and the solvent removed. The residue is purified by flash chromatography (0-100% EtOAc in cyclohexane) to give the title compound (260 mg, 90% content, 45%)

UPLC-MS (Method 2): $R_t$=1.17 min
MS (ESI pos): m/z=402 (M+H)$^+$

Example 21e

Example 20c (841 mg) is suspended in phosphorus oxychloride (17 mL, 177.39 mmol) and 8 drops of dry DMF are added. The mixture is heated at 100° C. for 3 h. The mixture is cooled and solvent evaporated. The residue is partioned in a mixture of 1N NaOH and EtOAc. The organic layer is washed with brine, dried filtered and evaporated to give a residue purified by flash chromatography (first eluent EtOAc 100%, second eluent MeOH 100%) to furnish the title compound (70 mg)

UPLC-MS (Method 2): $R_t$=0.73 min

MS (ESI pos): m/z=311 (M+H)$^+$

Example 21f

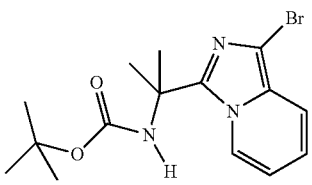 [SMILES: CC(C)(C)OC(=O)NC(C)(C)c1nc(Br)c2ccccn12]

Example 21a (998 mg, 3.62 mmol) is dissolved in dichloromethane (10 mL) and cooled to 0° C. N-bromosuccinimide (677 mg, 3.81 mmol) is added and the mixture is stirred for one hour. Saturated sodium thiosulfate aqueous solution is added, the mixture shaken, the phases separated, the organic phase dried and the solvent removed under vacuum. The residue is purified by flash chromatography (0-50% ethyl acetate in cyclohexane) to give the title compound (785 mg, 61%).

UPLC-MS (Method 2): $R_t$=1.13 min

MS (ESI pos): m/z=354/356 (M+H)$^+$

Example 21g

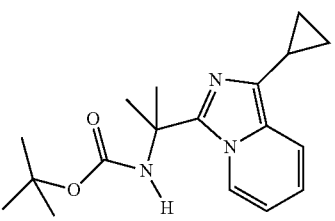 [SMILES: CC(C)(C)OC(=O)NC(C)(C)c1nc(C2CC2)c2ccccn12]

Example 21f (200 mg, 0.56 mmol), potassium cyclopropyltrifluoroborate (167 mg, 1.13 mmol), Potassium triphosphate (419 mg, 1.98 mmol), tricyclohexylphosphine (32 mg, 0.11 mmol) and palladium (II) acetate (13 mg, 0.06 mmol) are suspended in a mixture of toluene (5 mL) and water (0.2 mL) in a microwave vial and degassed for 5 minutes with a flow of nitrogen gas. The mixture is heated under microwave irradiation for 5 hours at 120° C. then allowed to cool and diluted with ethyl acetate and water. The phases are separated, the organic phase dried over sodium sulfate and the solvent removed under vacuum. The residue is purified by flash chromatography (0-2% methanol in dichloromethane) to give the title compound (40 mg, 23%).

UPLC-MS (Method 2): $R_t$=1.16 min

MS (ESI pos): m/z=316 (M+H)$^+$

Example 21h

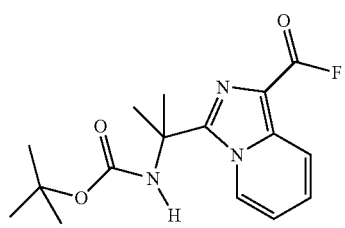 [SMILES: CC(C)(C)OC(=O)NC(C)(C)c1nc(C(=O)F)c2ccccn12]

The title compound is isolated as an impure byproduct in the preparation of Example 21d.

UPLC-MS (Method 2): $R_t$=1.03 min

MS (ESI pos): m/z=322 (M+H)$^+$

Example 21i

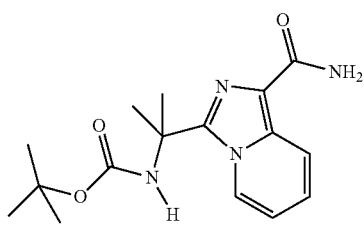 [SMILES: CC(C)(C)OC(=O)NC(C)(C)c1nc(C(N)=O)c2ccccn12]

Example 21h (52 mg, crude material) is suspended in 0.5 M ammonia solution in dry dioxane and the mixture stirred overnight. The solvent is removed under vacuum to give the title compound as a crude material which is used without further purification (52 mg, 50% content).

UPLC-MS (Method 2): $R_t$=0.86 min

MS (ESI pos): m/z=319 (M+H)$^+$

Example 21j

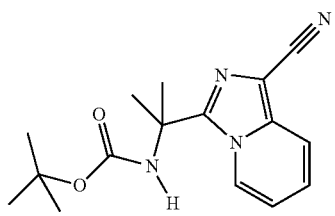 [SMILES: CC(C)(C)OC(=O)NC(C)(C)c1nc(C#N)c2ccccn12]

Example 21i (51 mg, 50% content) and Burgess reagent (38 mg, 0.16 mmol) are suspended in dry dichloromethane (5 mL) and the mixture stirred overnight. Water is added, the phases are separated, the organic phase dried over sodium sulfate and the solvent removed under vacuum. The residue is purified by flash chromatography (0-50% ethyl acetate in cyclohexane) to give the title compound (22 mg, 91%).

UPLC-MS (Method 2): $R_t$=1.00 min

MS (ESI pos): m/z=301 (M+H)$^+$

Example 21k

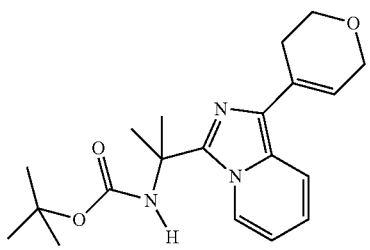 [SMILES: CC(C)(C)OC(=O)NC(C)(C)c1nc(C2=CCOCC2)c2ccccn12]

Example 21f (229 mg, 0.65 mmol), potassium 3,6-dihydro-2H-pyran-4-yl(trifluoro)boron (184 mg, 0.97 mmol), Potassium triphosphate (412 mg, 1.94 mmol) and tetrakis(triphenylphosphine)palladium(0) (75 mg, 0.06 mmol) are suspended in a mixture of dioxane (5 mL) and water (0.5 mL) in a screwtop tube and degassed for 5 minutes with a flow of argon gas. The mixture is heated 4 hours at 100° C. then allowed to cool and diluted with ethyl acetate and water. The phases are separated, the organic phase washed with brine and the solvent removed under vacuum. The residue is purified by flash chromatography (0-100% ethyl acetate in cyclohexane) to give the title compound (41 mg).

UPLC-MS (Method 1): $R_t$=0.81 min

MS (ESI pos): m/z=358 (M+H)$^+$

Example 21l

Example 20h (1.51 g, 4.67 mmol) is suspended in DCM (40 mL) and Burgess reagent (1.22 g, 5.14 mmol) is added. The mixture is allowed to stirred overnight then washed with 0.2M aqueous NaOH solution. The organic layer is dried, filtered and evaporated under reduced pressure to give a residue that is purified by flash chromatography (eluent 0-100% ethyl acetate in cyclohexane) to furnish the title compound (751 mg, 53%).

UPLC-MS (Method 1): $R_t$=0.77 min

MS (ESI pos): m/z=306 (M+H)$^+$

The following examples are synthesized in analogy to the preparation of example 21l:

| Example | Structure | Reactant(s) Conditions | LC-MS $R_t$ [min], method | MS (ESI pos or APCl, m/z) (M + H)$^+$ |
|---|---|---|---|---|
| 21m | 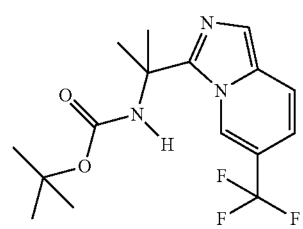 [SMILES: CC(C)(C)OC(=O)NC(C)(C)c1ncc2ccc(C(F)(F)F)cn12] | Example 20f (630 mg, 1.74 mmol) | 0.97 Method 1 | 344 |
| 21n | 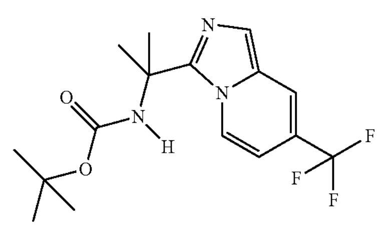 [SMILES: CC(C)(C)OC(=O)NC(C)(C)c1ncc2cc(C(F)(F)F)ccn12] | Example 20d (703 mg, 1.95 mmol) 2.3 equivalents of Burgess reagent. 3 days room temp then 8 h at 70° C. | 1.08 Method 2 | 344 |
| 21o | 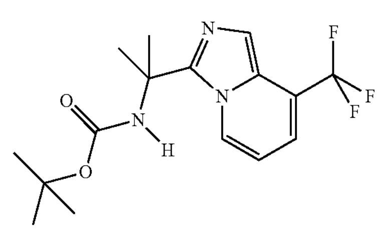 [SMILES: CC(C)(C)OC(=O)NC(C)(C)c1ncc2c(C(F)(F)F)cccn12] | Example 20e (495 mg, 1.37 mmol) 3 days reaction | 1.11 Method 2 | 344 |

-continued

| Example | Structure | Reactant(s) Conditions | LC-MS R$_t$ [min], method | MS (ESI pos or APCI, m/z) (M + H)$^+$ |
|---|---|---|---|---|
| 21p | 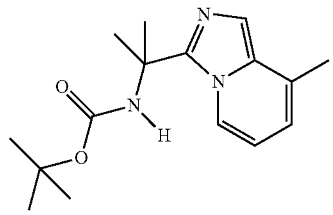 [SMILES: Cc1cccn2c(C(C)(C)NC(=O)OC(C)(C)C)ncc12] | Example 20n (1.20 g, 3.55 mmol) 4 days reaction | 4.02 Method 7a | 290 |
| 21q | 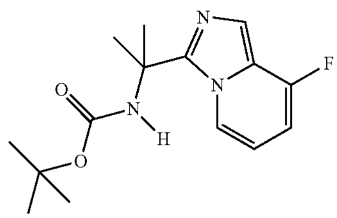 [SMILES: CC(C)(C)OC(=O)NC(C)(C)c1ncc2c(F)cccn12] | Example 20g (1.0 g, 3.21 mmol) 3 days reaction | 0.97 Method 2 | 294 |
| 21r | 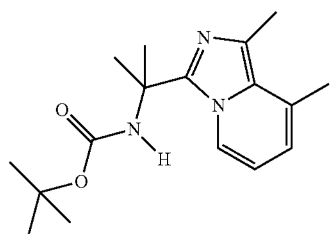 [SMILES: Cc1cccn2c(C(C)(C)NC(=O)OC(C)(C)C)nc(C)c12] | Example 20i (2.04 g, 6.33 mmol) | 1.05 Method 2 | 304 |
| 21s | 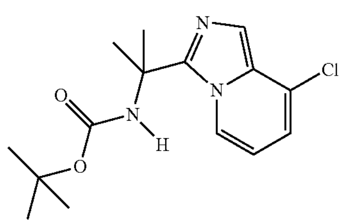 [SMILES: CC(C)(C)OC(=O)NC(C)(C)c1ncc2c(Cl)cccn12] | Example 20j (2.30 g, 7.02 mmol) | 0.84 Method 1 | 310/312 |
| 21t | 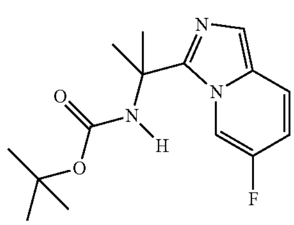 [SMILES: CC(C)(C)OC(=O)NC(C)(C)c1ncc2ccc(F)cn12] | Example 20k (0.55 g, 1.78 mmol) 28 days reaction | 0.93 Method 2 | 294 |
| 21u | 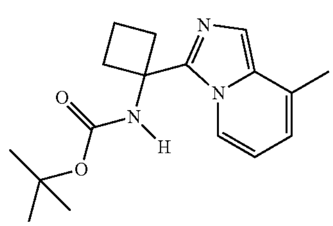 [SMILES: Cc1cccn2c(C3(NC(=O)OC(C)(C)C)CCC3)ncc12] | Example 20o (1.16 g, 3.63 mmol) | 1.12 Method 2 | 302 |
| 21v | 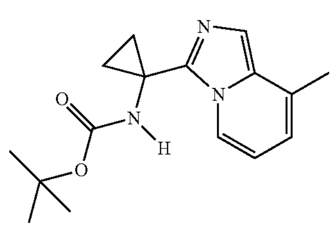 [SMILES: Cc1cccn2c(C3(NC(=O)OC(C)(C)C)CC3)ncc12] | Example 20p (0.77 g, 2.52 mmol) | $^1$H NMR (500 MHz, DMSO-d$_6$): (rotamers) δ 1.18 (br, m, 2H), 1.23 (br, m, 2H), 1.30 (br, s, 9H), 2.34 (s, 3H), 6.56 (ddd, J = 1.1, 2.0, 6.5 Hz, 1H), 6.63 (dd, J = 6.7 Hz, 1H), 7.22 (d, J = 0.6 Hz, 1H), 7.90 (br, s, 1H), 8.48 (br, d, J = 4.7 Hz, 1H) | |

-continued

| Example | Structure | Reactant(s) Conditions | LC-MS R<sub>t</sub> [min], method | MS (ESI pos or APCI, m/z) (M + H)<sup>+</sup> |
| --- | --- | --- | --- | --- |
| 21x | 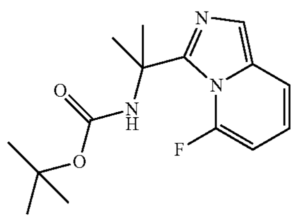 [SMILES: CC(C)(C)OC(=O)NC(C)(C)c1ncc2cccc(F)n12] | Example 20l (260 mg, 0.84 mmol) 3 days reaction | 0.75 Method 1 | 294 |
| 21y | 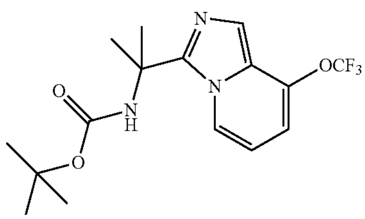 [SMILES: CC(C)(C)OC(=O)NC(C)(C)c1ncc2c(OC(F)(F)F)cccn12] | Example 20r (130 mg, 0.61 mmol) | 1.19 Method 2 | 360 |
| 21z | 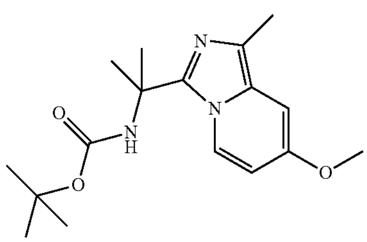 [SMILES: COc1ccn2c(C(C)(C)NC(=O)OC(C)(C)C)nc(C)c2c1] | Example 20m (260 mg, 0.77 mmol) 4 days reaction | 1.05 Method 2 | 320 |
| 21aa | 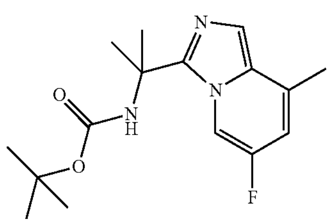 [SMILES: Cc1cc(F)cn2c(C(C)(C)NC(=O)OC(C)(C)C)ncc12] | Example 20q (102 mg, 0.31 mmol) | 1.11 Method 2 | 308 |
| 21ab | 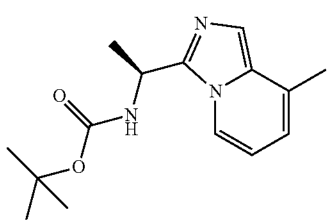 [SMILES: Cc1cccn2c([C@H](C)NC(=O)OC(C)(C)C)ncc12] | Example 20s (3.60 g, 12.3 mmol) | 1.11 Method 2 | 276 |
| 21ac | 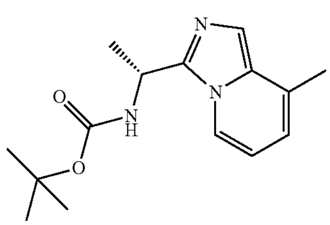 [SMILES: Cc1cccn2c([C@@H](C)NC(=O)OC(C)(C)C)ncc12] | Example 20t (3.50 g, 11.9 mmol) | 1.07 Method 2 | 276 |

Example 21ad

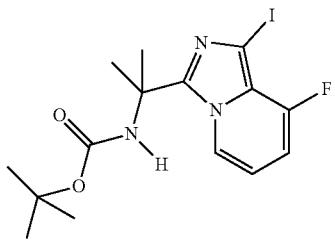 [SMILES: CC(C)(C)OC(=O)NC(C)(C)c1nc(I)c2c(F)cccn12]

Example 21q (200 mg, 0.68 mmol) is suspended in DCM (4 mL) and cooled to 0° C. N-iodosucciminide (153 mg, 0.68 mmol) is added and the mixture stirred at 0° C. for 30 minutes. 10% aqueous sodium thiosulfate solution is added, the mixture shaken and the phases separated. The organic layer is evaporated under reduced pressure to give a residue that is purified by flash chromatography (eluent 0-50% ethyl acetate in cyclohexane) to furnish the title compound (200 mg, 70%).

UPLC-MS (Method 2): $R_t$=1.17 min
MS (ESI pos): m/z=420 (M+H)$^+$

Example 21ae

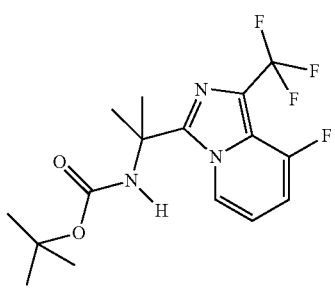 [SMILES: CC(C)(C)OC(=O)NC(C)(C)c1nc(C(F)(F)F)c2c(F)cccn12]

Example 21ad (200 mg, 0.48 mmol), methyl 2,2-difluoro-2-(fluorosulfonyl)acetate (182 µL, 1.43 mmol) and copper (I)iodide (136 mg, 0.72 mmol) are suspended in N-methylpyrrolidinone (4 mL) and heated at 110° C. for 50 minutes. The mixture is cooled in ice, diluted with water and extracted with ethyl acetate. The organic layer is evaporated under reduced pressure to give a residue that is purified by flash chromatography (eluent 0-50% ethyl acetate in cyclohexane) to furnish the title compound (150 mg, 78%).

UPLC-MS (Method 12): $R_t$=3.68 min
MS (ESI pos): m/z=462 (M+H)$^+$

Example 21af

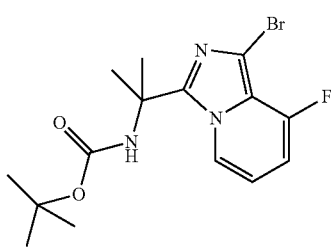 [SMILES: CC(C)(C)OC(=O)NC(C)(C)c1nc(Br)c2c(F)cccn12]

Example 21q (1.3 g, 4.43 mmol) is suspended in DCM (12 mL) and cooled to 0° C. N-bromosucciminide (0.83 g, 4.65 mmol) is added and the mixture stirred at 0° C. for 60 minutes. Saturated aqueous sodium thiosulfate solution is added, the mixture stirred for 30 minutes and the phases separated. The organic layer is evaporated under reduced pressure to give a residue that is purified by flash chromatography (eluent 0-50% ethyl acetate in cyclohexane) to furnish the title compound (600 mg, 36%).

UPLC-MS (Method 2): $R_t$=1.22 min
MS (ESI pos): m/z=372/374 (M+H)$^+$

Example 21ag

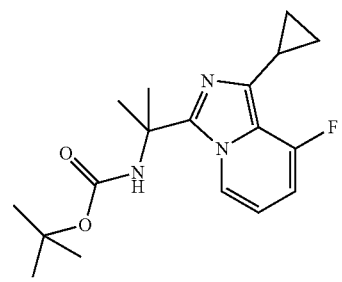 [SMILES: CC(C)(C)OC(=O)NC(C)(C)c1nc(C2CC2)c2c(F)cccn12]

Example 21af (600 mg, 1.61 mmol), potassium cyclopropyltrifluoroborate (477 mg, 3.22 mmol), Potassium triphosphate (1.20 g mg, 5.64 mmol), tricyclohexylphosphine (90 mg, 0.32 mmol) and palladium (II) acetate (36 mg, 0.16 mmol) are suspended in a mixture of toluene (17 mL) and water (0.2 mL) in a microwave vial and degassed for 5 minutes with a flow of nitrogen gas. The mixture is heated under microwave irradiation for 2×5 hours at 120° C. then allowed to cool and diluted with ethyl acetate and water. The phases are separated, the organic phase filtered through decalite and the solvent removed under vacuum. The residue is purified by flash chromatography (0-20% ethyl acetate in cyclohexane) to give the title compound (170 mg, 30%).

UPLC-MS (Method 2): $R_t$=1.34 min
MS (ESI pos): m/z=334 (M+H)$^+$

Example 21ah

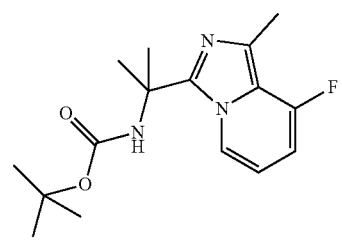 [SMILES: Cc1nc(C(C)(C)NC(=O)OC(C)(C)C)n2cccc(F)c12]

Example 21af (270 mg, 0.73 mmol), trimethylboroxine (274 mg, 2.18 mmol), potassium carbonate (1.20 g mg, 5.64 mmol), and palladium (II) (dppf) dichloride dichloromethane complex (59 mg, 0.07 mmol) are suspended in DMF (3 mL) and degassed for 5 minutes with a flow of nitrogen gas. The mixture is heated in a sealed tube for 2 hours at 100° C. then allowed to cool and diluted with ethyl acetate and water. The phases are separated and the solvent removed under vacuum. The residue is purified by flash chromatography (0-20% ethyl acetate in cyclohexane) to give the title compound (110 mg, 42%).
UPLC-MS (Method 2): $R_t$=1.11 min
MS (ESI pos): m/z=308 (M+H)$^+$ Example 21ai

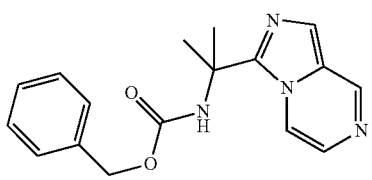 [SMILES: CC(C)(NC(=O)OCc1ccccc1)c1ncc2cnccn12]

The title compound is prepared in analogy to the procedure described for the synthesis of Example 20a and Example 21a starting from Cbz-Aib-OH in place of Boc-Aib-OH HPLC-MS (Method 2): $R_t$=1.04 min MS (ESI pos): m/z=310 (M+H)$^+$ The following examples are synthesized in analogy to the preparation of example 21l:

| Example | Structure | Reactant(s) Conditions | LC-MS $R_t$ [min], method | MS (ESI pos or APCI, m/z) (M + H)$^+$ |
|---|---|---|---|---|
| 21ak | 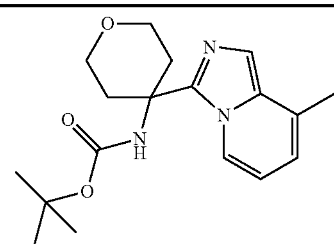 | Example 20v (1.29 g, 3.69 mmol) | 0.94 Method 2 | 332 |
| 21al | 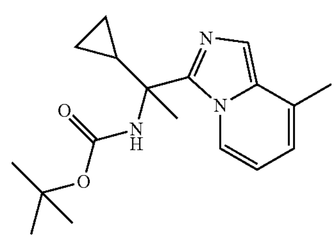 | Example 20w (1.40 g, 3.95 mmol) | 1.09 Method 2 | 316 |

Example 20u 220 mg, 0.67 mmol) is suspended in phosphorus oxychloride (3 mL) and heated at 100° C. for 2 h. The mixture is cooled and solvent evaporated. The residue is partioned in a mixture of 1N NaOH and EtOAc. The organic layer is washed with brine, dried, filtered and evaporated to give a residue purified by flash chromatography (eluent Ethyl acetate/cyclohexane 8:3) to furnish the title compound (38 mg)
HPLC-MS (Method 9): $R_t$=2.12 min
MS (ESI pos): m/z=311 (M+H)$^+$ Example 21aj

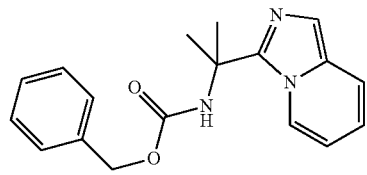 [SMILES: CC(C)(NC(=O)OCc1ccccc1)c1ncc2ccccn12]

Example 22a

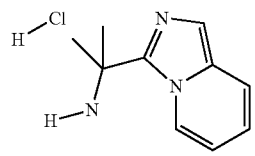

2M Hydrogen chloride in ethyl ether (3 mL, 6 mmol) is added to example 21a (258 mg, 0.937 mmol) dissolved in dry ethyl ether (7 mL). Stirring is continued at rt for 5 h. The solvent is evaporated and the residue is used as such (187 mg, 90%).
UPLC-MS (Method 2): $R_t$=0.57 min
MS (ESI pos): m/z=176 (M+H)$^+$ The following examples are synthesized in analogy to the preparation of example 22a:

| Example | Structure | Reactant(s) | UPLC-MS $R_t$ [min], method | MS (ESI pos, m/z) $(M + H)^+$ |
|---|---|---|---|---|
| 22b | 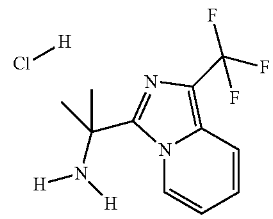 | Example 21d (51 mg, 90% content, 0.134 mmol) | 1.00 2 | 244 |
| 22c | 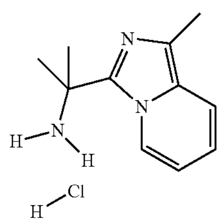 | Example 21b (280 mg, 0.968 mmol) | 0.62 2 | 226 |

Example 22d

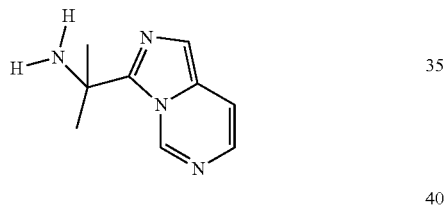

Example 21e (70 mg) is dissolved in MeOH (30 mL) and water (2 mL) and the solution is hydrogenated (3 bar) in the presence of palladium (10% on carbon, 46 mg) for 1 h.

The solids are removed by filtration through a dicalite pad and the resulting solution is evaporated to give the title compound (53 mg) that is used as such.

UPLC-MS (Method 2): $R_t$=0.28 min

MS (ESI pos): m/z=177 (M+H)$^+$

Example 22da

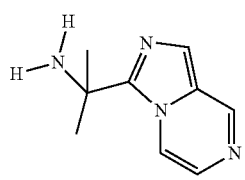

Example 21ai (34 mg) is dissolved in ethyl acetate (2 mL) and the solution is hydrogenated (1.6 bar) in the presence of palladium (10% on carbon, 24 mg) for 2 h. The solids are removed by filtration through a dicalite pad and the resulting solution is evaporated to give the title compound (13 mg) that is used as such. UPLC-MS (Method 1): $R_t$=0.73 min MS (ESI pos): m/z=159 (M-NH2)$^+$ Example 22e

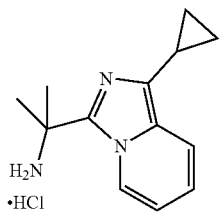 [SMILES: Cl ; CC(C)(N)c1nc(C2CC2)c2ccccn12]

4M Hydrogen chloride in 1,4-dioxane (1 mL, 4 mmol) is added to example 21g (40 mg, 0.12 mmol) and the mixture is stirred for 1 hour. The solvent is evaporated and the residue is used without purification (30 mg, 99%).

UPLC-MS (Method 1): $R_t$=0.571 min

MS (ESI pos): m/z=199 (M-NH2)$^+$

The following examples are synthesized in analogy to the preparation of example 22e:

| Example | Structure | Reactant(s) Conditions | LC-MS R$_t$ [min], method | MS (ESI pos or APCI, m/z) (M + H)$^+$ |
|---|---|---|---|---|
| 22f | 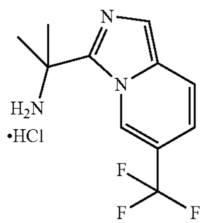 [SMILES: Cl ; CC(C)(N)c1ncc2ccc(C(F)(F)F)cn12] | Example 21m (40 mg, 0.10 mmol) | 0.73 Method 1 | 227 (M − NH2)$^+$ |
| 22g | 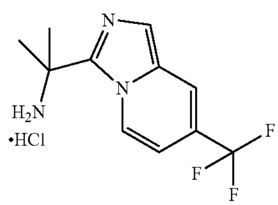 [SMILES: Cl ; CC(C)(N)c1ncc2cc(C(F)(F)F)ccn12] | Example 21n (60 mg, 0.16 mmol) | 0.71 Method 1 | 244 |
| 22h | 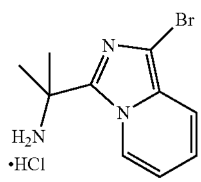 | Example 21f (50 mg, 0.14 mmol) | 0.73 Method 2 | 237/239 (M − NH2)$^+$ |
| 22i | 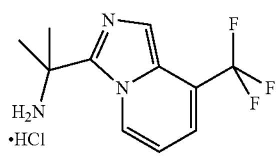 [SMILES: Cl ; CC(C)(N)c1ncc2c(C(F)(F)F)cccn12] | Example 21o (61 mg, 0.18 mmol) | 0.80 Method 2 | 227 (M − NH2)$^+$ |
| 22j | 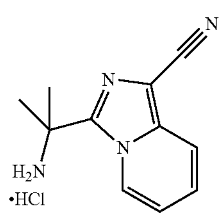 | Example 21j (22 mg, 0.07 mmol) | 0.79 Method 2 | 184 (M − NH2)$^+$ |
| 22k | 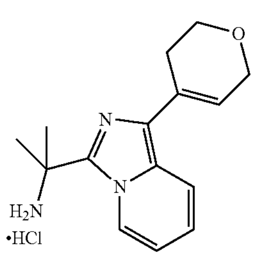 [SMILES: Cl ; CC(C)(N)c1nc(C2=CCOCC2)c2ccccn12] | Example 21k (41 mg, 0.11 mmol) | 0.69 Method 1 | 241 (M − NH2)$^+$ |
| 22l | 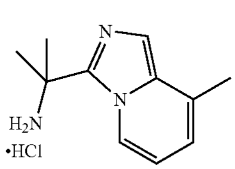 | Example 21p (585 mg, 2.02 mmol) 2M HCl in diethyl ether (10 mL), methanol (3 mL) | 0.67 Method 2 | 173 (M − NH2)$^+$ |

-continued

| Example | Structure | Reactant(s) Conditions | LC-MS R$_t$ [min], method | MS (ESI pos or APCl, m/z) (M + H)$^+$ |
|---|---|---|---|---|
| 22m | 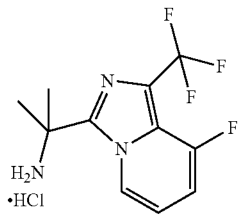 [SMILES: Cl ; CC(C)(N)c1nc(C(F)(F)F)c2c(F)cccn12] | Example 21ae (150 mg, 0.42 mmol) Overnight reaction | 0.97 Method 2 | 245 (M − NH2)$^+$ |
| 22n | 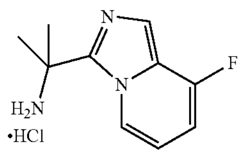 | Example 21q (60 mg, 0.20 mmol) | 0.59 Method 2 | 177 (M − NH2)$^+$ |
| 22o | 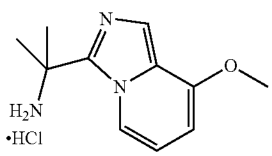 | Example 21l (150 mg, 0.49 mmol) | 0.62 Method 1 | 189 (M − NH2)$^+$ |
| 22p | 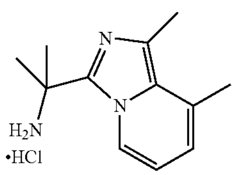 | Example 21r (300 mg, 0.99 mmol) 2M HCl in diethyl ether (5 mL), methanol (2 mL) Overnight reaction | 0.73 Method 2 | 187 (M − NH2)$^+$ |
| 22q | 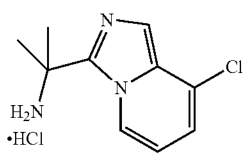 | Example 21s (448 mg, 1.45 mmol) | 0.67 Method 1 | 210/212 |
| 22r | 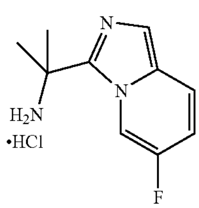 | Example 21t (44 mg, 0.15 mmol) 2M HCl in diethyl ether (0.75 mL), methanol (2 mL) Overnight reaction | 0.57 Method 2 | 194 |
| 22s | 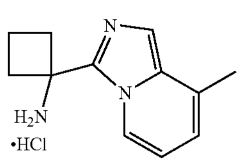 | Example 21u (588 mg, 1.95 mmol) 2M HCl in diethyl ether (9.75 mL), methanol (3 mL) Overnight reaction | 0.89 Method 2 | 185 (M − NH2)$^+$ |
| 22t | 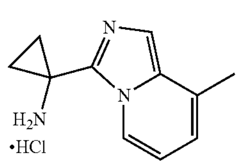 | Example 21v (570 mg, 1.98 mmol) 2M HCl in diethyl ether (9.75 mL), methanol (3 mL) Overnight reaction | 0.49 Method 1 | 188 |

-continued

| Example | Structure | Reactant(s) Conditions | LC-MS R$_t$ [min], method | MS (ESI pos or APCI, m/z) (M + H)$^+$ |
|---------|-----------|------------------------|---------------------------|---------------------------------------|
| 22u | 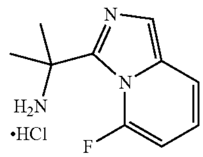 | Example 21x (40 mg, 0.14 mmol) 2M HCl in diethyl ether (0.5 mL), methanol (0.5 mL) | 0.59 Method 1 | 177 (M − NH2)$^+$ |
| 22v | 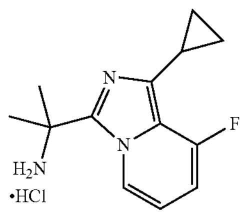 [SMILES: CC(C)(N)c1nc(C2CC2)c2c(F)cccn12 ; Cl] | Example 21ag (170 mg, 0.51 mmol) 2M HCl in diethyl ether (10 mL) | 1.14 Method 2 | 218 (M − NH2)$^+$ |
| 22w | 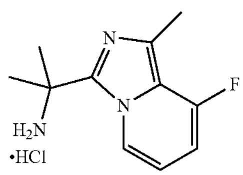 | Example 21ah (110 mg, 0.30 mmol) 2M HCl in diethyl ether (10 mL) | 0.93 Method 2 | 192 (M − NH2)$^+$ |
| 22x | 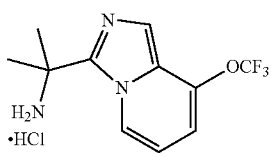 [SMILES: CC(C)(N)c1ncc2c(OC(F)(F)F)cccn12 ; Cl] | Example 21y (30 mg, 0.08 mmol) 2M HCl in diethyl ether (2 mL) | 1.03 Method 2 | 243 (M − NH2)$^+$ |
| 22y | 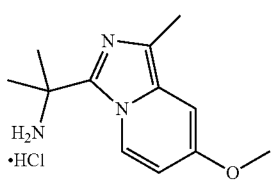 [SMILES: COc1ccn2c(C(C)(C)N)nc(C)c2c1 ; Cl] | Example 21z (98 mg, 0.3 mmol) 2M HCl in diethyl ether (1.5 mL), methanol (2 mL) Overnight reaction | 0.86 Method 2 | 203 (M − NH2)$^+$ |
| 22z | 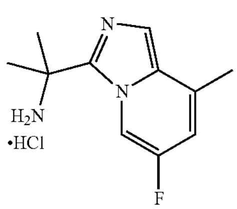 | Example 21aa (24 mg, 0.08 mmol) 2M HCl in diethyl ether (2 mL), 4 hour reaction | 0.94 Method 2 | 191 (M − NH2)$^+$ |
| 22aa | 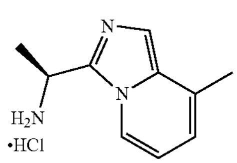 | Example 21ab (2.4 g, 8.7 mmol) 2M HCl in diethyl ether (44 mL), methanol overnight reaction | 0.77 Method 2 | 159 (M − NH2)$^+$ |
| 22ab | 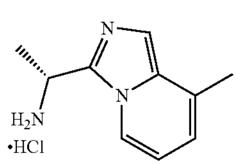 | Example 21ac (2.0 g, 7.3 mmol) 2M HCl in diethyl ether (36 mL), dichloromethane weekend reaction | 0.61 Method 2 | 159 (M − NH2)$^+$ |

Example 22ac

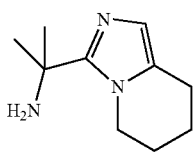

Example 21aj (99 mg, 0.30 mmol) is suspended in ethanol, 10% palladium on activated carbon (15 mg) is added an the mixture hydrogenated at 3.5 bar overnight. The mixture is filtered through celite and the solvent removed to give crude title compound (59 mg)
HPLC-MS (Method 2): $R_t$=0.72 min
MS (ESI pos): m/z=180 (M+H)$^+$
The following examples are synthesized in analogy to the preparation of example 22e:

TEA (600 µL, 4.300 mmol), HATU (360 mg, 0.946 mmol) are added in sequence to example 22a (182 mg, 0.817 mmol) dissolved in THF (10 mL). Stirring is continued for 72 h at rt. The reaction is washed with HCl 1N solution, then with NaOH 1N solution and brine. The organic layer is dried, filtered and evaporated under reduced pressure to give a residue that is purified by flash chromatography (eluent EtOAc/cyclohexane 15:85) to furnish the title compound (255 mg, 81%).

UPLC-MS (Method 2): $R_t$=0.94 min

MS (ESI pos): m/z=385 (M+H)$^+$

| Example | Structure | Reactant(s) Conditions | LC-MS $R_t$ [min], method | MS (ESI pos or APCI, m/z) (M + H)$^+$ |
|---|---|---|---|---|
| 22ad | 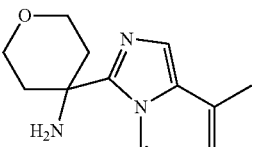 | Example 21ak (300 mg, 0.91 mmol) | 0.76 Method 1 | 215 (M − NH2)$^+$ |
| 22ae | 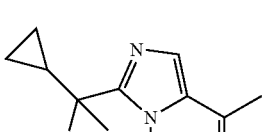 | Example 21al (1.0 g, 3.17 mmol) | 0.68 Method 2 | 199 (M − NH2)$^+$ |

Example 23a

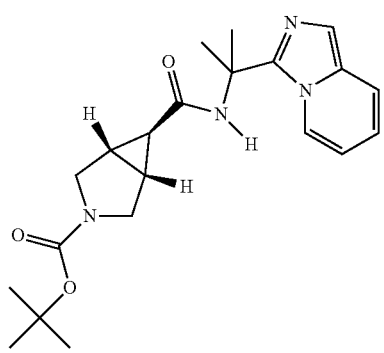 [SMILES: CC(C)(C)OC(=O)N1C[C@@H]2[C@H](C1)[C@H]2C(=O)NC(C)(C)c1ncc2ccccn12]

Meso-(1R,5S,6r)-3-(tert-butoxycarbonyl)-3-azabicyclo[3.1.0]hexane-6-carboxylic acid (215 mg, 0.946 mmol),

Example 23b

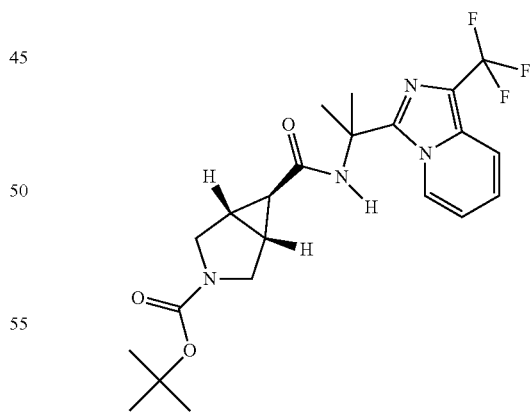

Example 23b is prepared in analogy to example 23a from example 22b (41 mg, 90% content, 0.132 mmol) as starting material. After stirring the reaction overnight, volatiles are removed and the resulting residue is purified by flash chromatography (eluent 0-60% EtOAc/cyclohexane) to furnish the title compound (41 mg, 95% content, 69%).
UPLC-MS (Method 2): $R_t$=1.20 min
MS (ESI pos): m/z=453 (M+H)$^+$ The following example is synthesized in analogy to the preparation of example 23b:

| Example | Structure | Reactant(s) | UPLC-MS R$_t$ [min], method | MS (ESI pos, m/z) (M + H)$^+$ |
|---|---|---|---|---|
| 23c | 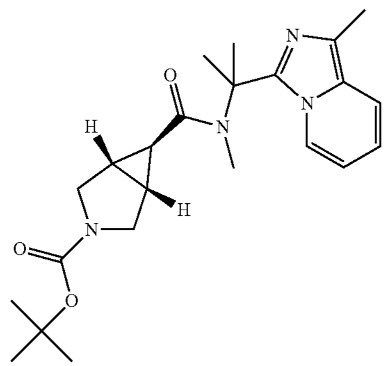 [SMILES: Cc1nc(C(C)(C)N(C)C(=O)[C@H]2[C@@H]3CN(C(=O)OC(C)(C)C)C[C@@H]32)n2ccccc12] | Example 22c (191 mg, 0.846 mmol) | 1.00 2 | 399 |

Example 23d

Example 23e

Meso-(1R,5S,6r)-3-(tert-butoxycarbonyl)-3-azabicyclo[3.1.0]hexane-6-carboxylic acid (66 mg, 0.290 mmol), TEA (167 μL, 1.20 mmol), HATU (110 mg, 0.290 mmol) are added in sequence to example 22d (51 mg) dissolved in dry DCM (7 mL). Stirring is continued for 20 h at rt. The reaction is washed first with water, then with NaOH 1N solution and brine. The aqueous layer is diluted with brine again and extracted with a mixture of EtOAc/MeOH 9:1. The organic layer is dried, filtered and evaporated under reduced pressure to give a residue that is purified by flash chromatography (eluent EtOAc/MeOH 9:2) to furnish the title compound (25 mg)

UPLC-MS (Method 2): R$_t$=0.74 min
MS (ESI pos): m/z=386 (M+H)$^+$

Example 22e (30 mg, 0.12 mmol), meso-(1R,5S,6r)-3-(tert-butoxycarbonyl)-3-azabicyclo[3.1.0]hexane-6-carboxylic acid (33 mg, 0.140 mmol), Et$_3$N (53 μL, 0.38 mmol) and HATU (54 mg, 0.140 mmol) are suspended in dry THF (5 mL) and the mixture stirred over a weekend. The solvent is removed, the residue redissolved in DCM, washed with 0.2M aqueous NaOH solution and brine. The organic layer is dried, filtered and evaporated under reduced pressure to give a residue that is purified by flash chromatography (eluent 0-100% EtOAc in cyclohexane) to give the title compound (Yield 35 mg)

UPLC-MS (Method 2): R$_t$=1.11 min
MS (ESI pos): m/z=425 (M+H)$^+$

The following examples are synthesized in analogy to the preparation of example 23e:

| Example | Structure | Reactant(s) Conditions | LC-MS R$_t$ [min], method | MS (ESI pos or APCI, m/z) (M + H)$^+$ |
|---------|-----------|------------------------|---------------------------|----------------------------------------|
| 23f | 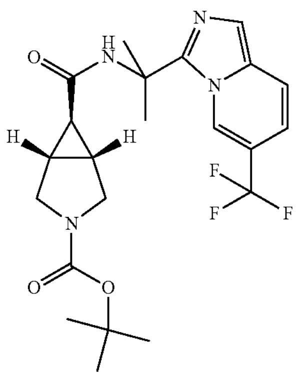 [SMILES: CC(C)(C)OC(=O)N1C[C@@H]2[C@H](C1)[C@H]2C(=O)NC(C)(C)c1ncc2ccc(C(F)(F)F)cn12] | Example 22f (30 mg, 0.10 mmol) 3 h reaction | 1.11 Method 2 | 453 |
| 23g | 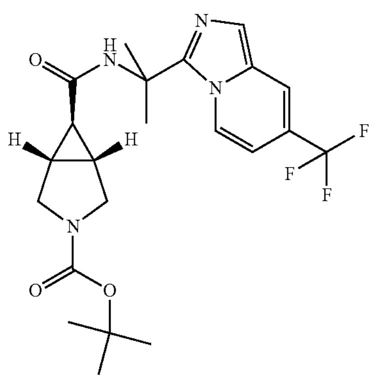 [SMILES: CC(C)(C)OC(=O)N1C[C@@H]2[C@H](C1)[C@H]2C(=O)NC(C)(C)c1ncc2cc(C(F)(F)F)ccn12] | Example 22g (45 mg, 0.14 mmol) 3 h reaction | 0.97 Method 1 | 453 |
| 23h | 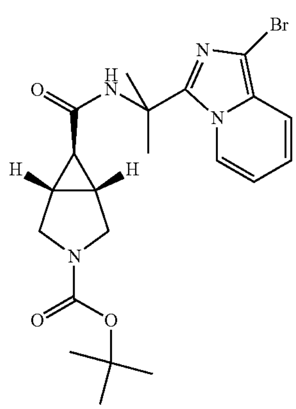 [SMILES: CC(C)(C)OC(=O)N1C[C@@H]2[C@H](C1)[C@H]2C(=O)NC(C)(C)c1nc(Br)c2ccccn12] | Example 22h (40 mg, 0.18 mmol) overnight reaction | 1.12 Method 2 | 463/465 |
| 23i | 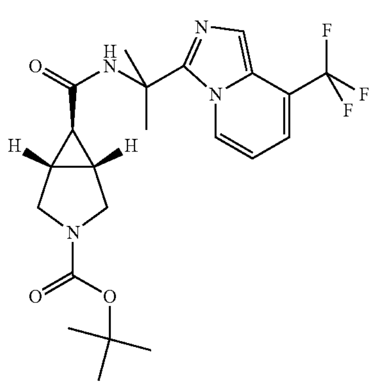 [SMILES: CC(C)(C)OC(=O)N1C[C@@H]2[C@H](C1)[C@H]2C(=O)NC(C)(C)c1ncc2c(C(F)(F)F)cccn12] | Example 22i (50 mg, 0.18 mmol) 3 h reaction | 1.10 Method 2 | 453 |

-continued

| Example | Structure | Reactant(s) Conditions | LC-MS R*t* [min], method | MS (ESI pos or APCl, m/z) (M + H)+ |
|---|---|---|---|---|
| 23j | 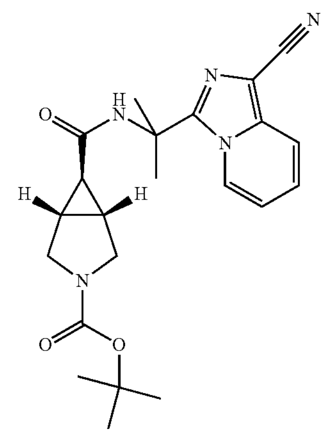 [SMILES: CC(C)(C)OC(=O)N1C[C@@H]2[C@H](C1)[C@H]2C(=O)NC(C)(C)c1nc(C#N)c2ccccn12] | Example 22j (19 mg, 0.07 mmol) DCM as solvent overnight reaction | 1.02 Method 2 | 410 |
| 23k | 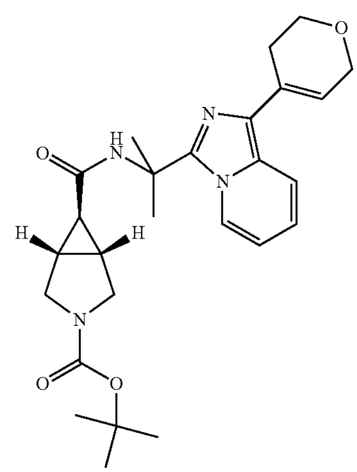 [SMILES: CC(C)(C)OC(=O)N1C[C@@H]2[C@H](C1)[C@H]2C(=O)NC(C)(C)c1nc(C2=CCOCC2)c2ccccn12] | Example 22k (35 mg, 0.12 mmol) DCM as solvent overnight reaction | 0.90 Method 1 | 467 |
| 23l | 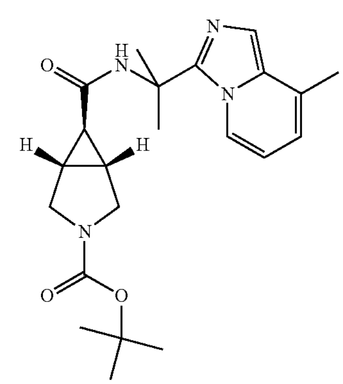 [SMILES: Cc1cccn2c(C(C)(C)NC(=O)[C@H]3[C@@H]4CN(C(=O)OC(C)(C)C)C[C@@H]43)ncc12] | Example 22l (456 mg, 2.02 mmol) DCM as solvent 3 h reaction | 0.98 Method 2 | 399 |

-continued

| Example | Structure | Reactant(s) Conditions | LC-MS R$_t$ [min], method | MS (ESI pos or APCl, m/z) (M + H)$^+$ |
|---|---|---|---|---|
| 23m | 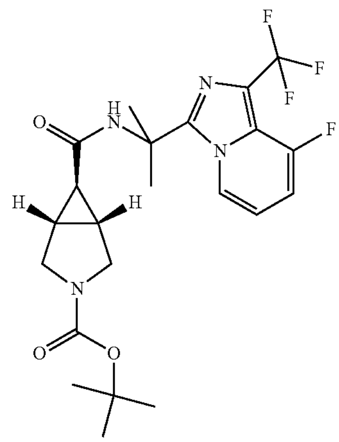 [SMILES: CC(C)(C)OC(=O)N1C[C@@H]2[C@H](C1)[C@H]2C(=O)NC(C)(C)c1nc(C(F)(F)F)c2c(F)cccn12] | Example 22m (70 mg, 0.24 mmol) DCM as solvent 3 h reaction | 1.19 Method 2 | 471 |
| 23n | 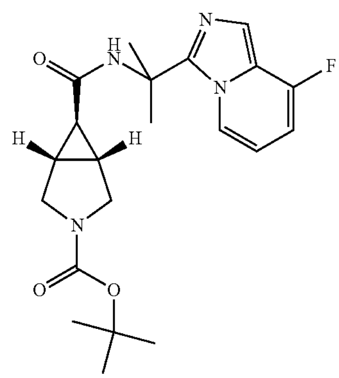 [SMILES: CC(C)(C)OC(=O)N1C[C@@H]2[C@H](C1)[C@H]2C(=O)NC(C)(C)c1ncc2c(F)cccn12] | Example 22n (55 mg, 0.21 mmol) DCM as solvent 3 h reaction | 0.97 Method 2 | 403 |
| 23o | 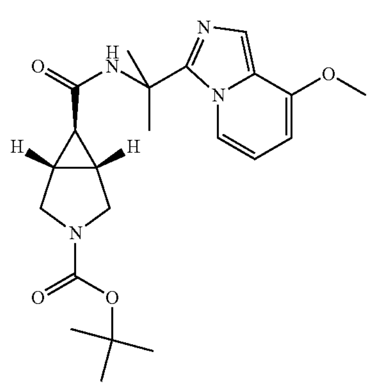 [SMILES: COc1cccn2c(C(C)(C)NC(=O)[C@H]3[C@@H]4CN(C(=O)OC(C)(C)C)C[C@@H]43)ncc12] | Example 22o (73 mg, 0.24 mmol) DCM as solvent overnight reaction | 0.86 Method 1 | 415 |

-continued

| Example | Structure | Reactant(s) Conditions | LC-MS R$_t$ [min], method | MS (ESI pos or APCI, m/z) (M + H)$^+$ |
|---|---|---|---|---|
| 23p | 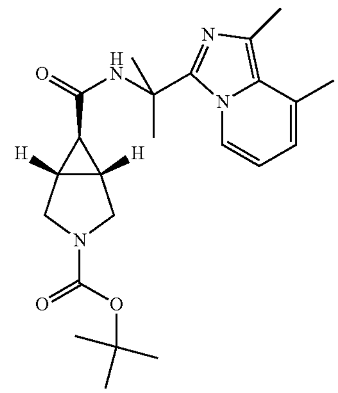 [SMILES: Cc1cccn2c(C(C)(C)NC(=O)[C@H]3[C@@H]4CN(C(=O)OC(C)(C)C)C[C@@H]43)nc(C)c12] | Example 22p (100 mg, 0.42 mmol) DCM as solvent 3 days reaction | 1.06 Method 2 | 413 |
| 23q | 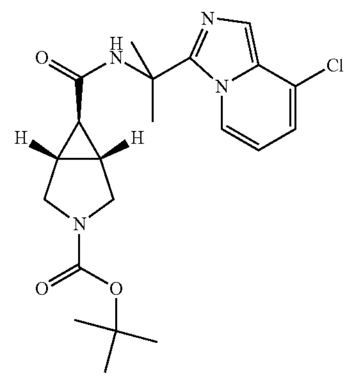 [SMILES: CC(C)(C)OC(=O)N1C[C@@H]2[C@H](C1)[C@H]2C(=O)NC(C)(C)c1ncc2c(Cl)cccn12] | Example 22q (120 mg, 0.46 mmol) DCM as solvent overnight reaction | 0.90 Method 1 | 419/421 |
| 23r | 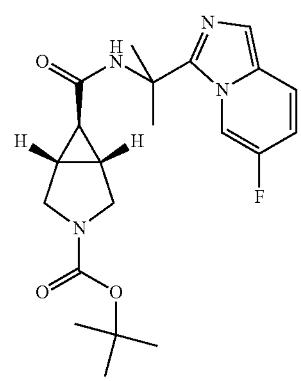 [SMILES: CC(C)(C)OC(=O)N1C[C@@H]2[C@H](C1)[C@H]2C(=O)NC(C)(C)c1ncc2ccc(F)cn12] | Example 22r (34 mg) DCM as solvent 3 days reaction | 1.06 Method 2 | 403 |
| 23s | 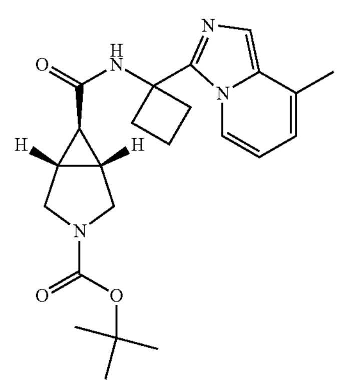 [SMILES: Cc1cccn2c(C3(NC(=O)[C@H]4[C@@H]5CN(C(=O)OC(C)(C)C)C[C@@H]54)CCC3)ncc12] | Example 22s (100 mg, 0.42 mmol) DCM as solvent overnight reaction | 1.12 Method 2 | 411 |

-continued

| Example | Structure | Reactant(s) Conditions | LC-MS R$_t$ [min], method | MS (ESI pos or APCl, m/z) (M + H)$^+$ |
|---|---|---|---|---|
| 23t | 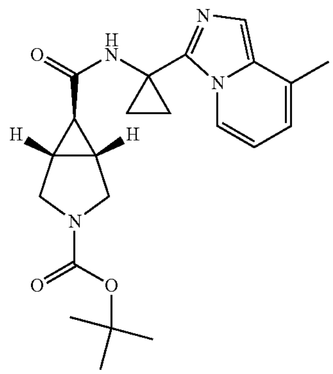 [SMILES: Cc1cccn2c(C3(NC(=O)[C@H]4[C@@H]5CN(C(=O)OC(C)(C)C)C[C@@H]54)CC3)ncc12] | Example 22t (100 mg, 0.45) DCM as solvent overnight reaction | 0.84 Method 1 | 397 |
| 23u | 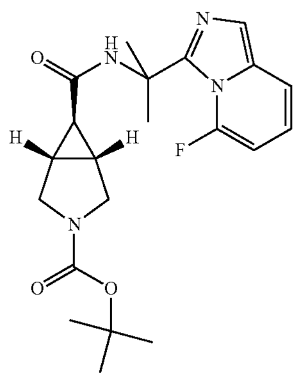 [SMILES: CC(C)(C)OC(=O)N1C[C@@H]2[C@H](C1)[C@H]2C(=O)NC(C)(C)c1ncc2cccc(F)n12] | Example 22u (35 mg, 0.15 mmol) DCM as solvent overnight reaction | 0.83 Method 1 | 403 |
| 23v | 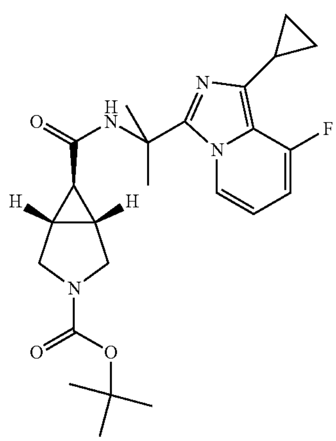 [SMILES: CC(C)(C)OC(=O)N1C[C@@H]2[C@H](C1)[C@H]2C(=O)NC(C)(C)c1nc(C2CC2)c2c(F)cccn12] | Example 22v (60 mg, 0.22 mmol) DCM as solvent overnight reaction | 1.29 Method 2 | 443 |
| 23w | 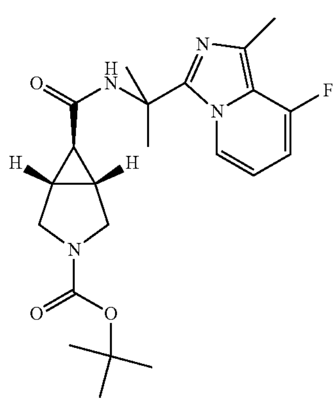 [SMILES: Cc1nc(C(C)(C)NC(=O)[C@H]2[C@@H]3CN(C(=O)OC(C)(C)C)C[C@@H]32)n2cccc(F)c12] | Example 22w (50 mg, 0.17 mmol) DCM as solvent overnight reaction | 1.12 Method 2 | 417 |

-continued

| Example | Structure | Reactant(s) Conditions | LC-MS R, [min], method | MS (ESI pos or APCl, m/z) (M + H)+ |
|---|---|---|---|---|
| 23x | 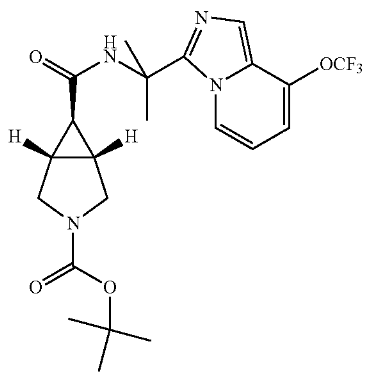 [SMILES: CC(C)(C)OC(=O)N1C[C@@H]2[C@H](C1)[C@H]2C(=O)NC(C)(C)c1ncc2c(OC(F)(F)F)cccn12] | Example 22x (22 mg, 0.07 mmol) DCM as solvent overnight reaction | 1.08 Method 2 | 469 |
| 23y | 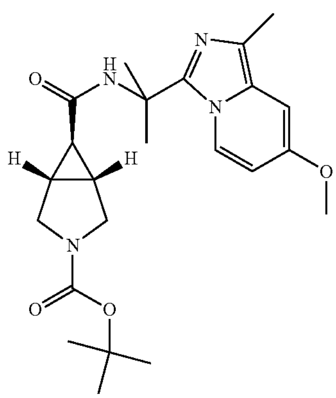 [SMILES: COc1ccn2c(C(C)(C)NC(=O)[C@H]3[C@@H]4CN(C(=O)OC(C)(C)C)C[C@@H]43)nc(C)c2c1] | Example 22y (78 mg) DCM as solvent overnight reaction | 1.04 Method 2 | 429 |
| 23z | 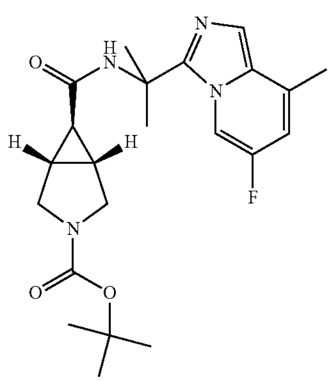 [SMILES: Cc1cc(F)cn2c(C(C)(C)NC(=O)[C@H]3[C@@H]4CN(C(=O)OC(C)(C)C)C[C@@H]43)ncc12] | Example 22z (19 mg, 0.08 mmol) DCM as solvent overnight reaction | 1.12 Method 2 | 417 |
| 23aa | 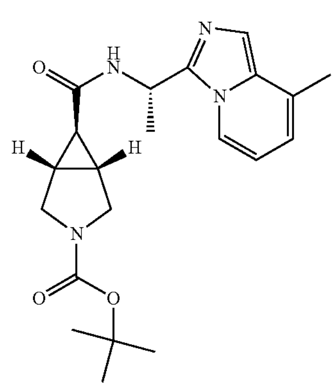 [SMILES: Cc1cccn2c([C@H](C)NC(=O)[C@H]3[C@@H]4CN(C(=O)OC(C)(C)C)C[C@@H]43)ncc12] | Example 22aa (100 mg 0.47) DCM as solvent overnight reaction | 1.09 Method 2 | 385 |

| Example | Structure | Reactant(s) Conditions | LC-MS R$_t$ [min], method | MS (ESI pos or APCl, m/z) (M + H)$^+$ |
|---|---|---|---|---|
| 23ab | 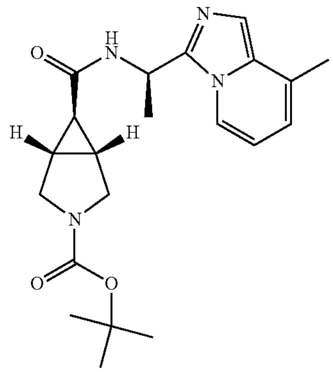 [SMILES: Cc1cccn2c([C@@H](C)NC(=O)[C@H]3[C@@H]4CN(C(=O)OC(C)(C)C)C[C@@H]43)ncc12] | Example 22ab (100 mg, 0.47 mmol) DCM as solvent overnight reaction | 1.02 Method 2 | 385 |
| 23ac | 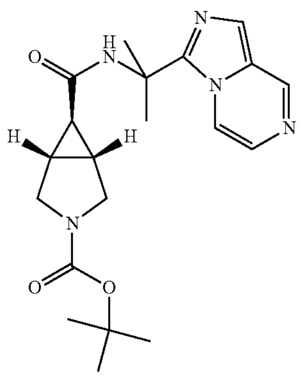 [SMILES: CC(C)(C)OC(=O)N1C[C@@H]2[C@H](C1)[C@H]2C(=O)NC(C)(C)c1ncc2cnccn12] | Example 22da (12 mg) DCM as solvent 4 day reaction EtOAc/MeOH 9:0.3 as eluent for purification | 0.81 Method 2 | 386 |

Example 23ad

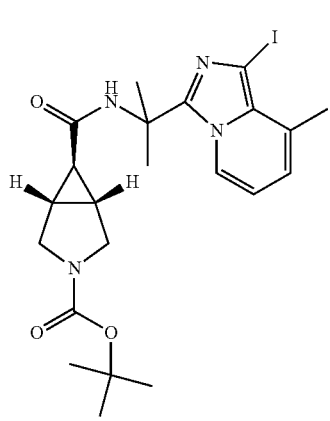 [SMILES: Cc1cccn2c(C(C)(C)NC(=O)[C@H]3[C@@H]4CN(C(=O)OC(C)(C)C)C[C@@H]43)nc(I)c12]

Example 23ae

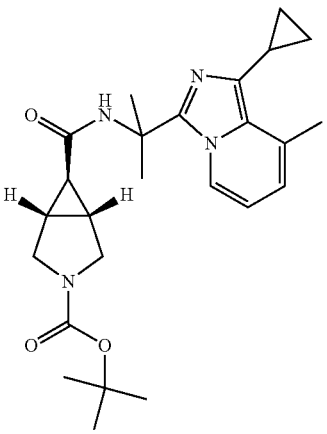 [SMILES: Cc1cccn2c(C(C)(C)NC(=O)[C@H]3[C@@H]4CN(C(=O)OC(C)(C)C)C[C@@H]43)nc(C3CC3)c12]

Example 23l (420 mg, 1.05 mmol) is suspended in dichloromethane (8 mL) at 0° C. and N-iodosuccinimide (236 mg, 1.05 mmol) is added. The mixture is stirred for 10 minutes then shaken with 5% sodium thiosulfate solution, the phases separated, the organic phase dried and the solvent removed. The residue is purified by flash chromatography (Eluent; 50% EtOAc in cyclohexane) to give the title compound (409 mg, 70%)

LC-MS (Method 2): R$_t$=1.22 min

MS (ESI pos): m/z=525 (M+H)$^+$

Example 23ad (100 mg, 0.18 mmol), potassium cyclopropyltrifluoroborate (266 mg, 1.80 mmol), Potassium triphosphate (670 mg, 3.15 mmol), tricyclohexylphosphine (56 mg, 0.20 mmol) and palladium (II) acetate (22 mg, 0.10 mmol) are suspended in a mixture of toluene (15 mL) and water (0.6 mL) and degassed for 5 minutes with a flow of nitrogen gas. The mixture is heated at 90° C. for 24 hours then allowed to cool and diluted with dichloromethane and water. The phases are separated, the organic dried, filtered and the solvent removed under vacuum. The residue is purified by flash chromatography (Eluent: 40% ethyl acetate in cyclohexane) to give the title compound (28 mg).

UPLC-MS (Method 2): $R_t$=1.26 min
MS (ESI pos): m/z=439 (M+H)$^+$

Example 23af

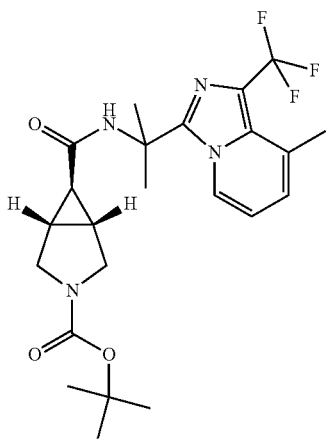 [SMILES: Cc1cccn2c(C(C)(C)NC(=O)[C@H]3[C@@H]4CN(C(=O)OC(C)(C)C)C[C@@H]43)nc(C(F)(F)F)c12]

Example 23ad (200 mg, 0.36 mmol), 2,2-difluoro-2-(fluorosulfonyl)acetate (219 mg, 3.13 mmol) and copper (I) iodide (108 mg, 1.56 mmol) are dissolved in dry 1-methyl-2-pyrrolidinone (4 mL) and the reaction is stirred at 110° for 60 minutes. The mixture is cooled, diluted with water and extracted with ethyl acetate. The organic extracts are dried and the solvent removed. The residue is purified by flash chromatography (Eluent: 0-50% EtOAc in cyclohexane) followed by reverse phase preparative HPLC to give the title compound (43 mg, 25%)

UPLC-MS (Method 2): $R_t$=1.24 min
MS (ESI pos): m/z=467 (M+H)$^+$

Example 23ag

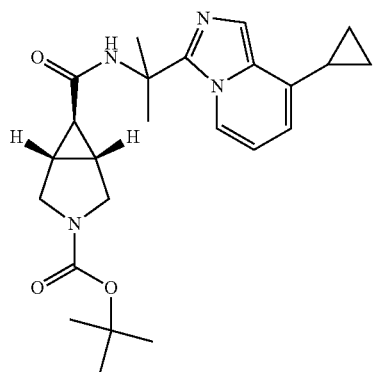 [SMILES: CC(C)(C)OC(=O)N1C[C@@H]2[C@H](C1)[C@H]2C(=O)NC(C)(C)c1ncc2c(C3CC3)cccn12]

Example 23q (140 mg, 50% content, 0.17 mmol), potassium cyclopropyltrifluoroborate (50 mg, 0.33 mmol), Potassium triphosphate (124 mg, 0.58 mmol), tricyclohexylphosphine (9 mg, 0.03 mmol) and palladium (II) acetate (4 mg, 0.02 mmol) are suspended in a mixture of toluene (0.7 mL) and water (0.2 mL) and degassed for 5 minutes with a flow of nitrogen gas. The mixture is heated under microwave irradiation at 120° C. for 2 hours. A further equivalent of potassium cyclopropyltrifluoroborate, potassium triphosphate, tricyclohexylphosphine and palladium (II) acetate are then added and the mixture heated under microwave irradiation at 140° C. for 5 hours then allowed to cool and diluted with ethyl acetate and water. The phases are separated, the organic phase dried, filtered and the solvent removed under vacuum. The residue is purified by flash chromatography (Eluent: 5% methanol in dichloromethane) to give the title compound (20 mg).

UPLC-MS (Method 1): $R_t$=0.91 min
MS (ESI pos): m/z=425 (M+H)$^+$

The following examples are synthesized in analogy to the preparation of example 23e:

| Example | Structure | Reactant(s) Conditions | LC-MS $R_t$ [min], method | MS (ESI pos or APCl, m/z) (M + H)$^+$ |
|---|---|---|---|---|
| 23ah | 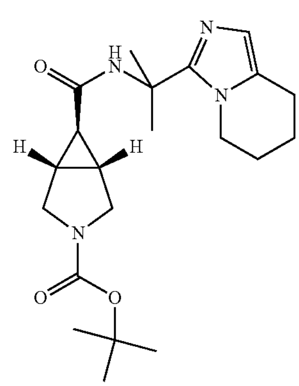 [SMILES: CC(C)(C)OC(=O)N1C[C@@H]2[C@H](C1)[C@H]2C(=O)NC(C)(C)c1ncc2n1CCCC2] | Example 22ac (59 mg, 0.30 mmol) | 0.85 Method 2 | 389 |

| Example | Structure | Reactant(s) Conditions | LC-MS R$_t$ [min], method | MS (ESI pos or APCl, m/z) (M + H)$^+$ |
|---|---|---|---|---|
| 23ai | 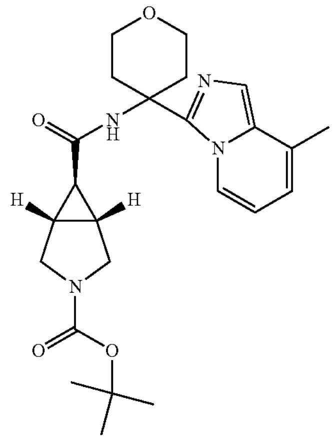 [SMILES: Cc1cccn2c(C3(NC(=O)[C@H]4[C@@H]5CN(C(=O)OC(C)(C)C)C[C@@H]54)CCOCC3)ncc12] | Example 22ad (242 mg, 0.30 mmol) | 0.99 Method 2 | 441 |
| 23aj | 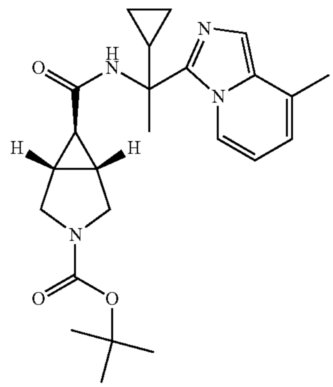 [SMILES: Cc1cccn2c(C(C)(NC(=O)[C@H]3[C@@H]4CN(C(=O)OC(C)(C)C)C[C@@H]43)C3CC3)ncc12] | Example 22ae (150 mg, 0.60 mmol) | 1.23 Method 2 | 425 |

Example 24a 3-aminopyridazine (1 g, 10.5 mmol) is dissolved in toluene (7 mL) and N,N-dimethylformamide dimethyl acetal (1.8 mL, 13.67 mmol) is added. The mixture is heated at 65° C. and stirring is continued overnight. Additional N,N-dimethylformamide dimethyl acetal (1.8 mL, 13.67 mmol) is added and stirring is continued at rt for 3 days. Additional N,N-dimethylformamide dimethyl acetal (3.6 mL, 27.34 mmol) is added and the reaction is heated at 85° C. for 5 h. Volatiles are removed under reduced pressure and the resulting residue is triturated with n-hexane to furnish the title compound (1.4 g, 91%)

UPLC-MS (Method 2): R$_t$=0.40 min

MS (ESI pos): m/z=151 (M+H)$^+$

Example 25a 3-bromo-2-formylpyridine (5 g, 26.88 mmol) and methylhydrazine (1.70 mL, 32.25 mmol) are dissolved in ethanol (10 mL) and heated at 80° C. for 2 h. Volatiles are removed under reduced pressure and the residue is re-evaporated several times to give N-[1-(3-Bromo-pyridin-2-yl)-methyl-idene]-N'-methyl-hydrazine (5.70 g, 99%)

UPLC-MS (Method 2): R$_t$=0.77 min

MS (ESI pos): m/z=215 (M+H)$^+$

N-[1-(3-Bromo-pyridin-2-yl)-methylidene]-N'-methyl-hydrazine (5.7 g, 26.63 mmol), copper (I) iodide (507 mg, 2.66 mmol), trans-N,N'-dimethylcyclohexane-1,2-diamine (76 mg, 0.533 mmol) and potassium carbonate (7.36 g, 53.25 mmol) are suspended in 1-methyl-2-pyrrolidinone (20 mL) and heated at 120° C. for 3 h. The mixture is diluted with saturated ammonium chloride solution and ethyl acetate. The resulting emulsion is filtered, the phases separated and the organic phase washed with brine, dried and volatiles evaporated under reduced pressure. The residue is redissolved in ethyl ether, washed with brine and the solvent removed. The residue is purified by flash chromatography (0-60% EtOAc in cyclohexane) to give 1-methyl-1H-pyrazolo[4,3-b]pyridine (580 mg, content 85%, 14%)

$^1$H NMR (300 MHz, DMSO-$d_6$): δ 4.08 (s, 3H), 7.40 (dd, J=4.60, 8.60 Hz, 1H), 8.14 (dd, J=1.10, 8.40 Hz, 1H), 8.25 (d, J=1.0 Hz, 1H), 8.53 (dd, J=1.40, 4.40 Hz, 1H) Bromine (2.37 g, 14.810 mmol) in NaOH solution (2M in water, 10 mL, 20 mmol) is added dropwise to 1-methyl-1H-pyrazolo[4,3-b]pyridine (580 mg, 85% content, 3.70 mmol) in dioxane (20 mL) cooled to 0° C. The mixture is allowed to reach rt and then stirred for 6 hours. Additional bromine (2.17 g, 13.570 mmol) is added dropwise and the mixture stirred for 30 minutes. The mixture is diluted with 100 mL of 10% sodium thiosulfate solution and extracted with EtOAc.

The combined organic extracts are dried over sodium sulfate and volatiles evaporated under reduced pressure. The resulting residue is suspended in DCM, the solids removed by filtration and the residue evaporated to give the title compound (630 mg, 80%)

$^1$H NMR (500 MHz, DMSO-$d_6$): δ 4.09 (s, 3H), 7.52 (dd, J=4.3, 8.6 Hz, 1H), 8.23 (dd, J=1.3, 8.6 Hz, 1H), 8.59 (dd, J=1.3, 4.3 Hz, 1H)

Example 26a

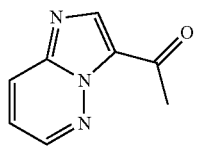

Example 24a (1.4 g, 9.59 mmol) is dissolved in dry DMF (80 mL) and sodium iodide (1.4 g, 9.59 mmol) and chloroacetone (1.6 g, 17.26 mmol) are added. The mixture is heated at 80° C. overnight. The reaction mixture is partitioned between water and ethyl acetate and filtered through a dicalite pad. The organic layer is washed with 1N NaOH, water and then dried over Na$_2$SO$_4$. Volatiles are evaporated and the resulting residue is purified by flash chromatography (eluent 70-100% EtOAc/cyclohexane) to furnish the title compound (132 mg, 9%)

UPLC-MS (Method 2): $R_t$=0.51 min
MS (ESI pos): m/z=162 (M+H)$^+$

Example 26b

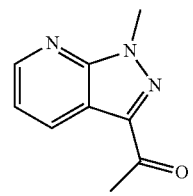

3-bromo-1-methyl-pyrazolo[3,4-b]pyridine (100 mg, 0.472 mmol) is dissolved in toluene (5 mL) and tributyl(1-ethoxyvinyl)tin (187 mg, 0.519 mmol) and tetrakis(triphenylphosphine) palladium(0) (54 mg, 0.047 mmol) are added to the solution and the reaction is refluxed for 2 h.

Volatiles are evaporated under reduced pressure and the resulting residue is suspended in THF/aqueous 2M HCl 1:1 and stirring is continued for 1 h. The reaction mixture is basified with Na$_2$CO$_3$ saturated solution, and extracted with ethyl acetate. The organic layer is dried, evaporated and the resulting residue is purified by flash chromatography (eluent 0-100% EtOAc/Cyclohexane) to give the title compound (70 mg, 85%)

UPLC-MS (Method 2): $R_t$=0.78 min
MS (ESI pos): m/z=176 (M+H)$^+$

The following example is synthesized in analogy to the preparation of example 26b:

| Example | Structure | Reactant(s) | UPLC-MS $R_t$ [min], method | MS (ESI pos, m/z) (M + H)$^+$ |
|---|---|---|---|---|
| 26c | 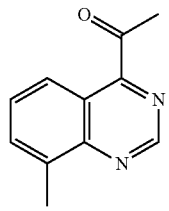 | Example 25a (400 mg, 1.89 mmol) | 0.61 2 | 176 |

Example 26d

4-Chloro-8-methylquinazoline (5.10 g, 25.13 mmol) is dissolved in toluene (50 mL) and tributyl(1-ethoxyvinyl)tin (9.98 g, 27.64 mmol) and tetrakis(triphenylphosphine) palladium(0) (1.45 g, 1.26 mmol) are added to the solution and the reaction is refluxed for 3 h. Volatiles are evaporated under reduced pressure and the resulting mixture is diluted with brine and ethyl acetate. The phases separated and the organic phase washed with brine, dried and volatiles evaporated under reduced pressure. The residue is purified by flash chromatography (0-30% EtOAc in cyclohexane) to give 4-(1-ethoxy-vinyl)-8-methyl-quinazoline (4.80 g, 89%).

UPLC-MS (Method 2): $R_t$=1.15 min
MS (ESI pos): m/z=215 (M+H)$^+$ 4-(1-Ethoxy-vinyl)-8-methyl-quinazoline (4.80 g, 22.40 mmol) is suspended in aqueous 1M HCl (100 mL) and stirring is continued for 3 h. The reaction mixture is basified with Na$_2$CO$_3$ saturated solution, and extracted with ethyl acetate. The organic layer is dried, evaporated to give the title compound (4.02 g, 96%) that is used as such.

UPLC-MS (Method 2): $R_t$=1.07 min
MS (ESI pos): m/z=187 (M+H)$^+$

Example 27a

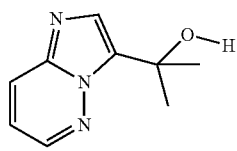

Methylmagnesium bromide (1.4M in THF, 1 mL, 1.4 mmol) is added to example 26a (132 mg, 0.819 mmol) in THF (10 mL) at 0° C. The mixture is stirred at 0° C. for 30 min and at rt for 60 min. Saturated NH$_4$Cl is added to the reaction mixture cooled to 0° C. followed by EtOAc. The organic layer is dried, filtered and evaporated to give a residue that is purified by flash chromatography (eluent EtOAc 100%) to furnish the title compound (94 mg, 65%)

UPLC-MS (Method 2): R$_t$=0.60 min

MS (ESI pos): m/z=178 (M+H)$^+$

The following example is synthesized in analogy to the preparation of example 27a:

| Example | Structure | Reactant(s) | UPLC-MS R$_t$ [min], method | MS (ESI pos, m/z) (M + H)$^+$ |
|---|---|---|---|---|
| 27b | 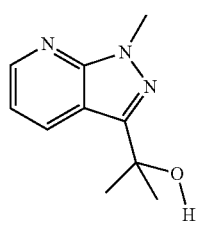 | Example 26c (180 mg, 1.03 mmol) | 0.64 2 | 192 |

Example 27c

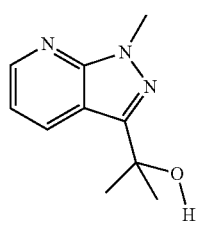

Example 27c is prepared from example 26b (70 mg, 0.400 mmol) in analogy to the example 27a without purification by flash chromatography. The title compound (68 mg, 89%) is used as such.

UPLC-MS (Method 2): R$_t$=0.64 min

MS (ESI pos): m/z=192 (M+H)$^+$

The following example is synthesized in analogy to the preparation of example 27a:

| Example | Structure | Reactant(s) | $^1$H-NMR |
|---|---|---|---|
| 27d | 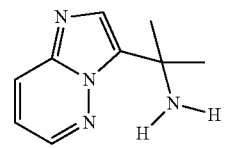 | Example 26d (4.02 g, 21.59 mmol) | $^1$H NMR (300 MHz, DMSO-d$_6$): δ 1.66 (s, 6H), δ 2.67 (s, 3H), 5.80 (s, 1H), 7.55 (dd, J = 6.9, 8.7 Hz, 1H), 7.78 (ddd, J = 1.1, 2.2, 7.1 Hz, 1H), 8.93 (dd, J = 1.1, 8.7 Hz, 1H), 9.19 (s, 1H) |

Example 28a

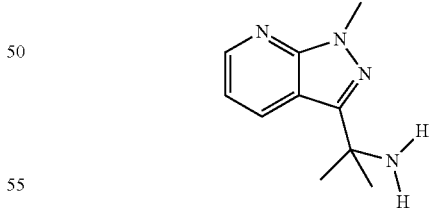

Sodium azide (172 mg, 2.65 mmol) is added to example 27a (94 mg, 0.531 mmol) in TFA (1.5 mL, 19.56 mmol) at 0° C. The reaction is allowed to reach rt and stirring is continued overnight. The reaction mixture is diluted with water, basified with saturated K$_2$CO$_3$ and taken up with EtOAc. The organic layer is dried and filtered to give 3-(1-azido-1-methyl-ethyl)-imidazo[1,2-b]pyridazine (as a solution in EtOAc).

UPLC-MS (Method 2): R$_t$=0.88 min

MS (ESI pos): m/z=203 (M+H)$^+$ 3-(1-Azido-1-methyl-ethyl)-imidazo[1,2-b]pyridazine (solution in ethyl acetate) is hydrogenated (1 bar) in presence of palladium (5% on carbon, 15 mg, 0.007 mmol) for 1 h.

The solids are removed by filtration through a dicalite pad and the resulting solution is evaporated to give the title compound (100 mg) that is used as such.

UPLC-MS (Method 2): R$_t$=0.34 min

MS (ESI pos): m/z=177 (M+H)$^+$

Example 28b

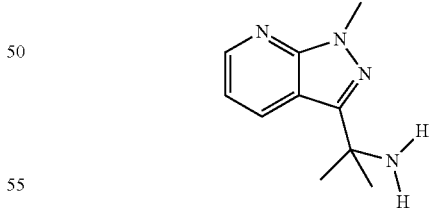

Sodium azide (116 mg, 1.78 mmol) is added portionwise to example 27c (68 mg, 0.356 mmol) in TFA (1 mL, 13.04 mmol) at 0° C. The reaction is allowed to reach rt and stirring is continued overnight. The reaction is cooled to 0° C., diluted with water and basified with saturated Na$_2$CO$_3$. EtOAc is added, the organic layer is dried and filtered to give 3-(1-Azido-1-methyl-ethyl)-1-methyl-1H-pyrazolo[3,4-b] pyridine (as a solution in ethyl acetate).

UPLC-MS (Method 2): R$_t$=1.06 min

MS (ESI pos): m/z=217 (M+H)$^+$ 3-(1-Azido-1-methyl-ethyl)-1-methyl-1H-pyrazolo[3,4-b]pyridine (solution in ethyl acetate) is hydrogenated (1 bar) in the presence of palladium (5% on carbon, 50 mg, 0.023 mmol), for 45 min.

The solids are removed by filtration through a dicalite pad and the resulting solution is evaporated to give the title compound (56 mg) that is used as such.

UPLC-MS (Method 2): $R_t$=0.55 min

MS (ESI pos): m/z=191 (M+H)$^+$

Example 28c

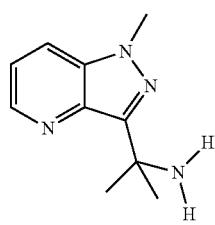

Sodium azide (175 mg, 2.69 mmol) is added to example 27b (103 mg, 0.54 mmol) in TFA (2 mL) at 0° C. The reaction is allowed to reach rt and stirring is continued for 2 h. Then additional TFA (2 mL) is added and stirring is continued for 2 h. The reaction mixture is cooled at 0° C., diluted with water, basified with saturated Na$_2$CO$_3$ and taken up with EtOAc. The organic layer is dried and filtered to give 3-(1-Azido-1-methyl-ethyl)-1-methyl-1H-pyrazolo[4,3-b]pyridine (as a solution in EtOAc).

UPLC-MS (Method 2): $R_t$=0.97 min

MS (ESI pos): m/z=217 (M+H)$^+$ 3-(1-Azido-1-methyl-ethyl)-1-methyl-1H-pyrazolo[4,3-b]pyridine (solution in EtOAc) is hydrogenated (1 bar) in presence of palladium (5% on carbon, 15 mg, 0.007 mmol) for 45 min. The solids are removed by filtration through a celite pad and the resulting solution is evaporated to give the title compound (101 mg, 99%)

UPLC-MS (Method 2): $R_t$=0.55 min

MS (ESI pos): m/z=191 (M+H)$^+$

Example 28d

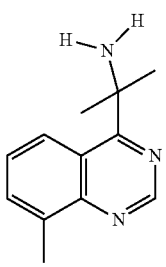

Methanesulfonyl chloride (0.61 mL, 7.91 mmol) is added dropwise to 27d (500 mg, 80% content, 1.98 mmol) and triethylamine (1.4 mL, 7.9 mmol) in THF (20 mL) at −78° C. Stirring is continued for 1.5 h at rt. The reaction mixture is diluted with water and ethyl acetate. The phases are separated and the organic phase is dried and volatiles are evaporated to give methanesulfonic acid 1-methyl-1-(8-methyl-quinazolin-4-yl)-ethyl ester (680 mg, 78% content, 96%) that is used as such.

UPLC-MS (Method 2): $R_t$=1.08 min

MS (ESI pos): m/z=281 (M+H)$^+$

Sodium azide (492 mg, 7.57 mmol) is added to methanesulfonic acid 1-methyl-1-(8-methyl-quinazolin-4-yl)-ethyl ester (680 mg, 78% content, 1.89 mmol) in DMF (1.5 mL, 19.56 mmol) and stirring is continued for 4 d. The reaction mixture is diluted with saturated Na$_2$CO$_3$ and EtOAc. The organic layer is washed with brine, dried and filtered to give 4-(1-azido-1-methyl-ethyl)-8-methyl-quinazoline (as a solution in EtOAc).

UPLC-MS (Method 2): $R_t$=1.39 min

MS (ESI pos): m/z=228 (M+H)$^+$ 4-(1-Azido-1-methyl-ethyl)-8-methyl-quinazoline (solution in ethyl acetate) is hydrogenated (1.5 bar) in presence of palladium (10% on carbon, 14 mg, 0.013 mmol) for 2 h.

The solids are removed by filtration through a celite pad and the resulting solution is evaporated to give the title compound (250 mg, 80% content) that is used as such.

UPLC-MS (Method 2): $R_t$=0.87 min

MS (ESI pos): m/z=202 (M+H)$^+$

Example 29a

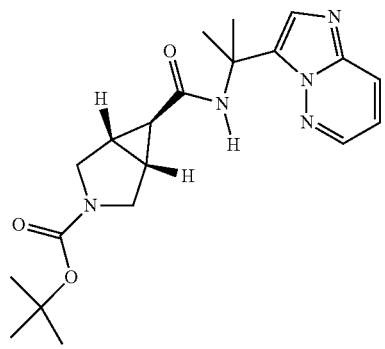 [SMILES: CC(C)(C)OC(=O)N1C[C@@H]2[C@H](C1)[C@H]2C(=O)NC(C)(C)c1cnc2cccnn12]

HATU (205 mg, 0.540 mmol) is added to meso-(1R,5S,6r)-3-(tert-butoxycarbonyl)-3-azabicyclo[3.1.0]hexane-6-carboxylic acid (123 mg, 0.540 mmol), example 28a (100 mg) and TEA (301 µl, 2.160 mmol) in dry DCM (1 mL) and stirring is continued for 1 h. The mixture is washed with 1N NaOH and brine. The organic phase is separated, dried and evaporated under reduced pressure. The resulting residue is purified by flash chromatography (eluent 0-5% MeOH/EtOAc) to furnish the title compound (118 mg).

UPLC-MS (Method 2): $R_t$=0.90 min

MS (ESI pos): m/z=386 (M+H)$^+$

Example 29b

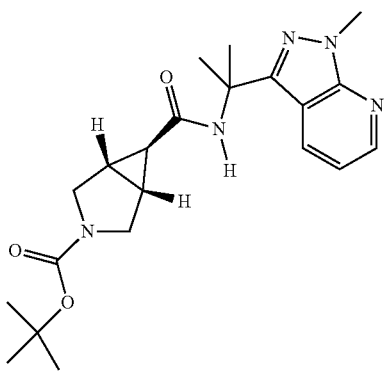 [SMILES: Cn1nc(C(C)(C)NC(=O)[C@H]2[C@@H]3CN(C(=O)OC(C)(C)C)C[C@@H]32)c2cccnc21]

HATU (134 mg, 0.353 mmol) is added to meso-(1R,5S,6r)-3-(tert-butoxycarbonyl)-3-azabicyclo[3.1.0]hexane-6-carboxylic acid (80 mg, 0.353 mmol), example 28b (56 mg, 0.294 mmol) and TEA (90 µl, 0.648 mmol) in dry THF (5 mL) and stirring is continued for 2 h. Solvent is removed and the resulting residue is purified by flash chromatography (eluent 0-100% EtOAc/Cyclohexane) to furnish the title compound (107 mg, 91%).

UPLC-MS (Method 2): $R_t$=0.96 min

MS (ESI pos): m/z=400 (M+H)$^+$

The following example is synthesized in analogy to the preparation of example 29b:

| Example | Structure | Reactant(s) | UPLC-MS $R_t$ [min], method | MS (ESI pos, m/z) (M + H)$^+$ |
|---|---|---|---|---|
| 29c | 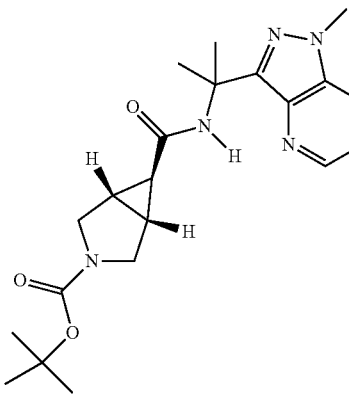 | Example 28c (101 mg, 0.53 mmol) | 0.95 2 | 400 |

Example 29d

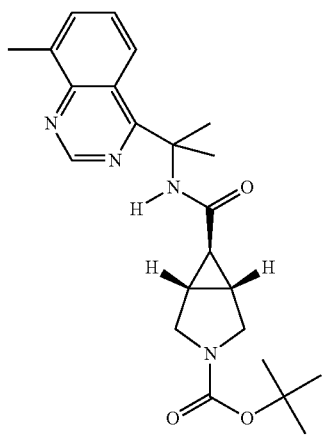 [SMILES: Cc1cccc2c(C(C)(C)NC(=O)[C@H]3[C@@H]4CN(C(=O)OC(C)(C)C)C[C@@H]43)ncnc12]

HATU (295 mg, 0.775 mmol) is added to meso-(1R,5S,6r)-3-(tert-butoxycarbonyl)-3-azabicyclo[3.1.0]hexane-6-carboxylic acid (136 mg, 0.596 mmol), example 28d (150 mg, 80% content, 0.596 mmol) and DIPEA (312 µl, 1.79 mmol) in DMF (2 mL) and stirring is continued overnight. Volatiles are evaporated under reduced pressure to furnish a residue that is diluted with ethyl acetate and washed with saturated NaHCO$_3$ and brine. The organic layers is separated, dried on a Phase separator cartridge and evaporated under reduce pressure to give a residue purified by flash chromatography (eluent 0-50% EtOAc/cyclohexane) to furnish the title compound (150 mg, 61%).

UPLC-MS (Method 2): R$_t$=1.17 min
MS (ESI pos): m/z=411 (M+H)$^+$

The following examples are synthesized in analogy to the preparation of example 29d:

| Example | Structure | Reactant(s) | UPLC-MS R$_t$ [min], method | MS (ESI pos or APCI, m/z) (M + H)$^+$ |
|---|---|---|---|---|
| 29e | 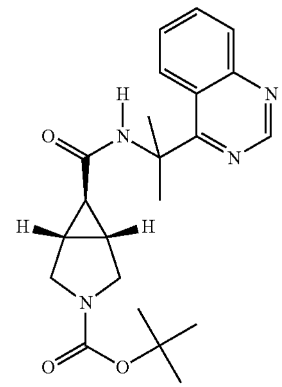 [SMILES: CC(C)(C)OC(=O)N1C[C@@H]2[C@H](C1)[C@H]2C(=O)NC(C)(C)c1ncnc2ccccc12] | 2-Quinazolin-4-ylpropan-2-amine (0.854 mmol) | 2.50 12 | 397 |
| 29f | 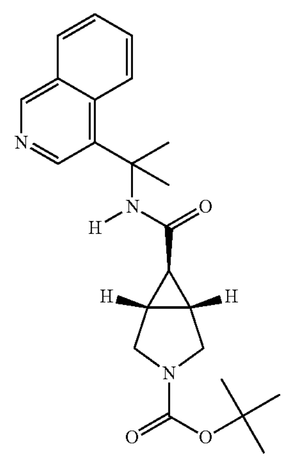 [SMILES: CC(C)(C)OC(=O)N1C[C@@H]2[C@H](C1)[C@H]2C(=O)NC(C)(C)c1cncc2ccccc12] | 2-isoquinolin-4-ylpropan-2-amine (0.899 mmol) | 2.93 7b | 396 |
| 29g | 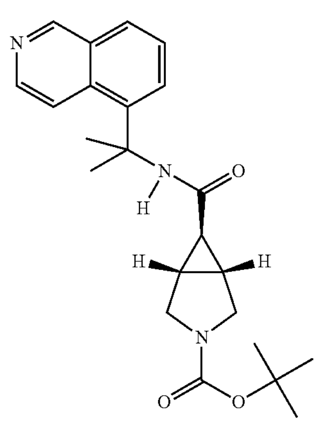 [SMILES: CC(C)(C)OC(=O)N1C[C@@H]2[C@H](C1)[C@H]2C(=O)NC(C)(C)c1cccc2cnccc12] | 2-(Isoquinolin-5-yl)propan-2-amine (0.359 mmol) | 2.83 7b | 396 |

Example 30a

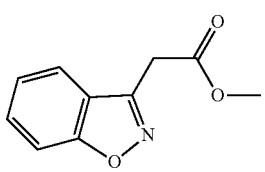

Hydroxylamine hydrochloride (7.5 g, 107.93 mmol) is added to a solution of hydroxy coumarin (5 g, 30.84 mmol) in MeOH (50 mL) at rt. Sodium acetate (8.8 g, 107.93 mmol) is added portionwise in 1.5 h. The reaction is stirred for 1.5 h at rt and then is heated at reflux overnight. Volatiles are evaporated, water is added and the mixture is cooled with ice-water bath. The aqueous layer is acidified to pH=3 with 4N HCl. A precipitate is filtered out and washed several times with water. The precipitate is dried under reduce pressure at 50° C. to give benzo[d]isoxazol-3-yl-acetic acid (4.3 g, 78%)

HPLC-MS (Method 11): $R_t$=0.32 min
MS (ESI pos): m/z=178 $(M+H)^+$

Trimethylsilydiazomethane (9.7 mL, 19.40 mmol) is added dropwise to benzo[d]isoxazol-3-yl-acetic acid (3.3 g, 17.64 mmol) in DCM/MeOH 11:1 (22 mL/2 mL) at 0° C. and stirring is continued for 1 h at 0° C. Volatiles are evaporated to give the title compound (3.3 g, 99%)

UPLC-MS (Method 2): $R_t$=0.88 min
MS (ESI pos): m/z=192 $(M+H)^+$

The following example is synthesized in analogy to the preparation of example 30a:

dried and evaporated to give a residue that is purified by flash chromatography (eluent 0-10% EtOAc/Cyclohexane) to furnish the title compound (870 mg, 51%).

UPLC-MS (Method 2): $R_t$=1.09 min
MS (ESI pos): m/z=220 $(M+H)^+$

Example 31b

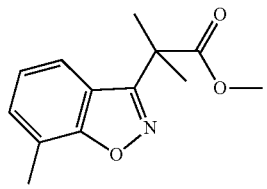

Sodium hydride (60% suspension in mineral oil, 973 mg, 24.32 mmol) is added portionwise to example 30b (1.42 g, 95% content, 6.57 mmol) in DMF (12 mL) at 0° C. The reaction is allowed to reach rt and stirred for 30 min. Iodomethane (2.1 mL, 33.20 mmol) is added dropwise to the reaction mixture cooled at 0° C. and the reaction is stirred at rt overnight.

Water is added and the reaction is extracted with EtOAc. Organic phase is washed with brine, dried and evaporated to give a residue that is purified by flash chromatography (eluent 0-40% EtOAc/Cyclohexane) to furnish the title compound (1.47 g, 96%).

GC-MS (Method 13): $R_t$=10.32 min
MS (EI pos): m/z=233 $[M]^+$

| Example | Structure | Reactant(s) | UPLC-MS $R_t$ [min], method | MS (ESI pos, m/z) |
|---|---|---|---|---|
| 30b | (structure) | 4-Hydroxy-8-methyl-2H-1-benzopyran-2-one (3.15 g, 17.88 mmol) | 3.49 11 | 146 $(M-CO_2H)^+$ |

Example 31a

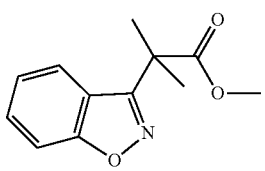 [SMILES: COC(=O)C(C)(C)c1noc2ccccc12]

Example 30a (1.5 g, 7.85 mmol) is dissolved in dry THF (30 mL) and the mixture is cooled at 0° C. Lithium bis(trimethylsilyl)amide 1M in THF (29 mL, 29 mmol) is added dropwise, the reaction is allowed to reach rt and stirred for 2 h. Iodomethane (1.8 mL, 29 mmol) is added dropwise and the reaction is stirred at rt overnight.

NH$_4$Cl saturated solution is added and the reaction is extracted with EtOAc. Organic phase is washed with brine,

Example 32a

Lithium hydroxide monohydrate (500 mg, 11.90 mmol) is added to example 31a (870 mg, 3.97 mmol) in water/THF 1:1 (9 mL) and the reaction is stirred at rt for 2 h. THF is evaporated, the mixture is cooled with ice-water bath. The aqueous layer is acidified to pH=4-5 with 1N HCl and extracted with DCM. Organic layer is dried on a phase separator cartridge and evaporated to give the title compound (810 mg, 98% content, 97%)

UPLC-MS (Method 2): $R_t$=0.53 min
MS (ESI pos): m/z=206 (M+H)$^+$

The following example is synthesized in analogy to the preparation of example 32a:

| Example | Structure | Reactant(s) | UPLC-MS $R_t$ [min], method | MS (APCI, m/z) (M + H)$^+$ |
|---|---|---|---|---|
| 32b | 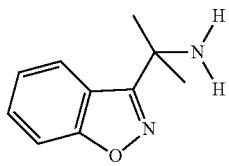 | Example 31b (1.47 g, 6.30 mmol) | 2.22 7a | 220 |

Example 33a

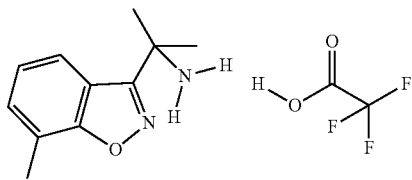

Diphenylphosphoryl azide (0.450 mL, 2.112 mmol) is added to example 32a (402 mg, 98% content, 1.92 mmol) and TEA (0.320 mL, 2.304 mmol) in toluene (3 mL) and the mixture is stirred at rt for 1 h. The mixture is added to toluene heated at 90° C. (3 mL) and heating is continued for 2 h at this temperature. Then the reaction is allowed to reach rt and stirred overnight. The mixture is poured into 4N HCl, phases are separated, the aqueous layer is basified with NaHCO$_3$ saturated solution to pH=10 and extracted with DCM. The organic layer is washed with brine, dried and evaporated to give a residue that is purified by preparative HPLC (stationary phase: Sunfire C18 ODB 5 µm 19×100 mm. Mobile phase: ACN/H2O+CF3COOH 0.05%). Fractions are combined, basified with NaHCO$_3$ saturated solution and ACN is evaporated. The aqueous layer is extracted with DCM, dried and evaporated to give the title compound (70 mg, 80% content, 18%).

UPLC-MS (Method 1): $R_t$=0.59 min
MS (ESI pos): m/z=177 (M+H)$^+$

Example 33b

Diphenylphosphoryl azide (0.596 mL, 2.773 mmol) is added to example 32b (640 mg, 2.919 mmol) and TEA (0.386 mL, 2.773 mmol) in toluene (5.4 mL) and the mixture is stirred at rt for 1 h and at 80° C. for 2 h. 4-Methoxybenzyl alcohol (0.364 mL, 2.919 mmol) and TEA (0.386 mL, 2.773 mmol) are added and stirring is continued overnight at 80° C. The mixture is diluted with EtOAc, washed with 10% citric acid, washed with brine, dried and evaporated to give a residue that is purified by flash chromatography (eluent 0-20% EtOAc/cyclohexane) to furnish [1-methyl-1-(7-methyl-benzo[d]isoxazol-3-yl)-ethyl]-carbamic acid 4-methoxy-benzyl ester (794 mg, 77%).

UPLC-MS (Method 12): $R_t$=3.73 min
MS (ESI pos): m/z=377 (M+Na)$^+$

TFA (4.3 mL) is added to [1-methyl-1-(7-methyl-benzo[d]isoxazol-3-yl)-ethyl]-carbamic acid 4-methoxy-benzyl ester (350 mg, 0.988 mmol) in DCM (4.4 mL) at 0° C. After stirring for 30 min at rt, volatiles are evaporated under reduced pressure to afford the title compound (300 mg, 98% content, 98%) that is used as such.

HPLC-MS (Method 2): $R_t$=0.66 min
MS (ESI pos): m/z=191 (M+H)$^+$

Example 34a

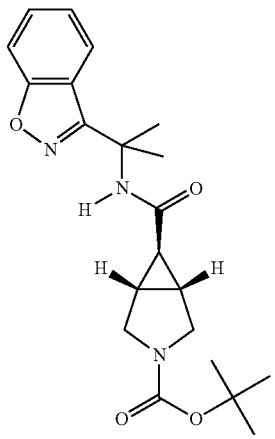 [SMILES: CC(C)(C)OC(=O)N1C[C@@H]2[C@H](C1)[C@H]2C(=O)NC(C)(C)c1noc2ccccc12]

HATU (184 mg, 0.484 mmol) is added to meso-(1R,5S,6r)-3-(tert-butoxycarbonyl)-3-azabicyclo[3.1.0]hexane-6-carboxylic acid (84 mg, 0.371 mmol), example 33a (77 mg, 85% content, 0.371 mmol) and DIPEA (194 µl, 1.114 mmol) in dry DMF (1 mL) and stirring is continued for 2 h. Volatiles are evaporated under reduced pressure and the crude is taken up with ethyl acetate and washed with saturated NaHCO$_3$ and brine. The organic layers is separated, dried on a Phase separator cartridge and evaporated under reduce pressure to give a residue that is purified by flash chromatography (eluent 0-40% EtOAc/cyclohexane) to furnish the title compound (60 mg, 98% content, 41%).

HPLC-MS (Method 12): $R_t$=3.43 min
MS (ESI pos): m/z=408 (M+Na)$^+$

Example 34b

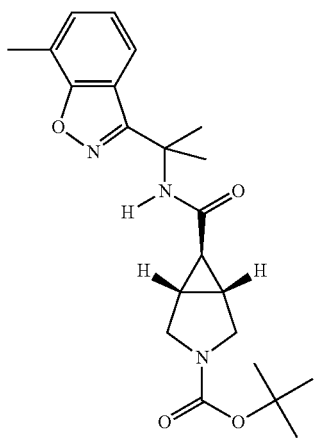 [SMILES: Cc1cccc2c(C(C)(C)NC(=O)[C@H]3[C@@H]4CN(C(=O)OC(C)(C)C)C[C@@H]43)noc12]

HATU (378 mg, 1.26 mmol) is added to meso-(1R,5S,6r)-3-(tert-butoxycarbonyl)-3-azabicyclo[3.1.0]hexane-6-carboxylic acid (220 mg, 0.966 mmol), example 33b (300 mg, 98% content, 0.966 mmol) and DIPEA (505 µl, 2.90 mmol) in dry DMF (2 mL) and stirring is continued for 2 h. Volatiles are evaporated under reduced pressure and the crude is taken up with ethyl acetate and washed with saturated NaHCO$_3$ and brine. The organic layers is separated, dried on a Phase separator cartridge and evaporated under reduce pressure to give a residue that is purified by flash chromatography (eluent 0-40% EtOAc/cyclohexane) to furnish the title compound (276 mg, 72%).

HPLC-MS (Method 11): R$_t$=2.97 min
MS (ESI pos): m/z=400 (M+H)$^+$

Example 35a

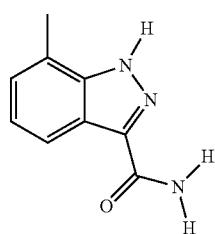

Example 35a is prepared from 7-methyl-1H-indazole-3-carboxylic acid (13.1 mmol) in analogy to example 6a to give the title compound (730 mg, 77% content, 25%)

HPLC-MS (Method 2): R$_t$=0.69 min
MS (ESI pos): m/z=176 (M+H)$^+$

Example 36a

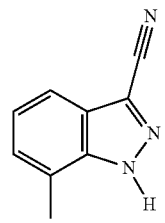

Example 36a is prepared from example 35a (650 mg, 77% content, 2.86 mmol) in analogy to example 7e to give the title compound (109 mg, 91% content, 22%)

HPLC-MS (Method 2): R$_t$=0.96 min
MS (ESI pos): m/z=158 (M+H)$^+$

Example 37a

Sodium hydride (60% suspension in mineral oil, 31 mg, 0.76 mmol) is added to a solution of 36a (109 mg, 91% content, 0.63 mmol) in DMF (1 mL) at 0° C. After 20 min, 2-(trimethylsilyl)ethoxymethyl chloride (157 µl, 0.88 mmol) is added dropwise to the reaction mixture. After stirring for 1 h at rt, the reaction is diluted with EtOAc, washed with NaHCO$_3$ saturated solution and brine. The organic layer is separated and dried with a Phase separator cartridge and evaporated under vacuum to give a residue that is purified by flash chromatography (eluent 0-10% EtOAc/cyclohexane) to furnish the title compound (182 mg).

UPLC-MS (Method 2): R$_t$=1.61
MS (ESI pos): m/z=288 (M+H)$^+$

The following example is synthesized in analogy to the preparation of example 39c:

| Example | Structure | Reactant(s) | GC-MS R$_t$ [min], method | MS (EI pos, m/z) [M]$^+$ |
|---|---|---|---|---|
| 37b | 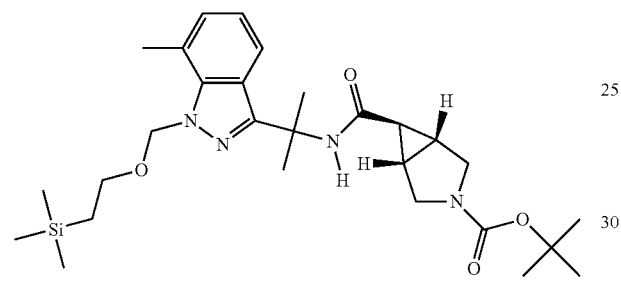 | 1H-Indazole-3-carbonitrile (1.90 g, 13.3 mmol) | 11.61-11.80 13 | 273 |

Example 38a

Under nitrogen atmosphere, dry THF (7.6 mL) is added to anhydrous Cerium (III) chloride (410 mg, 1.66 mmol) at 0° C. The reaction is allowed to reach RT and stirred for 2 h. At −78° C. methyllithium as a complex with Lithium Iodide (1.6 M in ethyl ether, 1.1 mL, 1.7 mmol) is added and stirring is continued for 30 minutes at −78° C. A solution of 37a (160 mg, 0.56 mmol) in THF dry (3 mL) is added to the mixture and stirring is continued for 30 minutes at −78° C. and then overnight at RT. Saturated NH$_4$Cl and NaOH (32% in water) are added to the mixture at −30° C. until a precipitate forms. Undissolved material is filtered away on a celite pad. The filtrate is washed with DCM, separated and dried with a phase separator cartridge. The solvent is evaporated under reduce pressure to obtain a crude that is used as such. HATU (263 mg, 0.692 mmol) is added to meso-(1R,5S,6r)-3-(tert-butoxycarbonyl)-3-azabicyclo[3.1.0]hexane-6-carboxylic acid (121 mg, 0.379 mmol), the crude from the previous step and DIPEA (278 µl, 1.60 mmol) in dry DMF (1 mL) and stirring is continued overnight. Volatiles are evaporated under reduced pressure to furnish a residue that is diluted with ethyl acetate and washed with saturated NaHCO$_3$ and brine. The organic layers is separated, dried on a Phase separator cartridge and evaporated under reduce pressure to give a residue purified by flash chromatography (eluent 10-40% EtOAc/cyclohexane) to furnish the title compound (160 mg, 54% over 2 steps).

UPLC-MS (Method 7a): R$_t$=6.32-6.62 min
MS (ESI pos): m/z=529 (M+H)$^+$

The following example is synthesized in analogy to the preparation of example 38a:

| Example | Structure | Reactant(s) | UPLC-MS R$_t$ [min], method | MS (ESI pos, m/z) (M + Na)$^+$ |
|---|---|---|---|---|
| 38b | 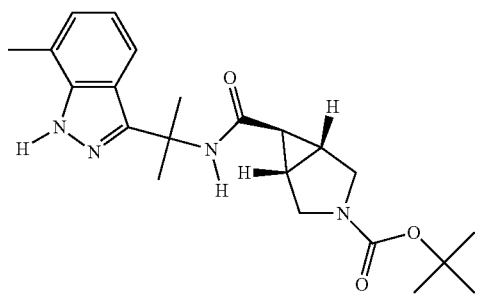 [SMILES: Cc1cccc2c(C(C)(C)NC(=O)[C@H]3[C@@H]4CN(C(=O)OC(C)(C)C)C[C@@H]43)n[nH]c12] | Example 37b (3.73 g, 13.6 mmol) | 4.31 12 | 537 |

Example 39a

Example 38a (160 mg, 0.303 mmol), tetrabutylammonium fluoride (1.0 M in THF, 3.9 mL, 3.9 mmol) and ethylenediamine (121 µl, 1.82 mmol) are refluxed overnight Volatiles are evaporated under reduced pressure to furnish a residue that is diluted with ethyl acetate and washed with water. The organic layers is separated, dried on a Phase separator cartridge and evaporated under reduce pressure to give a residue purified by flash chromatography (eluent 0-80% DCM:MeOH:NH$_3$ 95:5:0.5/DCM) to furnish the title compound (62 mg, 51%).

UPLC-MS (Method 7a): R$_t$=4.39 min

MS (APCI): m/z=399 (M+H)$^+$

The following example is synthesized in analogy to the preparation of example 39a:

| Example | Structure | Reactant(s) | UPLC-MS R$_t$ [min], method | MS (ESI pos, m/z) (M + H)$^+$ |
|---|---|---|---|---|
| 39b | 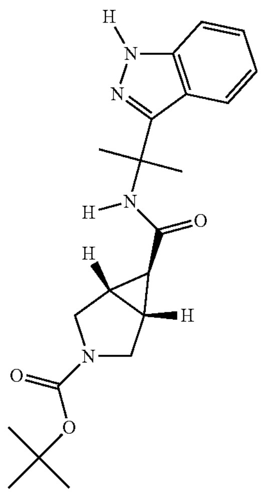 [SMILES: CC(C)(C)OC(=O)N1C[C@@H]2[C@H](C1)[C@H]2C(=O)NC(C)(C)c1n[nH]c2ccccc12] | Example 38b (1.60 g, 3.11 mmol) | 2.58 11 | 385 |

Example 39c

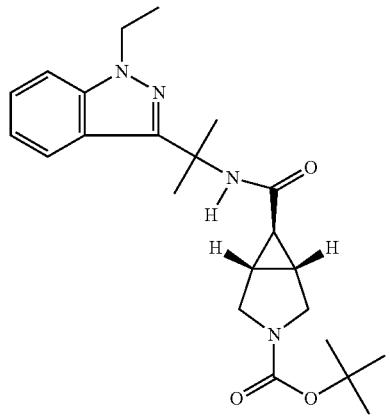 [SMILES: CCn1nc(C(C)(C)NC(=O)[C@H]2[C@@H]3CN(C(=O)OC(C)(C)C)C[C@@H]32)c2ccccc21]

Cesium carbonate (149 mg, 0.46 mmol) is added to a solution of example 39b (156 mg, 94% content, 0.38 mmol) in DMF (5 mL). After 15 min, iodoethane (31 µl, 0.38 mmol) is added dropwise to the reaction mixture. After stirring over weekend, volatiles are evaporated under reduced pressure, the reaction is diluted with EtOAc, washed with NaHCO$_3$ saturated solution and brine. The organic layer is separated and dried with a Phase separator cartridge and evaporated under vacuum to give a residue that is purified by flash chromatography (eluent 10-60% EtOAc/cyclohexane) to furnish the title compound (147 mg, 93%).

UPLC-MS (Method 11): R$_t$=3.01

MS (ESI neg): m/z=411 (M−H)$^−$

The following examples are synthesized in analogy to the preparation of example 37a:

| Example | Structure | Reactant(s) | UPLC-MS R$_t$ [min], method | MS (ESI neg, m/z) (M − H)$^−$ |
|---|---|---|---|---|
| 39d | 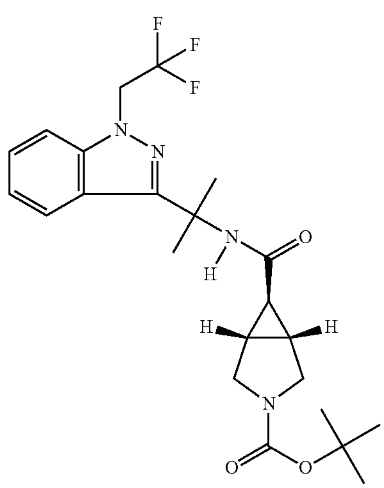 [SMILES: CC(C)(C)OC(=O)N1C[C@@H]2[C@H](C1)[C@H]2C(=O)NC(C)(C)c1nn(CC(F)(F)F)c2ccccc12] | Example 39b (156 mg, 94% content, 0.38 mmol), 2,2,2-trifluoroethyl iodide (113 µl, 1.14 mmol), cesium carbonate (447 mg, 1.37 mmol) | 3.09 11 | 465 |

| Example | Structure | Reactant(s) | UPLC-MS $R_t$ [min], method | MS (ESI neg, m/z) $(M - H)^-$ |
|---|---|---|---|---|
| 39e | 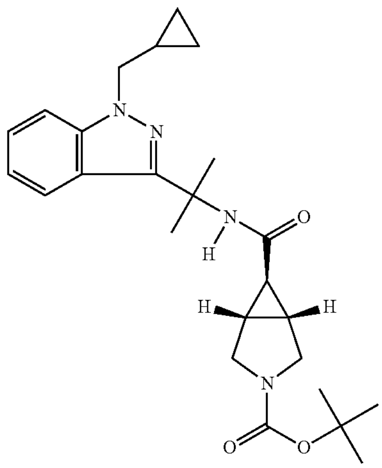 [SMILES: CC(C)(C)OC(=O)N1C[C@@H]2[C@H](C1)[C@H]2C(=O)NC(C)(C)c1nn(CC2CC2)c2ccccc12] | Example 39b (150 mg, 94% content, 0.37 mmol), cyclopropylmethyl bromide (36 μl, 0.37 mmol) | 3.20 11 | 439 (ESI pos, m/z) $(M + H)^+$ |
| 39f | 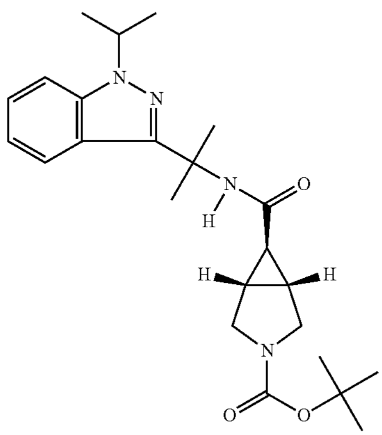 [SMILES: CC(C)n1nc(C(C)(C)NC(=O)[C@H]2[C@@H]3CN(C(=O)OC(C)(C)C)C[C@@H]32)c2ccccc21] | Example 39b (152 mg, 94% content, 0.37 mmol), 2-bromopropane (246 μl, 0.74 mmol), cesium carbonate (290 mg, 0.89 mmol) | 3.32 11 | 425 |
| 39g | 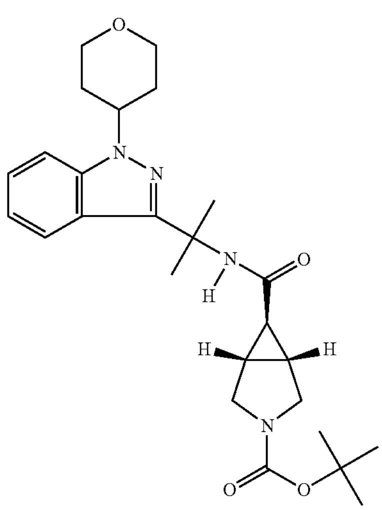 [SMILES: CC(C)(C)OC(=O)N1C[C@@H]2[C@H](C1)[C@H]2C(=O)NC(C)(C)c1nn(C2CCOCC2)c2ccccc12] | Example 39b (156 mg, 94% content, 0.38 mmol), 4-bromo-tetrahydropyran (215 μl, 1.91 mmol), cesium carbonate (746 mg, 2.29 mmol); after addition of 4-bromo-tetrahydropyran, stirring is continued for 4d at 40° C. | 3.01 11 | 467 |

Example 40a

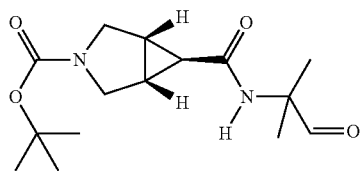 [SMILES: CC(C)(C=O)NC(=O)[C@H]1[C@@H]2CN(C(=O)OC(C)(C)C)C[C@@H]21]

Dess-Martin periodinane (54.7 g, 129.0 mmol) is added portionwise to example 4a (35.0 g, 117.3 mmol) in DCM (240 mL) cooled to 0° C. and stirring is continued at RT overnight. 10% sodium thiosulfate solution (200 mL) is added and stirring is continued for 30 min. The organic layers is separated, washed with saturated NaHCO$_3$ solution, dried on a Phase separator cartridge and evaporated under reduced pressure to furnish the title compound (34.7 g, 100%), that is used as such.

UPLC-MS (Method 7a): R$_t$=3.63 min
MS (AFCI): m/z=297 (M+H)$^+$

Example 41a

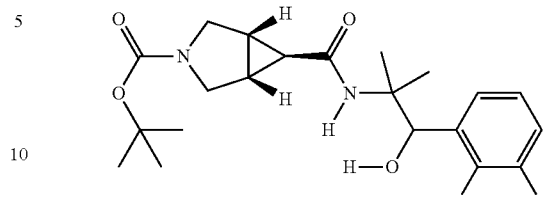

n-Butyllithium (2.0 M in cyclohexane, 67.5 mL, 135 mmol) is added to 1,2-difluorobenzene (12.3 g, 108 mmol) in THF (250 mL) at −78° C. Stirring is continued for 1 h. Example 40a (16.0 g, 54.0 mmol) in THF (5 mL) is added to the reaction mixture at −78° C. and stirring is continued for 3 h at that temperature. Saturated NH$_4$Cl (15 mL) is added to the reaction mixture at −78° C. The reaction mixture is warmed to RT. The organic layer is separated, washed with brine, dried with a Phase separator cartridge and evaporated under vacuum to give a residue that is purified by flash chromatography (eluent 20-40% EtOAc/cyclohexane) to furnish the title compound (11.2 g, 50%).

$^1$H NMR (300 MHz, DMSO-d$_6$): δ 1.13 (s, 3H), 1.24 (br s, 3H), 1.33-1.42 (m, 10H), 1.83 (d, J=2.7 Hz, 2H), 3.29 (br s, 2H), 3.46 (d, J=10.9 Hz, 2H), 5.23 (d, J=5.6 Hz, 1H), 5.99 (d, J=5.6 Hz, 1H), 7.11-7.39 (m, 3H), 7.62 (br s, 1H).

The following examples are synthesized in analogy to the preparation of example 41a:

| Example | Structure | Reactant(s) | UPLC-MS R$_t$ [min], method | MS (ESI pos, m/z) (M + H)$^+$ |
|---|---|---|---|---|
| 41b | 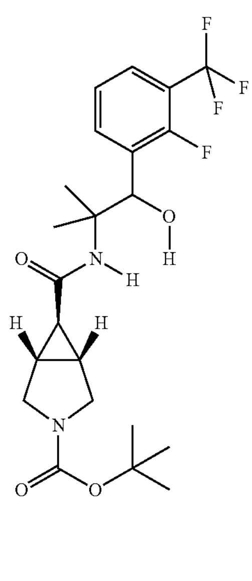 [SMILES: CC(C)(C)OC(=O)N1C[C@@H]2[C@H](C1)[C@H]2C(=O)NC(C)(C)C(O)c1cccc(C(F)(F)F)c1F] | Example 40a (2.49 g, 8.40 mmol); 2-fluoro-benzotrifluoride (2.76 g, 16.8 mmol) | 3.33 11 | 461 |

-continued

| Example | Structure | Reactant(s) | UPLC-MS R$_t$ [min], method | MS (ESI pos, m/z) (M + H)$^+$ |
|---|---|---|---|---|
| 41c | 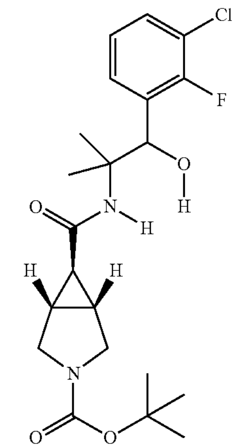 [SMILES: CC(C)(C)OC(=O)N1C[C@@H]2[C@H](C1)[C@H]2C(=O)NC(C)(C)C(O)c1cccc(Cl)c1F] | Example 40a (1.98 g, 6.68 mmol); 1-chloro-2-fluorobenzene (1.74 g, 13.4 mmol) | 3.22 11 | 427 |

Example 41d

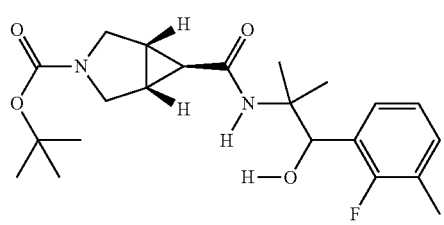 [SMILES: Cc1cccc(C(O)C(C)(C)NC(=O)[C@H]2[C@@H]3CN(C(=O)OC(C)(C)C)C[C@@H]32)c1F]

n-Butyllithium (2.0 M in cyclohexane, 19.4 mL, 38.9 mmol) is added to 2-fluorotoluene (3.4 mL, 31 mmol) in THF (65 mL) at −78° C. Stirring is continued for 1 h. Example 40a (4.70 g, 98% content, 15.54 mmol) in THF (5 mL) is added to the reaction mixture at −78° C. and stirring is continued for 1 h at that temperature. n-Butyllithium (2.0 M in cyclohexane, 15.5 mL, 31.1 mmol) is added to potassium tert-butoxide (3.49 g, 31.08 mmol) in THF (15 mL) at −78° C. and the resulting mixture added to the reaction mixture containing example 40 at −78° C. After 1 h saturated NH$_4$Cl (50 mL) is added to the reaction mixture at −78° C. The reaction mixture is warmed to RT. The organic layer is separated, washed with brine, dried with a Phase separator cartridge and evaporated under vacuum to give a residue that is purified by flash chromatography (eluent 0-40% EtOAc/cyclohexane) to furnish the title compound (1.70 g, 97% content, 26%).

UPLC-MS (Method 7a): R$_t$=4.95 min
MS (APCI): m/z=407 (M+H)$^+$

Example 42a

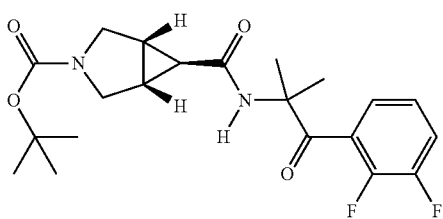 [SMILES: CC(C)(C)OC(=O)N1C[C@@H]2[C@H](C1)[C@H]2C(=O)NC(C)(C)C(=O)c1cccc(F)c1F]

Dess-Martin periodinane (12.7 g, 29.9 mmol) is added portionwise to example 41a (11.2 g, 27.2 mmol) in DCM (200 mL) cooled to 0° C. and stirring is continued at RT overnight. 10% sodium thiosulfate solution is added and stirring is continued for 30 min. The organic layers is separated, washed with saturated NaHCO$_3$ solution, dried on a Phase separator cartridge and evaporated under reduce pressure to furnish the title compound (10.4 g, 94%), that is used as such.

UPLC-MS (Method 7a): R$_t$=4.72 min
MS (APCI): m/z=409 (M+H)$^+$

The following examples are synthesized in analogy to the preparation of example 42a:

| Example | Structure | Reactant(s) | UPLC-MS $R_t$ [min], method | MS (ESI pos or APCI, m/z) (M + H)⁺ |
|---|---|---|---|---|
| 42b | 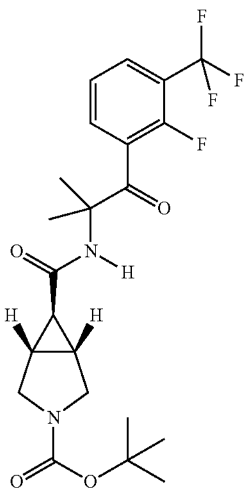 [SMILES: CC(C)(C)OC(=O)N1C[C@@H]2[C@H](C1)[C@H]2C(=O)NC(C)(C)C(=O)c1cccc(C(F)(F)F)c1F] | Example 41b (2.06 g, 4.47 mmol) | 5.40 7a | 459 |
| 42c | 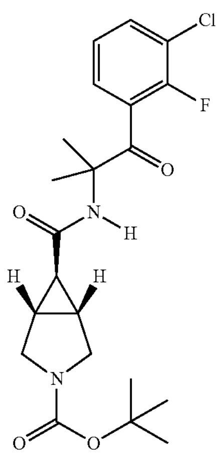 [SMILES: CC(C)(C)OC(=O)N1C[C@@H]2[C@H](C1)[C@H]2C(=O)NC(C)(C)C(=O)c1cccc(Cl)c1F] | Example 41c (1.07 g, 2.51 mmol) | 3.25 11 | 425 |
| 42d | 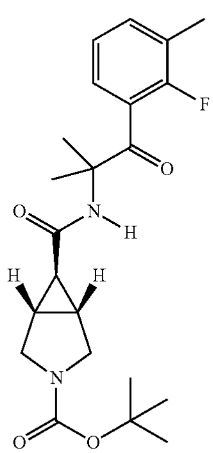 [SMILES: Cc1cccc(C(=O)C(C)(C)NC(=O)[C@H]2[C@@H]3CN(C(=O)OC(C)(C)C)C[C@@H]32)c1F] | Example 41d (1.70 g, 97% content, 4.06 mmol) | 4.89 7a | 405 |

Example 43a

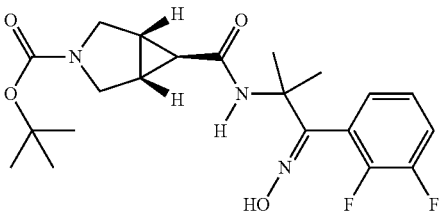 [SMILES: CC(C)(C)OC(=O)N1C[C@@H]2[C@H](C1)[C@H]2C(=O)NC(C)(C)C(=NO)c1cccc(F)c1F]

Hydroxylamine hydrochloride (3.93 g, 56.62 mmol) is added to example 42a (9.25 g, 22.65 mmol) in pyridine (30 mL) and stirring is continued at 50° C. over weekend. Volatiles are evaporated under reduced pressure, DCM and water are added. The organic layers is separated, washed with brine, dried on a Phase separator cartridge and evaporated under reduce pressure to furnish the title compound (8.85 g, 92%), that is used as such.

UPLC-MS (Method 7a): $R_t$=4.52 min
MS (APCI): m/z=424 (M+H)⁺

The following example is synthesized in analogy to the preparation of example 43a:

| Example | Structure | Reactant(s) | UPLC-MS $R_t$ [min], method | MS (ESI pos or APCI, m/z) (M + H)⁺ |
|---|---|---|---|---|
| 43b | 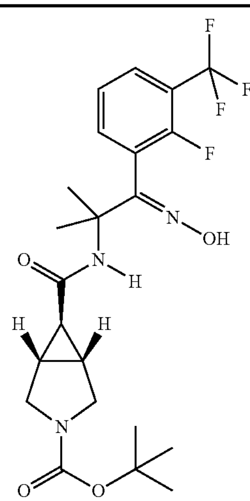 | Example 42b (1.00 g, 2.18 mmol) | 4.88 7a | 474 |

Example 43c

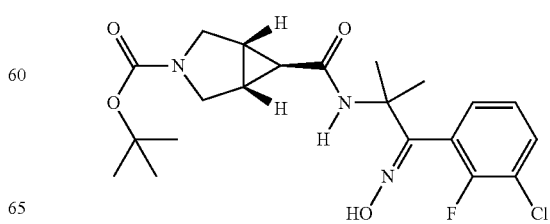

Hydroxylamine hydrochloride (429 mg, 6.18 mmol) is added to example 42c (1.05 g, 2.47 mmol) in pyridine (20 mL) and stirring is continued at RT for 2 h and at 50° C. over weekend. Volatiles are evaporated under reduced pressure and the residue is triturated with DCM at RT first and then with boiling AcOEt/acetone to furnish the title compound (550 mg, 51%).

$^1$H NMR (300 MHz, DMSO-d$_6$): δ 1.13-1.43 (m, 13H), 1.57 (br s, 3H), 1.79 (br s, 2H), 3.30 (br s, 4H), 7.00 (t, J=7.9 Hz, 1H), 7.26 (t, J=7.9 Hz, 1H), 7.52-7.66 (m, 1H), 7.97 (s, 1H), 10.95 (s, 1H).

Example 44a

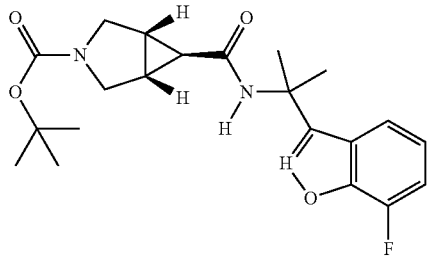

Potassium tert-butoxide (175 mg, 1.56 mmol) is added to example 43a (600 mg, 1.42 mmol) in THF (30 mL) and the reaction mixture is refluxed for 2 h. The reaction is diluted with EtOAc, washed with water and brine. The organic layer is separated and dried with a Phase separator cartridge and evaporated under vacuum to give a residue that is purified by flash chromatography (eluent 0-30% EtOAc/cyclohexane) to furnish the title compound (340 mg, 60%).

UPLC-MS (Method 1): R$_t$=1.22 min

MS (ESI pos): m/z=404 (M+H)$^+$

The following examples are synthesized in analogy to the preparation of example 44a:

| Example | Structure | Reactant(s) | UPLC-MS R$_t$ [min], method | MS (ESI pos or APCI, m/z) (M + H)$^+$ |
|---|---|---|---|---|
| 44b | 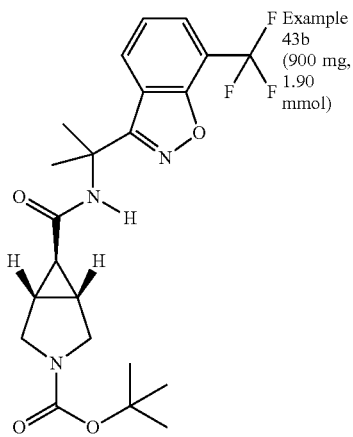 | Example 43b (900 mg, 1.90 mmol) | 5.21 7a | 454 |
| 44c | 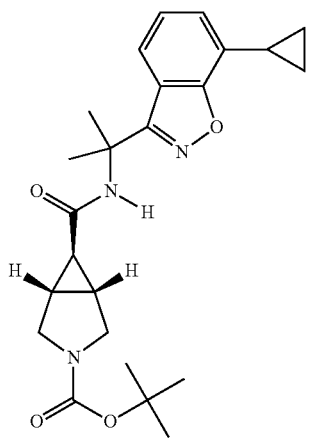 [SMILES: CC(C)(C)OC(=O)N1C[C@@H]2[C@H](C1)[C@H]2C(=O)NC(C)(C)c1noc2c(C3CC3)cccc12] | Example 43c (100 mg, 0.23 mmol) | 1.22 2 | 420 |

Example 44d

Cyclopentyl methyl ether (2 mL) and water (0.2 mL) are added to example 44c (140 mg, 0.32 mmol), potassium cyclopropyltrifluoroborate (47 mg, 0.32 mmol), palladium (II) acetate (2 mg, 0.01 mmol), X-Phos (9 mg, 0.02 mmol) and Potassium carbonate (13 mg, 0.10 mmol) and the reaction mixture is heated at 100° C. overnight. The reaction is diluted with EtOAc/brine. The organic layer is separated, dried and evaporated under reduce pressure to give a residue that is purified by flash chromatography (eluent 0-30% EtOAc/cyclohexane) to furnish the title compound (105 mg, 78%).

UPLC-MS (Method 7a): R$_t$=5.37 min

MS (APCI): m/z=426 (M+H)$^+$

Example 45a

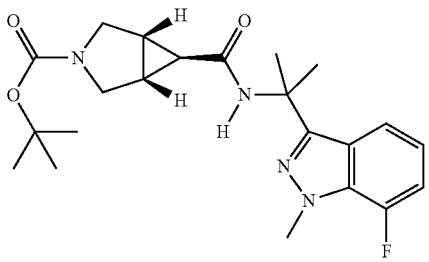 [SMILES: Cn1nc(C(C)(C)NC(=O)[C@H]2[C@@H]3CN(C(=O)OC(C)(C)C)C[C@@H]32)c2cccc(F)c21]

Example 42a (1.00 g, 2.45 mmol) and methylhydrazine (645 µl, 12.2 mmol) in EtOH (2 mL) are heated under microwaves irradation (160° C.) for 20 min. Volatiles are evaporated under reduce pressure to give a residue that is purified by flash chromatography (eluent 0-40% EtOAc/cyclohexane) to furnish the title compound (630 mg, 62%).
UPLC-MS (Method 2): $R_t$=1.20 min
MS (ESI pos): m/z=417 (M+H)$^+$

Example 45b

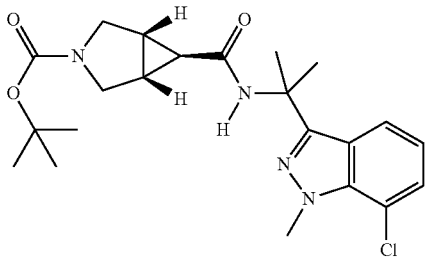

Example 42c (350 mg, 0.82 mmol) and methylhydrazine (217 µl, 4.12 mmol) in EtOH (3 mL) are heated under microwaves irradation (150° C.) for 60 min. Volatiles are evaporated under reduce pressure to give a residue that is purified by flash chromatography (eluent 0-40% EtOAc/cyclohexane) to furnish the title compound (220 mg, 62%).
UPLC-MS (Method 2): $R_t$=1.31 min
MS (ESI pos): m/z=433 (M+H)$^+$

Example 45c

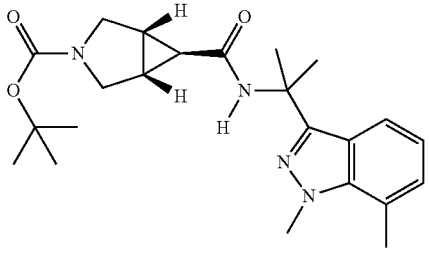 [SMILES: Cc1cccc2c(C(C)(C)NC(=O)[C@H]3[C@@H]4CN(C(=O)OC(C)(C)C)C[C@@H]43)nn(C)c12]

Example 45b (1.50 g, 98% content, 3.40 mmol), tetrakis(triphenylphosphine)palladium(0) (157 mg, 0.136 mmol) and tetramethyltin (1.3 mL, 9.5 mmol) are dissolved in DMF (12 mL), split in 2 equal batches and heated under microwaves irradation (175° C.) for 35 min. The reaction is diluted with EtOAc/brine. The organic layer is separated, dried and evaporated under reduced pressure to give a residue that is purified by flash chromatography (eluent 0-40% EtOAc/cyclohexane) to furnish a residue that is in turn purified by C18 chromatography (eluent 25-90% ACN/H$_2$O) to afford the title compound (1.16 g, 83%).
UPLC-MS (Method 2): $R_t$=1.22 min
MS (ESI pos): m/z=413 (M+H)$^+$

Example 45d

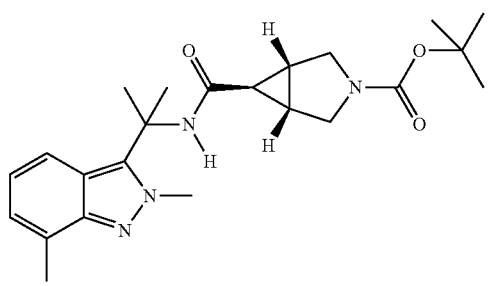 [SMILES: Cc1cccc2c(C(C)(C)NC(=O)[C@H]3[C@@H]4CN(C(=O)OC(C)(C)C)C[C@@H]43)n(C)nc12]

Example 42d (1.10 g, 2.72 mmol), copper (II) oxide (11 mg, 0.14 mmol), potassium carbonate (564 mg, 4.08 mmol) and methylhydrazine (917 µl, 17.41 mmol) are heated at 110° C. for 3 d. The reaction is filtered on a celite pad, which is washed with EtOAc. The filtrate is washed with water and then dried. Volatiles are evaporated under reduce pressure to give a residue that is purified by flash chromatography (eluent 0-100% EtOAc/cyclohexane) to furnish the title compound (95 mg, 9%). Example 45c is also obtained as by-product.
UPLC-MS (Method 2): $R_t$=1.11 min
MS (ESI pos): m/z=413 (M+H)$^+$

Example 45e

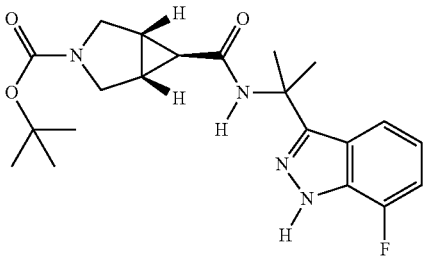

Example 42a (1.50 g, 3.67 mmol) and hydrazine hydrate (3 mL, 60 mmol) in EtOH (2 mL) are heated under microwaves irradation (120° C.) for 8 h. Volatiles are evaporated under reduce pressure to give a residue that is purified by preparative HPLC (stationary phase: XBridge C18 5 µm 19×100 mm. Mobile phase: ACN/H$_2$O+NH$_4$COOH 5 mM). Fractions containing the title compound are combined and lyophilised to furnish the title compound (40 mg, 3%).
UPLC-MS (Method 2): $R_t$=1.05 min
MS (ESI pos): m/z=403 (M+H)$^+$

Example 45f

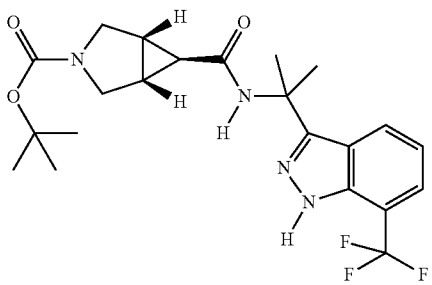 [SMILES: CC(C)(C)OC(=O)N1C[C@@H]2[C@H](C1)[C@H]2C(=O)NC(C)(C)c1n[nH]c2c(C(F)(F)F)cccc12]

Example 42b (150 mg, 0.327 mmol) and hydrazine hydrate (56 μl, 1.15 mmol) in EtOH (2 mL) are heated under microwaves irradation (140° C.) for 15 min. Volatiles are evaporated under reduce pressure to give a residue that is dissolved with EtOAc/water. The organic layer is separated, washed with brine, dried and evaporated under reduce pressure to furnish the title compound (132 mg, 89%) that is used as such.
UPLC-MS (Method 7a): $R_t$=4.73 min
MS (AFCI): m/z=453 (M+H)$^+$

Example 46a

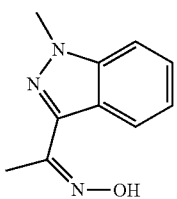

1-(1-Methyl-1H-indazol-3-yl)ethanone (800 mg, 4.59 mmol), hydroxylamine hydrochloride (479 mg, 6.89 mmol) and TEA (958 μl, 6.89 mmol) in EtOH (4 mL) are heated under microwaves irradation (120° C.) for 20 min. The reaction mixture is diluted with EtOAc/water. The organic layer is separated, washed with brine, dried and evaporated under reduce pressure to furnish the title compound (800 mg, 92%) that is used as such.
UPLC-MS (Method 2): $R_t$=0.91 min
MS (ESI pos): m/z=190 (M+H)$^+$

Example 47a (racemic mixture)

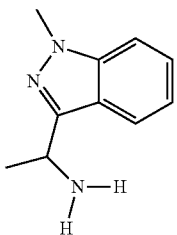

Raney Nickel (100 mg, 1.17 mmol) is added to example 46a (200 mg, 1.06 mmol) and ammonium hydroxide (300 μl, 2.31 mmol) in EtOH (10 mL) and the mixture is hydrogenated at 3.5 bar for 3 h. The catalyst is removed by filtration on a celite pad washing with EtOH and water. EtOH is evaporated under reduced and DCM is added. The organic layer is separated, dried and evaporated under reduce pressure to furnish the title compound (140 mg, 76%) that is used as such.
UPLC-MS (Method 2): $R_t$=0.62 min
MS (ESI pos): m/z=159 (M-NH$_2$)$^+$

Example 48a (mixture of stereoisomers)

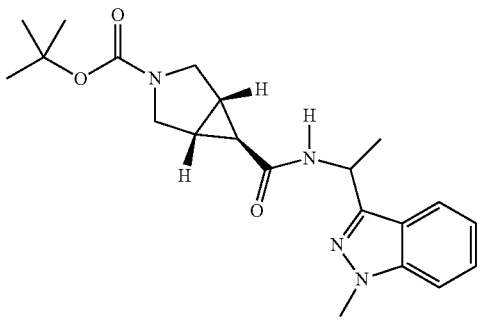 [SMILES: CC(NC(=O)[C@H]1[C@@H]2CN(C(=O)OC(C)(C)C)C[C@@H]21)c1nn(C)c2ccccc12]

HATU (414 mg, 1.09 mmol) is added to meso-(1R,5S,6r)-3-(tert-butoxycarbonyl)-3-azabicyclo[3.1.0]hexane-6-carboxylic acid (165 mg, 0.726 mmol), example 47a (140 mg, 0.799 mmol) and DIPEA (379 μl, 2.18 mmol) in dry DMF (5 mL) and stirring is continued overnight. The reaction mixture is diluted with ethyl acetate and washed with water and brine. The organic layers is separated, dried on a Phase separator cartridge and evaporated under reduce pressure to furnish the title compound (250 mg, 90%) that is used as such.
UPLC-MS (Method 2): $R_t$=1.09 min
MS (ESI pos): m/z=385 (M+H)$^+$ The stereoisomers of the title compound are separated by HPLC using a chiral stationary phase.
Method for Separation:
HPLC apparatus type: Waters 600 Pump, 2767 Autosampler, UV Detector 2489; column: Daicel chiralpack AD-H, 5.0 μm, 250 mm×20 mm; method: eluent hexane/IPA 90:10; flow rate: 12 mL/min, temperature: 21-22° C.; UV Detection: 220 nm

---

Example 48b: stereoisomer 1
Unknown absolute stereochemistry at
NH—C marked with an asterisk

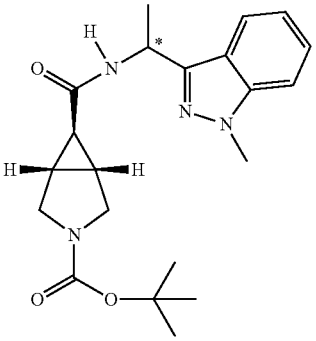 [SMILES: CC(NC(=O)[C@H]1[C@@H]2CN(C(=O)OC(C)(C)C)C[C@@H]21)c1nn(C)c2ccccc12]

---

Example 48c: stereoisomer 2
Unknown absolute stereochemistry at
NH—C marked with an asterisk

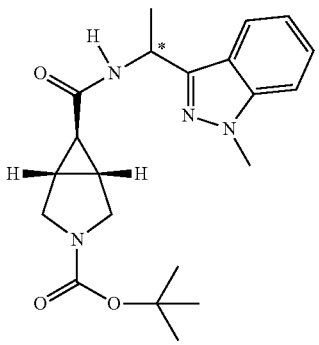 [SMILES: CC(NC(=O)[C@H]1[C@@H]2CN(C(=O)OC(C)(C)C)C[C@@H]21)c1nn(C)c2ccccc12]

| Example | Chiral HPLC (Method 14) R$_t$ [min] | HPLC-MS (Method 12): R$_t$ [min] | MS (ESI pos): m/z |
|---|---|---|---|
| 48b | 3.80 | 3.32 | 385 |
| 48c | 4.56 | 3.32 | 385 |

Example 49a (racemic mixture)

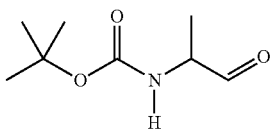

Dess-Martin periodinane (12.3 g, 29.1 mmol) is added portionwise to N-BOC-2-amino-1-propanol (5.00 g, 28.5 mmol) in DCM (75 mL) cooled to 0° C. and stirring is continued at RT overnight. 10% sodium thiosulfate solution is added and stirring is continued for 30 min. The organic layers is separated, washed with saturated NaHCO$_3$ solution, dried on a Phase separator cartridge and evaporated under reduce pressure to furnish the title compound (4.68 g, 95%), that is used as such.

$^1$H NMR (300 MHz, DMSO-d$_6$): δ 1.12 (d, J=7.3 Hz, 3H), 1.39 (br, s, 9H), 3.86 (m, 1H), 7.31 (br, d, J=6.4 Hz, 1H), 9.42 (d, J=0.7, 1H)

Example 50a (mixture of stereoisomers)

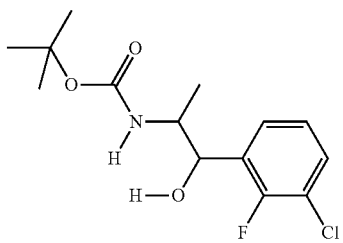 [SMILES: CC(NC(=O)OC(C)(C)C)C(O)c1cccc(Cl)c1F]

n-Butyllithium (2.5 M in hexanes, 16.2 mL, 40.4 mmol) is added to 1-chloro-2-fluorobenzene (3.6 mL, 34.6 mmol) in THF (76 mL) at −78° C. Stirring is continued for 1 h.

Example 49a (2.00 g, 11.6 mmol) in THF (15 mL) is added to the reaction mixture at −78° C. and stirring is continued for 1 h at that temperature. Saturated NH$_4$Cl (100 mL) is added to the reaction mixture at −78° C. The reaction mixture is warmed to RT. The organic layer is separated, washed with brine, dried with a Phase separator cartridge and evaporated under vacuum to give a residue that is purified by flash chromatography (eluent 0-30% EtOAc/cyclohexane) to furnish the title compound (1.65 g, 47%).

UPLC-MS (Method 2): R$_t$=1.15 min

MS (ESI pos): m/z=304 (M+H)$^+$

Example 51a (racemic mixture)

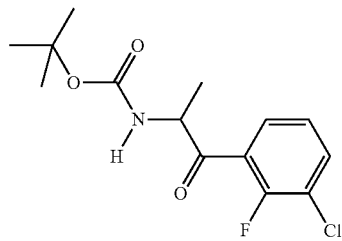 [SMILES: CC(NC(=O)OC(C)(C)C)C(=O)c1cccc(Cl)c1F]

Dess-Martin periodinane (2.46 g, 5.79 mmol) is added portionwise to example 50a (1.60, 5.27 mmol) in DCM (10 mL) cooled to 0° C. and stirring is continued at RT for 2 h. 10% sodium thiosulfate solution is added and stirring is continued for 30 min. The organic layers is separated, washed with saturated NaHCO$_3$ solution, dried on a Phase separator cartridge and evaporated under reduce pressure to furnish the title compound (1.50 g, 89% content, 84%), that is used as such.

UPLC-MS (Method 2): R$_t$=1.25 min

MS (ESI pos): m/z=302 (M+H)$^+$

Example 52a (racemic mixture)

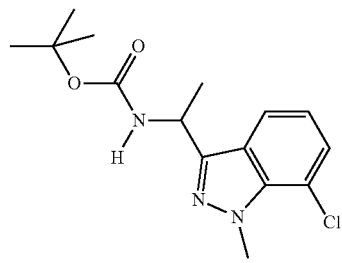 [SMILES: CC(NC(=O)OC(C)(C)C)c1nn(C)c2c(Cl)cccc12]

Example 51a (1.50 g, 89% content, 4.42 mmol) and methylhydrazine (2.8 mL, 53 mmol) in EtOH (7 mL) are heated at 75° C. overnight followed by 4 h at 80° C. Volatiles are evaporated under reduce pressure to give a residue that is purified by flash chromatography (eluent 0-30% EtOAc/cyclohexane) to furnish the title compound (620 mg, 45%).

$^1$H NMR (300 MHz, DMSO-d$_6$): δ 1.37 (br, s, 9H), 1.48 (d, J=7.0 Hz, 3H), 4.26 (s, 3H), 5.06 (m, 1H), 7.08 (dd, J=7.6, 8.2 Hz, 1H), 7.42 (m, 2H), 7.83 (dd, J=0.9, 8.0 Hz, 1H).

Example 52b (racemic mixture)

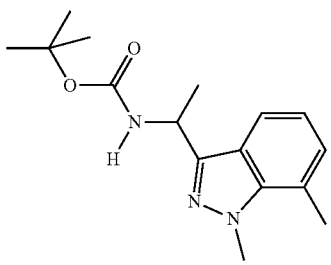 [SMILES: Cc1cccc2c(C(C)NC(=O)OC(C)(C)C)nn(C)c12]

Trimethylboroxine (542 μl, 3.87 mmol) is added to example 52a (400 mg, 1.291 mmol), potassium carbonate (892 mg, 6.46 mmol) and 1,1'-bis(diphenylphosphino)ferrocene-palladium(II)dichloride dichloromethane complex (105 mg, 0.129 mmol) in DMF (6 mL) and the reaction mixture is heated at 100° C. overnight. Trimethylboroxine (542 μl, 3.87 mmol), potassium carbonate (892 mg, 6.46 mmol) and 1,1'-bis(diphenylphosphino)ferrocene-palladium (II)dichloride dichloromethane complex (105 mg, 0.129 mmol) are added to the reaction mixture cooled to RT and) and the reaction mixture is heated at 100° C. for 1 d. Volatiles are evaporated under reduced pressure and the residue dissolved with EtOAc/water. The organic layer is separated, dried and evaporated under reduce pressure to give a residue that is purified by flash chromatography (eluent 0-20% EtOAc/cyclohexane) to furnish the title compound (175 mg, 95% content, 45%).

UPLC-MS (Method 2): $R_t$=1.21 min
MS (ESI pos): m/z=290 (M+H)$^+$

Example 53a (racemic mixture)

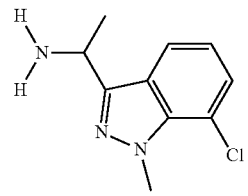

Example 52a (220 mg, 0.710 mmol) is suspended in MeOH/Water 1:1 (1 mL/1 mL), and heated under microwaves irradation (140° C.) for 50 min. The reaction mixture is purified on a SCX cartridge, which is washed with MeOH and DCM, and then eluted with $NH_3$ in MeOH to give the title compound (145 mg, 97%)

UPLC-MS (Method 2): $R_t$=0.71 min
MS (ESI pos): m/z=193 (M-$NH_2$)$^+$

The following example is synthesized in analogy to the preparation of example 53a:

| Example | Structure | Reactant(s) | HPLC-MS $R_t$ [min], method | MS (ESI pos, m/z) (M – $NH_2$)$^+$ |
|---|---|---|---|---|
| 53b (racemic mixture) | 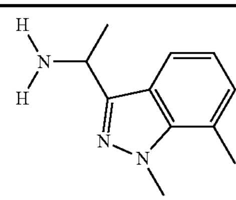 | Example 52b (175 mg, 95% content, 0.575 mmol) | 0.66 2 | 173 |

The following example is synthesized in analogy to the preparation of example 34b:

| Example | Structure | Reactant(s) | HPLC-MS $R_t$ [min], method | MS (APCI, m/z) (M + H)$^+$ |
|---|---|---|---|---|
| 54a (mixture of stereoisomers) | | Example 53a (145 mg, 0.692 mmol) | 4.85 7a | 419 |

The stereoisomers of the example 54a are separated by HPLC using a chiral stationary phase.

Method for Separation:

HPLC apparatus type: Waters 600 Pump, 2767 Autosampler, UV Detector 2489; column: Deicel chiralpack AD-H, 5.0 μm, 250 mm×20 mm; method: eluent hexane/IPA 85:15; flow rate: 10 mL/min, temperature: 25° C.; UV Detection: 230 nm Example 54b: stereoisomer 1
Unknown absolute stereochemistry at
NH—C marked with an asterisk

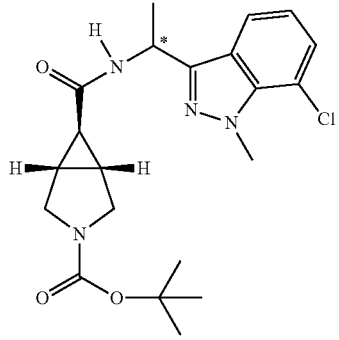 [SMILES: CC(NC(=O)[C@H]1[C@@H]2CN(C(=O)OC(C)(C)C)C[C@@H]21)c1nn(C)c2c(Cl)cccc12]

Example 54c: stereoisomer 2
Unknown absolute stereochemistry at
NH—C marked with an asterisk

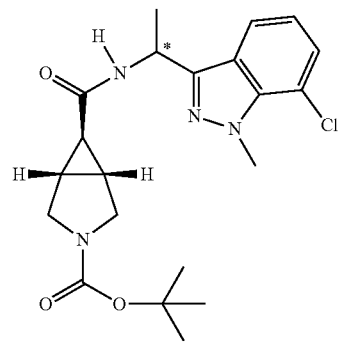 [SMILES: CC(NC(=O)[C@H]1[C@@H]2CN(C(=O)OC(C)(C)C)C[C@@H]21)c1nn(C)c2c(Cl)cccc12]

| Example | Chiral HPLC (Method 15) R$_t$ [min] | HPLC-MS (Method 11): R$_t$ [min] | MS (ESI pos): m/z |
|---|---|---|---|
| 54b | 8.87 | 3.25 | 419 |
| 54c | 9.86 | 3.24 | 419 |

The following example is synthesized in analogy to the preparation of example 34b:

| Example | Structure | Reactant(s) | HPLC-MS R$_t$ [min], method | MS (ESI pos, m/z) (M + H)$^+$ |
|---|---|---|---|---|
| 54d (mixture of stereoisomers) | | Example 53b (114 mg, 0.602 mmol) | 3.05 11 | 399 |

The stereoisomers of the example 54d are separated by HPLC using a chiral stationary phase.

Method for Separation:

HPLC apparatus type: Waters 600 Pump, 2767 Autosampler, UV Detector 2489; column: Daicel chiralpack AD-H, 5.0 μm, 250 mm×20 mm; method: eluent hexane/IPA 85:15; flow rate: 15 mL/min, temperature: 25° C.; UV Detection: 230 nm Example 54e: stereoisomer 1
Unknown absolute stereochemistry at
NH—C marked with an asterisk

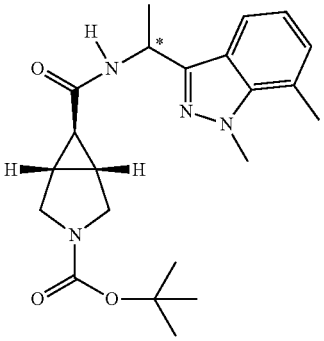 [SMILES: Cc1cccc2c(C(C)NC(=O)[C@H]3[C@@H]4CN(C(=O)OC(C)(C)C)C[C@@H]43)nn(C)c12]

Example 54f: stereoisomer 2
Unknown absolute stereochemistry at
NH—C marked with an asterisk

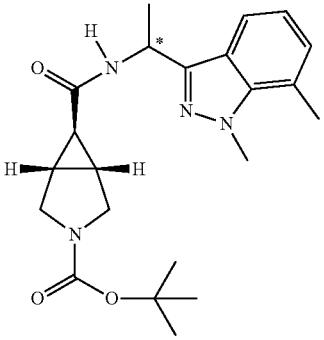 [SMILES: Cc1cccc2c(C(C)NC(=O)[C@H]3[C@@H]4CN(C(=O)OC(C)(C)C)C[C@@H]43)nn(C)c12]

| Example | Chiral HPLC (Method 15) R$_t$ [min] | HPLC-MS (Method 11): R$_t$ [min] | MS (ESI pos): m/z |
|---|---|---|---|
| 54e | 6.00 | 2.88 | 399 |
| 54f | 7.16 | 2.87 | 399 |

Example 55a

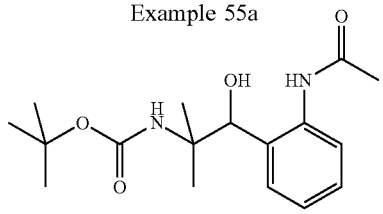

2-Bromoacetanilide (1.68 g, 90% content, 7.06 mmol) is dissolved in dry THF (15 mL) and cooled to −78° C. under a nitrogen atmosphere. n-Butyllithium (2.5 M solution in hexane, 5.93 mL, 14.8 mmol) is added dropwise and the mixture stirred at −78° C. for 30 minutes. tert-Butyl 2-formylpropan-2-ylcarbamate (1.39 g, 7.42 mmol) in dry THF (10 mL) is added dropwise and the mixture stirred for 30 minutes at −78° C. then allowed to warm to −50° C. over 1 hour. Saturated aqueous ammonium chloride solution (20 mL) is added, the mixture allowed to warm to room temperature and the phases separated. The organic phase is washed with brine, dried and the solvent removed. The residue is purified by flash chromatography (Eluent 0-2% MeOH in DCM) to give the title product (370 mg, 16%).

LC-MS (Method 1): R$_t$=1.02 min
MS (ESI pos): m/z=323 (M+H)$^+$

The following examples are synthesized in analogy to the preparation of example 55a:

| Example | Structure | Reactant(s) Conditions | LC-MS R$_t$ [min], method | MS (ESI pos or APCI, m/z) (M + H)$^+$ |
|---|---|---|---|---|
| 55b | 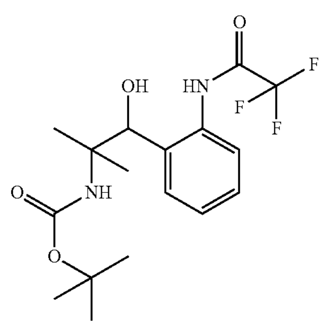 [SMILES: CC(C)(C)OC(=O)NC(C)(C)C(O)c1ccccc1NC(=O)C(F)(F)F] | N-(2-bromophenyl)-2,2,2-trifluoroacetamide (3.63 g, 13.5 mmol) Eluent for purification 10% EtOAc in cyclohexane | 1.33 Method 1 | 377 |
| 55c | 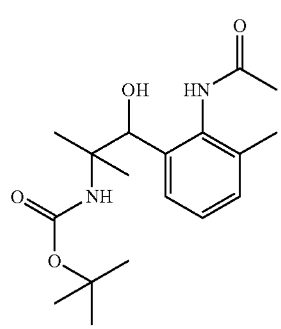 [SMILES: CC(=O)Nc1c(C)cccc1C(O)C(C)(C)NC(=O)OC(C)(C)C] | N-(2-bromo-6-methylphenyl)-acetamide (3.70 g, 50% content, 8.11 mmol) Eluent for purification 0-100% EtOAc in cyclohexane | 0.96 Method 1 | 337 |

-continued

| Example | Structure | Reactant(s) Conditions | LC-MS R$_t$ [min], method | MS (ESI pos or APCI, m/z) (M + H)$^+$ |
|---|---|---|---|---|
| 55d | 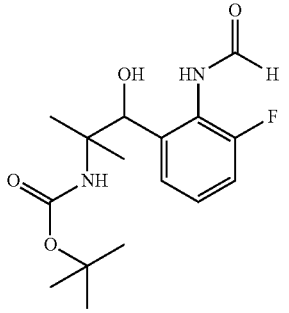 | N-(2-bromo-6-fluorophenyl)-formamide (1.81 g, 8.30 mmol) Eluent for purification 0-40% EtOAc in cyclohexane | 1.01 Method 2 | 327 |
| 55e | 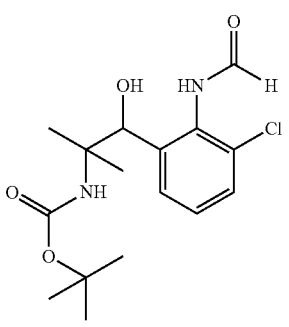 [SMILES: CC(C)(C)OC(=O)NC(C)(C)C(O)c1cccc(Cl)c1NC=O] | N-(2-bromo-6-Chlorophenyl)-formamide (2.67 g, 9.11 mmol) Eluent for purification 0-40% EtOAc in cyclohexane | 1.03 Method 2 | 343, 345 |
| 55f | 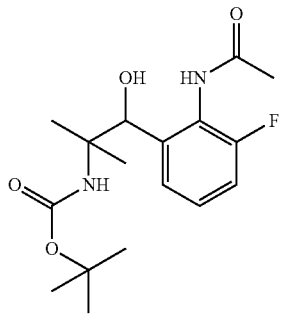 [SMILES: CC(=O)Nc1c(F)cccc1C(O)C(C)(C)NC(=O)OC(C)(C)C] | N-(2-bromo-6-fluorophenyl)-acetamide (6.0 g, 20.7 mmol) Eluent for purification 0-40% EtOAc in cyclohexane | 0.96 Method 2 | 341 |
| 55g | 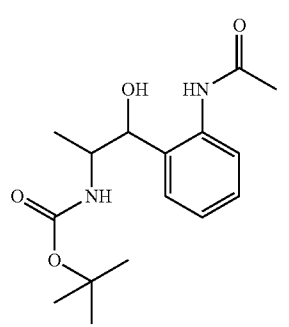 [SMILES: CC(=O)Nc1ccccc1C(O)C(C)NC(=O)OC(C)(C)C] | Bromoacetanilide (3.09 g, 14.4 mmol) and tert-butyl (1-oxopropan-2-yl)carbamate (1.25 g, 7.22 mmol | 0.83 and 0.91 Method 2 | 309 |

-continued

| Example | Structure | Reactant(s) Conditions | LC-MS R$_t$ [min], method | MS (ESI pos or APCI, m/z) (M + H)$^+$ |
|---|---|---|---|---|
| 55h | 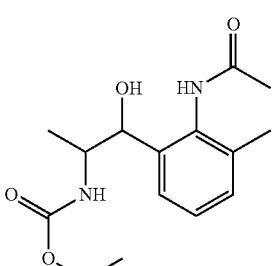 | N-(2-bromo-6-methylphenyl)-acetamide (1.97 g, 8.64 mmol) and tert-butyl (1-oxopropan-2-yl)carbamate (1.25 g, 7.22 mmol | 0.84 and 0.89 Method 2 | 323 |

Example 56a

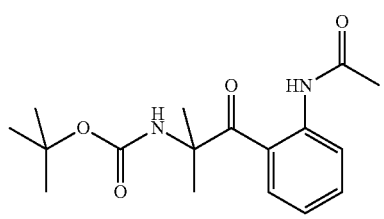 [SMILES: CC(=O)Nc1ccccc1C(=O)C(C)(C)NC(=O)OC(C)(C)C]

Example 55a (210 mg, 0.65 mmol) is suspended in DCM and Dess Martin periodinane (304 mg, 0.72 mmol) is added.

The mixture is stirred for 10 minutes and then shaken with 10% aqueous sodium thiosulfate solution and the phases separated. The organic phase is washed with saturated aqueous sodium bicarbonate solution, dried and the solvent removed to give the title product (208 mg, 100%).

LC-MS (Method 1): R$_t$=1.13 min

MS (ESI pos): m/z=321 (M+H)$^+$

The following examples are synthesized in analogy to the preparation of example 56a:

| Example | Structure | Reactant(s) Conditions | LC-MS R$_t$ [min], method | MS (ESI pos or APCI, m/z) (M + H)$^+$ |
|---|---|---|---|---|
| 56b | 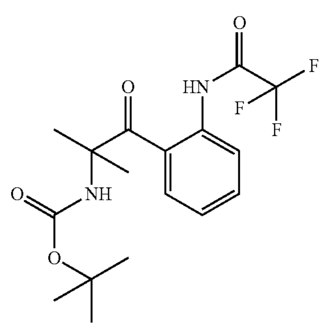 [SMILES: CC(C)(C)OC(=O)NC(C)(C)C(=O)c1ccccc1NC(=O)C(F)(F)F] | Example 55b (1.65 g, 85% content, 3.73 mmol) Eluent for purification 5% EtOAc in cyclohexane | 1.39 Method 1 | 375 |
| 56c | 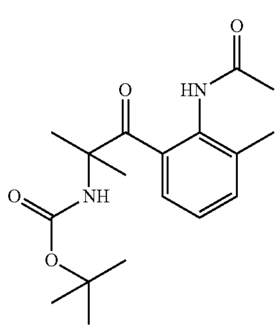 [SMILES: CC(=O)Nc1c(C)cccc1C(=O)C(C)(C)NC(=O)OC(C)(C)C] | Example 55c (356 mg, 85% content, 0.90 mmol), 4 hour reaction Eluent for purification 0-50% EtOAc in cyclohexane | 1.05 Method 1 | 335 |

-continued

| Example | Structure | Reactant(s) Conditions | LC-MS R$_t$ [min], method | MS (ESI pos or APCI, m/z) (M + H)$^+$ |
|---|---|---|---|---|
| 56d | 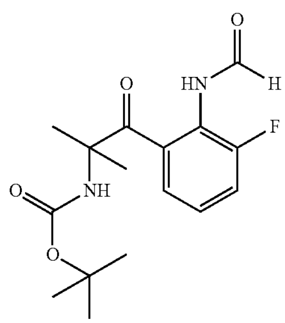 [SMILES: CC(C)(C)OC(=O)NC(C)(C)C(=O)c1cccc(F)c1NC=O] | Example 55d (724 mg), 4 hour reaction Eluent for purification 0-50% EtOAc in cyclohexane | 1.06 Method 2 | 325 |
| 56e | 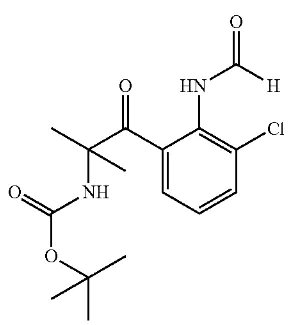 [SMILES: CC(C)(C)OC(=O)NC(C)(C)C(=O)c1cccc(Cl)c1NC=O] | Example 55e (600 mg, 1.75 mmol), 4 hour reaction Eluent for purification 0-50% EtOAc in cyclohexane | 1.09 Method 2 | 341, 343 |
| 56f | 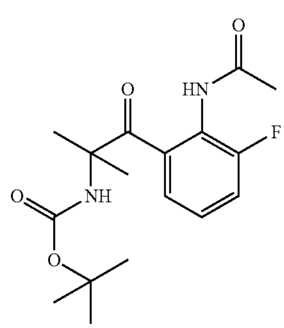 [SMILES: CC(=O)Nc1c(F)cccc1C(=O)C(C)(C)NC(=O)OC(C)(C)C] | Example 55f (350 mg), 4 hour reaction Eluent for purification 0-50% EtOAc in cyclohexane | 1.17 Method 2 | 339 |
| 56g | 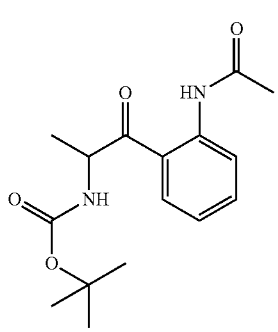 [SMILES: CC(=O)Nc1ccccc1C(=O)C(C)NC(=O)OC(C)(C)C] | Example 55g (450 mg, 1.46 mmol), 2 hour reaction No purification | 1.03 Method 2 | 307 |

| Example | Structure | Reactant(s) Conditions | LC-MS $R_t$ [min], method | MS (ESI pos or APCI, m/z) $(M + H)^+$ |
|---|---|---|---|---|
| 56h | 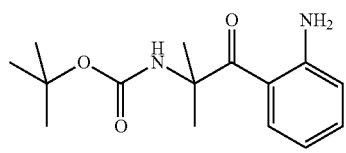 [SMILES: CC(C)(C)OC(=O)NC(C)(C)C(=O)c1ccccc1N] | Example 55h (580 mg, 1.80 mmol), 1 hour reaction No purification | 0.96 Method 2 | 321 |

Example 56i

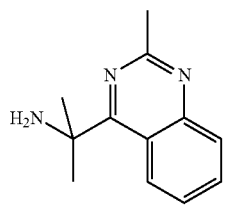

The title compound is isolated as a byproduct in the preparation of Example 57b step 1. (see later) (157 mg, 85% content).

LC-MS (Method 1): $R_t$=1.09 min
MS (ESI pos): m/z=279 (M+H)$^+$

Example 56j

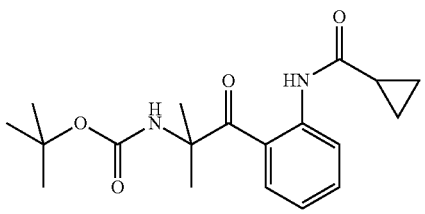 [SMILES: CC(C)(C)OC(=O)NC(C)(C)C(=O)c1ccccc1NC(=O)C1CC1]

Example 56i (157 mg, 85% content, 0.48 mmol) is suspended in DCM (5 mL) and cyclopropylcarbanoyl chloride (65 μL, 0.71 mmol) and triethylamine (200 μLm 1.44 mmol) are added. The mixture is stirred overnight then diluted with DCM, washed with 0.2 M aqueous HCl, 0.2 M NaOH and brine, dried and the solvent removed under vacuum. The residue is purified by flash chromatography (Eluent: 10% EtOAc in cyclohexane) to give the title product (166 mg, 92%).

LC-MS (Method 1): $R_t$=1.28 min
MS (ESI pos): m/z=347 (M+H)$^+$

Example 57a

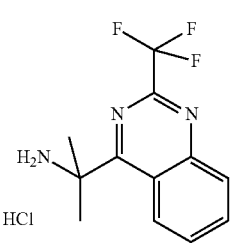 [SMILES: Cl ; CC(C)(N)c1nc(C(F)(F)F)nc2ccccc12]

Example 56a (205 mg, 0.64 mmol) and ammonium chloride (300 mg, 5.58 mmol) are suspended in 7M ammonia in methanol (4 mL) and heated under microwave irradiation at 140° C. for 16 hours. The solvent is removed, the residue suspended in methanol and filtered to remove excess ammonium chloride then loaded onto a prewashed SCX cartridge, washed with water and methanol and eluted with 7M ammonia in methanol. The solvent is removed under vacuum to give the crude title product (106 mg).

LC-MS (Method 1): $R_t$=0.58 min
MS (ESI pos): m/z=202 (M+H)$^+$

Example 57b

Step 1:

Example 56b (1.25 g, 3.34 mmol) and ammonium chloride (0.9 g, 16.5 mmol) are suspended in 7M ammonia in methanol (30 mL) and heated under microwave irradiation at 120° C. for 40 minutes. The mixture is diluted with ethyl acetate, washed with water, the organic phase is dried and the solvent removed. The residue is purified by flash chromatography (eluent DCM) to give the Boc protected product, 112 mg).

LC-MS (Method 1): R$_t$=1.38 min
MS (ESI pos): m/z=356 (M+H)$^+$

Step 2:
The intermediate from step 1 is suspended in 4M HCl in dioxane and stirred for 30 minutes. The solvent is evaporated and the residue dried under vacuum to give the title product (90 mg)

LC-MS (Method 1): R$_t$=0.69 min

MS (ESI pos): m/z=256 (M+H)$^+$

The following examples are synthesized in analogy to the preparation of example 57a:

| Example | Structure | Reactant(s) Conditions | LC-MS R$_t$ [min], method | MS (ESI pos or APCI, m/z) (M + H)$^+$ |
|---|---|---|---|---|
| 57c | 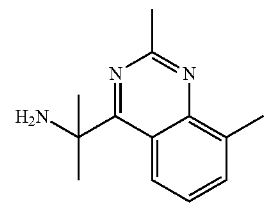 [SMILES: Cc1nc(C(C)(C)N)c2cccc(C)c2n1] | Example 56c (265 mg, 0.79 mmol), | 0.70 Method 1 | 216 |
| 57d | 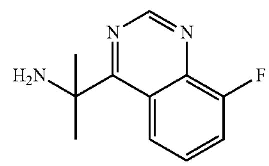 | Example 56d (580 mg, 1.79 mmol), | 0.75 Method 2 | 206 |
| 57e | 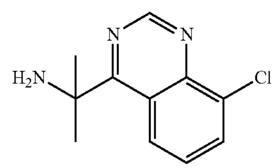 | Example 56e (320 mg) | 0.61 Method 2 | 222, 224 |
| 57f | 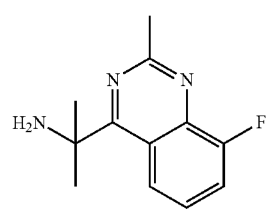 [SMILES: Cc1nc(C(C)(C)N)c2cccc(F)c2n1] | Example 56f (230 mg) | 0.55 Method 2 | 220 |
| 57g | 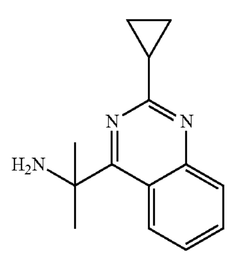 [SMILES: CC(C)(N)c1nc(C2CC2)nc2ccccc12] | Example 56j (166 mg) | 0.64 Method 1 | 228 |

The following examples are synthesized in analogy to the preparation of example 57b:

| Example | Structure | Reactant(s) Conditions | LC-MS $R_t$ [min], method | MS (ESI pos or APCI, m/z) $(M + H)^+$ |
|---|---|---|---|---|
| 57h | 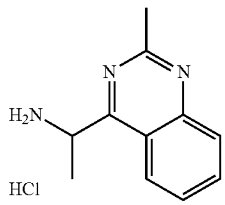 | Example 56g (440 mg, 1.36 mmol), HCl 2M in diethyl ether | 0.52 Method 2 | 188 |
| 57i | 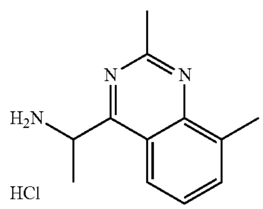 | Example 56h (575 mg, 1.79 mmol), HCl 2M in diethyl ether | 0.90 Method 2 | 202 |

Example 58a

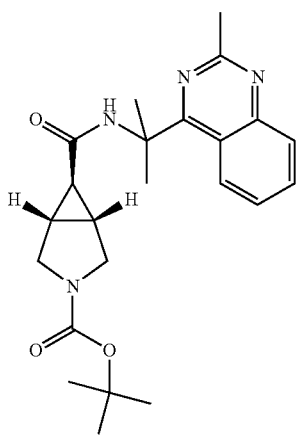 [SMILES: Cc1nc(C(C)(C)NC(=O)[C@H]2[C@@H]3CN(C(=O)OC(C)(C)C)C[C@@H]32)c2ccccc2n1]

Example 57a (80 mg, 0.40 mmol), meso-(1R,5S,6r)-3-(tert-butoxycarbonyl)-3-azabicyclo[3.1.0]hexane-6-carboxylic acid (108 mg, 0.48 mmol), Et$_3$N (138 μL, 0.99 mmol) and HATU (181 mg, 0.48 mmol) are suspended in DCM (5 mL) and the mixture stirred overnight. The mixture is diluted with DCM, and washed with water The organic layer is dried, filtered and evaporated under reduced pressure to give a residue that is purified by flash chromatography (eluent 0-3% MeOH in DCM) to give the title compound (Yield 140 mg, 86%)

UPLC-MS (Method 1): $R_t$=0.92 min

MS (ESI pos): m/z=411 (M+H)$^+$

The following examples are synthesized in analogy to the preparation of example 58a:

| Example | Structure | Reactant(s) Conditions | LC-MS $R_t$ [min], method | MS (ESI pos or APCI, m/z) $(M + H)^+$ |
|---|---|---|---|---|
| 58b | 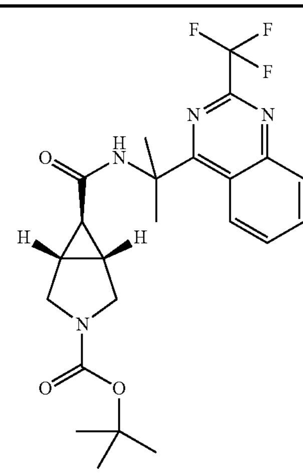 | Example 57b (90 mg) Eluent for purification 0-30% EtOAC in cyclohexane | 1.36 Method 1 | 465 |

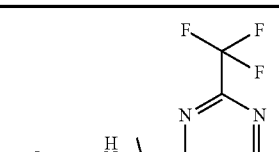

| Example | Structure | Reactant(s) Conditions | LC-MS R_t [min], method | MS (ESI pos or APCI, m/z) (M + H)+ |
|---|---|---|---|---|
| 58c | 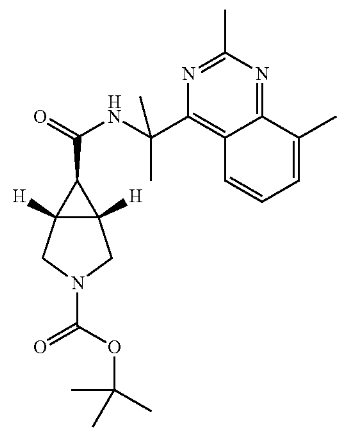 [SMILES: Cc1nc(C(C)(C)NC(=O)[C@H]2[C@@H]3CN(C(=O)OC(C)(C)C)C[C@@H]32)c2cccc(C)c2n1] | Example 57c (70 mg) Eluent for purification 0-50% EtOAC in cyclohexane | 1.11 Method 1 | 425 |
| 58d | 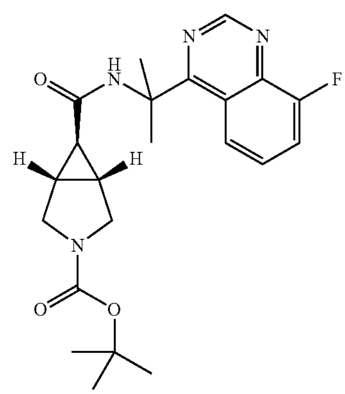 [SMILES: CC(C)(C)OC(=O)N1C[C@@H]2[C@H](C1)[C@H]2C(=O)NC(C)(C)c1ncnc2c(F)cccc12] | Example 57d (70 mg) No purification, used as crude | 1.02 Method 2 | 415 |
| 58e | 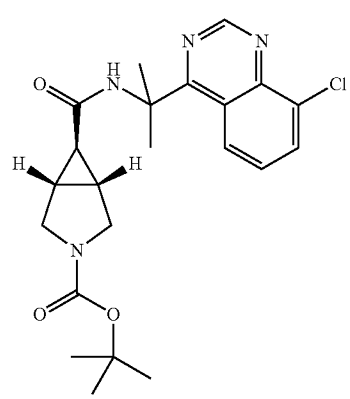 [SMILES: CC(C)(C)OC(=O)N1C[C@@H]2[C@H](C1)[C@H]2C(=O)NC(C)(C)c1ncnc2c(Cl)cccc12] | Example 57e (60 mg) No purification, used as crude | 1.12 Method 2 | 431/433 |

-continued
| Example | Structure | Reactant(s) Conditions | LC-MS R$_t$ [min], method | MS (ESI pos or APCI, m/z) (M + H)$^+$ |
|---|---|---|---|---|
| 58f | 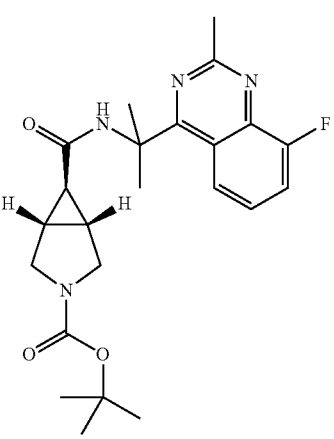 [SMILES: Cc1nc(C(C)(C)NC(=O)[C@H]2[C@@H]3CN(C(=O)OC(C)(C)C)C[C@@H]32)c2cccc(F)c2n1] | Example 57f (50 mg) No purification, used as crude | 1.10 Method 2 | 429 |
| 58g | 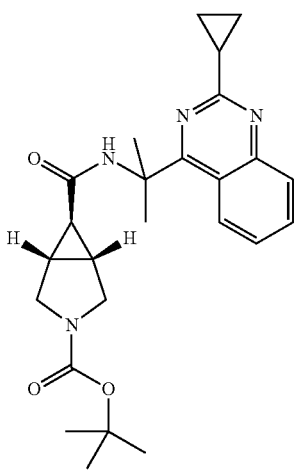 [SMILES: CC(C)(C)OC(=O)N1C[C@@H]2[C@H](C1)[C@H]2C(=O)NC(C)(C)c1nc(C2CC2)nc2ccccc12] | Example 57g (56 mg) Eluent for purification 0-30% EtOAC in cyclohexane | 1.06 Method 1 | 437 |
| 58h | 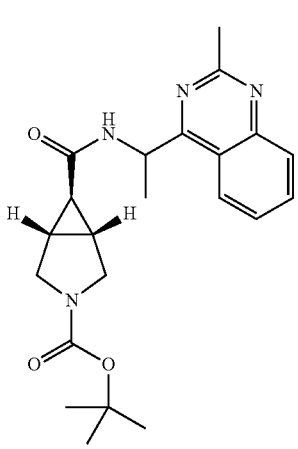 [SMILES: Cc1nc(C(C)NC(=O)[C@H]2[C@@H]3CN(C(=O)OC(C)(C)C)C[C@@H]32)c2ccccc2n1] | Example 57h (125 mg) Eluent for purification 0-100% EtOAC in cyclohexane | 1.02 Method 2 | 397 |

-continued

| Example | Structure | Reactant(s) Conditions | LC-MS R$_t$ [min], method | MS (ESI pos or APCI, m/z) (M + H)$^+$ |
|---|---|---|---|---|
| 58i | 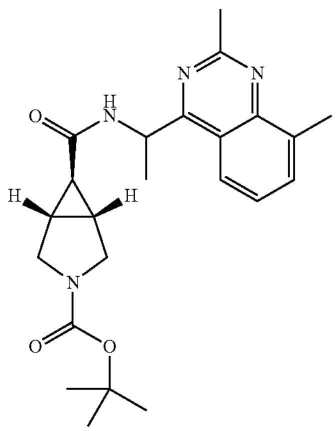 [SMILES: Cc1nc(C(C)NC(=O)[C@H]2[C@@H]3CN(C(=O)OC(C)(C)C)C[C@@H]32)c2cccc(C)c2n1] | Example 57i (200 mg) Eluent for purification 0-100% EtOAC in cyclohexane | 1.29 Method 2 | 411 |

The stereoisomers of the example 58h are separated by HPLC using a chiral stationary phase.

Method for Separation:

HPLC apparatus type: Waters 600 Pump, 2767 Autosampler, UV Detector 2489; column: Daicel chiralpack OJ-H, 5.0 μm, 250 mm×20 mm; method: eluent hexane/ethanol 93:7; flow rate: 15 mL/min, temperature: 25° C.; UV Detection: 230 nm Example 58j: stereoisomer 1
Unknown absolute stereochemistry at
NH—C marked with an asterisk

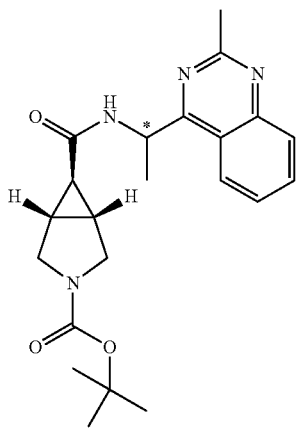 [SMILES: Cc1nc(C(C)NC(=O)[C@H]2[C@@H]3CN(C(=O)OC(C)(C)C)C[C@@H]32)c2ccccc2n1]

Example 58k: stereoisomer 2
Unknown absolute stereochemistry at
NH—C marked with an asterisk -continued

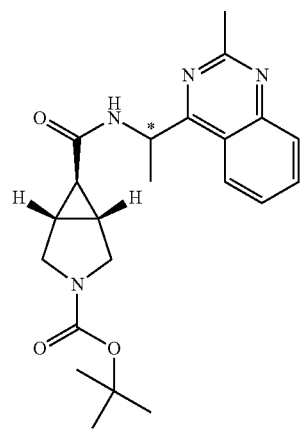 [SMILES: Cc1nc(C(C)NC(=O)[C@H]2[C@@H]3CN(C(=O)OC(C)(C)C)C[C@@H]32)c2ccccc2n1]

| Example | Chiral HPLC (Method 17) R$_t$ [min] | HPLC-MS (Method 2): R$_t$ [min] | MS (ESI pos): m/z |
|---|---|---|---|
| 58j | 9.84 | 1.10 | 397 |
| 58k | 9.97 | 1.10 | 397 |

The stereoisomers of the example 58i are separated by HPLC using a chiral stationary phase.

Method for Separation:

HPLC apparatus type: Waters 600 Pump, 2767 Autosampler, UV Detector 2489; column: Daicel chiralpack AS-H, 5.0 μm, 250 mm×20 mm; method: eluent hexane/ethanol 95:5; flow rate: 8 mL/min, temperature: 25° C.; UV Detection: 230 nm Example 58l: stereoisomer 1
Unknown absolute stereochemistry at
NH—C marked with an asterisk -continued

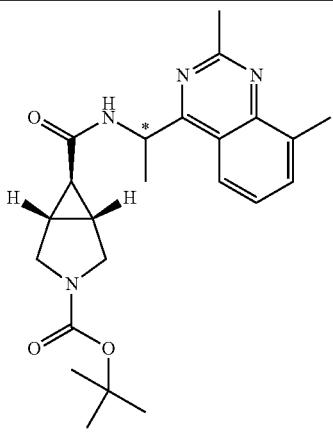

Example 58m: stereoisomer 2
Unknown absolute stereochemistry at
NH—C marked with an asterisk

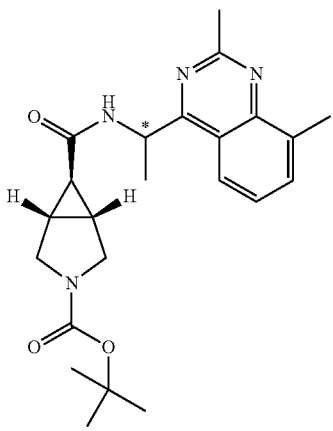 [SMILES: Cc1nc(C(C)NC(=O)[C@H]2[C@@H]3CN(C(=O)OC(C)(C)C)C[C@@H]32)c2cccc(C)c2n1]

| Example | Chiral HPLC (Method 18) R$_t$ [min] | HPLC-MS (Method 2): R$_t$ [min] | MS (ESI pos): m/z |
|---------|----|----|----|
| 58l | 5.08 | 1.25 | 411 |
| 58m | 5.94 | 1.25 | 411 |

Example 59a

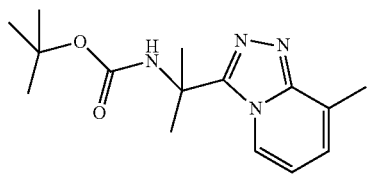 [SMILES: Cc1cccn2c(C(C)(C)NC(=O)OC(C)(C)C)nnc12]

Step 1:
Boc-AIB-OH (0.50 g, 2.44 mmol), 2-hydrazino-3-methylpyridine (1.0 g, 8.24 mmol), HATU (3.70 g, 9.73 mmol) and triethyl amine (2.48 mL, 17.8 mmol) are suspended in DCM and the mixture stirred overnight, The mixture is filtered, the solvent removed and the residue purified by flash chromatography (eluent 0-100% ethyl acetate in cyclohexane) to give impure hydrazide intermediate (800 mg) which is used directly in the following step.

Step 2:
The material from step 1 is suspended in dry DCM (20 ML) and polymer supported triphenylphosphine (3 mmol/g, 1.3 g. 3.9 mmol), trimethylsilylazide (520 µL, 3.9 mmol) and diethylazodicarboxylate (2.03 mL, 4.7 mmol) are added. The mixture is stirred overnight, filtered and the solvent removed. The residue is purified by flash chromatography (eluent 0-100% ethyl acetate in cyclohexane) to give the title product (Yield 180 mg).
UPLC-MS (Method 2): R$_t$=0.76 min
MS (ESI pos): m/z=291 (M+H)$^+$ Example 60a

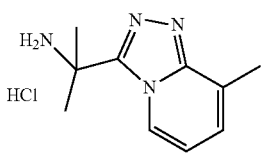

Example 59a (180 mg, 0.62 mmol) is suspended in 4M HCl in dioxane (4 ML) and stirred for 3 hours. The solvent is removed under vacuum to give the title product (150 mg, 90% content)
UPLC-MS (Method 2): R$_t$=0.49 min
MS (ESI pos): m/z=191 (M+H)$^+$ Example 61a

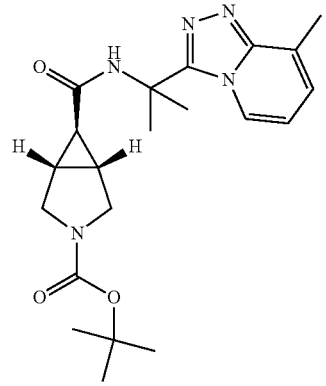 [SMILES: Cc1cccn2c(C(C)(C)NC(=O)[C@H]3[C@@H]4CN(C(=O)OC(C)(C)C)C[C@@H]43)nnc12]

The title product is synthesised from Example 60a (100 mg, 0.44 mmol) in analogy to the procedure described for the synthesis of Example 58a (Yield 150 mg, 85%)
UPLC-MS (Method 2): R$_t$=0.84 min
MS (ESI pos): m/z=400 (M+H)$^+$ Example 62a

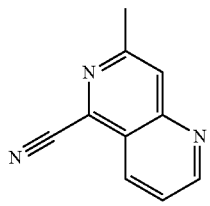

5-Chloro-7-methyl-[1,6]naphthyridine (J. Chem. Soc. Perkin 1, 1972, 705-709, 340 mg, 1.9 mmol), zinc cyanide (246 mg, 2.09 mmol), 1,1-bis(diphenylphosphino)ferrocene (95 mg, 0.17 mmol) and tris(dibenzylideneacetone)dipalladium (0) (70 mg, 0.08 mmol) are suspended in dry DMF (5 mL) and heated overnight at 100° C. The mixture is cooled to room temperature, diluted with water and extracted with ethyl acetate. The organic extracts are washed with brine, dried and the solvent removed under vacuum. The residue is purified by flash chromatography (eluent 20% EtOAc in cyclohexane) to give the title compound (Yield 240 mg)

UPLC-MS (Method 2): $R_t$=0.78 min
MS (ESI pos): m/z=170 (M+H)$^+$

Example 62b

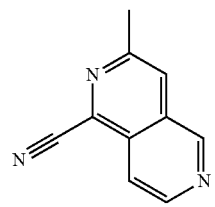

The title product is synthesised from 1-Chloro-3-methyl-[2,6]naphthyridine (J. Chem. Soc. Perkin 1, 1972, 705-709, 726 mg, 4.06 mmol), in analogy to the procedure described for the synthesis of Example 62a using 0-50% EtOAc in cyclohexane as eluent for the purification (Yield 380 mg).

LC-MS (Method 12): $R_t$=2.52 min
MS (ESI pos): m/z=170 (M+H)$^+$

Example 63a

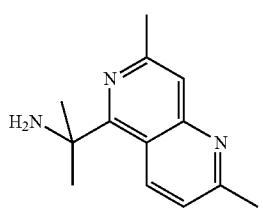 [SMILES: Cc1cc2nc(C)ccc2c(C(C)(C)N)n1]

Cerium(III) chloride (1.05 g, 4.26 mmol) is heated under vacuum at 140° C. for 10 minutes then cooled to 0° C. under nitrogen atmosphere and dry THF (12 mL) are added. The mixture is stirred at room temperature for 2 hours then cooled to −78° C. Methyl lithium LiCl complex (1.6 M in diethyl ether, 2.66 mL, 4.26 mmol) is added and the mixture stirred at −78° C. for 30 minutes. Example 62a (240 mg, 1.42 mmol) dissolved in dry THF (3 mL) is added dropwise, the mixture stirred for 40 minutes at −78° C. then allowed to warm slowly to −20° C. and saturated ammonium chloride solution is added dropwise until a precipitate is formed. The mixture is filtered through celite, washing with abundant DCM. The organic phase is washed with water, dried and the solvent removed to give a crude mixture containing the title compound (Yield 230 mg)

UPLC-MS (Method 2): $R_t$=0.59 min
MS (ESI pos): m/z=216 (M+H)$^+$

Example 63b

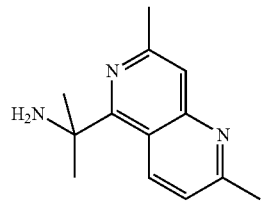 [SMILES: Cc1cc2nc(C)ccc2c(C(C)(C)N)n1]

The title product is synthesised from Example 62b (380 mg, 2.25 mmol), in analogy to the procedure described for the synthesis of Example 63a (crude yield 560 mg).

LC-MS (Method 2): $R_t$=0.56 min
MS (ESI pos): m/z=170 (M+H)$^+$

Example 64a

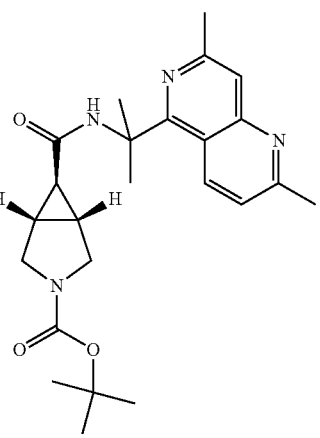

The title product is synthesised from Example 63a (230 mg), in analogy to the procedure described for the synthesis of Example 58a (yield 21 mg).

LC-MS (Method 2): $R_t$=1.15 min
MS (ESI pos): m/z=425 (M+H)$^+$

Example 64b

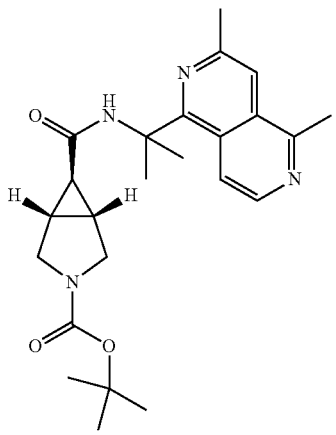 [SMILES: Cc1cc2c(C)nccc2c(C(C)(C)NC(=O)[C@H]2[C@@H]3CN(C(=O)OC(C)(C)C)C[C@@H]32)n1]

The title product is synthesised from Example 63b (200 mg), in analogy to the procedure described for the synthesis of Example 58a (yield 51 mg).
LC-MS (Method 1): R$_f$=0.91 min
MS (ESI pos): m/z=425 (M+H)$^+$ Example 65a

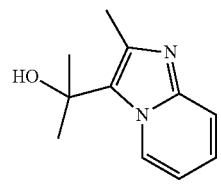

Ethyl 2-methylimidazo[1,2-a]pyridine-3-carboxylate (3.30 g, 16.1 mmol) is suspended in dry THF and cooled to −20° C. under nitrogen atmosphere. Methylmagnesium bromide (1.4 M in THF/toluene, 35 mL, 48.5 mmol) is added dropwise, the mixture allowed to warm to room temperature and stirred overnight. Saturated aqueous ammonium chloride solution is added and the mixture extracted with ethyl acetate. The organic extracts are dried and the solvent removed. The residue is purified by flash chromatography (eluent 0-100% EtOAc in cyclohexane) to give the title product (yield 1.20 g, 39%)
$^1$H NMR (500 MHz, DMSO-d$_6$): δ 1.64 (s, 6H), 2.44 (s, 3H), 5.40 (s, 1H), 6.82 (dd, 1H), 7.16 (dd, 1H), 7.43 (d, 1H), 8.84 (dd, 1H).

Example 66a

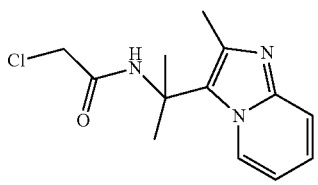 [SMILES: Cc1nc2ccccn2c1C(C)(C)NC(=O)CCl]

Example 65a (1.2 g, 6.31 mmol) is suspended in chloroacetonitrile (15 mL) and TFA (15 mL) and the mixture stirred overnight, The solvent is evaporated and the residue is purified by flash chromatography (eluent 0-10% MeOH in DCM) to give the title product (yield 0.5 g, 30%
LC-MS (Method 1): R$_f$=0.60 min
MS (ESI pos): m/z=266/268 (M+H)$^+$ Example 67a

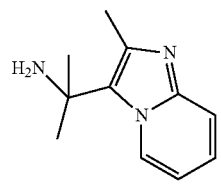

Example 66a (100 mg, 0.38 mmol) is suspended in 6M aqueous HCl (2 mL) and heated at 80° C. overnight, The mixture is loaded onto a prewashed SCX cartridge, washed with water and methanol and eluted with 7M NH3 in methanol. The solvent is removed to give the title product (yield 70 g, 98%).
$^1$H NMR (500 MHz, DMSO-d$_6$): δ 1.57 (s, 6H), 2.44 (s, 3H), 6.74 (dd, 1H), 7.08 (dd, 1H), 7.34 (d, 1H), 9.15 (dd, 1H). NH2 not observed.

Example 68a

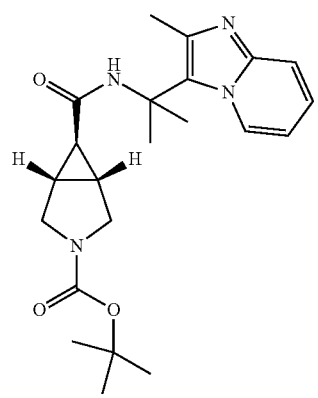 [SMILES: Cc1nc2ccccn2c1C(C)(C)NC(=O)[C@H]1[C@@H]2CN(C(=O)OC(C)(C)C)C[C@@H]21]

The title product is synthesised from Example 67a (70 mg), in analogy to the procedure described for the synthesis of Example 58a (yield 40 mg).
LC-MS (Method 1): R$_f$=0.80 min
MS (ESI pos): m/z=399 (M+H)$^+$

Example 69a

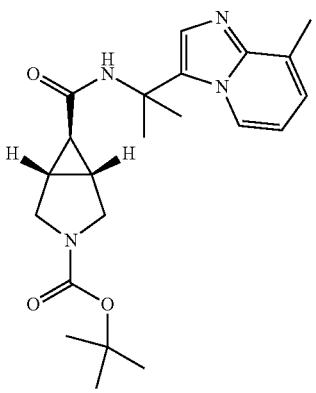 [SMILES: Cc1cccn2c(C(C)(C)NC(=O)[C@H]3[C@@H]4CN(C(=O)OC(C)(C)C)C[C@@H]43)cnc12]

The title product is synthesised from ethyl 8-methylimidazo[1,2-a]pyridine-3-carboxylate (1.0 g, prepared in analogy to the procedure described in Bioorg. Med. Chem. Lett, 2012, 1870-1873), in analogy to the procedure described for the synthesis of Example 65a through to Example 68a (yield 68 mg).

LC-MS (Method 2): $R_t$=1.02 min
MS (ESI pos): m/z=399 (M+H)$^+$

Example 70a

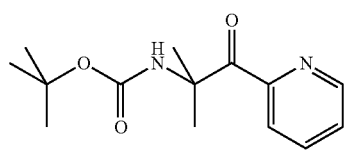 [SMILES: CC(C)(C)OC(=O)NC(C)(C)C(=O)c1ccccn1]

The title product is synthesised from 2-bromopyridine in analogy to the procedure described for the synthesis of Example 55a through to Example 56a (yield 218 mg).

LC-MS (Method 2): $R_t$=1.14 min
MS (ESI pos): m/z=265 (M+H)$^+$

Example 71a

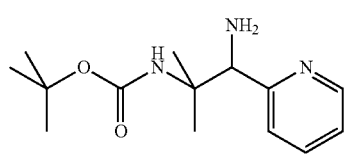 [SMILES: CC(C)(C)OC(=O)NC(C)(C)C(N)c1ccccn1]

Example 70a (218 mg, 0.82 mmol), ammonium acetate (326 mg, 8.25 mmol) and sodiumcyanoborohydride (62 mg. 0.99 mmol) are combined in dry methanol (5 mL) and the mixture stirred overnight then heated in a sealed tube at 90° C. for 6 hours. The solvent is removed, the residue dissolved in ethyl acetate, washed with water and brine, dried and the solvent removed to give crude title product (yield 220 mg).

LC-MS (Method 2): $R_t$=0.97 min
MS (ESI pos): m/z=266 (M+H)$^+$

Example 72a

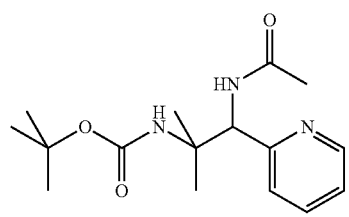 [SMILES: CC(=O)NC(c1ccccn1)C(C)(C)NC(=O)OC(C)(C)C]

Example 71a (220 mg), acetyl chloride (89 μL, 1.24 mmol) and triethylamine (345 μL, 2.49 mmol) are combined in dry DCM (5 mL) and the mixture stirred for 2 hours The mixture is diluted with DCM, washed with water, dried and the solvent removed. The residue is purified by flash chromatography (eluent 0-100% EtOAc in cyclohexane) to give the title product (yield 77 mg).

LC-MS (Method 2): $R_t$=0.97 min
MS (ESI pos): m/z=308 (M+H)$^+$

Example 73a

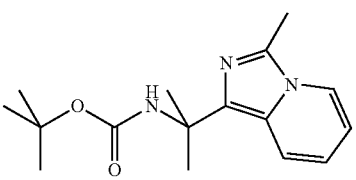 [SMILES: Cc1nc(C(C)(C)NC(=O)OC(C)(C)C)c2ccccn12]

Example 72a (77 mg, 0.25 mmol), and Burgess reagent (90 mg, 0.38 mmol) are combined in dry DCM (5 mL) and the mixture stirred overnight The mixture is diluted with DCM, washed with water, dried and the solvent removed. The residue is purified by flash chromatography (eluent 0-50% EtOAc in cyclohexane) to give the title product (yield 54 mg).

LC-MS (Method 2): $R_t$=1.06 min
MS (ESI pos): m/z=290 (M+H)$^+$

Example 74a

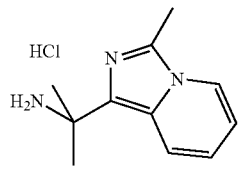

Example 73a (54 mg), is suspended in 2M HCl in diethyl ether and the mixture stirred overnight. The solvent is removed under vacuum to give crude title product (yield 42 mg).

LC-MS (Method 2): $R_t$=0.75 min
MS (ESI pos): m/z=173 (M-NH2)+

Example 75a

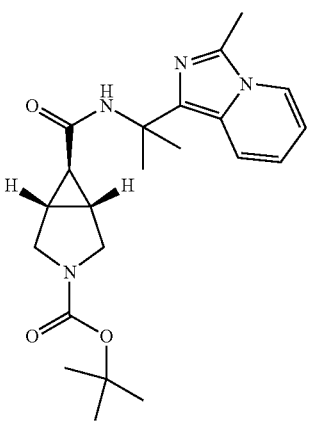 [SMILES: Cc1nc(C(C)(C)NC(=O)[C@H]2[C@@H]3CN(C(=O)OC(C)(C)C)C[C@@H]32)c2ccccn12]

The title product is synthesised from Example 74a (42 mg), in analogy to the procedure described for the synthesis of Example 58a using 0-5% MeOH in DCM as eluent for the purification (yield 37 mg).

LC-MS (Method 2): $R_t$=1.05 min
MS (ESI pos): m/z=399 (M+H)$^+$

Example 76a

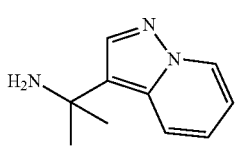

Cerium(III) chloride (18.12 g, 74 mmol) is heated under vacuum at 140° C. for 3 hours then cooled to room temperature under nitrogen atmosphere and dry THF (200 mL) are added. The mixture is stirred at room temperature overnight then cooled to −78° C. Methyl lithium LiCl complex (1.6 M in diethyl ether, 46 mL, 74 mmol) is added and the mixture stirred at −78° C. for 2 hours. Pyrazolo[1,5-a]pyridine-3-carbonitrile (1.05 g) in dry THF (25 mL) is added dropwise, the mixture stirred for 2 hours at −78° C. then saturated ammonium chloride solution is added followed by concentrated aqueous ammonia. The mixture is warmed to room temperature, filtered through celite, washing with abundant DCM. The organic phase is washed with water, dried and the solvent removed to give a crude mixture containing the title compound (Yield 1.27 g)

UPLC-MS (Method 2): $R_t$=0.55 min
MS (ESI pos): m/z=159 (M-NH2)$^+$

Example 77a

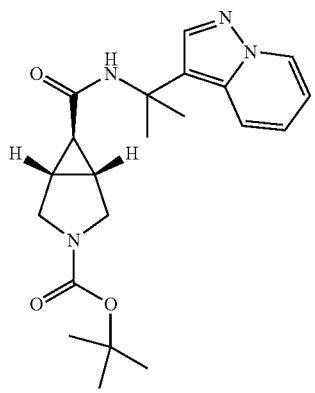 [SMILES: CC(C)(C)OC(=O)N1C[C@@H]2[C@H](C1)[C@H]2C(=O)NC(C)(C)c1cnn2ccccc12]

The title product is synthesised from Example 76a (154 mg), in analogy to the procedure described for the synthesis of Example 58a using 50-70% EtOAc in cyclohexane as eluent for the purification (yield 246 mg).

LC-MS (Method 2): $R_t$=1.00 min
MS (ESI pos): m/z=385 (M+H)$^+$

Example 78a

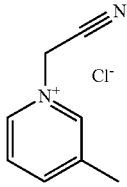

3-picoline (5.0 g, 53.7 mmol) is suspended in acetonitrile and chloroacetonitrile (6.76 mL, 107.4 mmol) is added. The mixture is stirred at room temperature for 4 hours and the precipitate is collected by filtration and dried under vacuum to give the title compound (7.0 g)

$^1$H NMR (500 MHz, DMSO-d$_6$): δ 2.53 (s, 3H), δ 6.04 (s, 2H), 8.16 (dd, J=6.0, 8.0 Hz, 1H), 8.58 (d, J=8.0, 1H), 9.09 (d, J=6.0 Hz, 1H), 9.17 (s, 1H).

Example 79a

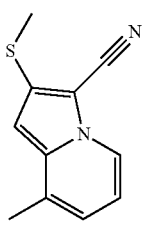

Example 78a (2.0 g, 11.9 mmol), 1-nitro-2,2-bis-metil-mercapto-etilene (1.96 g, 11.9 mmol) and triethylamine (3.30 mL, 23.7) are suspended in ethanol (30 mL) and refluxed for 6 hours. The solvent is evaporated and the

Example 80a

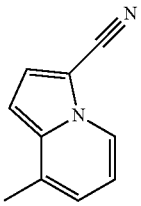

Example 79a (0.5 g, 2.47 mmol and excess raney nickel (approx. 2 g) are suspended in ethanol and stirred for 6 hours. The solvent is evaporated and the residue purified by flash chromatography (eluent 0-10% ethyl acetate in cyclohexane) to give the title compound (88 mg)

LC-MS (Method 2): $R_t$=1.15 min

MS (ESI pos): m/z=157 (M+H)$^+$

Example 81a residue purified by flash chromatography (eluent 0-10% ethyl acetate in cyclohexane) to give the title compound (0.75 g)

$^1$H NMR (500 MHz, DMSO-d$_6$): δ 2.42 (s, 3H), 2.62 (s, 3H), 6.69 (2, 1H), 6.90 (dd, 1H), 7.00 (d, 1H), 8.24 (d, 1H).

Cerium(III) chloride (1.39 g, 5.63 mmol) is heated under vacuum at 140° C. for 3 hours then cooled to room temperature under nitrogen atmosphere and dry THF (10 mL) are added. The mixture is stirred at room temperature overnight then cooled to −78° C. Methyl lithium LiCl complex (1.6 M in diethyl ether, 3.52 mL, 5.63 mmol) is added and the mixture stirred at −78° C. for 2 hours. Example 80a (88 mg, 0.56 mmol) in dry THF (5 mL) is added dropwise, the mixture stirred for 2 hours at −78° C. then saturated ammonium chloride solution is added followed by 32% aqueous ammonia. The mixture is warmed to room temperature, filtered through celite, washing with abundant DCM. The organic phase is washed with water, dried and the solvent removed to give a crude mixture containing the title compound (88 mg)

UPLC-MS (Method 2): $R_t$=1.12 min

MS (ESI pos): m/z=172 (M-NH2)$^+$

Example 82a

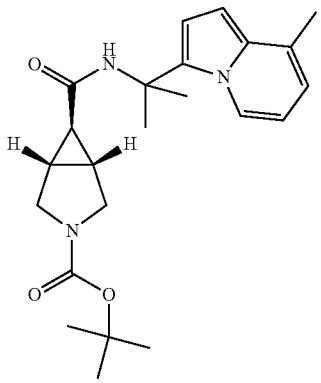 [SMILES: Cc1cccn2c(C(C)(C)NC(=O)[C@H]3[C@@H]4CN(C(=O)OC(C)(C)C)C[C@@H]43)ccc12]

The title product is synthesised from Example 81a (88 mg), in analogy to the procedure described for the synthesis of Example 58a using 0-50% EtOAc in cyclohexane as eluent for the purification (yield 60 mg).

LC-MS (Method 2): $R_t$=1.30 min

MS (ESI pos): m/z=398 (M+H)$^+$

Exemplary Embodiments

Example 1

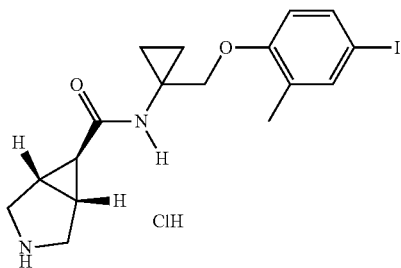 [SMILES: Cc1cc(I)ccc1OCC1(NC(=O)[C@H]2[C@@H]3CNC[C@@H]32)CC1 ; Cl]

HATU (8 mg, 0.022 mmol) is added to meso-(1R,5S,6r)-3-(tert-butoxycarbonyl)-3-azabicyclo[3.1.0]hexane-6-carboxylic acid (4.5 mg, 0.020 mmol), 1-(4-iodo2-methylphenoxymethyl)-cyclopropylamine (3 mg, 0.010 mmol; prepared as described in WO 2012/028676) and DIPEA (6 μl, 0.035 mmol) in DMF (0.200 mL) and stirring is continued for 18 h at rt. The reaction is filtered on a basic aluminum oxide pad, washed with DMF/MeOH 9:1 (600 μl) and then dried. The residue is diluted with dioxane 0.500 ml and 0.200 mL of 4N HCl solution in dioxane and stirring is continued overnight. Solvent is evaporated to give the title compound (4.8 mg, 100%).

UPLC-MS (Method 3): $R_t$=1.36

MS (ESI pos): m/z=413 (M+H)$^+$

The following examples are synthesized in analogy to the preparation of example 1:
| Example | Structure | Reactant(s) | UPLC-MS $R_t$ [min], method | MS (ESI pos, m/z) $(M + H)^+$ |
|---|---|---|---|---|
| 2 | 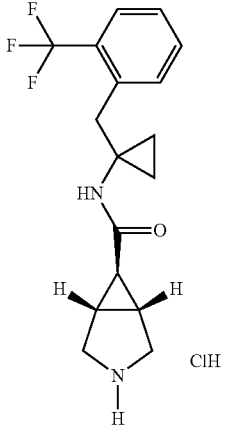 [SMILES: O=C(NC1(Cc2ccccc2C(F)(F)F)CC1)[C@H]1[C@@H]2CNC[C@@H]21 ; Cl] | 1-(2-trifluoromethyl-benzyl)-cylopropylamine (43 mg, 0.200 mmol; prepared as described in WO 2007/134862) Using 1 eq. of carboxylic acid | 1.06 4 | 324 |
| 3 | 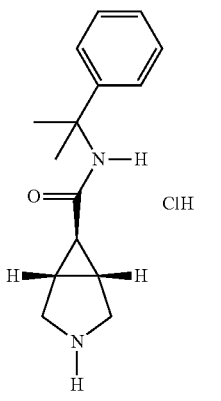 [SMILES: CC(C)(NC(=O)[C@H]1[C@@H]2CNC[C@@H]21)c1ccccc1 ; Cl] | 1-methyl-1-phenyl-ethylamine (1.35 mg, 0.010 mmol) | 0.92 3 | 245 |
| 4 | 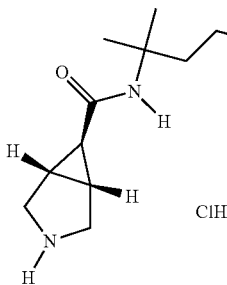 | 2-methyl-4-phenyl-butan-2-amine (1.63 mg, 0.010 mmol) | 1.21 3 | 273 |

Example 5

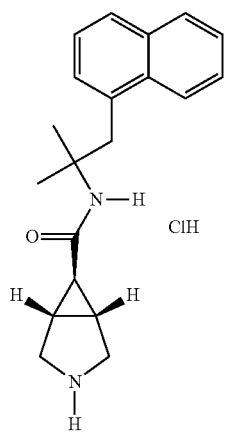 [SMILES: CC(C)(Cc1cccc2ccccc12)NC(=O)[C@H]1[C@@H]2CNC[C@@H]21 ; Cl]

HATU (84 mg, 0.220 mmol) is added to meso-(1R,5S,6r)-3-(tert-butoxycarbonyl)-3-azabicyclo[3.1.0]hexane-6-carboxylic acid (45 mg, 0.200 mmol), 2-methyl-1-(naphtha-len-1-yl)propan-2-amine (47 mg, 0.200 mmol and DIPEA (120 µl, 0.700 mmol) in DMF (3 mL) and stirring is continued overnight at rt. The reaction is purified by preparative HPLC (stationary phase: Xbridge C18 5 µm 19×100 mm. Mobile phase: ACN/$H_2O$+$NH_4COOH$ 5 mM). Fractions containing the title compound are combined and lyophilised. The residue in MeOH (3 mL) is treated with HCl in ethyl ether (2M, 1.2 mL, 25.610 mmol). After stirring for 3 h, volatiles are evaporated under reduced pressure and the resulting residue redissolved in ACN/$H_2O$ 1:1 and lyophilised to furnish the title compound (44.7 mg, 65%)

UPLC-MS (Method 4): $R_t$=1.25

MS (ESI pos): m/z=309 $(M+H)^+$

The following examples are synthesized in analogy to the preparation of example 5:

| Example | Structure | Reactant(s) | UPLC-MS $R_t$ [min], method | MS (ESI pos, m/z) $(M + H)^+$ |
|---------|-----------|-------------|----------------------------|-------------------------------|
| 6 | 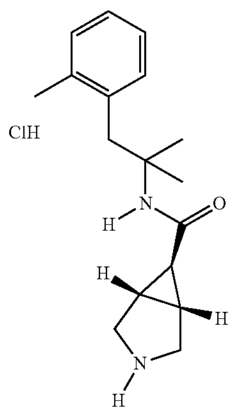 [SMILES: Cl ; Cc1ccccc1CC(C)(C)NC(=O)[C@H]1[C@@H]2CNC[C@@H]21] | 2-methyl-1-(o-tolyl)propan-2-amine hydrochloride (40 mg, 0.200 mmol) | 1.22 3 | 273 |
| 7 | 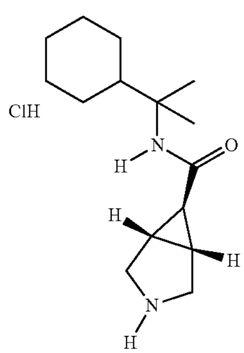 [SMILES: Cl ; CC(C)(NC(=O)[C@H]1[C@@H]2CNC[C@@H]21)C1CCCCC1] | 2-cyclohexylpropan-2-amine hydrochloride (36 mg, 0.200 mmol) | 1.21 3 | 251 |

| Example | Structure | Reactant(s) | UPLC-MS R$_t$ [min], method | MS (ESI pos, m/z) (M + H)$^+$ |
|---|---|---|---|---|
| 8 | 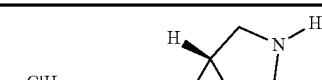 | 2-(3,4-dichloro-phenyl)propan-2-amine (41 mg, 0.200 mmol) | 1.31 3 | 313 |

Example 9

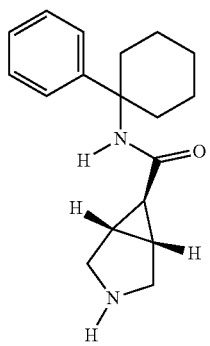 [SMILES: O=C(NC1(c2ccccc2)CCCCC1)[C@H]1[C@@H]2CNC[C@@H]21]

Example 9 is prepared from 1-phenylcyclohexan-1-amine hydrochloride (42 mg, 0.200 mmol) as described for the example 5 but after the first purification, the compound is purified again first by preparative HPLC (stationary phase: Xbridge C18 5 μm 19×100 mm. Mobile phase: ACN/H$_2$O+ NH$_4$COOH 5 mM) and then over a Water CX 0.4 g cartridge to furnish the title compound. (22.9 mg, 40%)

UPLC-MS (Method 4): R$_t$=1.23
MS (ESI pos): m/z=285 (M+H)$^+$

Example 10

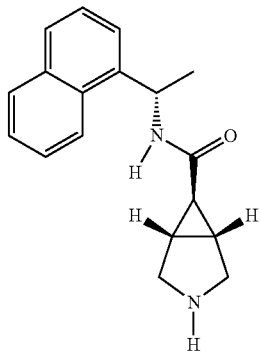 [SMILES: C[C@H](NC(=O)[C@H]1[C@@H]2CNC[C@@H]21)c1cccc2ccccc12]

HATU (125 mg, 0.330 mmol) is added to meso-(1R,5S,6r)-3-(tert-butoxycarbonyl)-3-azabicyclo[3.1.0]hexane-6-carboxylic acid (68 mg, 0.300 mmol), (S) 1-(1-napthyl)ethylamine (56 mg, 0.330 mmol and DIPEA (78 μl, 0.450 mmol) in DMF (3 mL) and stirring is continued for 18 h at rt. The reaction is filtered on a basic aluminum oxide pad, washed with DMF/MeOH 9:1 (6 ml) and then dried. The residue is diluted with DMF (1 mL) and loaded over a Waters RP 2 g cartridge, washed with H$_2$O/MeOH 95:5 (20 mL) and eluted with MeOH (10 mL). The crude is evaporated and dissolved in DCM (2 mL), then TFA (100 μL, 13 mmol) is added and stirring is continued for 4 h at rt. The solvent is evaporated and the residue is diluted with H$_2$O/ACN 1:1, then purified over a Waters CX 2 g cartridge, washed with MeOH/H$_2$O 95:5 (40 mL), eluted with NH$_4$OH 5% solution in MeOH (10 mL). Solvents are evaporated and the crude is redissolved in ACN/H$_2$O 1:1 (4 mL) and freeze-dried to give the title compound (84 mg, 100%)

UPLC-MS (Method 3): R$_t$=1.19
MS (ESI pos): m/z=281 (M+H)$^+$

Example 11

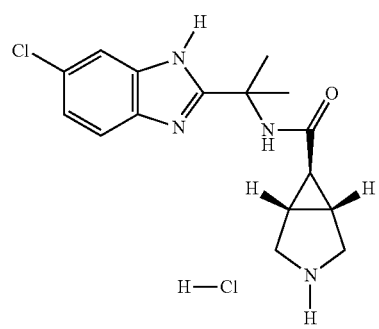 [SMILES: CC(C)(NC(=O)[C@H]1[C@@H]2CNC[C@@H]21)c1nc2ccc(Cl)cc2[nH]1 ; Cl]

TEA (6 mL, 44.985 mmol) followed by TBTU (5.3 g, 16.511 mmol) are added to 4-chloro-o-phenylenediamine (2.1 g, 15.001 mmol) and α-(Boc-amino)isobutyric acid, Boc-a-methylalanine (3.3 g, 16.247 mmol) in THF (50 mL). After stirring for 3 d at rt, volatiles are evaporated under reduced pressure, the residue taken up in EtOAc, washed with 5% citric acid, 2M NaOH, dried over Na$_2$SO$_4$, filtered and evaporate under reduce pressure to give a residue that is purified by flash chromatography (eluent 50% EtOAc/cyclohexane) to furnish a mixture of adducts (4.2 g, 85%). Such mixture is heated at 60° C. overnight in acetic acid (35 mL). Volatiles are evaporated under reduced pressure to give a residue that is taken up in EtOAc, washed with 2M NaOH, dried over MgSO$_4$, filtered and evaporate under reduce pressure to give a residue. Such residue is suspended in DCM (25 mL) and treated with TFA (10 mL). Stirring is continued for 2 h. Volatiles are evaporated under reduced pressure and the resulting residue taken up with methyl tert-butyl ether, washed with 0.5 M HCl and evaporated under reduced pressure. The resulting mixture is taken up and evaporated twice with EtOH to give a residue (3.4 g). 57 mg of such residue (0.2 mmol) and DIPEA (65 μl, 0.4 mmol) in DMF (1 mL) are added to HATU (84 mg, 0.220 mmol), meso-(1R,5S,6r)-3-(tert-butoxycarbonyl)-3-azabicyclo [3.1.0]hexane-6-carboxylic acid (45 mg, 0.200 mmol) and DIPEA (113 μl, 0.700 mmol) in DMF (2 mL) and stirring is continued overnight at rt and the reaction mixture purified by preparative HPLC (stationary phase: XBridge C18 5 μm 19×100 mm. Mobile phase: ACN/H$_2$O+NH$_4$COOH 5 mM). Fractions containing the title compound are combined and lyophilised. The residue in MeOH (3 mL) is treated with HCl in ethyl ether (2M, 1.2 mL, 25.610 mmol). After stirring for 3 h, volatiles are evaporated under reduced pressure and the resulting residue redissolved in ACN/H$_2$O 1:1 and lyophilised to furnish the title compound (86 mg, 100%)

UPLC-MS (Method 4): R$_t$=0.83 min

MS (ESI pos): m/z=319 (M+H)$^+$

Example 12

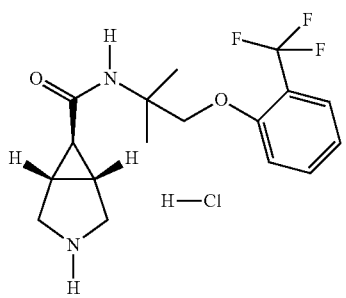

Example 3b (84 mg, 0.19 mmol) is dissolved in ethyl ether (1 mL), cooled to 0° C. and then hydrogen chloride 2M in ethyl ether (1 mL, 2 mmol) is added dropwise. Stirring is continued overnight at rt. Solvents are removed and the crude product is taken up with ethyl ether twice and then dried and evaporated under reduce pressure to furnish the title compound (60 mg, 84%).

HPLC-MS (Method 7): R$_t$=6.32 min

MS (AFCI): m/z=343 (M+H)$^+$

The following examples are synthesized in analogy to the preparation of example 12:

| Example | Structure | Reactant(s) | HPLC-MS R$_t$ [min], method | MS (ESI pos or APCI, m/z) (M + H)$^+$ |
|---|---|---|---|---|
| 13 | 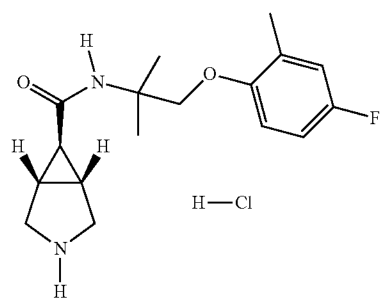 [SMILES: Cc1cc(F)ccc1OCC(C)(C)NC(=O)[C@H]1[C@@H]2CNC[C@@H]21 ; Cl] | Example 3a (72 mg, 0.177 mmol) | 6.91 6 | 307 |
| 14 | 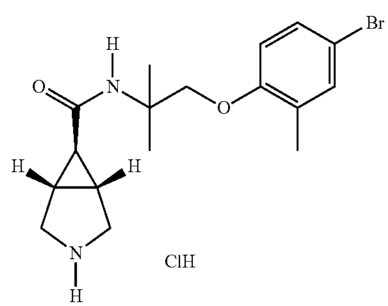 [SMILES: Cc1cc(Br)ccc1OCC(C)(C)NC(=O)[C@H]1[C@@H]2CNC[C@@H]21 ; Cl] | Example 3k (80 mg, 0.17 mmol); using dioxane as solvent | 3.20 8 | 367 |

-continued

| Example | Structure | Reactant(s) | HPLC-MS R$_t$ [min], method | MS (ESI pos or APCI, m/z) (M + H)$^+$ |
|---|---|---|---|---|
| 15 | 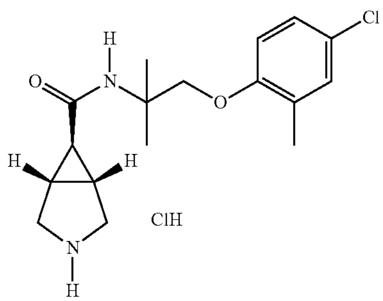 [SMILES: Cc1cc(Cl)ccc1OCC(C)(C)NC(=O)[C@H]1[C@@H]2CNC[C@@H]21 ; Cl] | Example 3l (150 mg. 0.355 mmol); using dioxane as solvent | 2.31 12 | 323 |
| 16 | 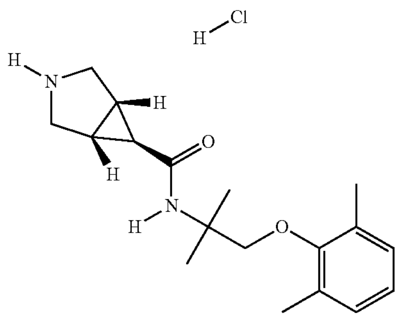 [SMILES: Cl ; Cc1cccc(C)c1OCC(C)(C)NC(=O)[C@H]1[C@@H]2CNC[C@@H]21] | Example 3s (95 mg, 0.219 mmol); using MeOH as solvent | 5.71 7 | 302 |
| 17 | 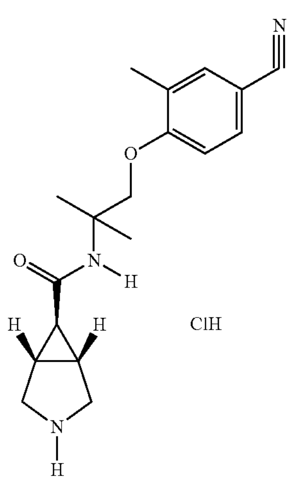 [SMILES: Cc1cc(C#N)ccc1OCC(C)(C)NC(=O)[C@H]1[C@@H]2CNC[C@@H]21 ; Cl] | Example 5a (60 mg. 0.145 mmol) | 5.98 7 | 314 |

-continued
| Example | Structure | Reactant(s) | HPLC-MS R_t [min], method | MS (ESI pos or APCI, m/z) (M + H)+ |
|---|---|---|---|---|
| 18 | 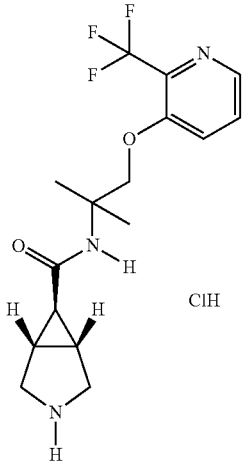 | Example 5b (110 mg. 0.248 mmol) | 5.47 7 | 344 |
| 19 | 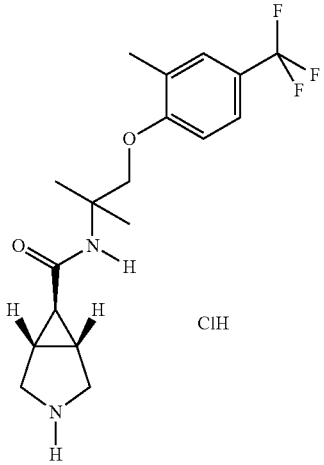 [SMILES: Cc1cc(C(F)(F)F)ccc1OCC(C)(C)NC(=O)[C@H]1[C@@H]2CNC[C@@H]21 ; Cl] | Example 5e (13.5 mg. 0.03 mmol) | 3.09 8 | 357 |
| 20 | 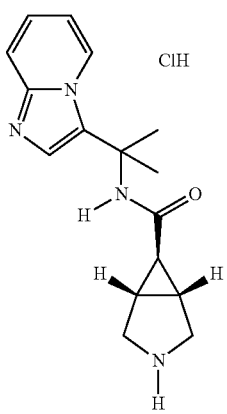 [SMILES: CC(C)(NC(=O)[C@H]1[C@@H]2CNC[C@@H]21)c1cnc2ccccn12 ; Cl] | Example 9g (142 mg, 0.370 mmol); using MeOH as solvent | 0.76-0.92 10 | 285 |

-continued

| Example | Structure | Reactant(s) | HPLC-MS R_t [min], method | MS (ESI pos or APCI, m/z) (M + H)+ |
|---|---|---|---|---|
| 21 | 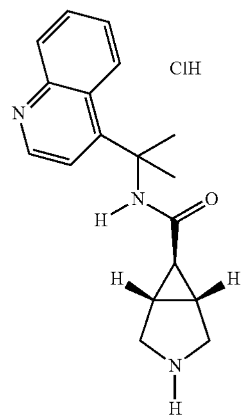 [SMILES: CC(C)(NC(=O)[C@H]1[C@@H]2CNC[C@@H]21)c1ccnc2ccccc12 ; Cl] | Example 9h (144 mg, 0.365 mmol); using MeOH as solvent | 1.48 11 | 296 |
| 22 | 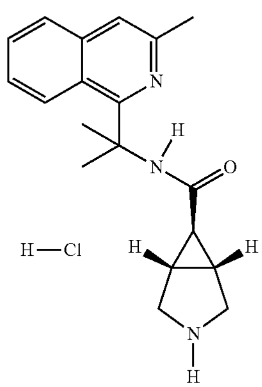 [SMILES: Cc1cc2ccccc2c(C(C)(C)NC(=O)[C@H]2[C@@H]3CNC[C@@H]32)n1 ; Cl] | Example 9d (299 mg, 0.730 mmol); using DCM as solvent | 2.40 11 | 310 |
| 23 | 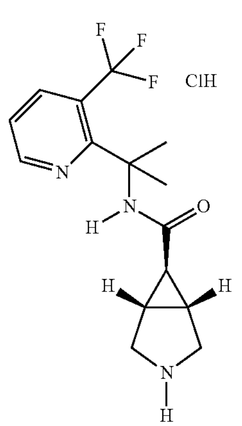 [SMILES: CC(C)(NC(=O)[C@H]1[C@@H]2CNC[C@@H]21)c1ncccc1C(F)(F)F ; Cl] | Example 9e (48 mg, 0.113 mmol); using MeOH as solvent | 2.70 10 | 314 |

-continued
| Example | Structure | Reactant(s) | HPLC-MS R*t* [min], method | MS (ESI pos or APCI, m/z) (M + H)+ |
|---|---|---|---|---|
| 24 | 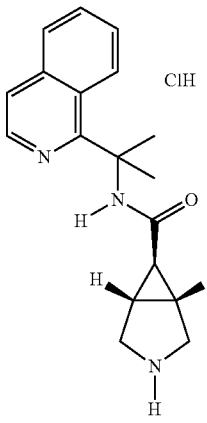 | Example 9f (40 mg, 0.095 mmol); using MeOH as solvent | 2.10 8 | 296 |
| 25 | 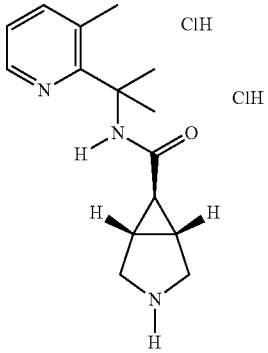 [SMILES: Cc1cccnc1C(C)(C)NC(=O)[C@H]1[C@@H]2CNC[C@@H]21 ; Cl ; Cl] | Example 9a (104 mg, 0.275 mmol); using MeOH as solvent | 1.54 8 | 260 |
| 26 | 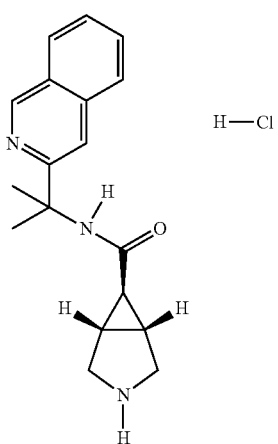 [SMILES: CC(C)(NC(=O)[C@H]1[C@@H]2CNC[C@@H]21)c1cc2ccccc2cn1 ; Cl] | Example 9l (60 mg, 98% content, 0.149 mmol) | 1.92 10 | 296 |

-continued

| Example | Structure | Reactant(s) | HPLC-MS R$_t$ [min], method | MS (ESI pos or APCI, m/z) (M + H)$^+$ |
|---|---|---|---|---|
| 27 | 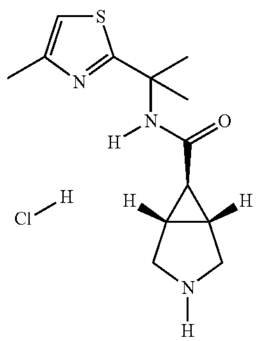 [SMILES: Cc1csc(C(C)(C)NC(=O)[C@H]2[C@@H]3CNC[C@@H]32)n1 ; Cl] | Example 9k (161 mg, 97% content, 0.427 mmol) using MeOH as solvent | 1.65 10 | 266 |
| 28 | 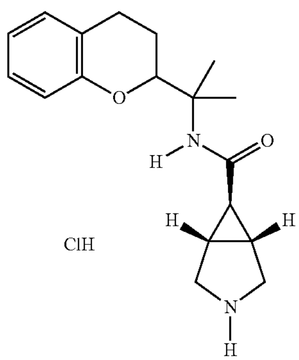 [SMILES: CC(C)(NC(=O)[C@H]1[C@@H]2CNC[C@@H]21)C1CCc2ccccc2O1 ; Cl] | Example 14a (48 mg, 0.117 mmol); using MeOH as solvent | 2.58 9 | 301 |
| 29 | 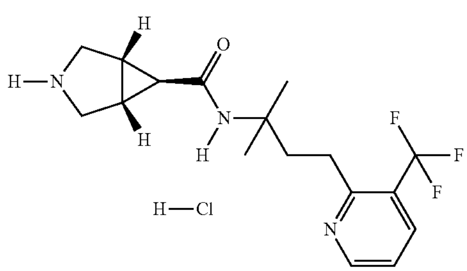 | Example 19a (142 mg, 0.322 mmol) | 2.48 8 | 342 |
| 30 | 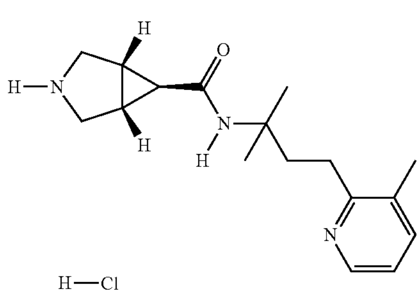 [SMILES: Cc1cccnc1CCC(C)(C)NC(=O)[C@H]1[C@@H]2CNC[C@@H]21 ; Cl] | Example 19b (130 mg, 0.335 mmol); using MeOH as solvent | 2.06 8 | 288 |

-continued

| Example | Structure | Reactant(s) | HPLC-MS $R_t$ [min], method | MS (ESI pos or APCI, m/z) $(M + H)^+$ |
|---|---|---|---|---|
| 31 | 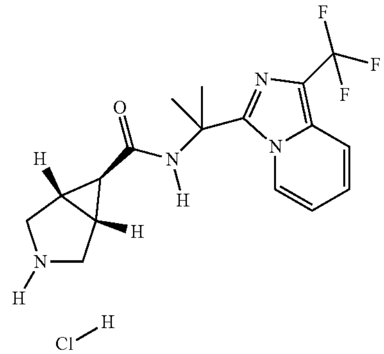 [SMILES: CC(C)(NC(=O)[C@H]1[C@@H]2CNC[C@@H]21)c1nc(C(F)(F)F)c2ccccn12 ; Cl] | Example 23b (41 mg, 95% content, 0.086 mmol) | 2.13 11 | 353 |

Example 32

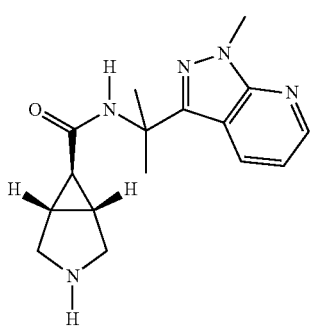 [SMILES: Cn1nc(C(C)(C)NC(=O)[C@H]2[C@@H]3CNC[C@@H]32)c2cccnc21]

Example 32 is prepared from example 29b (107 mg, 0.268 mmol) in analogy to example 12 using SCX cartridge purification of the residue resulting from reaction. Fractions obtained upon eluting with metanolic ammonia are evaporated under reduced pressure to give the title compound (59 mg, 74%)

HPLC-MS (Method 10): $R_t$=2.40 min

MS (ESI pos): m/z=300 $(M+H)^+$

The following examples are synthesized in analogy to the preparation of example 32:

| Example | Structure | Reactant(s) | HPLC-MS $R_t$ [min], method | MS (ESI pos or APCI, m/z) $(M + H)^+$ |
|---|---|---|---|---|
| 33 | 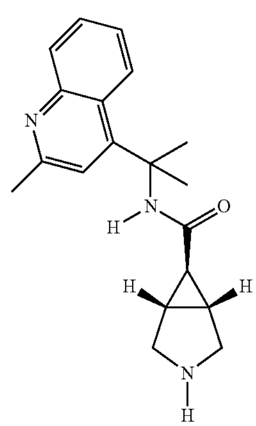 [SMILES: Cc1cc(C(C)(C)NC(=O)[C@H]2[C@@H]3CNC[C@@H]32)c2ccccc2n1] | Example 9i (240 mg, 97% content, 0.568 mmol) Using MeOH as solvent) | 1.57 11 | 310 |

| Example | Structure | Reactant(s) | HPLC-MS R$_t$ [min], method | MS (ESI pos or APCI, m/z) (M + H)$^+$ |
|---|---|---|---|---|
| 34 | 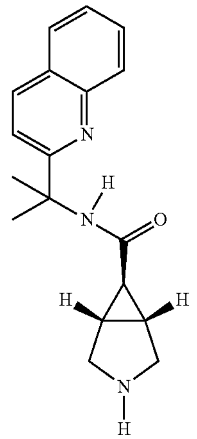 [SMILES: CC(C)(NC(=O)[C@H]1[C@@H]2CNC[C@@H]21)c1ccc2ccccc2n1] | Example 9j (126 mg, 0.319 mmol) Using DCM as solvent | 2.02 11 | 296 |
| 35 | 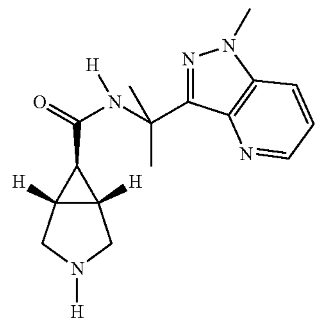 [SMILES: Cn1nc(C(C)(C)NC(=O)[C@H]2[C@@H]3CNC[C@@H]32)c2ncccc21] | Example 29c (184 mg, 0.461 mmol) Using MeOH/Ethyl ether as solvents | 1.87 8 | 300 |

Example 36

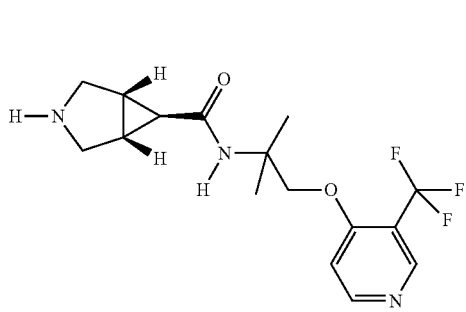 [SMILES: CC(C)(COc1ccncc1C(F)(F)F)NC(=O)[C@H]1[C@@H]2CNC[C@@H]21]

Example 37

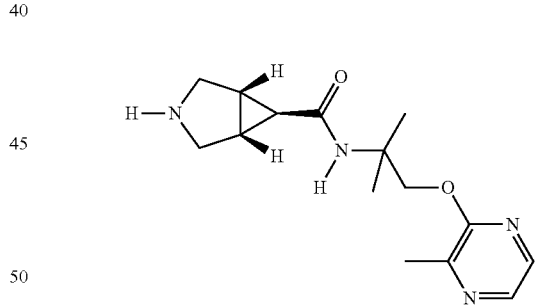

Example 36 is prepared from example 5c (75 mg, 0.169 mmol) in analogy to example 12 using preparative HPLC purification of the residue (stationary phase: Xbridge C18 5 µm 19×100 mm. Mobile phase: ACN/H$_2$O+NH$_4$COOH 5 mM). Fractions containing the title compound are combined and ACN is evaporated under reduced pressure. Aqueous layer is extracted with DCM, separated and DCM is evaporated. The residue is dissolved in MeOH and loaded on a SCX cartridge. Fractions obtained upon eluting with methanolic ammonia are evaporated to furnish the title compound (15 mg, 26%).

HPLC-MS (Method 8): R$_t$=2.17 min

MS (APCI): m/z=344 (M+H)$^+$

Example 37 is prepared from example 5k (42 mg, 0.108 mmol) in analogy to example 12 using MeOH as solvent. Then the reaction mixture is basified with NH$_3$ in MeOH and purified with preparative HPLC (stationary phase: Xbridge C18 5 µm 19×100 mm. Mobile phase: ACN/H$_2$O+ NH$_4$COOH 5 mM). Fractions containing the title compound are combined and ACN is evaporated under reduced pressure. Aqueous layer is extracted with DCM, separated and the organic layer is evaporated to furnish the title compound (5.5 mg, 18%).

HPLC-MS (Method 8): R$_t$=1.89 min

MS (APCI): m/z=291 (M+H)$^+$

Example 38

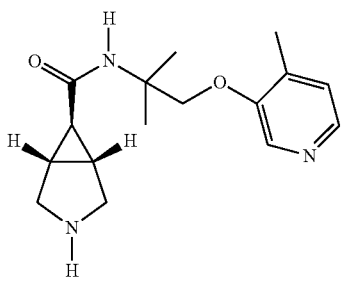 [SMILES: Cc1ccncc1OCC(C)(C)NC(=O)[C@H]1[C@@H]2CNC[C@@H]21]

Example 39

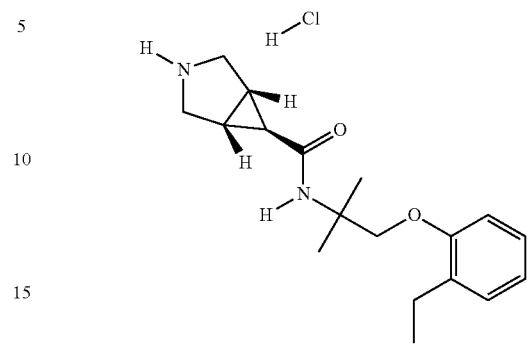

Example 3i (85 mg, 81% content, 0.17 mmol) is dissolved in methanol (4 mL) and then hydrogen chloride 2M in ethyl ether (0.86 mL, 1.71 mmol) is added. Stirring is continued overnight at rt. Solvents are removed under reduce pressure to give a residue that is purified by preparative HPLC (stationary phase: Sunfire C18 ODB 5 μm 19×100 mm. Mobile phase: ACN/$H_2O$+$CF_3COOH$ 0.05%). Fractions containing the title compound are combined and evaporated under reduced pressure. The residue is taken up with HCl in ethyl ether (1 mL), then evaporated under reduced pressure to furnish the title compound (28 mg, 48%)

HPLC-MS (Method 7): $R_t$=5.91 min

MS (APCI): m/z=303 (M+H)$^+$

The following examples are synthesized in analogy to the preparation of example 39:

Example 38 is prepared from example 3d (109 mg, 98% content, 0.274 mmol) in analogy to example 12. The residue is dissolved in HCl in MeOH and purified by preparative HPLC (stationary phase: Xbridge C18 5 μm 19×100 mm. Mobile phase: ACN/$H_2O$+$NH_4COOH$ 5 mM). Fractions containing the title compound are combined and evaporated, redissolved in MeOH, purified on SCX cartridge and eluted with metanolic ammonia to furnish the title compound (26 mg, 33%)

HPLC-MS (Method 7): $R_t$=5.45 min

MS (APCI): m/z=290 (M+H)$^+$

| Example | Structure | Reactant(s) | HPLC-MS $R_t$ [min], method | MS (ESI pos or APCI, m/z) (M + H)$^+$ |
|---|---|---|---|---|
| 40 | 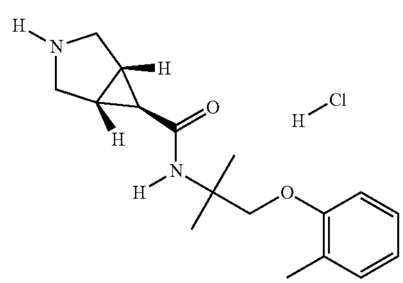 [SMILES: Cc1ccccc1OCC(C)(C)NC(=O)[C@H]1[C@@H]2CNC[C@@H]21 ; Cl] | Example 3j (130 mg, 95% content, 0.318 mmol) | 3.46 10 | 289 |
| 41 | 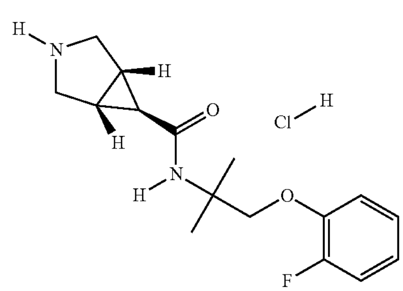 [SMILES: CC(C)(COc1ccccc1F)NC(=O)[C@H]1[C@@H]2CNC[C@@H]21 ; Cl] | Example 3q (80 mg, 0.167 mmol) | 5.33 7 | 293 |

Example 42

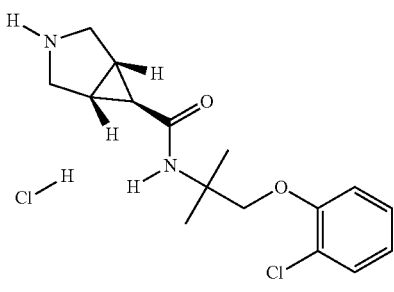 [SMILES: CC(C)(COc1ccccc1Cl)NC(=O)[C@H]1[C@@H]2CNC[C@@H]21 ; Cl]

Example 42 is prepared from example 3t (65 mg, 0.159 mmol) in analogy to example 39 using SCX cartridge purification of the residue obtained from preparative HPLC. Fractions obtained upon eluting with metanolic ammonia are evaporated under reduced pressure to give a residue. The residue is taken up with MeOH and hydrogen chloride 2M in ethyl ether is added. The residue is evaporated under reduced pressure to give the title compound (47 mg, 86%).

HPLC-MS (Method 7): $R_t$=5.47 min
MS (APCI): m/z=309 (M+H)$^+$

Example 43

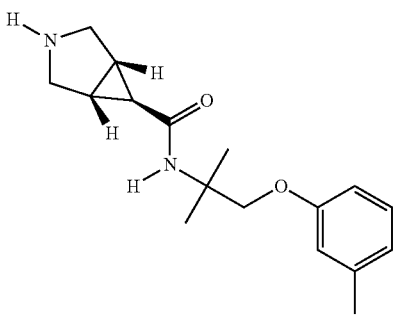 [SMILES: Cc1cccc(OCC(C)(C)NC(=O)[C@H]2[C@@H]3CNC[C@@H]32)c1]

Example 43 is prepared from example 3n (85 mg, 87% content, 0.190 mmol) in analogy to example 39 purifying on SCX cartridge the residue obtained from preparative HPLC purification. Fractions obtained upon eluting with metanolic ammonia are evaporated under reduced pressure to give the title compound (27 mg, 49%).

HPLC-MS (Method 6): $R_t$=6.55 min
MS (ESI pos): m/z=289 (M+H)$^+$

Example 44

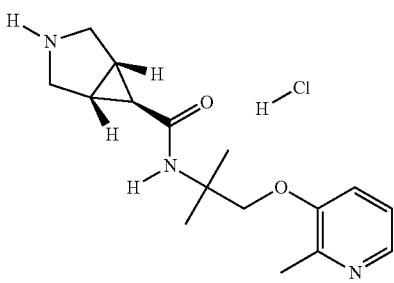

Example 44 is prepared from example 3p (92 mg, 0.210 mmol) in analogy to example 12 using MeOH as solvent. The solution is decanted, the remaining precipitate is dissolved in MeOH and reprecipitated with ethyl ether. The precipitate is filtered and dried to furnish the title compound (61 mg, 89%)

HPLC-MS (Method 7): $R_t$=4.45 min
MS (APCI): m/z=290 (M+H)$^+$

Example 45

Example 45 is prepared from example 23c (220 mg, 0.552 mmol) in analogy to example 39 using with MeOH (1 mL) and ethyl ether (8 mL) as solvents. The mixture is evaporated and the residue is partitioned between water and DCM. The aqueous layer is evaporated to furnish the title compound (50 mg, 27%)

HPLC-MS (Method 11): $R_t$=1.48 min
MS (ESI pos): m/z=297 (M+H)$^+$

Example 46

Example 46 is prepared from example 29a (115 mg, 0.298 mmol) in analogy to example 39 using with MeOH (1 mL) and ethyl ether (8 mL) as solvents. The mixture is evaporated and the residue is partitioned between water and DCM. The aqueous layer is evaporated, the resulting residue redissolved in MeOH and purified on SCX cartridge and eluted with metanolic ammonia to furnish the title compound (33 mg, 82%)

HPLC-MS (Method 8): $R_t$=1.82 min
MS (APCI): m/z=286 (M+H)$^+$

Example 47

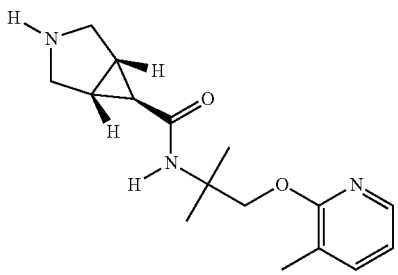 [SMILES: Cc1cccnc1OCC(C)(C)NC(=O)[C@H]1[C@@H]2CNC[C@@H]21]

Example 3v (13 g, 33.37 mmol) is suspended in MeOH/Water 1:1 (35 mL/35 mL), split in 7 equal batches and heated under microwaves irradation (150° C.) for 70 min. Solvents are removed under reduce pressure to give a residue that is purified by flash chromatography (eluent 100% DCM to 93:7:0.7 DCM/MeOH/NH$_3$) to furnish the title compound (7 g, 72%).

UPLC-MS (Method 2): R$_t$=0.68 min
MS (ESI pos): m/z=290 (M+H)$^+$

The following examples are synthesized in analogy to the preparation of example 47:

| Example | Structure | Reactant(s) | HPLC-MS R$_t$ [min], method | MS (ESI pos, m/z) (M + H)$^+$ |
|---|---|---|---|---|
| 48 | 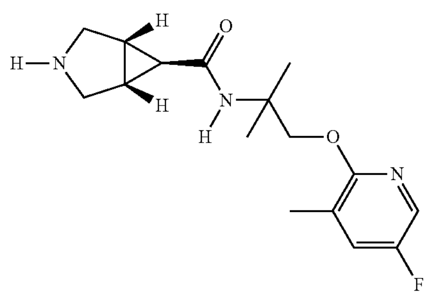 [SMILES: Cc1cc(F)cnc1OCC(C)(C)NC(=O)[C@H]1[C@@H]2CNC[C@@H]21] | Example 3h (25 mg, 0.061 mmol) | 2.14 11 | 308 |
| 49 | 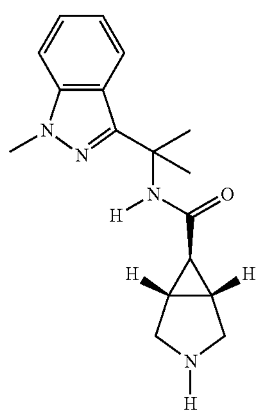 [SMILES: Cn1nc(C(C)(C)NC(=O)[C@H]2[C@@H]3CNC[C@@H]32)c2ccccc21] | Example 9b (730 mg, 1.832 mmol) | 1.61 11 | 299 |

Example 50

Example 50 is prepared from example 9c (30 mg, 0.062 mmol) as described for the example 47 purifying the reaction residue on a SCX cartridge, which is washed with MeOH and DCM, and then eluted with NH$_3$ in MeOH to give the title compound (22 mg, 95%)

HPLC-MS (Method 10): R$_t$=3.63 min

MS (ESI pos): m/z=375 (M+H)$^+$

The following example is synthesized in analogy to the preparation of example 50:

Example 52

Example 5h (200 mg, 0.451 mmol) is suspended in MeOH (1 mL) and water (1.5 mL) and the mixture is heated under microwaves irradation (150° C.) for 50 min and then for one additional hour. Volatiles are removed under reduce pressure to give a residue that is purified by Preparative HPLC (stationary phase: Sunfire C18 ODB 5 μm 19×100 mm. Mobile phase: ACN/H2O+CF3COOH 0.05%). Fractions containing the title compound are combined and ACN is evaporated under reduced pressure. The aqueous layer is basified and extracted with DCM. The separated organic layer is evaporated to furnish the title compound (95 mg, 61%)

HPLC-MS (Method 11): R$_t$=2.33 min

MS (ESI pos): m/z=344 (M+H)$^+$

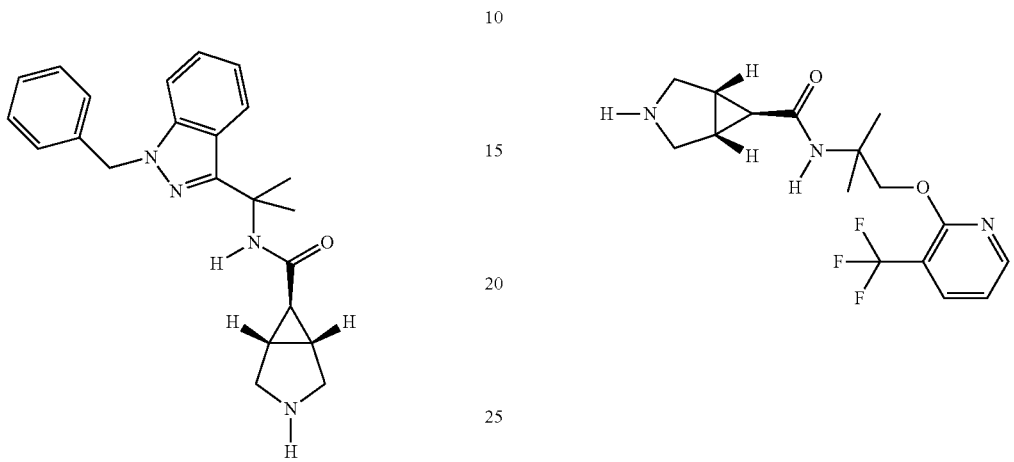

| Example | Structure | Reactant(s) | HPLC-MS R$_t$ [min], method | MS (ESI pos, m/z) (M + H)$^+$ |
|---------|-----------|-------------|------------------------------|-------------------------------|
| 51 | 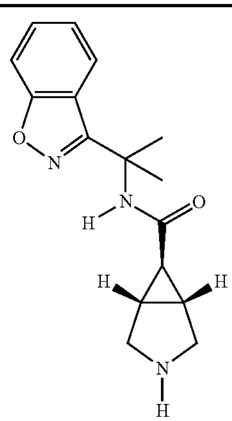 | Example 34a (60 mg, 98% content, 0.153 mmol) | 1.68 11 | 286 |

Example 53

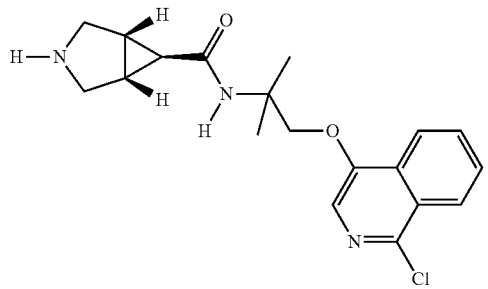 [SMILES: CC(C)(COc1cnc(Cl)c2ccccc12)NC(=O)[C@H]1[C@@H]2CNC[C@@H]21]

Example 3c (95 mg, 0.208 mmol) is dissolved in dry DCM (1 mL), cooled to 0° C. and then hydrogen chloride 2M in ethyl ether (1 mL, 2 mmol) is added. Stirring is continued for 5 h at rt resulting in formation of a precipitate. The solution is decanted and the remaining precipitate is dissolved in MeOH and loaded on an SCX cartridge. Fractions obtained upon eluting with metanolic ammonia are evaporated under reduced pressure to give the title compound (64 mg, 86%).

HPLC-MS (Method 10): $R_t$=3.51 min
MS (ESI pos): m/z=360 (M+H)$^+$

The following examples are synthesized in analogy to the preparation of example 53:

Example 56

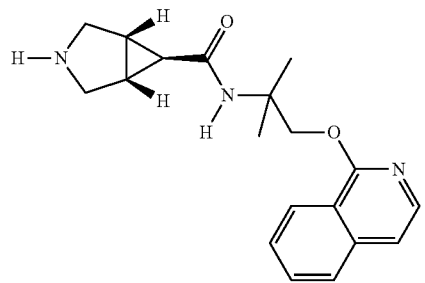

Example 56 is prepared from example 5f (158 mg, 0.371 mmol) in analogy to example 53. The reaction mixture is basified with NH$_3$ in MeOH and purified by preparative HPLC (stationary phase: Sunfire C18 ODB 5 μm 19×100 mm. Mobile phase: ACN/H2O+CF3COOH 0.05%). Fractions containing the title compound are combined and basified with NaHCO$_3$ saturated solution. Solvents are removed and the residue is loaded on an SCX cartridge. Fractions obtained upon eluting with metanolic ammonia are evaporated under reduced pressure to give the title compound (38 mg, 31%).

HPLC-MS (Method 8): $R_t$=2.80 min
MS (APCI): m/z=326 (M+H)$^+$

| Example | Structure | Reactant(s) | HPLC-MS $R_t$ [min], method | MS (APCI, m/z) (M + H)$^+$ |
|---|---|---|---|---|
| 54 | 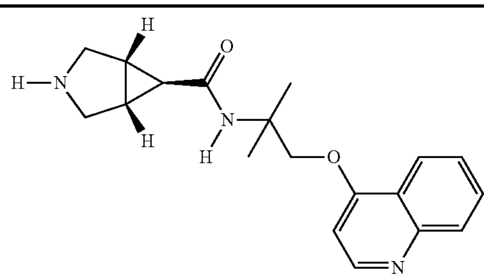 | Example 3f (156 mg, 95% content, 0.341 mmol) | 2.48  8 | 326 |
| 55 | 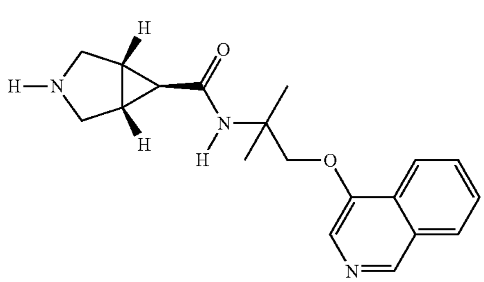 [SMILES: CC(C)(COc1cncc2ccccc12)NC(=O)[C@H]1[C@@H]2CNC[C@@H]21] | Example 3g (108 mg, 96% content, 0.244 mmol) | 2.61  8 | 326 |

Example 57

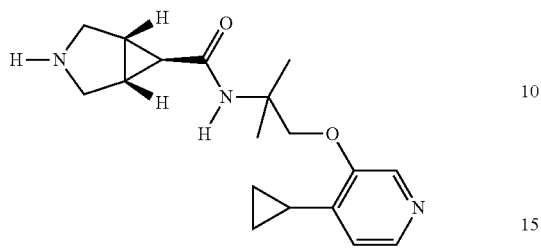

Example 57 is prepared from example 15c (94 mg, 83% content, 0.197 mmol) in analogy to example 53. The reaction mixture is basified with NH$_3$ in MeOH and purified by preparative HPLC (stationary phase: Xbridge C18 5 μm 19×100 mm. Mobile phase: ACN/H2O+NH$_4$COOH 5 mM). Fractions containing the title compound are combined and basified with NH$_3$ in MeOH, then purified by flash chromatography (eluent 95:5:0.5 DCM/MeOH/NH$_4$OH) to furnish the title compound (15 mg, 24%).

HPLC-MS (Method 8): R$_t$=2.19 min
MS (APCI): m/z=316 (M+H)$^+$

The following example is synthesized in analogy to the preparation of example 57:

| Example | Structure | Reactant(s) | HPLC-MS R$_t$ [min], method | MS (ESI pos, m/z) (M + H)$^+$ |
|---|---|---|---|---|
| 58 | 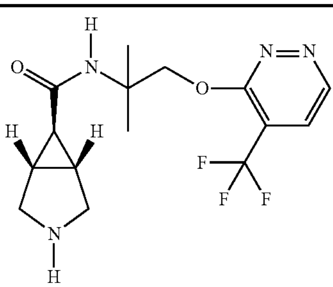 | Example 5j (280 mg, 0.630 mmol) | 2.97 10 | 345 |

Example 59

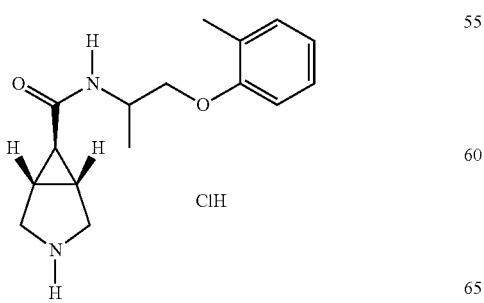

Hydrogen chloride 4M in dioxane (3 mL, 12 mmol) is added to example 3r (30 mg, 0.080 mmol) and stirring is continued for 3 h. Solvents are evaporated and the residue is dried under reduce pressure to give the title compound (10 mg, 40%)

HPLC-MS (Method 8): $R_t$=2.50 min
MS (AFCI): m/z=275 (M+H)$^+$

The following examples are synthesized in analogy to the preparation of example 59:

| Example | Structure | Reactant(s) | HPLC-MS $R_t$ [min], method | MS (ESI pos or APCI, m/z) (M + H)$^+$ |
|---|---|---|---|---|
| 60 | 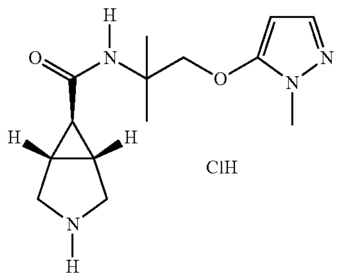 [SMILES: Cn1nccc1OCC(C)(C)NC(=O)[C@H]1[C@@H]2CNC[C@@H]21 ; Cl] | Example 3m (170 mg, 0.418 mmol) | 1.70 8 | 279 |
| 61 | 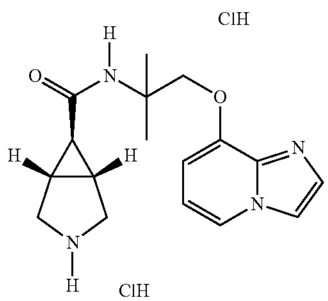 [SMILES: Cl ; CC(C)(COc1cccn2ccnc12)NC(=O)[C@H]1[C@@H]2CNC[C@@H]21 ; Cl] | Example 3u (110 mg, 0.265 mmol) | 1.70 11 | 315 |
| 62 | 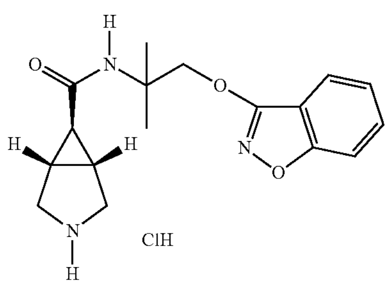 [SMILES: CC(C)(COc1noc2ccccc12)NC(=O)[C@H]1[C@@H]2CNC[C@@H]21 ; Cl] | Example 30 (200 mg, 75% content, 0.361 mmol) | 3.34 10 | 316 |

Example 63

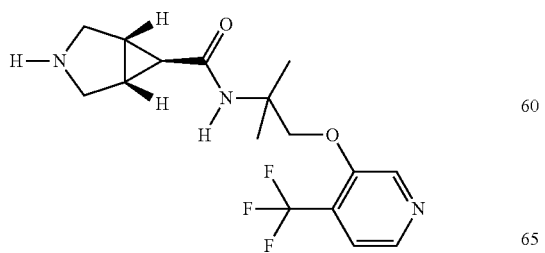

Example 3w (25.9 g 58.4 mmol) is split in 4 equal parts and each of them is dissolved in MeOH (6.5 mL), cooled to 0° C. and treated with Hydrogen chloride 2M in ether (37 mL, 73 mmol). Stirring is continued overnight. Volatiles are removed under reduced pressure and the residues redissolved in MeOH, purified over SCX cartridges, washed with DCM/MeOH 1:1 and eluted with 2N metanolic ammonia and combined to furnish the title compound (20.05 g, 100%).

HPLC-MS (Method 10): $R_t$=3.09 min
MS (ESI pos): m/z=344 (M+H)$^+$

Example 64

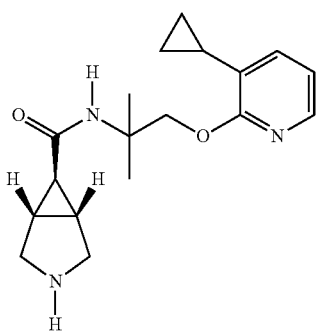

Example 64 is prepared from example 5l (90 mg, 0.195 mmol) in analogy to example 59. Following evaporation of volatiles, the residue is purified by Preparative HPLC (stationary phase: Sunfire C18 ODB 5 μm 19×100 mm. Mobile phase: ACN/H$_2$O+CF$_3$COOH 0.05%). Fractions containing the title compound are combined and ACN is evaporated under reduced pressure. The aqueous layer is basified and extracted with DCM. The separated organic layer is evaporated to furnish the title compound (35 mg, 57%)

HPLC-MS (Method 10): $R_t$=3.28 min

MS (ESI pos): m/z=316 (M+H)$^+$

The following example is synthesized in analogy to the preparation of example 64:

| Example | Structure | Reactant(s) | HPLC-MS $R_t$ [min], method | MS (ESI pos, m/z) (M + H)$^+$ |
|---|---|---|---|---|
| 65 | 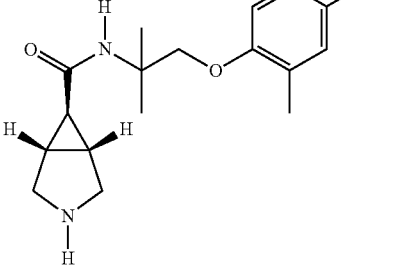 | Example 15b (60 mg, 0.140 mmol) | 2.32 12 | 329 |

The following example is synthesized in analogy to the preparation of example 47:

| Example | Structure | Reactant(s) | HPLC-MS $R_t$ [min], method | MS (APCI, m/z) (M + H)$^+$ |
|---|---|---|---|---|
| 66 | 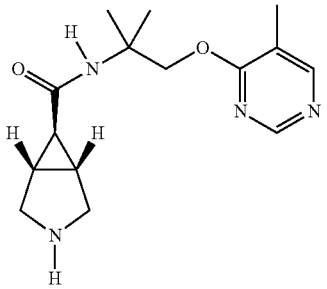 | Example 15d (58 mg, 0.149 mmol) | 1.83 8 | 291 |

Example 67

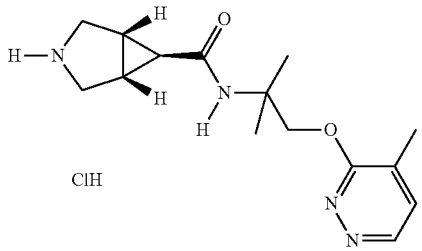 [SMILES: Cc1ccnnc1OCC(C)(C)NC(=O)[C@H]1[C@@H]2CNC[C@@H]21 ; Cl]

Example 5d (20 mg, 98% content, 0.05 mmol) is dissolved in MeOH (0.5 mL), cooled to 0° C. and then hydrogen chloride 2M in ethyl ether (1 mL, 2 mmol) is added dropwise. Stirring is continued for 1 h at rt. Hydrogen chloride 2M in ethyl ether (1 mL, 2 mmol) is added dropwise and stirring is further continued for 2 h at rt. Volatiles are evaporated under reduced pressure to furnish the title compound (16 mg, 97%).

HPLC-MS (Method 8): $R_t$=1.78 min
MS (APCI): m/z=291 (M+H)$^+$

Example 68

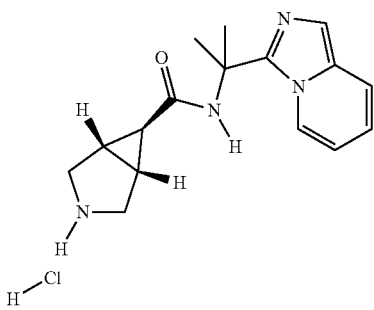

Example 68 is prepared from example 23a (105 mg, 0.273 mmol) as described for example 67 using ethyl ether as solvent. The precipitate formed during the reaction is filtered and washed with ethyl ether and dried. Then the residue is dissolved in water and washed with DCM. The aqueous layer is lyophilized to furnish the title compound (55 mg, 63%)

HPLC-MS (Method 12): $R_t$=0.27 min
MS (ESI pos): m/z=285 (M+H)$^+$

Example 69

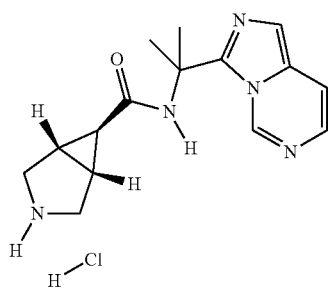

Example 69 is prepared from example 23d (25 mg, 0.065 mmol) as described for example 67 using MeOH as solvent (1 mL). Volatiles are evaporated, then the residue is dissolved in water and washed with DCM. The aqueous layer is lyophilized to furnish the title compound (16 mg, 78%)

HPLC-MS (Method 12): $R_t$=0.25 min
MS (ESI pos): m/z=286 (M+H)$^+$

Example 70

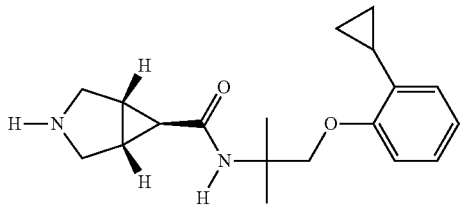 [SMILES: CC(C)(COc1ccccc1C1CC1)NC(=O)[C@H]1[C@@H]2CNC[C@@H]21]

Example 15a (105 mg, 0.253 mmol) is dissolved in DCM (2 mL) and Hydrogen chloride 4M in dioxane (1.2 mL, 0.506 mmol) is added and stirring is continued overnight. Volatiles are removed under reduce pressure to give a residue that is purified by Preparative HPLC (stationary phase: Sunfire C18 ODB 5 μm 19×100 mm. Mobile phase: ACN/H2O+CF3COOH 0.05%). Fractions containing the title compound are combined and ACN is evaporated under reduced pressure. The aqueous layer is basified with 10% NaOH and extracted with DCM. The separated organic layer is evaporated under reduced pressure. The resulting residue is dissolved in EtOH and Hydrogen chloride 4M in dioxane (0.200 mL) is added. Volatiles are evaporated under reduced pressure to furnish the title compound (53 mg, 59%)

HPLC-MS (Method 8): $R_t$=3.27 min
MS (APCI): m/z=315 (M+H)$^+$

Example 71

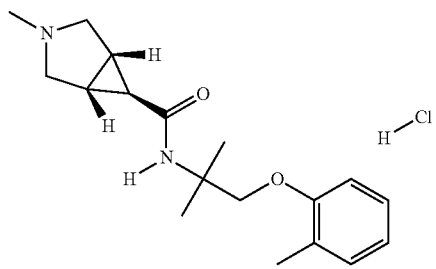

TEA (0.144 mL, 1.041 mmol) and iodomethane (0.032 mL, 0.521 mmol) are added to example 40 (110 mg, 0.347 mmol) dissolved in DMF and stirring is continued for 2 days.

The reaction mixture is diluted with water and ethyl ether. The separated organic layer is dried and evaporated under reduced pressure to give a residue that is purified by flash chromatography (eluent 98:2:0.2 to 80:20:2 DCM/MeOH/NH$_4$OH). The resulting residue is dissolved in EtOH and treated with HCl 4M in dioxane. Volatiles are evaporated under reduced pressure to furnish the title compound (23 mg, 22%).

HPLC-MS (Method 7): $R_t$=6.04 min
MS (APCI): m/z=303 (M+H)$^+$

Example 72

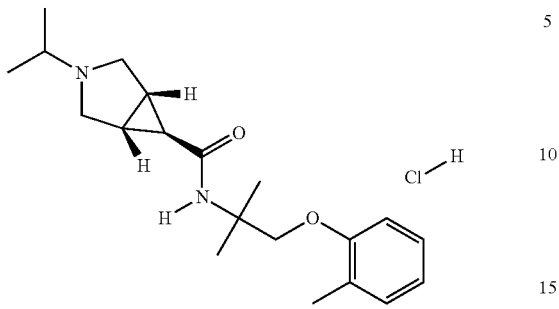

Acetic acid (104 μL, 1.734 mmol) and acetone (51 μL, 0.694 mmol) are added to example 40 (100 mg, 0.347) dissolved in DMF (2 mL). After 1 h, sodium triacetoxyborohydride (147 mg, 0.694 mmol) is added to the mixture and stirring overnight. The reaction mixture is diluted with water and extracted with ethyl ether. Volatiles are removed under reduced pressure and the residue is purified by Preparative HPLC (stationary phase: Sunfire C18 ODB 5 μm 19×100 mm. Mobile phase: ACN/$H_2O$+$CF_3COOH$ 0.05%), then by preparative HPLC (stationary phase: Xbridge C18 5 μm 19×100 mm. Mobile phase: ACN/$H_2O$+$NH_4COOH$ 5 mM). Fractions containing the title compound are combined and evaporated under reduced pressure. The resulting residue is dissolved in DCM and washed with water. Volatiles are removed under reduced pressure and the residue is purified by flash chromatography (eluent 98:2:0.2 to 90:10:1 DCM/MeOH/$NH_4OH$). The residue is dissolved in MeOH and treated with HCl 4M in dioxane. Volatiles are evaporated under reduced pressure to furnish the title compound (22 mg, 17%).

HPLC-MS (Method 7): $R_t$=5.97 min

MS (APCI): m/z=331 (M+H)$^+$

The following example is synthesized in analogy to the preparation of example 47:

Example 74

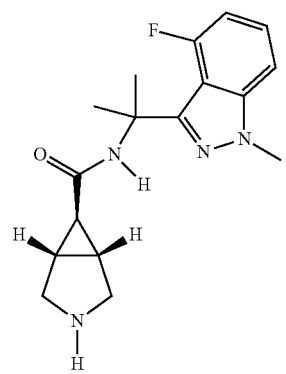 [SMILES: Cn1nc(C(C)(C)NC(=O)[C@H]2[C@@H]3CNC[C@@H]32)c2c(F)cccc21]

Hydrogen chloride 4M in dioxane (2 mL, 8.0 mmol) is added to example 9n (80 mg, 22% content, 0.042 mmol) and stirring is continued for 5 h. The reaction mixture is basified by addition of methanolic ammonia, water and DCM are added, the organic layer is separated, dried by Phase separator cartridge and solvent evaporated affording a residue that is purified by preparative HPLC (stationary phase XTerra C18 OBD 5 μm 30×100 mm. Mobile phase: ACN/$H_2O$+$NH_4COOH$ 5 mM). Fractions containing the title compound are combined and ACN is evaporated under reduced pressure. The aqueous layer is extracted with DCM, separated and the DCM is evaporated to furnish the title compound (12 mg, 90%)

HPLC-MS (Method 7a): $R_t$=2.75 min

MS (APCI): m/z=317 (M+H)$^+$

| Example | Structure | Reactant(s) | HPLC-MS $R_t$ [min], method | MS (ESI neg, m/z) |
|---|---|---|---|---|
| 73 | 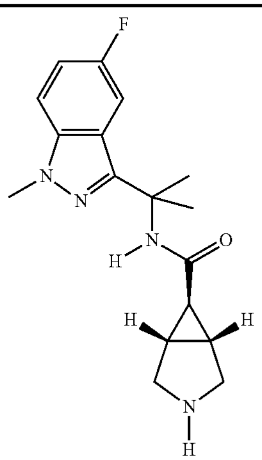 | Example 9m (225 mg, 97% content, 0.52 mmol) | 1.81 11 | 315 [M − H]− |

The following examples are synthesized in analogy to the preparation of example 74:

| Example | Structure | Reactant(s) | HPLC-MS R_t [min], method | MS (ESI pos or APCI, m/z) (M + H)+ |
|---|---|---|---|---|
| 75 | (structure) | Example 9o (100 mg, 50% content 0.12 mmol) | 2.83 7a | 317 |
| 76 | (structure) | Example 9p (360 mg, 69% content 0.53 mmol) | 3.43 7a | 367 |

The following example is synthesized in analogy to the preparation of example 50:

| Example | Structure | Reactant(s) | HPLC-MS R_t [min], method | MS (APCI, m/z) (M + H)+ |
|---|---|---|---|---|
| 77 | (structure) | Example 9q (170 mg, 99% content, 0.41 mmol) | 1.90 7a | 311 |

Example 78

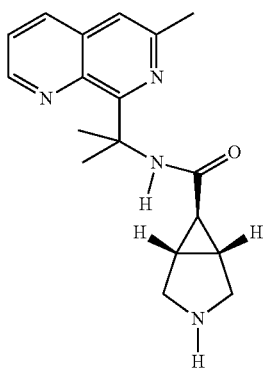 [SMILES: Cc1cc2cccnc2c(C(C)(C)NC(=O)[C@H]2[C@@H]3CNC[C@@H]32)n1]

Example 78 is prepared from example 9r (120 mg, 98% content, 0.29 mmol) as described for the example 50 purifying the residue from SCX cartridge by flash chromatography (eluent 95:5:0.5 DCM/MeOH/NH$_4$OH) to furnish the title compound (81 mg, 91%).

HPLC-MS (Method 11): R$_t$=2.19 min
MS (ESI pos): m/z=311 (M+H)$^+$

The following example is synthesized in analogy to the preparation of example 50:

| Example | Structure | Reactant(s) | HPLC-MS R$_t$ [min], method | MS (ESI pos, m/z) (M + H)$^+$ |
|---|---|---|---|---|
| 79 | 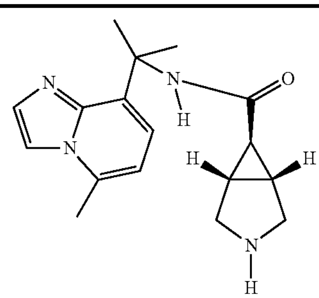 | Example 9s (20 mg, 0.05 mmol) | 1.48 11 | 299 |

The following examples are synthesized in analogy to the preparation of example 32:

| Example | Structure | Reactant(s) | HPLC-MS R$_t$ [min], method | MS (ESI pos or APCl, m/z) (M + H)$^+$ |
|---|---|---|---|---|
| 80 | 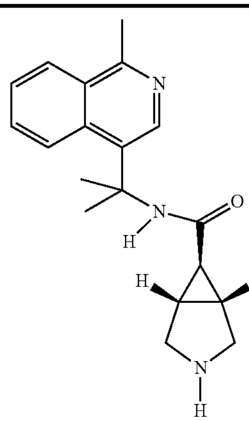 | Example 9t (300 mg, 0.733 mmol), using DCM as solvent | 0.26 12 | 310 |

| Example | Structure | Reactant(s) | HPLC-MS R_t [min], method | MS (ESI pos or APCl, m/z) (M + H)+ |
|---|---|---|---|---|
| 81 | 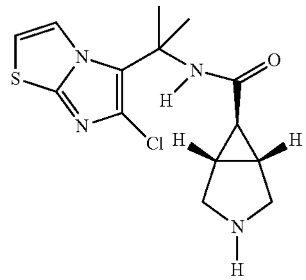 [SMILES: CC(C)(NC(=O)[C@H]1[C@@H]2CNC[C@@H]21)c1c(Cl)nc2sccn12] | Example 9u (39 mg, 98% content, 0.09 mmol), using DCM as solvent | 1.58 11 | 325 |

Example 82

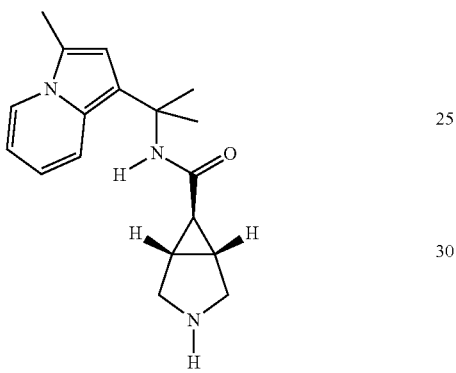

Example 9v (65 mg, 98% content, 0.148 mmol) is dissolved in MeOH and palladium (16 mg, 0.015 mmol) is added. The mixture is hydrogenated at 1 bar for 2 h. The catalyst is removed by filtration and washed with MeOH. The resulting solution is evaporated under reduced pressure to afford a residue that is purified by flash chromatography (eluent 0-4% MeOH+1% NH$_4$OH/DCM) to furnish the title compound (28 mg, 64%).

HPLC-MS (Method 12): R$_t$=2.16 min
MS (ESI pos): m/z=298 (M+H)+

The following examples are synthesized in analogy to the preparation of example 50:

| Example | Structure | Reactant(s) | HPLC-MS R_t [min], method | MS (ESI pos or APCl, m/z) (M + H)+ |
|---|---|---|---|---|
| 83 | 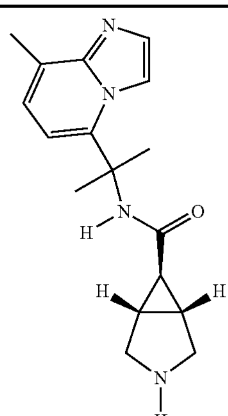 | Example 9w (127 mg, 0.319 mmol) | 1.63 10 | 299 |

| Example | Structure | Reactant(s) | HPLC-MS R$_t$ [min], method | MS (ESI pos or APCI, m/z) (M + H)$^+$ |
|---|---|---|---|---|
| 84 | 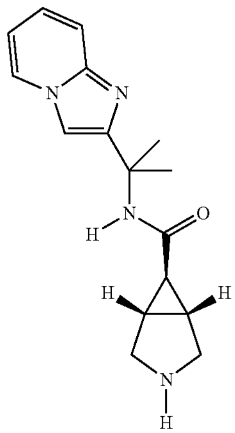 [SMILES: CC(C)(NC(=O)[C@H]1[C@@H]2CNC[C@@H]21)c1cn2ccccc2n1] | Example 9x (190 mg, 0.494 mmol) | 2.40 7a | 285 |

The following examples are synthesized in analogy to the preparation of example 47:

| Example | Structure | Reactant(s) | HPLC-MS R$_t$ [min], method | MS (ESI pos, m/z) (M + H)$^+$ |
|---|---|---|---|---|
| 85 | 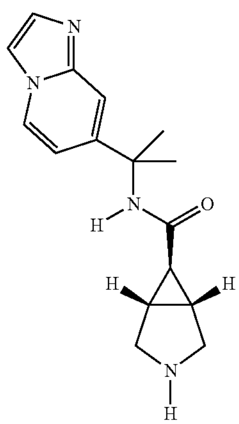 [SMILES: CC(C)(NC(=O)[C@H]1[C@@H]2CNC[C@@H]21)c1ccn2ccnc2c1] | Example 9y (95 mg, 70% content, 0.17 mmol) | 1.50 11 | 285 |
| 86 | 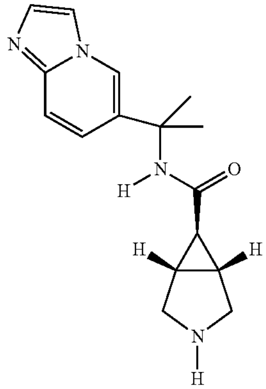 [SMILES: CC(C)(NC(=O)[C@H]1[C@@H]2CNC[C@@H]21)c1ccc2nccn2c1] | Example 9z (95 mg, 87% content, 0.22 mmol) | 1.55 11 | 285 |

-continued

| Example | Structure | Reactant(s) | HPLC-MS $R_t$ [min], method | MS (ESI pos, m/z) $(M + H)^+$ |
|---|---|---|---|---|
| 87 | 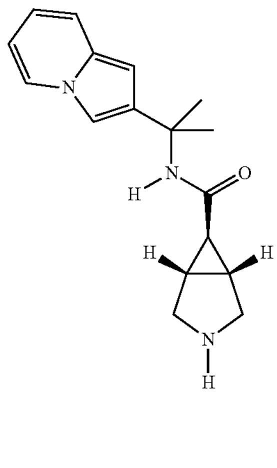 [SMILES: CC(C)(NC(=O)[C@H]1[C@@H]2CNC[C@@H]21)c1cc2ccccn2c1] | Example 9aa (80 mg, 98% content, 0.20 mmol) | 2.55 12a | 284 |
| 88 | 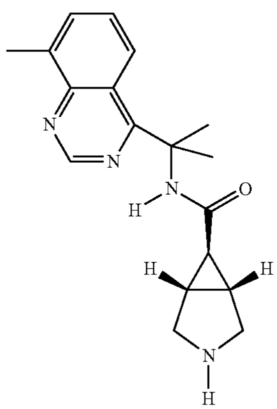 [SMILES: Cc1cccc2c(C(C)(C)NC(=O)[C@H]3[C@@H]4CNC[C@@H]43)ncnc12] | Example 29d (150 mg, 0.365 mmol) | 1.81 11 | 311 |

The following example is synthesized in analogy to the preparation of example 50:

| Example | Structure | Reactant(s) | HPLC-MS $R_t$ [min], method | MS (ESI pos, m/z) $(M + H)^+$ |
|---|---|---|---|---|
| 89 | 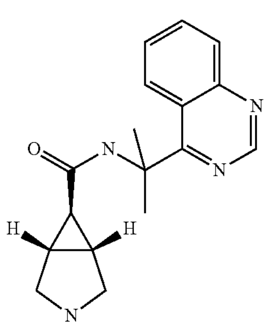 [SMILES: CC(C)(NC(=O)[C@H]1[C@@H]2CNC[C@@H]21)c1ncnc2ccccc12] | Example 29e (250 mg, 95% content, 0.599 mmol) | 2.42 12 | 297 |

The following example is synthesized in analogy to the preparation of example 32:

| Example | Structure | Reactant(s) | HPLC-MS $R_t$ [min], method | MS (APCI, m/z) $(M + H)^+$ |
|---|---|---|---|---|
| 90 | 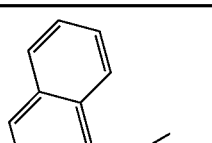 | Example 29f (160 mg, 98% content, 0.396 mmol) Using MeOH as solvent | 2.09 7b | 296 |

The following examples is synthesized in analogy to the preparation of example 12:

| Example | Structure | Reactant(s) | HPLC-MS $R_t$ [min], method | MS (ESI pos, m/z) $(M + H)^+$ |
|---|---|---|---|---|
| 91 | 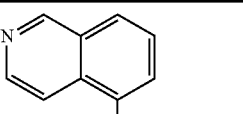 | Example 29g (126 mg, 0.319 mmol) using DCM as solvent | 1.65 11 | 296 |

The following example is synthesized in analogy to the preparation of example 50:

| Example | Structure | Reactant(s) | HPLC-MS $R_t$ [min], method | MS (ESI pos, m/z) $(M + H)^+$ |
|---|---|---|---|---|
| 92 | 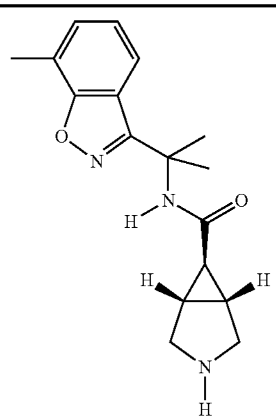 | Example 34b (180 mg, 0.451 mmol) | 2.58 12a | 300 |

The following example is synthesized in analogy to the preparation of example 47:

| Example | Structure | Reactant(s) | HPLC-MS R$_t$ [min], method | MS (APCI, m/z) (M + H)$^+$ |
|---|---|---|---|---|
| 93 | 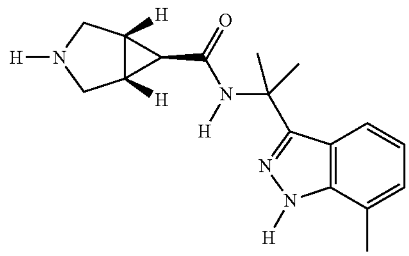 [SMILES: Cc1cccc2c(C(C)(C)NC(=O)[C@H]3[C@@H]4CNC[C@@H]43)n[nH]c12] | Example 39a (60 mg, 0.15 mmol) | 2.68 7a | 299 |

The following example is synthesized in analogy to the preparation of example 32:

| Example | Structure | Reactant(s) | HPLC-MS R$_t$ [min], method | MS (ESI pos, m/z) (M + H)$^+$ |
|---|---|---|---|---|
| 94 | 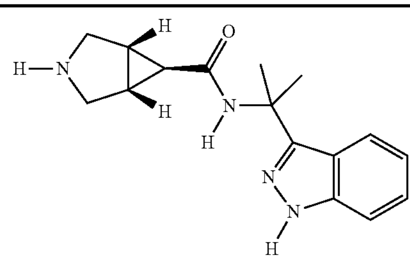 | Example 39b (62 mg, 94% content, 0.15 mmol) | 1.29 11 | 285 |

The following example is synthesized in analogy to the preparation of example 50:

| Example | Structure | Reactant(s) | HPLC-MS R$_t$ [min], method | MS (m/z) |
|---|---|---|---|---|
| 95 | 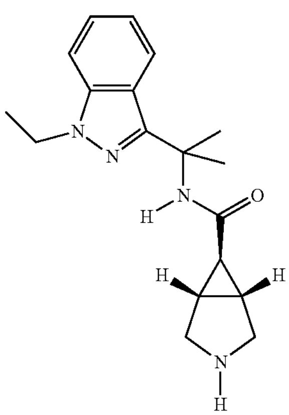 [SMILES: CCn1nc(C(C)(C)NC(=O)[C@H]2[C@@H]3CNC[C@@H]32)c2ccccc21] | Example 39c (84 mg, 0.20 mmol) | 1.95 11 | 311 (ESI neg) (M − H)$^-$ |

-continued

| Example | Structure | Reactant(s) | HPLC-MS R$_t$ [min], method | MS (m/z) |
|---------|-----------|-------------|------------------------------|----------|
| 96 | 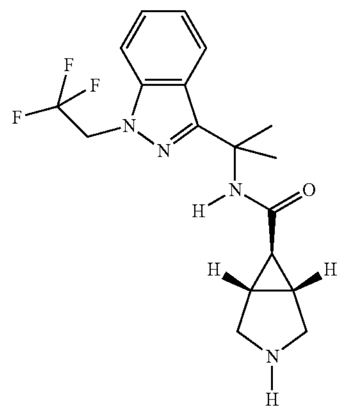 [SMILES: CC(C)(NC(=O)[C@H]1[C@@H]2CNC[C@@H]21)c1nn(CC(F)(F)F)c2ccccc12] | Example 39d (60 mg, 0.13 mmol) | 2.24 11 | 367 (ESI pos) (M + H)$^+$ |
| 97 | 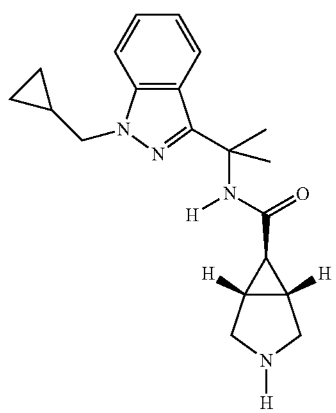 [SMILES: CC(C)(NC(=O)[C@H]1[C@@H]2CNC[C@@H]21)c1nn(CC2CC2)c2ccccc12] | Example 39e (90 mg, 0.21 mmol) | 2.13 11 | 339 (ESI pos) (M + H)$^+$ |
| 98 | 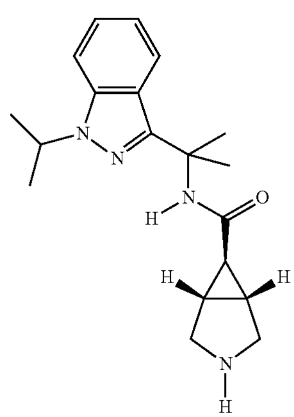 [SMILES: CC(C)n1nc(C(C)(C)NC(=O)[C@H]2[C@@H]3CNC[C@@H]32)c2ccccc21] | Example 39f (70 mg, 0.16 mmol) | 2.39 11 | 325 (ESI neg) (M − H)$^-$ |

-continued

| Example | Structure | Reactant(s) | HPLC-MS $R_t$ [min], method | MS (m/z) |
|---|---|---|---|---|
| 99 | 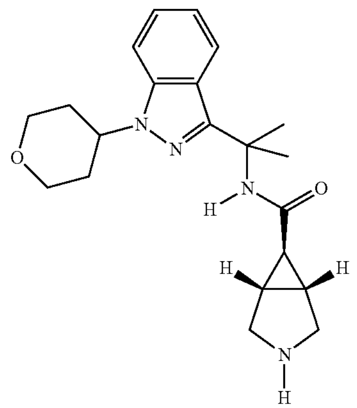 [SMILES: CC(C)(NC(=O)[C@H]1[C@@H]2CNC[C@@H]21)c1nn(C2CCOCC2)c2ccccc12] | Example 39g (60 mg, 0.13 mmol) | 1.97 11 | 369 (ESI pos) (M + H)+ |

Example 100

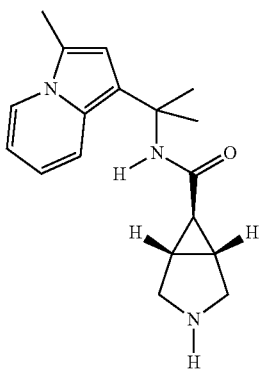 [SMILES: Cc1cc(C(C)(C)NC(=O)[C@H]2[C@@H]3CNC[C@@H]32)c2ccccn12]

tert-Butyldimethylsilyl trifluoromethanesulfonate (162 μL, 0.71 mmol) is added to example 9ab (92 mg, 0.23 mmol) and 2,6-lutidine (108 μL, 0.92 mmol) in DCM (2.8 mL). After 2 h the reaction mixture is washed with saturated ammonium chloride and brine. The organic layer is separated and dried with a Phase separator cartridge and evaporated under vacuum to obtain a residue that is dissolved in THF (1 mL) at −30° C. and treated with tetrabutylammonium fluoride (1.0 M in THF, 87 μL, 0.087 mmol). After stirring 30 min at −30° C., volatiles are evaporated under reduced pressure and the resulting residue is purified by flash chromatography (eluent 0-10% MeOH+1% NH₄OH/DCM). Fractions containing the title compound are combined and further purified over SCX cartridge, washed with MeOH and eluted with methanolic ammonia. Volatiles are removed under reduced pressure to furnish the title compound (21 mg, 30%).

UPLC-MS (Method 11): $R_t$=1.67

MS (ESI pos): m/z=299 (M+H)+

The following examples are synthesized in analogy to the preparation of example 47:

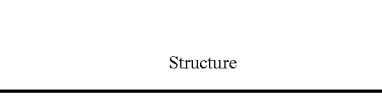

| Example | Structure | Reactant(s) | HPLC-MS $R_t$ [min], method | MS (APCl, m/z) (M + H)+ |
|---|---|---|---|---|
| 101 | 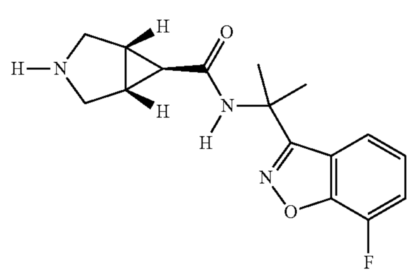 [SMILES: CC(C)(NC(=O)[C@H]1[C@@H]2CNC[C@@H]21)c1noc2c(F)cccc12] | Example 44a (4.93 g, 96% content, 11.73 mmol) | 3.04 7a | 304 |

| Example | Structure | Reactant(s) | HPLC-MS $R_t$ [min], method | MS (APCI, m/z) $(M + H)^+$ |
|---|---|---|---|---|
| 102 | 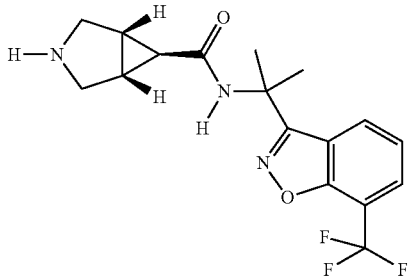 [SMILES: CC(C)(NC(=O)[C@H]1[C@@H]2CNC[C@@H]21)c1noc2c(C(F)(F)F)cccc12] | Example 44b (800 mg, 1.76 mmol) | 3.35 7a | 354 |

The following example is synthesized in analogy to the preparation of example 50:

| Example | Structure | Reactant(s) | HPLC-MS $R_t$ [min], method | MS (APCI, m/z) $(M + H)^+$ |
|---|---|---|---|---|
| 103 | 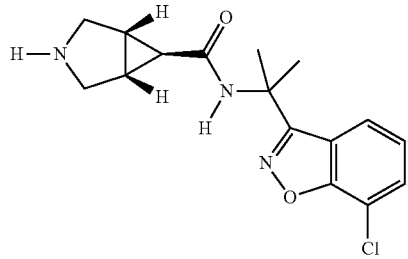 [SMILES: CC(C)(NC(=O)[C@H]1[C@@H]2CNC[C@@H]21)c1noc2c(Cl)cccc12] | Example 44c (290 mg, 95% content, 0.66 mmol) | 3.19 7a | 320 |

The following example is synthesized in analogy to the preparation of example 78:

| Example | Structure | Reactant(s) | HPLC-MS $R_t$ [min], method | MS (APCI, m/z) $(M + H)^+$ |
|---|---|---|---|---|
| 104 | 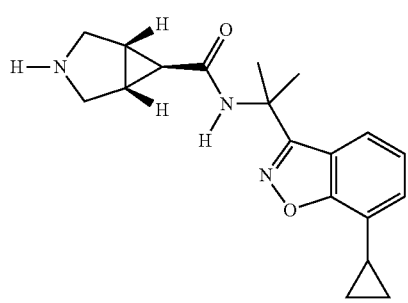 [SMILES: CC(C)(NC(=O)[C@H]1[C@@H]2CNC[C@@H]21)c1noc2c(C3CC3)cccc12] | Example 44d (105 mg, 0.25 mmol) | 3.50 7a | 326 |

Example 105

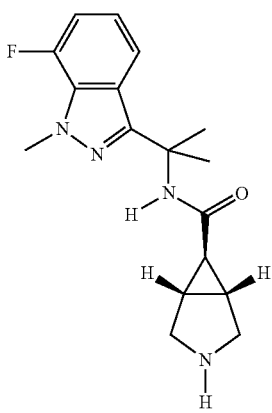 [SMILES: Cn1nc(C(C)(C)NC(=O)[C@H]2[C@@H]3CNC[C@@H]32)c2cccc(F)c21]

Hydrogen chloride 4M in dioxane (15 mL, 60 mmol) is added to example 45a (2.45 g, 5.88 mmol) in MeOH (5 mL) and stirring is continued for 5 h. The reaction mixture is basified by addition of methanolic ammonia (7N). Solids are removed by filtration and washed with DCM. Volatiles are evaporated affording a residue that is triturated with ethyl ether to furnish the title compound (1.60 g, 86%)

HPLC-MS (Method 7a): $R_t$=3.06 min
MS (AFCI): m/z=317 (M+H)$^+$

Example 106

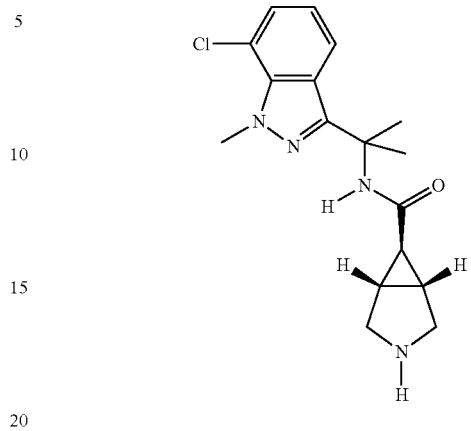

Hydrogen chloride 4M in dioxane (3 mL, 12 mmol) is added to example 45b (220 mg, 0.51 mmol) in MeOH (5 mL) and stirring is continued for 4 h. The reaction mixture is basified by addition of methanolic ammonia (7N). Solids are removed by filtration and washed with DCM. Volatiles are evaporated affording a residue that is purified by flash chromatography (10/1/90 MeOH/NH$_4$OH/DCM) followed by preparative HPLC (stationary phase: Xbridge C18 5 μm 19×100 mm. Mobile phase: ACN/H$_2$O+NH$_4$HCO$_3$ 5 mM). Fractions containing the title compound are combined and ACN is evaporated under reduced pressure. The aqueous layer is extracted with DCM, separated and the DCM is evaporated to furnish the title compound (30 mg, 18%)

HPLC-MS (Method 11): $R_t$=2.38 min
MS (ESI pos): m/z=333 (M+H)$^+$

The following examples are synthesized in analogy to the preparation of example 50:

| Example | Structure | Reactant(s) | HPLC-MS $R_t$ [min], method | MS (APCI, m/z) (M + H)$^+$ |
|---|---|---|---|---|
| 107 | 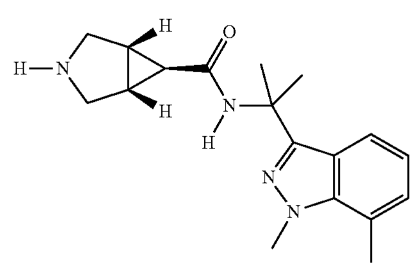 [SMILES: Cc1cccc2c(C(C)(C)NC(=O)[C@H]3[C@@H]4CNC[C@@H]43)nn(C)c12] | Example 45c (1.16 g, 2.81 mmol) | 3.21 7a | 313 |
| 108 | 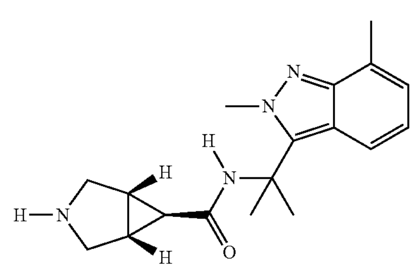 [SMILES: Cc1cccc2c(C(C)(C)NC(=O)[C@H]3[C@@H]4CNC[C@@H]43)n(C)nc12] | Example 45d (140 mg, 0.34 mmol) | 3.02 7a | 313 |

Example 109

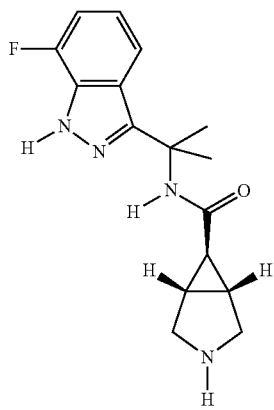 [SMILES: CC(C)(NC(=O)[C@H]1[C@@H]2CNC[C@@H]21)c1n[nH]c2c(F)cccc12]

Hydrogen chloride 4M in dioxane (2 mL, 8 mmol) is added to example 45e (40 mg, 0.10 mmol) and stirring is continued for 4 h. The reaction mixture is basified by addition of ammonium hydroxide. The reaction mixture is diluted with DCM. The organic layer is separated, volatiles are evaporated under reduced pressure affording a residue that is purified by preparative HPLC (stationary phase Xbridge C18 5 µm 19×100 mm. Mobile phase: ACN/H$_2$O+ NH$_4$COOH 5 mM). Fractions containing the title compound are combined and ACN is evaporated under reduced pressure. The aqueous layer is extracted with DCM, separated and the DCM is evaporated to afford a residue that is purified by flash chromatography (10/1/90 MeOH/NH$_4$OH/DCM) to furnish the title compound (10 mg, 33%)

HPLC-MS (Method 7a): R$_t$=2.41 min
MS (AFCI): m/z=303 (M+H)$^+$

The following example is synthesized in analogy to the preparation of example 47:

Example 111

Mixture of Stereoisomers

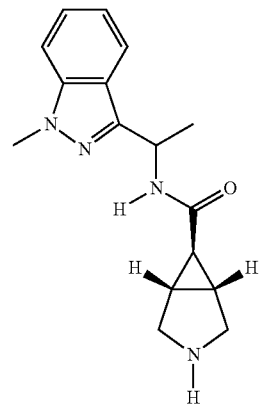 [SMILES: CC(NC(=O)[C@H]1[C@@H]2CNC[C@@H]21)c1nn(C)c2ccccc12]

Hydrogen chloride 4M in dioxane (3 mL, 12 mmol) is added to example 48a (220 mg, 0.51 mmol) in DCM (2 mL) and stirring is continued for 4 h. The reaction mixture is basified by addition of NH$_4$OH (30%). The reaction mixture is diluted with DCM. The organic layer is separated, washed with brine, volatiles are evaporated under reduced pressure affording a residue that is triturated with ethyl ether to furnish the title compound (100 mg, 56%)

HPLC-MS (Method 10): R$_t$=2.88 min
MS (ESI pos): m/z=285 (M+H)$^+$

| Example | Structure | Reactant(s) | HPLC-MS R$_t$ [min], method | MS (APCI, m/z) (M + H)$^+$ |
|---|---|---|---|---|
| 110 | (structure shown) | Example 45f (171 mg, 0.38 mmol) | 2.88 7a | 353 |

The following examples are synthesized in analogy to the preparation of example 111:

| Example | Structure | Reactant(s) | HPLC-MS | MS (APCI, m/z) (M + H)+ |
|---|---|---|---|---|
| 112 (single stereoisomer, unknown absolute stereochemistry at NH—C marked with an asterisk) | 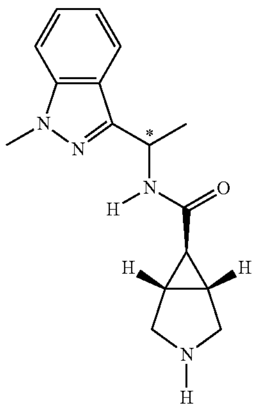 [SMILES: CC(NC(=O)[C@H]1[C@@H]2CNC[C@@H]21)c1nn(C)c2ccccc12] | Example 48b (70 mg, 0.18 mmol) 7a | 3.09 | 285 |
| 113 (single stereoisomer, unknown absolute stereochemistry at NH—C marked with an asterisk) | 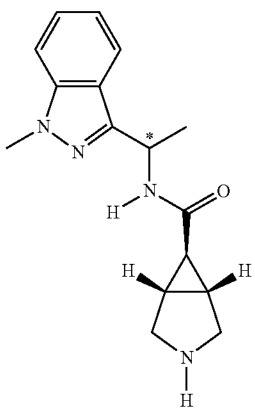 [SMILES: CC(NC(=O)[C@H]1[C@@H]2CNC[C@@H]21)c1nn(C)c2ccccc12] | Example 48c (70 mg, 0.18 mmol) 7a | 3.00 | 285 |

The following examples are synthesized in analogy to the preparation of example 50:

| Example | Structure | Reactant(s) | HPLC-MS | MS (ESI pos or APCI, m/z) (M + H)+ |
|---|---|---|---|---|
| 114 (mixture of stereoisomers) | 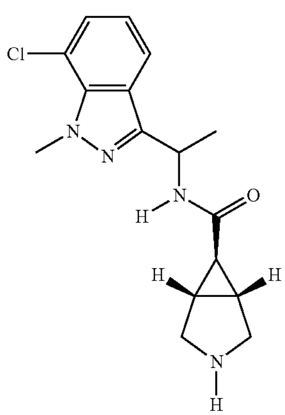 [SMILES: CC(NC(=O)[C@H]1[C@@H]2CNC[C@@H]21)c1nn(C)c2c(Cl)cccc12] | Example 54a (50 mg, 0.12 mmol) 7a | 3.90 | 319 |

-continued
| Example | Structure | Reactant(s) | HPLC-MS | MS (ESI pos or APCI, m/z) (M + H)+ |
|---|---|---|---|---|
| 115 (single stereoisomer, unknown absolute stereochemistry at NH—C marked with an asterisk) | 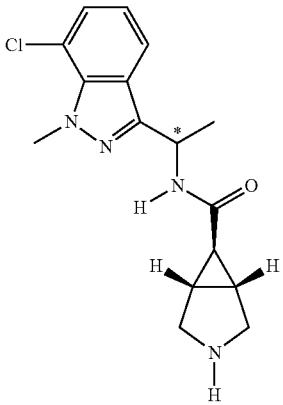 | Example 54b (82 mg, 0.20 mmol) | 2.19 11 | 319 |
| 116 (single stereoisomer, unknown absolute stereochemistry at NH—C marked with an asterisk) | 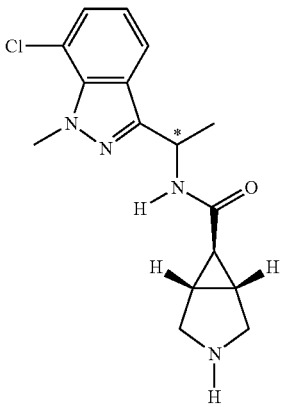 | Example 54c (86 mg, 0.21 mmol) | 2.22 11 | 319 |
| 117 (mixture of stereoisomers) | 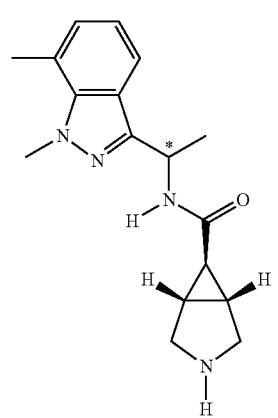 [SMILES: Cc1cccc2c(C(C)NC(=O)[C@H]3[C@@H]4CNC[C@@H]43)nn(C)c12] | Example 54d (40 mg, 93% content, 0.09 mmol) | 2.02 11 | 299 |

| Example | Structure | Reactant(s) | HPLC-MS | MS (ESI pos or APCI, m/z) (M + H)+ |
|---|---|---|---|---|
| 118 (single stereoisomer, unknown absolute stereochemistry at NH—C marked with an asterisk) | 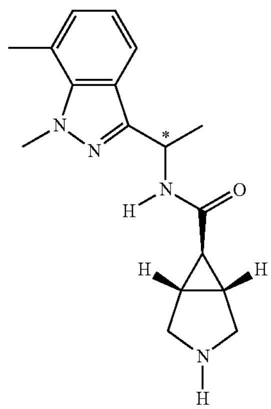 [SMILES: Cc1cccc2c(C(C)NC(=O)[C@H]3[C@@H]4CNC[C@@H]43)nn(C)c12] | Example 54e (41 mg, 0.10 mmol) | 2.03 11 | 299 |
| 119 (single stereoisomer, unknown absolute stereochemistry at NH—C marked with an asterisk) | 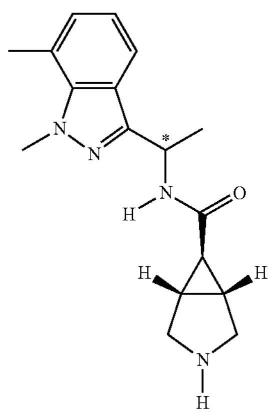 [SMILES: Cc1cccc2c(C(C)NC(=O)[C@H]3[C@@H]4CNC[C@@H]43)nn(C)c12] | Example 54f (42 mg, 0.11 mmol) | 2.05 11 | 299 |

Example 120

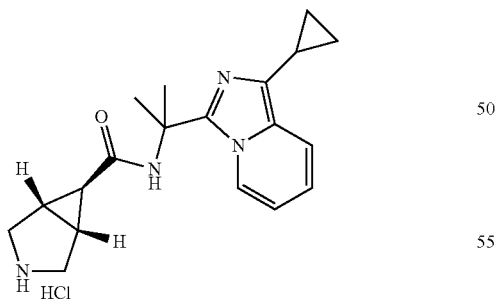

Example 23e (35 mg, 0.08 mmol) is suspended in 4M HCl in dioxane (2 mL) and stirred for 1 hour. The solvent is removed, the residue redissolved in water, washed with DCM and the aqueous phase evaporated to give the title compound (29 mg, 98%).

HPLC-MS (Method 11): $R_t$=2.04 min

MS (ESI neg): m/z=323 [M−H]−

The following examples are synthesized in analogy to the preparation of example 120:
| Example | Structure | Reactant(s) | HPLC-MS | MS (ESI pos or APCI, m/z) (M + H)+ |
|---|---|---|---|---|
| 121 | 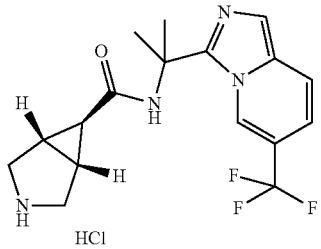 [SMILES: CC(C)(NC(=O)[C@H]1[C@@H]2CNC[C@@H]21)c1ncc2ccc(C(F)(F)F)cn12 ; Cl] | Example 23f (29 mg, 0.06 mmol) | 2.35 Method 7b | 353 |
| 122 | 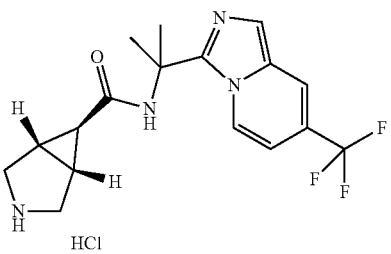 [SMILES: CC(C)(NC(=O)[C@H]1[C@@H]2CNC[C@@H]21)c1ncc2cc(C(F)(F)F)ccn12 ; Cl] | Example 23g (55 mg, 0.12 mmol) | 2.35 Method 10 | 353 |
| 123 | 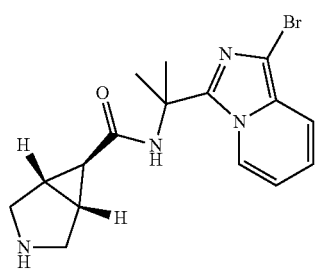 | Example 23h (38 mg, 0.08 mmol) | 2.32 Method 7b | 363/365 |
| 124 | 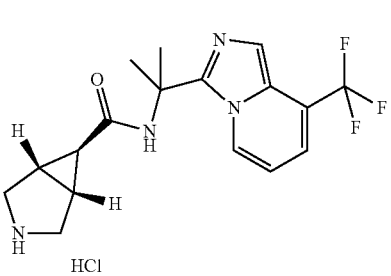 [SMILES: CC(C)(NC(=O)[C@H]1[C@@H]2CNC[C@@H]21)c1ncc2c(C(F)(F)F)cccn12 ; Cl] | Example 23i (76 mg, 0.17 mmol) | 2.32 Method 11 | 353 |
| 125 | 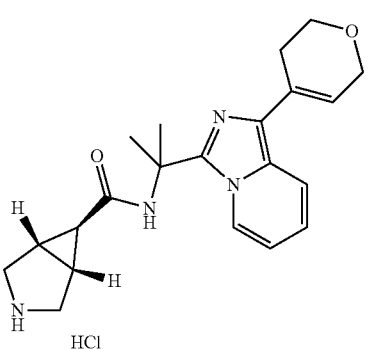 [SMILES: CC(C)(NC(=O)[C@H]1[C@@H]2CNC[C@@H]21)c1nc(C2=CCOCC2)c2ccccn12 ; Cl] | Example 23k (25 mg, 0.05 mmol) 2M HCl in diethylether (2 mL), MeCN (1 mL) | 1.67 Method 11 | 365 [M − H]− |

| Example | Structure | Reactant(s) | HPLC-MS | MS (ESI pos or APCI, m/z) (M + H)+ |
|---|---|---|---|---|
| 126 | 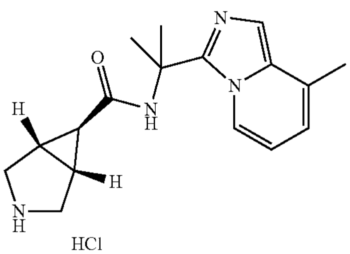 [SMILES: Cc1cccn2c(C(C)(C)NC(=O)[C@H]3[C@@H]4CNC[C@@H]43)ncc12 ; Cl] | Example 23l (261 mg, 0.65 mmol) 2M HCl in diethylether (3.25 mL), MeOH (5 mL) overnght | 2.91 Method 7a | 299 |
| 127 | 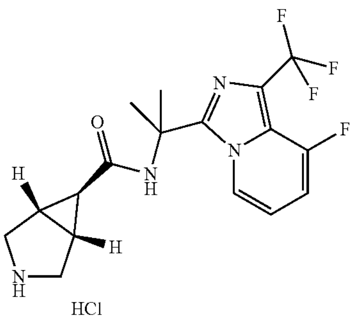 [SMILES: CC(C)(NC(=O)[C@H]1[C@@H]2CNC[C@@H]21)c1nc(C(F)(F)F)c2c(F)cccn12 ; Cl] | Example 23m (67 mg, 0.14 mmol) 3h reaction | 2.34 Method 11 | 369 [M − H]− |
| 128 | 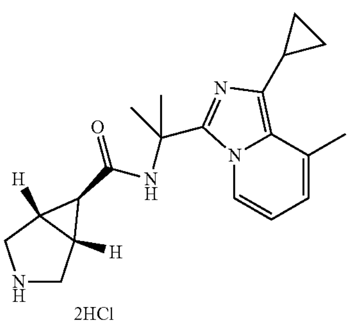 [SMILES: Cc1cccn2c(C(C)(C)NC(=O)[C@H]3[C@@H]4CNC[C@@H]43)nc(C3CC3)c12 ; "2HCl"] | Example 23ae (28 mg) MeOH as co-solvent (1 mL) Overnight reaction | 2.23 Method 11 | 339 |
| 129 | 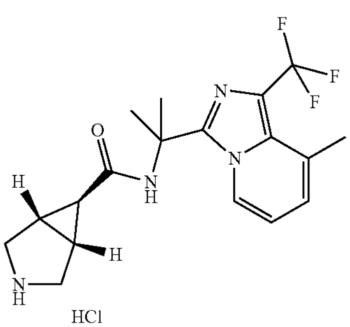 [SMILES: Cc1cccn2c(C(C)(C)NC(=O)[C@H]3[C@@H]4CNC[C@@H]43)nc(C(F)(F)F)c12 ; Cl] | Example 23af (43 mg) MeOH as co-solvent (2 mL) Overnight reaction | 3.40 Method 11 | 367 |
| 130 | 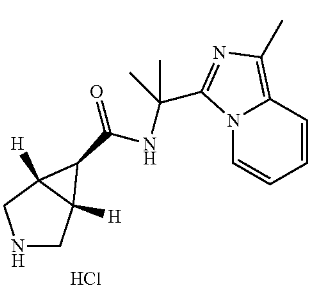 [SMILES: Cc1nc(C(C)(C)NC(=O)[C@H]2[C@@H]3CNC[C@@H]32)n2ccccc12 ; Cl] | Example 23p (141 mg) MeOH as co-solvent (2 mL) Overnight reaction | 2.39 Method 10 | 313 |

-continued

| Example | Structure | Reactant(s) | HPLC-MS | MS (ESI pos or APCI, m/z) (M + H)+ |
|---|---|---|---|---|
| 131 | 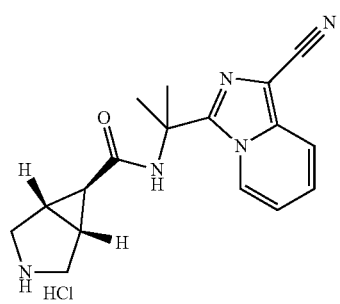 [SMILES: CC(C)(NC(=O)[C@H]1[C@@H]2CNC[C@@H]21)c1nc(C#N)c2ccccn12 ; Cl] | Example 23ac (11 mg) MeOH as co-solvent (1 mL) purified by SCX | 0.58 Method 12a | 286 |

Example 132

Example 23j (26 mg, 0.06 mmol) is suspended in 2M HCl in diethyl ether (1 mL) and stirred for 1 hour. The solvent is removed under vacuum to give the title compound (22 mg, 100%).

HPLC-MS (Method 10): $R_t$=2.63 min

MS (ESI pos): m/z=310 [M+H]+

The following examples are synthesized in analogy to the preparation of example 132:

| Example | Structure | Reactant(s) | HPLC-MS | MS (ESI pos or APCI, m/z) (M + H)+ |
|---|---|---|---|---|
| 133 | 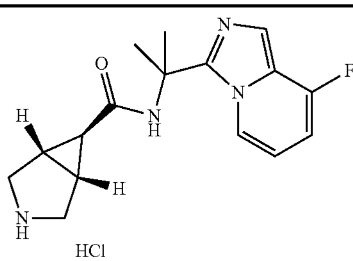 | Example 23n (76 mg, 0.19 mmol) 4M HCl in dioxane | 1.93 Method 12a | 303 |
| 134 | 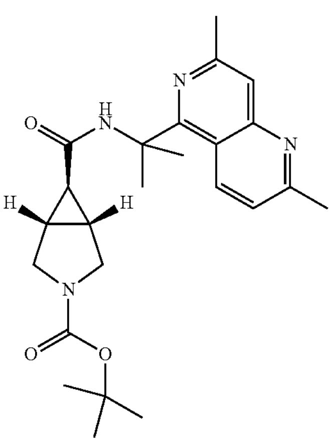 [SMILES: Cc1cc2nc(C)ccc2c(C(C)(C)NC(=O)[C@H]2[C@@H]3CN(C(=O)OC(C)(C)C)C[C@@H]32)n1] | Example 64a (21 mg) MeOH as co-solvent (2 ml) | 2.58 Method 7a | 325 |

| Example | Structure | Reactant(s) | HPLC-MS | MS (ESI pos or APCI, m/z) (M + H)+ |
|---|---|---|---|---|
| 135 | 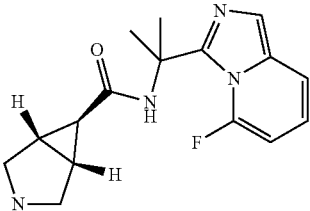 | Example 23u (8 mg, 0.02 mmol) purified by SCX | 1.44 Method 11 | 303 |
| 136 | 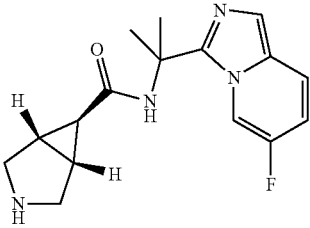 [SMILES: CC(C)(NC(=O)[C@H]1[C@@H]2CNC[C@@H]21)c1ncc2ccc(F)cn12] | Example 23r (12 mg, 0.04 mmol) purified by SCX | 1.37 Method 11 | 301 [M − H]− |
| 137 | 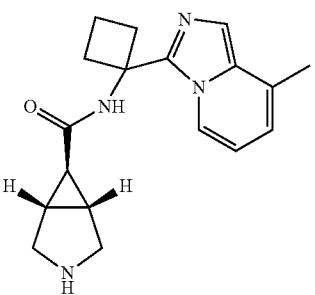 [SMILES: Cc1cccn2c(C3(NC(=O)[C@H]4[C@@H]5CNC[C@@H]54)CCC3)ncc12] | Example 23s (160 mg, 0.34 mmol) MeOH as co-solvent (2 ml) purified by SCX | 2.77 Method 7a | 311 |

Example 138

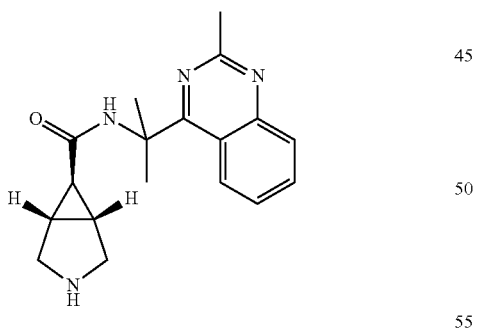

Example 58a (100 mg, 0.24 mmol) is suspended in DCM (5 mL) and TFA (0.5 mL) is added. The mixture is stirred for 30 minutes and the solvent removed under vacuum. The residue is loaded onto an SCX cartridge, washed with methanol and eluted with 7M ammonia in methanol. The solvent is removed under vacuum to give the title compound (72 mg, 95%).

HPLC-MS (Method 11): $R_t$=2.05 min

MS (ESI pos): m/z=311 [M+H]+

The following examples are synthesized in analogy to the preparation of example 138:

| Example | Structure | Reactant(s) | HPLC-MS | MS (ESI pos or APCI, m/z) $(M + H)^+$ |
|---|---|---|---|---|
| 139 | 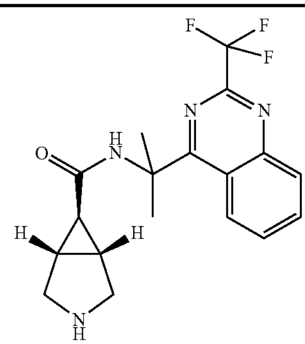 | Example 58b (81 mg, 0.17 mmol) | 2.49 Method 11 | 365 |
| 140 | 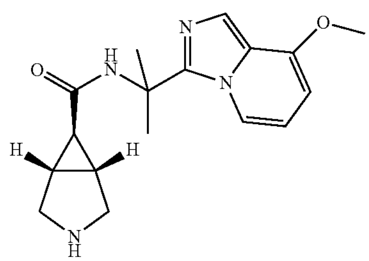 [SMILES: COc1cccn2c(C(C)(C)NC(=O)[C@H]3[C@@H]4CNC[C@@H]43)ncc12] | Example 23o (88 mg, 0.21 mmol) | 1.48 Method 11 | 315 |
| 141 | 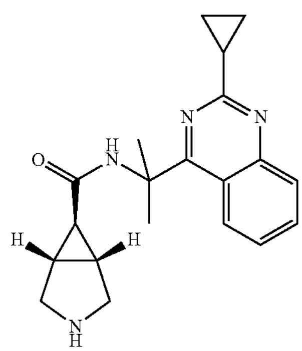 [SMILES: CC(C)(NC(=O)[C@H]1[C@@H]2CNC[C@@H]21)c1nc(C2CC2)nc2ccccc12] | Example 58g (75 mg, 0.17 mmol) | 2.24 Method 11 | 337 |
| 142 | 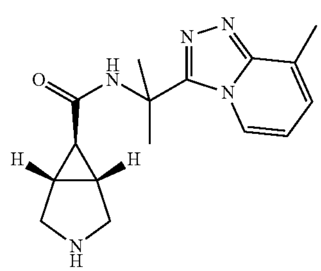 [SMILES: Cc1cccn2c(C(C)(C)NC(=O)[C@H]3[C@@H]4CNC[C@@H]43)nnc12] | Example 61a (150 mg, 0.38 mmol) | 1.48 Method 7a | 300 |
| 143 | 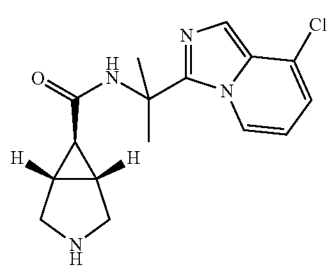 [SMILES: CC(C)(NC(=O)[C@H]1[C@@H]2CNC[C@@H]21)c1ncc2c(Cl)cccn12] | Example 23q (131 mg, 0.3 mmol) | 1.74 Method 11 | 317 [M − H]− |

-continued

| Example | Structure | Reactant(s) | HPLC-MS | MS (ESI pos or APCI, m/z) (M + H)+ |
|---------|-----------|-------------|---------|-------------------------------------|
| 144 | 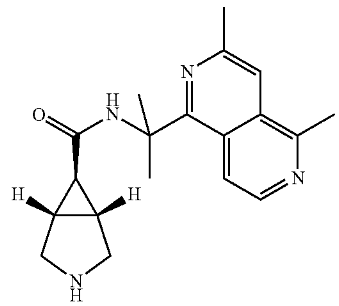 | Example 64b (51 mg, 0.12 mmol) | 1.96 Method 11 | 325 |
| 145 | 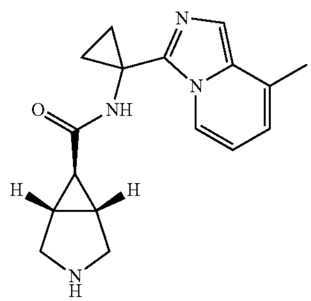 [SMILES: Cc1cccn2c(C3(NC(=O)[C@H]4[C@@H]5CNC[C@@H]54)CC3)ncc12] | Example 23t (100 mg, 0.25 mmol) Neat TFA (2 mL) | 2.80 Method 7a | 297 |
| 146 | 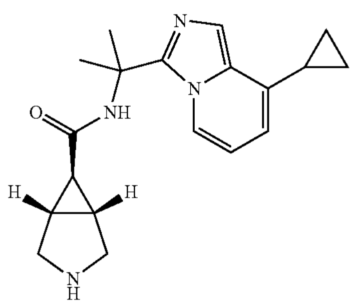 [SMILES: CC(C)(NC(=O)[C@H]1[C@@H]2CNC[C@@H]21)c1ncc2c(C3CC3)cccn12] | Example 23ag (20 mg, 0.05 mmol) Neat TFA (2 mL) | 2.88 Method 7a | 325 |
| 147 | 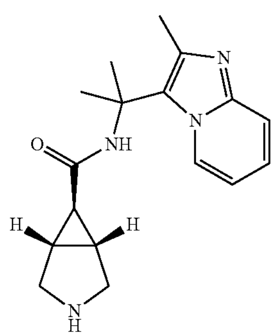 [SMILES: Cc1nc2ccccn2c1C(C)(C)NC(=O)[C@H]1[C@@H]2CNC[C@@H]21] | Example 68a (40 mg, 0.10 mmol) Neat TFA (2 mL) | 0.26 Method 12 | 299 |
| 148 | 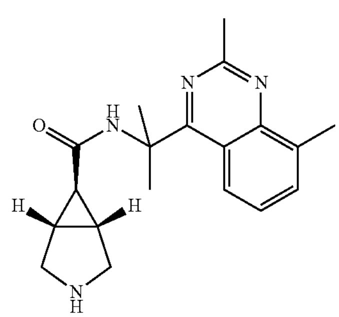 | Example 58c (74 mg, 0.17 mmol) Neat TFA (2 mL) | 3.03 Method 7a | 325 |

-continued

| Example | Structure | Reactant(s) | HPLC-MS | MS (ESI pos or APCI, m/z) (M + H)+ |
|---------|-----------|-------------|---------|-----------------------------------|
| 149 | 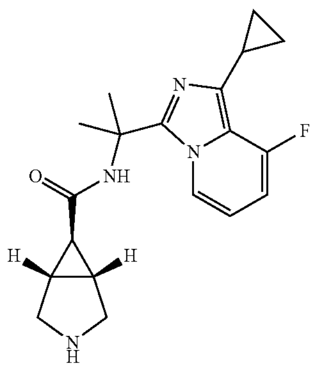 [SMILES: CC(C)(NC(=O)[C@H]1[C@@H]2CNC[C@@H]21)c1nc(C2CC2)c2c(F)cccn12] | Example 23v (64 mg, 0.14 mmol) Neat TFA (2 mL) | 2.47 Method 11 | 343 |
| 150 | 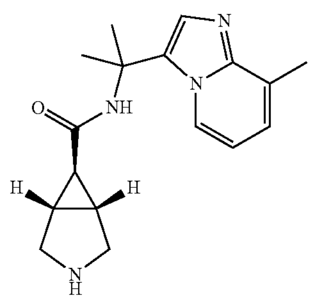 [SMILES: Cc1cccn2c(C(C)(C)NC(=O)[C@H]3[C@@H]4CNC[C@@H]43)cnc12] | Example 69a (68 mg, 0.17 mmol) | 2.30 Method 7a | 299 |
| 151 | 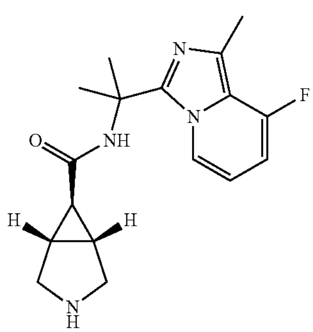 [SMILES: Cc1nc(C(C)(C)NC(=O)[C@H]2[C@@H]3CNC[C@@H]32)n2cccc(F)c12] | Example 23w (55 mg, 0.12 mmol) | 2.80 Method 7a | 317 |
| 152 | 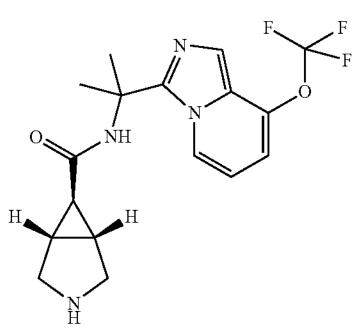 [SMILES: CC(C)(NC(=O)[C@H]1[C@@H]2CNC[C@@H]21)c1ncc2c(OC(F)(F)F)cccn12] | Example 23x (23 mg, 0.04 mmol) Neat TFA (2 mL) | 3.19 Method 7a | 369 |

-continued

| Example | Structure | Reactant(s) | HPLC-MS | MS (ESI pos or APCI, m/z) (M + H)+ |
|---------|-----------|-------------|---------|------------------------------------|
| 153 | 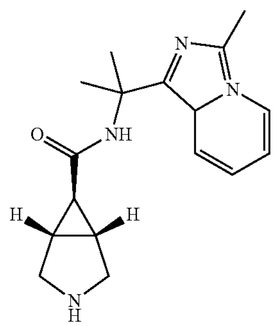 | Example 75a (37 mg, 0.09 mmol) | 2.77 Method 7a | 299 |
| 154 | 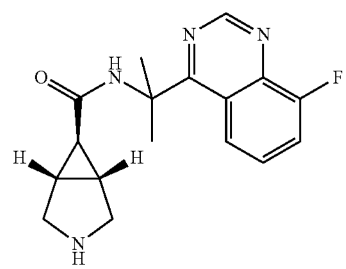 [SMILES: CC(C)(NC(=O)[C@H]1[C@@H]2CNC[C@@H]21)c1ncnc2c(F)cccc12] | Example 58d (60 mg, 0.14 mmol) Purified by preperative HPLC | 1.90 Method 7a | 315 |
| 155 | 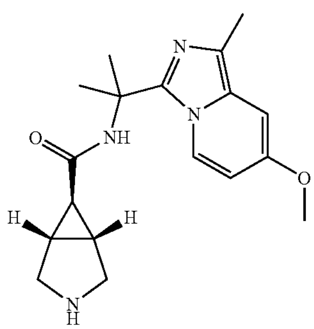 [SMILES: COc1ccn2c(C(C)(C)NC(=O)[C@H]3[C@@H]4CNC[C@@H]43)nc(C)c2c1] | Example 23y (76 mg) Purified by preperative HPLC | 1.77 Method 11 | 329 |
| 156 | 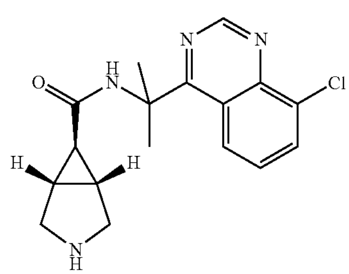 [SMILES: CC(C)(NC(=O)[C@H]1[C@@H]2CNC[C@@H]21)c1ncnc2c(Cl)cccc12] | Example 58e (100 mg, 0.23 mmol) Purified by preperative HPLC | 2.75 Method 10 | 331 |
| 157 | 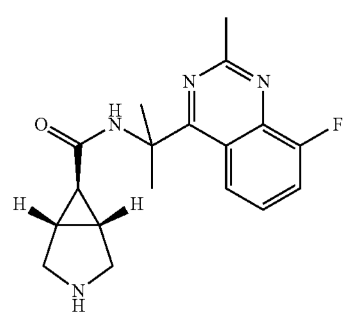 [SMILES: Cc1nc(C(C)(C)NC(=O)[C@H]2[C@@H]3CNC[C@@H]32)c2cccc(F)c2n1] | Example 58f (60 mg, 0.14 mmol) Purified by preperative TLC | 2.82 Method 7a | 329 |

-continued
| Example | Structure | Reactant(s) | HPLC-MS | MS (ESI pos or APCI, m/z) (M + H)+ |
|---|---|---|---|---|
| 158 | 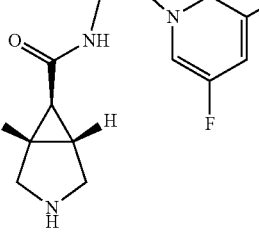 | Example 23z (22 mg, 0.05 mmol) | 2.70 Method 7a | 317 |
| 159 | 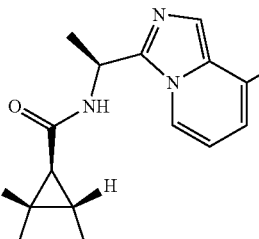 | Example 23aa (150 mg, 0.39 mmol) | 2.98 Method 7a | 285 |
| 160 | 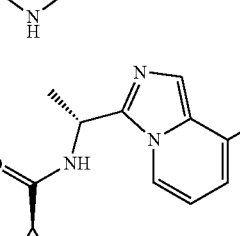 | Example 23ab (167 mg, 0.43 mmol) | 3.27 Method 7a | 285 |
| 161 (mixture of stereoisomers) | 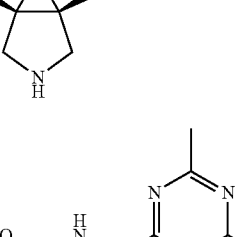 | Example 58h (50 mg, 0.13 mmol) | 2.95 Method 7a | 297 |
| 162 (mixture of stereoisomers) | 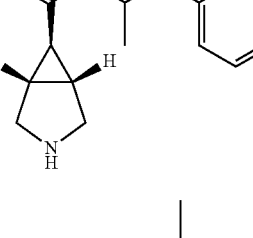 | Example 58i (50 mg, 0.12 mmol) | 3.55 Method 7a | 311 |

| Example | Structure | Reactant(s) | HPLC-MS | MS (ESI pos or APCI, m/z) (M + H)+ |
|---|---|---|---|---|
| 163 Single stereoisomer of unknown absolute configuration at CH marked with asterisk | 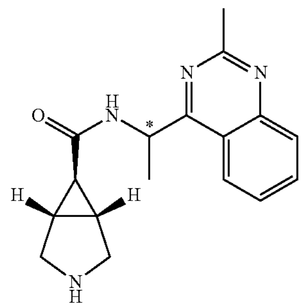 [SMILES: Cc1nc(C(C)NC(=O)[C@H]2[C@@H]3CNC[C@@H]32)c2ccccc2n1] | Example 58j (55 mg, 0.14 mmol) | 3.03 Method 7a | 297 |
| 164 Single stereoisomer of unknown absolute configuration at CH marked with asterisk | 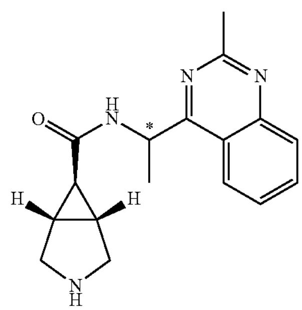 [SMILES: Cc1nc(C(C)NC(=O)[C@H]2[C@@H]3CNC[C@@H]32)c2ccccc2n1] | Example 58k (55 mg, 0.14 mmol) | 2.98 Method 7a | 297 |
| 165 Single stereoisomer of unknown absolute configuration at CH marked with asterisk | 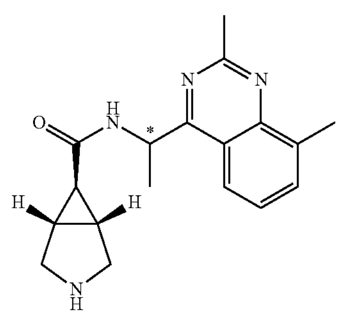 | Example 58l (70 mg, 0.17 mmol) | 2.26 Method 11 | 311 |
| 166 Single stereoisomer of unknown absolute configuration at CH marked with asterisk | 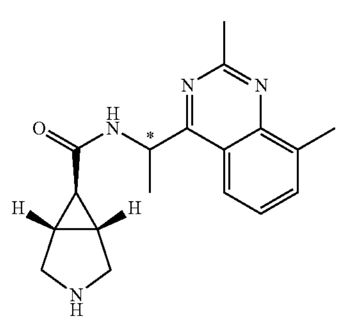 | Example 58m (70 mg, 0.17 mmol) | 2.28 Method 11 | 311 |

Example 167

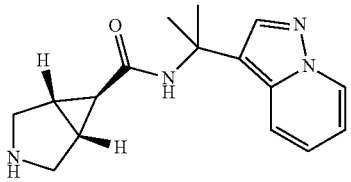 [SMILES: CC(C)(NC(=O)[C@H]1[C@@H]2CNC[C@@H]21)c1cnn2ccccc12]

2,6-Lutidine (212 mg, 1.98 mmol) and tert-butyldimethylsilyltrifluoromethanesulfonate (290 mg, 1.1 mmol) are added to example 77a (85 mg) suspended in dry DCM (7 mL) and the mixture is stirred for 15 minutes. The solution is washed with water, dried and the solvent removed. The residue is suspended in dry THF (5 mL) and tetrabutylammonium fluoride (1 M in THF, 220 µL, 0.22 mmol) is added and the mixture stirred for 15 minutes. The solvent is evaporated, the mixture partitioned between water and DCM, the phases separated, the organic phase dried and the solvent removed. The product is purified by preparative HPLC to give the title compound (28 mg).

HPLC-MS (Method 7a): $R_t$=2.70 min

MS (ESI pos): m/z=285 [M+H]$^+$

Example 168

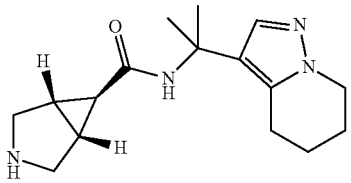 [SMILES: CC(C)(NC(=O)[C@H]1[C@@H]2CNC[C@@H]21)c1cnn2c1CCCC2]

Example 167 (148 mg) is suspended in ethanol (25 mL) and hydrogenated at 3.5 bar overnight using 10% palladium on activated carbon as the catalyst. The mixture is filtered through celite and the solvent removed. The residue is purified by flash chromatography (eluent DCM/MeOH/NH$_4$OH 90:10:1) to give the title compound (88 mg).

HPLC-MS (Method 11): $R_t$=1.71 min

MS (ESI pos): m/z=289 [M+H]$^+$

Example 169

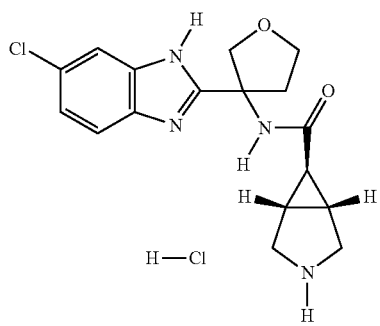 [SMILES: O=C(NC1(c2nc3ccc(Cl)cc3[nH]2)CCOC1)[C@H]1[C@@H]2CNC[C@@H]21 ; Cl]

N,N'-Dicyclohexylcarbodiimide (1.75 g, 8.5 mmol) is added portionwise at 0° C. to 4-chloro-o-phenylenediamine (1.21 g, 8.5 mmol) and 3-tert-Butoxycarbonylamino-tetrahydro-furan-3-carboxylic acid (1.97 g, 8.5 mmol) in THF (50 mL). After stirring overnight at rt, the reaction mixture was filtered and evaporated under reduced pressure to give a residue that is purified by flash chromatography (eluent 0-5% EtOH/DCM) to furnish [3-(5-Chloro-1H-benzoimidazol-2-yl)-tetrahydro-furan-3-yl]-carbamic acid tert-butyl ester (2.35 g, 78%).

[3-(5-Chloro-1H-benzoimidazol-2-yl)-tetrahydro-furan-3-yl]-carbamic acid tert-butyl ester (2.09 g, 6.19 mmol) is dissolved in DCM (100 mL) and treated with TFA (10 mL). Stirring is continued for 2 h. Volatiles are evaporated under reduced pressure and the resulting residue taken up twice with ethyl ether and evaporated under reduced pressure to give 3-(5-Chloro-1H-benzoimidazol-2-yl)-tetrahydro-furan-3-ylamine as trifluoroacetic salt crude (2.2 g).

meso-(1R,5S,6r)-3-(tert-butoxycarbonyl)-3-azabicyclo[3.1.0]hexane-6-carboxylic acid (43 mg, 0.19 mmol) is dissolved in DMF (1 mL) and HATU (143 mg, 0.38 mmol) and DIPEA (146 µl, 0.85 mmol) are added. After stirring 15 minutes, 3-(5-Chloro-1H-benzoimidazol-2-yl)-tetrahydro-furan-3-ylamine as trifluoroacetic salt crude (60 mg, 0.17 mmol) is added and continued to be stirred overnight at rt. The reaction mixture is purified by preparative HPLC (stationary phase: XBridge C18 5 µm 19×100 mm. Mobile phase: ACN/H$_2$O+NH$_4$HCO$_3$ 5 mM). Fractions containing meso-(1R,5S,6r)-6-[3-(6-Chloro-1H-benzoimidazol-2-yl)-tetrahydro-furan-3-ylcarbamoyl]-3-aza-bicyclo[3.1.0]hexane-3-carboxylic acid tert-butyl ester are combined and lyophilized. The residue in dioxane (1 mL) is treated with HCl in dioxane (4M, 0.43 mL, 1.71 mmol). After stirring overnight at rt, volatiles are evaporated under reduced pressure and the resulting residue is dissolved in ACN/H$_2$O 1:1 and lyophilized to furnish the title compound (40 mg, 61%)

UPLC-MS (Method 3): $R_t$=0.77 min

MS (ESI pos): m/z=347 (M+H)$^+$

The following example is synthesized in analogy to the preparation of example 50:
| Example | Structure | Reactant(s) | HPLC-MS $R_t$ [min], method | MS (ESI pos, m/z) $(M + H)^+$ |
|---|---|---|---|---|
| 170 | 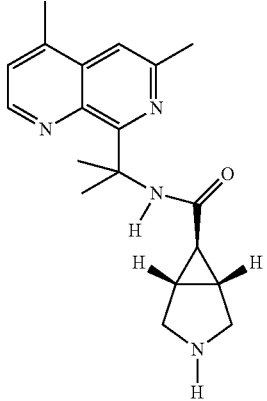 [SMILES: Cc1cc2c(C)ccnc2c(C(C)(C)NC(=O)[C@H]2[C@@H]3CNC[C@@H]32)n1] | Example 9ac (170 mg, 0.400 mmol) | 2.47 11 | 325 |
The following example is synthesized in analogy to the preparation of example 100:
| Example | Structure | Reactant(s) | HPLC-MS $R_t$ [min], method | MS (ESI pos, m/z) $(M + H)^+$ |
|---|---|---|---|---|
| 171 | 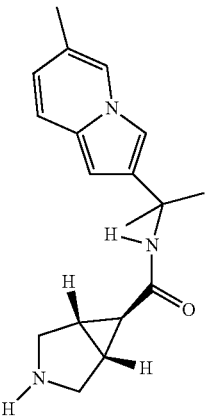 [SMILES: Cc1ccc2cc(C(C)(C)NC(=O)[C@H]3[C@@H]4CNC[C@@H]43)cn2c1] | Example 9ad (72 mg, 0.18 mmol) | 2.56 11 | 298 |

The following examples are synthesized in analogy to the preparation of example 50:

| Example | Structure | Reactant(s) | HPLC-MS R$_t$ [min], method | MS (ESI pos, m/z) (M + H)$^+$ |
|---|---|---|---|---|
| 172 | 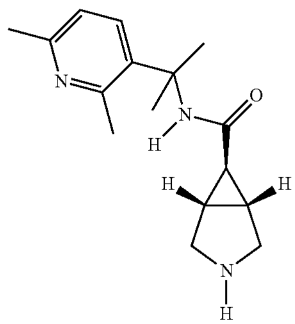 [SMILES: Cc1ccc(C(C)(C)NC(=O)[C@H]2[C@@H]3CNC[C@@H]32)c(C)n1] | Example 9ae (350 mg, 80% content, 0.750 mmol) | 1.42 11 | 274 |
| 173 (mixture of stereoisomers) | 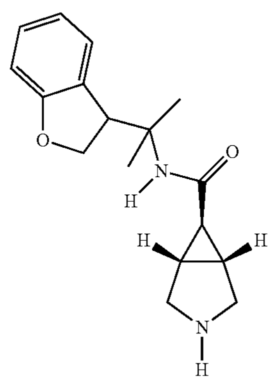 [SMILES: CC(C)(NC(=O)[C@H]1[C@@H]2CNC[C@@H]21)C1COc2ccccc21] | Example 9af (50 mg, 0.13 mmol) | 2.08 11 | 287 |
| 174 (single stereoisomer, unknown absolute stereochemistry at NH—C marked with an asterisk) | 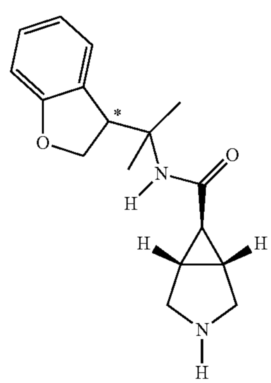 [SMILES: CC(C)(NC(=O)[C@H]1[C@@H]2CNC[C@@H]21)C1COc2ccccc21] | Example 9ag (71 mg, 0.18 mmol) | 2.00 11 | 287 |
| 175 (single stereoisomer, unknown absolute stereochemistry at NH—C marked with an asterisk) | 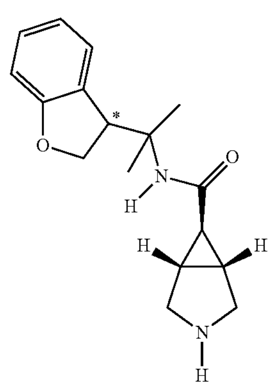 [SMILES: CC(C)(NC(=O)[C@H]1[C@@H]2CNC[C@@H]21)C1COc2ccccc21] | Example 9ah (77 mg, 0.20 mmol) | 2.03 11 | 287 |

Example 176

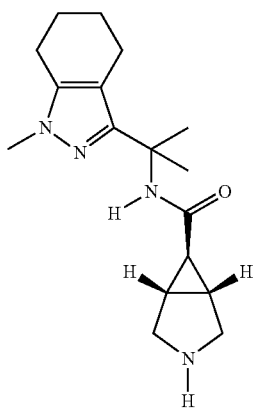 [SMILES: Cn1nc(C(C)(C)NC(=O)[C@H]2[C@@H]3CNC[C@@H]32)c2c1CCCC2]

Example 49 (61 mg, 93% content, 0.19 mmol) is dissolved in acetic acid (3 mL and Platinum(IV) oxide hydrate (25 mg, 0.10 mmol) is added. The mixture is hydrogenated at 3 bar for 3 h. The reaction mixture is purified over SCX cartridge, washed with MeOH and eluted with methanolic ammonia. Volatiles are removed under reduced pressure to afford a residue that is purified by flash chromatography (eluent 0-10% MeOH+1% NH$_4$OH/DCM) to furnish the title compound (44 mg, 77%).

HPLC-MS (Method 11): R$_t$=1.73 min

MS (ESI pos): m/z=303 (M+H)$^+$

The following examples are synthesized in analogy to the preparation of example 50:

| Example | Structure | Reactant(s) | HPLC-MS R$_t$ [min], method | MS (ESI pos, m/z) (M + H)$^+$ |
|---|---|---|---|---|
| 177 | 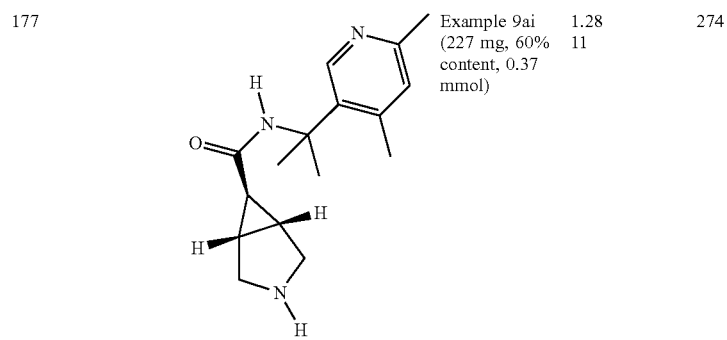 | Example 9ai (227 mg, 60% content, 0.37 mmol) | 1.28 11 | 274 |
| 178 (mixture of stereoisomers) | 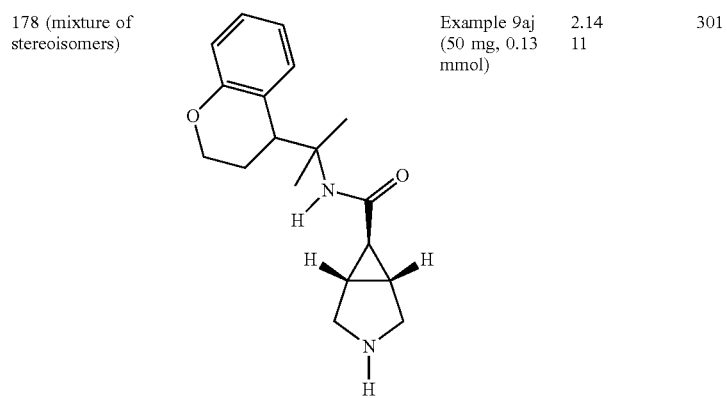 | Example 9aj (50 mg, 0.13 mmol) | 2.14 11 | 301 |

| Example | Structure | Reactant(s) | HPLC-MS R$_t$ [min], method | MS (ESI pos, m/z) (M + H)$^+$ |
|---|---|---|---|---|
| 179 (single stereoisomer, unknown absolute stereochemistry at CH$_2$CH$_2$—C marked with an asterisk) | | Example 9ak (120 mg, 97% content, 0.29 mmol) | 2.14 11 | 301 |
| 180 (single stereoisomer, unknown absolute stereochemistry at CH$_2$CH$_2$—C marked with an asterisk) | | Example 9al (120 mg, 96% content, 0.27 mmol) | 2.17 11 | 301 |

The following examples are synthesized in analogy to the preparation of example 138:

| Example | Structure | Reactant(s) | HPLC-MS | MS (ESI pos or APCI, m/z) (M + H)$^+$ |
|---|---|---|---|---|
| 181 | 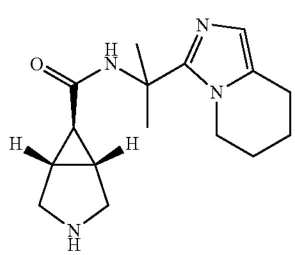 [SMILES: CC(C)(NC(=O)[C@H]1[C@@H]2CNC[C@@H]21)c1ncc2n1CCCC2] | Example 23ah (81 mg, 0.17 mmol) | 1.51 Method 11 | 289 |

| Example | Structure | Reactant(s) | HPLC-MS | MS (ESI pos or APCI, m/z) (M + H)+ |
|---|---|---|---|---|
| 182 | 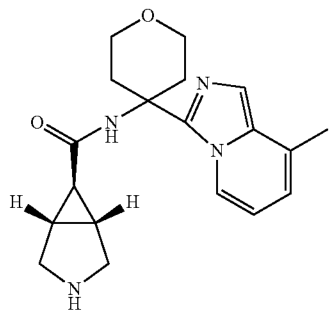 [SMILES: Cc1cccn2c(C3(NC(=O)[C@H]4[C@@H]5CNC[C@@H]54)CCOCC3)ncc12] | Example 23ai 348 mg, | 1.54 Method 11 | 341 |
| 183 (mixture of stereoisomers) | 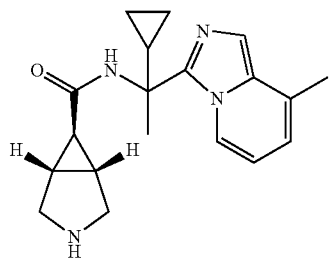 [SMILES: Cc1cccn2c(C(C)(NC(=O)[C@H]3[C@@H]4CNC[C@@H]43)C3CC3)ncc12] | Example 23aj (120 mg, 0.14 mmol) | 1.80 Method 11 | 325 |
| 184 | 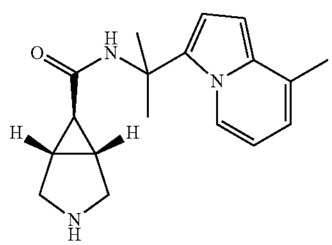 [SMILES: Cc1cccn2c(C(C)(C)NC(=O)[C@H]3[C@@H]4CNC[C@@H]43)ccc12] | Example 82a (60 mg, 0.15 mmol) | 2.42 Method 11 | 298 |

Camp Assay
Method Description for cAMP Assay with Human Somatostatin 4 Receptor

The activation of the SSTR4 receptor (Gi coupled) causes an inhibition of intracellular cAMP after stimulation with Forskolin, which can be quantifiable by use of a suitable assay Kit and an adequate plate reader. This technique is used to characterize pharmacological effects of the SSTR4 receptor agonists by use of hSSTR4 expressing H4 cells.
Description:

Compounds are dissolved and diluted in DMSO. The final test solution contains 1% DMSO. The cAMP standard (Lance cAMP 384 Kit; PerkinElmer, Cat# AD0264) is prepared in assay buffer (HBSS with 0.1% BSA, 5 mM HEPES, 0.5 M IBMX, pH 7.4) containing 1% DMSO and the cAMP standard curve is included at least on one plate. Cells are centrifuged and suspended in assay buffer (incl. 1:100 diluted Alexa antibody).

For the assay 5 μl of a cell suspension (approximately 5000 cells/well)—incl. Alexa antibody (diluted 1:100) are added into a 384 well MTP microtitre plate excepting one row or column (depending on the plate layout), which is reserved for the standard curve. Then 2 μl of compound sample is added as concentration response curve (e.g. 1e-5 M to 6e-10 M), usually in triplicates. Each assay contains incubations with vehicle controls instead of compound as controls for non-inhibited cAMP generation (100% CTL; 'high values') and incubations with 1 μM Somatosatin as controls for full inhibition and background (0% CTL; 'values'). After approximately 10-15 min incubation time 3 μl Forskolin (dissolved in DMSO, final conc. 15 μM) is added. Then the plates are shaken briefly and incubated for 60 min at room temperature. After 60 min 10 μl of the detection mix is added into all wells followed by an additional incubation period of 1 h. The plates are read in a suitable plate reader.

The analysis of the data is based on the "ratio" of the time-resolved fluorescence measurements of donor and acceptor fluorophore (Ex: 320 nm; Em1: 665 nm; Em2: 615 nm; ratio 665/615). From this ratio, cAMP concentrations are calculated from standard curve and the EC50 is estimated by least square curve fit program.

Radioligand Binding Assays
Method Description for Binding Assays with Human Somatostatin Receptors by Use of CHO Cell Membranes Expressing Recombinant Human SSTR1 or Human SSTR2 or Human SSTR3 or Human SSTR4 or Human SSTR5

Receptor binding assays refer to a technique in which labeled receptor ligands are used to detect binding to a receptor. In competition experiments test compounds, which are not labeled, compete with the binding side of a labeled ligand. The displacement of the labeled ligand by the test compound leads to a decreased signal.

Procedure:

For the binding experiments 200 μL of membrane homogenate from one of the following protein amounts is used: hSSTR1 (40 μg/well); hSSTR2 (25 μg/well); hSSTR3 (1.5 μg/well); hSSTR4 (0.5 μg/well); hSSTR5 (25 μg/well). The homogenate is incubated with 0.05 nM of radioligand ([3-125I-Tyr]-Somatostatin-(1-14)) in addition to increasing concentrations of a test compound or vehicle (100% binding) in a total volume of 250 μL using a Hepes buffer (10 mM, EDTA 1 mM, $MgCl_2$ 5 mM, pH7.6, BSA 0.5%, Bacitracin 0.003%, DMSO 1%) for 180 min at room temperature. The incubation is terminated by filtration with ice cold NaCl 0.9% through polyethyleneimine treated (0.3%) GF/B glass fiber filters using a cell harvester. The protein-bound radioactivity is measured in a suitable reader. The non-specific binding is defined as radioactivity bound in the presence of 1 μM Somatostatin-14 during the incubation period.

The analysis of the concentration-binding curves is performed by computer-assisted nonlinear least square curve fitting method using the model of one receptor binding site.

Metabolic Stability

The metabolic stability of the compounds according to the invention may be investigated as follows:

The metabolic degradation of the test compound is assayed at 37° C. with pooled human liver microsomes. The final incubation volume of 100 μl per time point contains TRIS buffer pH 7.6 at room temperature (0.1 M), magnesium chloride (5 mM), microsomal protein (1 mg/mL) and the test compound at a final concentration of 1 μM. Following a short preincubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life is determined by the slope of the semi-logarithmic plot of the concentration-time profile.

Biological Activity

The agonstic activity of the above described examples is demonstrated by the data in Table 2. The EC50 values were obtained with the aid of the above described cAMP ASSAY.

TABLE 2

Agonistic activity of compounds of the present invention.

| Example | SSTR4 agonism EC50 [nM] |
|---|---|
| 1 | 237.5 |
| 2 | 56.5 |
| 3 | 179.0 |
| 4 | 315.0 |
| 5 | 26.6 |
| 6 | 59.6 |
| 7 | 435.3 |
| 8 | 2.8 |
| 9 | 536.0 |
| 10 | 10.7 |
| 11 | 8.1 |
| 12 | 0.6 |
| 13 | 2.4 |
| 14 | 7.2 |
| 15 | 7.8 |
| 16 | 192.5 |
| 17 | 1.0 |
| 18 | 20.4 |
| 19 | 140.8 |
| 20 | 8.5 |
| 21 | 0.7 |
| 22 | 0.4 |
| 23 | 17.5 |
| 24 | 0.5 |
| 25 | 14.8 |
| 26 | 46.5 |
| 27 | 284.6 |
| 28 | 11.3 |
| 29 | 60.4 |
| 30 | 202.0 |
| 31 | 1.9 |
| 32 | 9.9 |
| 33 | 4.6 |
| 34 | 41.1 |
| 35 | 375.5 |
| 36 | 21.8 |
| 37 | 161.8 |
| 38 | 27.8 |
| 39 | 3.0 |
| 40 | 5.0 |
| 41 | 194.0 |
| 42 | 14.7 |
| 43 | 184.7 |
| 44 | 361.0 |
| 45 | 1.2 |
| 46 | 240.7 |
| 47 | 3.7 |
| 48 | 3.7 |
| 49 | 0.4 |
| 50 | 8.4 |
| 51 | 7.4 |
| 52 | 2.4 |
| 53 | 9.8 |
| 54 | 66.6 |
| 55 | 30.9 |
| 56 | 5.5 |
| 57 | 16.3 |
| 58 | 22.0 |
| 59 | 64.3 |
| 60 | 76.9 |
| 61 | 1085.5 |
| 62 | 206.5 |
| 63 | 4.1 |
| 64 | 2.0 |
| 65 | 29.8 |
| 66 | 142.5 |
| 67 | 66.3 |
| 68 | 4.7 |
| 69 | 749.0 |
| 70 | 5.7 |
| 71 | 26.9 |
| 72 | 362.0 |
| 73 | 11.9 |
| 74 | 1.6 |
| 75 | 0.4 |
| 76 | 0.8 |
| 77 | 0.5 |
| 78 | 3.2 |
| 79 | 83.7 |
| 80 | 0.3 |
| 81 | 143.4 |
| 82 | 24.6 |
| 83 | 11.0 |
| 84 | 839.7 |
| 85 | 143.5 |
| 86 | 93.9 |
| 87 | 22.9 |
| 88 | 0.8 |
| 89 | 2.6 |
| 90 | 1.4 |
| 91 | 87.2 |
| 92 | 0.4 |
| 93 | 0.1 |
| 94 | 1.6 |
| 95 | 3.6 |

TABLE 2-continued

Agonistic activity of compounds of the present invention.

| Example | SSTR4 agonism EC50 [nM] |
|---|---|
| 96 | 9.2 |
| 97 | 12.4 |
| 98 | 19.9 |
| 99 | 102.0 |
| 100 | 0.6 |
| 101 | 1.2 |
| 102 | 2.3 |
| 103 | 0.3 |
| 104 | 1.7 |
| 105 | 0.4 |
| 106 | 0.1 |
| 107 | 0.2 |
| 108 | 4.0 |
| 109 | 0.3 |
| 110 | 0.7 |
| 111 | 14.5 |
| 112 | 118.6 |
| 113 | 19.2 |
| 114 | 4.7 |
| 115 | 21.3 |
| 116 | 2.1 |
| 117 | 6.1 |
| 118 | 39.2 |
| 119 | 3.2 |
| 120 | 1.9 |
| 121 | 61.5 |
| 122 | 1336.3 |
| 123 | 1.5 |
| 124 | 15.4 |
| 125 | 97.6 |
| 126 | 0.4 |
| 127 | 31.9 |
| 128 | 0.4 |
| 129 | 6.8 |
| 130 | 0.3 |
| 131 | 484.0 |
| 132 | 72.3 |
| 133 | 7.1 |
| 134 | 34.7 |
| 135 | 7.6 |
| 136 | 6.4 |
| 137 | 0.8 |
| 138 | 4.3 |
| 139 | 10.9 |
| 140 | 0.6 |
| 141 | 3.3 |
| 142 | 4.0 |
| 143 | 0.3 |
| 144 | 47.7 |
| 145 | 0.9 |
| 146 | 2.6 |
| 147 | 13.3 |
| 148 | 1.1 |
| 149 | 1.0 |
| 150 | 0.9 |
| 151 | 0.6 |
| 152 | 26.1 |
| 153 | 1.6 |
| 154 | 7.6 |
| 155 | 94.7 |
| 156 | 7.4 |
| 157 | 36.9 |
| 158 | 0.8 |
| 159 | 15.4 |
| 160 | 42.4 |
| 161 | 763.9 |
| 162 | 128.3 |
| 163 | 338.1 |
| 164 | 6662.5 |
| 165 | 88.8 |
| 166 | 1401.8 |
| 167 | 4.9 |
| 168 | 47.3 |
| 169 | 312.5 |
| 170 | 10.9 |
| 171 | 61.5 |
| 172 | 519.6 |
| 173 | 236.8 |
| 174 | 100.2 |
| 175 | 1003.3 |
| 176 | 1.2 |
| 177 | 9.1 |
| 178 | 22.4 |
| 179 | 10.3 |
| 180 | 400.5 |
| 181 | 41.3 |
| 182 | 68.5 |
| 183 | 9.9 |
| 184 | 0.4 |

Selectivity

Selectivity data was obtained with the aid of the above described radioligand binding assays.

TABLE 3

Selectivity of compounds of the present invention for SSTR4 over other SSTRs.

| Ex | SSTR4 binding Ki [nM] | SSTR1 binding Ki [nM] | SSTR2 binding Ki [nM] | SSTR3 binding Ki [nM] | SSTR5 binding Ki [nM] |
|---|---|---|---|---|---|
| 11 | 106.5 | >8910 | >9590 | >8580 | >9850 |
| 21 | 10.8 | >8910 | >9590 | >8580 | >9850 |
| 22 | 3.7 | 848 | >9590 | >8580 | >9850 |
| 24 | 2.9 | 2820 | >9610 | >8650 | >9860 |
| 25 | 114.4 | >8960 | >9610 | >8640 | >9855 |
| 40 | 37.1 | >9760 | >9600 | >8630 | >9850 |
| 47 | 39.9 | >9148 | >9603 | >8618 | >9853 |
| 49 | 4.5 | 4535 | >9600 | >8615 | >9855 |
| 56 | 100.0 | 3460 | >9610 | >8630 | >9850 |
| 63 | 68.9 | >7514 | >7875 | >7068 | >8079 |
| 78 | 97.2 | 6640 | >9630 | >8710 | >9860 |
| 80 | 1.2 | 508 | >9630 | >8710 | >9860 |
| 93 | 3.6 | 7030 | >9630 | >8690 | >9770 |
| 94 | 15.9 | >9480 | >9630 | >8690 | >9770 |
| 101 | 46.2 | >9090 | >9600 | >8597 | >9853 |
| 107 | 3.4 | 4300 | >9600 | >8597 | >9853 |
| 126 | 3.0 | 6630 | >9630 | >8710 | >9860 |
| 128 | 7.6 | 1100 | >9630 | 6180 | >9860 |
| 138 | 70.3 | 7360 | >9630 | >8710 | >9860 |
| 148 | 32.3 | 6670 | >9630 | >8690 | >9770 |

Stability

Stability data was obtained with the above described experimental procedure.

TABLE 4

Stability of compounds of the present invention in human liver microsomes.

| Example | Half-life $t_{1/2}$ [min] |
|---|---|
| 2 | >130 |
| 8 | >130 |
| 10 | >130 |
| 11 | >130 |
| 12 | >130 |
| 13 | >130 |
| 15 | >130 |
| 17 | >130 |
| 18 | >130 |
| 20 | >130 |

TABLE 4-continued

Stability of compounds of the present invention in human liver microsomes.

| Example | Half-life $t_{1/2}$ [min] |
|---|---|
| 21 | >130 |
| 22 | >130 |
| 23 | >130 |
| 24 | >130 |
| 25 | >130 |
| 28 | >130 |
| 31 | >130 |
| 32 | >130 |
| 33 | >130 |
| 38 | >130 |
| 39 | >130 |
| 40 | >130 |
| 42 | >130 |
| 43 | >130 |
| 44 | >130 |
| 45 | >130 |
| 47 | >130 |
| 48 | >130 |
| 49 | >130 |
| 51 | >130 |
| 52 | >130 |
| 53 | 47 |
| 56 | >130 |
| 57 | >130 |
| 58 | >130 |
| 59 | >130 |
| 60 | >130 |
| 63 | >130 |
| 64 | >130 |
| 65 | >130 |
| 67 | >130 |
| 68 | >130 |
| 70 | >130 |
| 71 | 120 |
| 74 | 36 |
| 75 | >130 |
| 76 | >130 |
| 77 | >130 |
| 78 | >130 |
| 80 | >130 |
| 83 | >130 |
| 87 | >130 |
| 88 | >130 |
| 89 | >130 |
| 90 | >130 |
| 92 | >130 |
| 93 | >130 |
| 94 | >130 |
| 95 | >130 |
| 100 | >130 |
| 101 | >130 |
| 102 | >130 |
| 103 | >130 |
| 104 | >130 |
| 105 | >130 |
| 106 | >130 |
| 107 | >130 |
| 108 | >130 |
| 109 | >130 |
| 110 | >130 |
| 111 | >130 |
| 113 | >130 |
| 114 | >130 |
| 116 | >130 |
| 119 | >130 |
| 120 | >130 |
| 126 | >130 |
| 128 | >130 |
| 129 | >130 |
| 130 | >130 |
| 133 | >130 |
| 137 | >130 |
| 138 | >130 |
| 139 | >130 |
| 140 | >130 |
| 141 | >130 |
| 142 | >130 |
| 143 | >130 |
| 145 | >130 |
| 146 | >130 |
| 148 | >130 |
| 149 | >130 |
| 150 | >130 |
| 151 | >130 |
| 156 | >130 |
| 158 | >130 |
| 159 | >130 |
| 167 | >130 |
| 168 | >130 |

The invention claimed is:

1. A method for the treatment of pain which comprises administering to a host suffering from pain a therapeutically effective amount of a compound of Formula I to treat the pain, wherein Formula I is represented by:

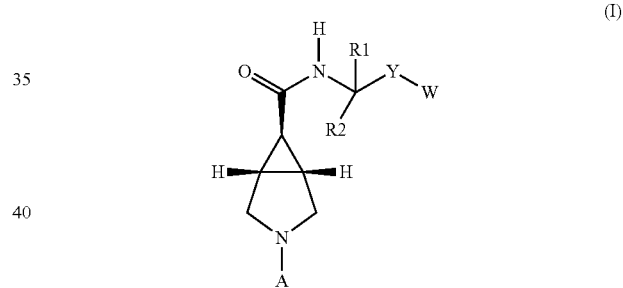

(I)

or a salt thereof, wherein:

A is selected from the group consisting of H and $C_{1-6}$-alkyl;

$R^1$ and $R^2$ are independently selected from the group consisting of H, $C_{1-6}$-alkyl and $C_{3-6}$-cycloalkyl, wherein at least one of $R^1$ or $R^2$ is $C_{1-6}$-alkyl or $C_{3-6}$-cycloalkyl, and the $C_{1-6}$-alkyl or the $C_{3-6}$-cycloalkyl is optionally substituted with halogens or MeO—;

W is a mono- or bicyclic heteroaryl, each of which is optionally substituted with one or more $R^3$, and wherein the heteroaryl comprises up to 4 heteroatoms and one or two 5- or 6-membered ring(s);

$R^3$ is independently selected from the group consisting of $C_{1-6}$-alkyl, $C_{1-6}$-alkyl-O—, halogen, HO—, and NC—; and Y is selected from the group consisting of a bond, —CH$_2$—, —CH$_2$CH$_2$—, and —CH$_2$O—.

2. The method of claim 1, wherein A is H; and $R^1$ and $R^2$ are $C_{1-6}$ alkyl.

3. The method of claim 2, wherein W is selected from the group consisting of

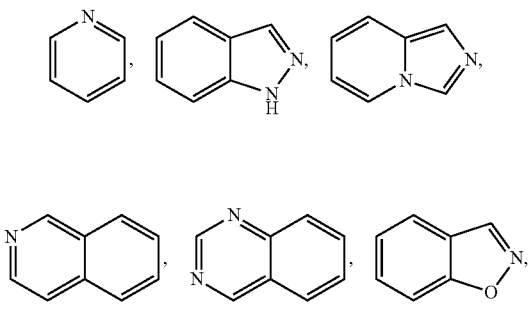

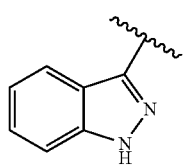 [SMILES: *c1n[nH]c2ccccc12]

wherein each of these ring systems are optionally substituted with one or more $R^3$.

4. The method of claim 2, wherein Y is —CH$_2$O—; and W is

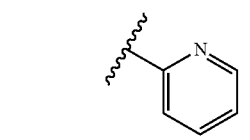

optionally substituted with one $R^3$.

5. The method of claim 2, wherein Y is a bond; and W is

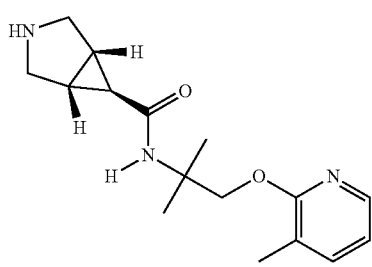 [SMILES: Cc1cccnc1OCC(C)(C)NC(=O)[C@H]1[C@@H]2CNC[C@@H]21]

optionally substituted with one $R^3$.

6. The method of claim 1, wherein the compound is

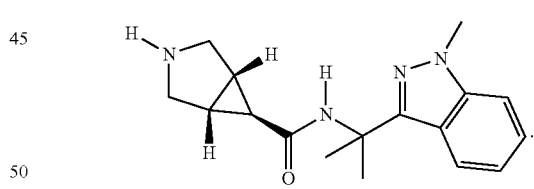

or a pharmaceutically acceptable salt thereof.

7. The method of claim 1, wherein the compound is a pharmaceutically acceptable salt of

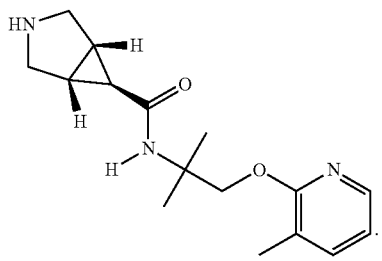 [SMILES: Cc1cccnc1OCC(C)(C)NC(=O)[C@H]1[C@@H]2CNC[C@@H]21]

8. The method of claim 1, wherein the compound is

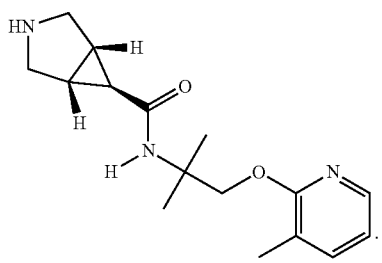 [SMILES: Cc1cccnc1OCC(C)(C)NC(=O)[C@H]1[C@@H]2CNC[C@@H]21]

9. The method of claim 1, wherein the compound is

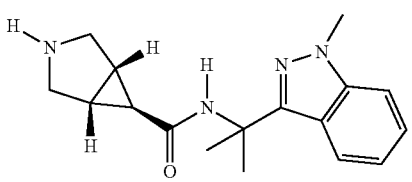 [SMILES: Cn1nc(C(C)(C)NC(=O)[C@H]2[C@@H]3CNC[C@@H]32)c2ccccc21]

or a pharmaceutically acceptable salt thereof.

10. The method of claim 1, wherein the compound is

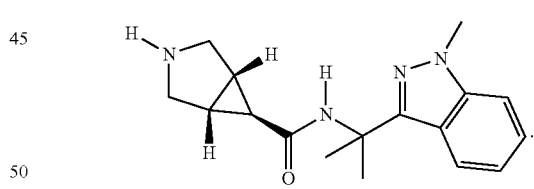

11. The method of claim 3, wherein the pain is neuropathic pain.

12. The method of claim 6, wherein the pain is neuropathic pain.

13. The method of claim 7, wherein the pain is neuropathic pain.

14. The method of claim 9, wherein the pain is neuropathic pain.

15. The method of claim 11, wherein the neuropathic pain is post-stroke pain, pain due to central nervous system injury, or pain due to multiple sclerosis.

16. The method of claim 6, wherein the pain is low back pain.

17. The method of claim 7, wherein the pain is low back pain.

18. The method of claim 9, wherein the pain is low back pain.

19. The method of claim 6, wherein the pain is chronic back pain.

20. The method of claim 7, wherein the pain is chronic back pain.

21. The method of claim 6, wherein the pain is fibromyalgia.

22. The method of claim 7, wherein the pain is fibromyalgia.

23. The method of claim 6, wherein the pain is caused by irritable bowel or diabetic neuropathy.

24. The method of claim 7, wherein the pain is caused by irritable bowel or diabetic neuropathy.

25. The method of claim 6, wherein pain is trigeminal neuralgia, complex regional pain syndrome Type I, or complex regional pain syndrome Type II.

26. The method of claim 7, wherein pain is trigeminal neuralgia, complex regional pain syndrome Type I, or complex regional pain syndrome Type II.

27. The method of claim 6, wherein the pain is caused by osteoarthritis.

28. The method of claim 6, wherein the pain is tumour pain.

29. The method of claim 3, wherein the pain is chronic pain.

30. The method of claim 6, wherein the pain is chronic pain.

31. The method of claim 3, wherein the pain is inflammatory pain.

32. The method of claim 6, wherein the pain is inflammatory pain.

33. The method of claim 12, wherein the host is a human being.

34. The method of claim 16, wherein the host is a human being.

35. The method of claim 21, wherein the host is a human being.

36. The method of claim 23, wherein the host is a human being.

37. The method of claim 25, wherein the host is a human being.

38. The method of claim 30, wherein the host is a human being.

* * * * *